United States Patent [19]

Furukawa et al.

[11] Patent Number: 5,674,856
[45] Date of Patent: Oct. 7, 1997

[54] MODIFIED OLIGODEOXYRIBONUCLEODITIDES

[75] Inventors: Hidehiko Furukawa; Kenji Momota; Hitoshi Hotoda; Makoto Koizumi; Masakatsu Kaneko, all of Tokyo, Japan

[73] Assignee: Sankyo Company, Limited, Tokyo, Japan

[21] Appl. No.: 393,510

[22] Filed: Feb. 23, 1995

Related U.S. Application Data

[63] Continuation of Ser. No. 189,046, Jan. 31, 1994, abandoned.

[30] Foreign Application Priority Data

| Jan. 29, 1993 | [JP] | Japan | 5-013509 |
| Jun. 7, 1993 | [JP] | Japan | 5-135573 |
| Jun. 10, 1993 | [JP] | Japan | 5-138517 |

[51] Int. Cl.$^6$ .......... A61K 48/00; C07H 21/02; C07H 21/04
[52] U.S. Cl. .......... 514/44; 536/24.1; 536/24.5; 536/25.3
[58] Field of Search .......... 536/24.1, 24.5, 536/25.3; 514/44

[56] References Cited

U.S. PATENT DOCUMENTS 5,220,003  6/1993  Jung et al. .......... 536/27.11

FOREIGN PATENT DOCUMENTS

| 2087818 | 7/1993 | Canada . |
| 2087817 | 7/1993 | Canada . |
| 0 097 805 | 11/1984 | European Pat. Off. . |
| 0 169 787 | 1/1986 | European Pat. Off. . |
| 0 289 619 | 11/1988 | European Pat. Off. . |
| 0 304 215 | 2/1989 | European Pat. Off. . |
| 0 552 767 | 7/1993 | European Pat. Off. . |
| 0 552 766 | 7/1993 | European Pat. Off. . |
| WO92/08729 | 5/1992 | Japan . |
| 88/00201 | 1/1988 | WIPO . |
| 88/04301 | 6/1988 | WIPO . |
| 88/07544 | 10/1988 | WIPO . |
| 90/12022 | 10/1990 | WIPO . |
| WO92/13869 | 8/1992 | WIPO . |

OTHER PUBLICATIONS

Bergstrom et al, "Organoiron mediated alkylation of phosphite esters: Synthesis of (Dicarbonyl)(n5-cyckopentadienyl)iron–derived nucleoside phosphonate esters", J. Org. Chem. 57:873–876 1992.

Mitchell et al, "Boron trifluoride–methanol complex as a nondepurinating detritylating agent in DNA synthesis", Nucleic Acids Res. 18(17) 5321 (Abstract Only) 1990.

Caruthers, "Synthesis of oligonucleotides and oligonucleotide analogues" in (Antisense inhibitors of Gene Expression, pp. 7–24, J.S. Cohen ed., CRC press, Boca Raton, FL) 1989.

Niedlein et al, "Synthesen und Untersuchungen von [Oxazolo[2,3-a]isoindol-9b(2HJ)-yl]phosphonten und –phosphinaten: eine neue klasse von heterocyclen", Helv. Chim. Acta 76:2407–2417 1993.

Renault et al, "Synthesis and antiviral evaluation of furopyrimidine diones cyclic and acyclic, nucleoside analogues", Heterocycles 41(5):937–945 1995.

Jois et al, "Synthesis and antiviral evaluation of some novel [1,2,4]triazolo[4,3-b][1,2,4]triazole nucleoside analogs", J. Heterocyclic Chem. 30:1289–1292 1993.

Verheggen et al, "Synthesis and antiherpes virus activity of 1,5 anhydrohexitol nucleosides", J. Med. chem. 36:2033–2040 1993.

Taunton–Riby et al, "Oligonucleotide synthesis: II. The use of substituted trityl groups", J. Org. Chem. 37(7):956–964 1972.

Paul C. Zamecnik et al, "Inhibition of Rous sarcoma virus replication and cell transformation by a specific oligodeoxynucleotide", Proc. Natl. Acad. Sci. USA, vol. 75, No. 1, pp. 280–284 (1978).

(List continued on next page.)

Primary Examiner—George C. Elliott
Assistant Examiner—Jeffrey Fredman
Attorney, Agent, or Firm—Frishauf, Holtz, Goodman, Langer & Chick, P.C.

[57] ABSTRACT

Compounds for the treatment or prophylaxis of a viral infection in a mammal, which may be human, are provided. The compounds are oligodeoxyribonucleic acid derivatives, and a novel route to such compounds is also provided together with intermediates of more general utility.

The active compounds are of the general formula (1):

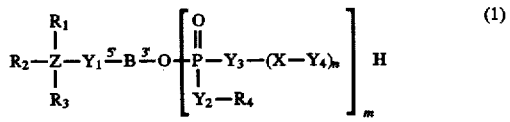

wherein $R_1$, $R_2$ and $R_3$ are hydrogen atoms, alkyl groups, aryl groups as defined, and anthraquinonyl groups as defined; Z is carbon or silicon; or $R_2$, $R_3$ and Z together represent fluorenyl or xanthenyl; $R_4$ is a hydrogen atom, an alkyl group as defined, an aryl group as defined; $Y_1$, $Y_3$ and $Y_4$ are oxygen, sulfur or >NH; $Y_2$ is oxygen, sulfur, >NH, alkylene or phenylene; X is alkylene group as defined; m and n are 0 to 10; and B is an oligodeoxyribonucleotide of chain length 3 to 9; or salts thereof.

32 Claims, No Drawings

OTHER PUBLICATIONS

Paul C. Zamecnik et al, "Inhibition of replication and expression of human T–cell lymphotropic virus type III in cultured cells by exogenous synthetic oligonucleotides complementary to viral RNA", *Proc. Natl. Acad. Sci. USA*, vol. 83, pp. 4143–4146 (1986).

Chemical Abstracts, vol. 98, No. 11, 1983, abstract No. 89801f, N. Balgobin et al, "An Efficient Chemical Synthesis of a Biologically Functional DNA Molecule . . . ", p. 599.

Chemical Abstracts, vol. 98, No. 11, 1983, abstract No. 89808p, N. Balgobin et al, "A Novel Strategy for the Chemical Synthesis of DNA and RNA Fragments using 2–Oxymethyleneanthraquinone (MAQ) as a 3'–Terminal Phosphate Protecting Group", p. 599.

Chemical Abstracts, vol. 97, No. 21, 1982, abstract No. 182794v, C. Gioeli et al, "Fluorene-9-methyl-, a Phosphate Protecting Group: its Application in the Phosphotriester Approach through the Synthesis of Tetracosathymidylic Acid", p. 868.

Journal of the Chemical Society, Chemical Communications, vol. 12, 1982, pp. 672–674, C. Gioeli et al, "The Fluoren–9–ylmethoxycarbonyl Group for the Protection of Hydroxy Groups: Its Application in the Synthesis of an Octathymidylic Acid Fragment".

Chemical Abstracts, vol. 119, No. 21, 1993, abstract No. 226347f, R. Ishido et al, "2–(2–(monomethoxytrityloxy)ethylthio)ethyl Group and its use as a Protecting Group for Phosphoric Acid Residue in oligonucleotide Synthesis", p. 1059; of JP–A–0 532 614.

Tetrahedron Letters, vol. 27, No. 39, 1986, T. Horn et al, "A Chemical 5'-Phosphorylation of Oligodeoxyribonucleotides that can be Monitored by trityl Cation Release", p. 4705 to 4708.

MODIFIED OLIGODEOXYRIBONUCLEODITIDES

This application is a continuation of application Ser. No. 08/189,046, filed Jan. 31, 1994, now abandoned.

BACKGROUND TO THE INVENTION

The present invention relates to a series of new modified oligodeoxyribonucleotides which have excellent anti-viral activity. The invention also provides methods and compositions using these oligodeoxyribonucleotides for the therapy and prophylaxis of viral infections and for inhibiting the proliferation of neoplastic cells. The invention also provides processes for the preparation of these compounds. The compounds of the present invention are particularly effective against the Human Immunodeficiency Virus (HIV), now generally accepted to be the cause of AIDS.

It is known that oligodeoxyribonucleotides (anti-sense oligodeoxyribonucleotides) having a sequence complementary to a gene inhibit the functional expression of that gene. Also it has been reported that anti-sense oligodeoxyribonucleotides complementary to a virus gene or oncogene can inhibit the replication of the virus or the multiplication of the cell by inhibiting the function of the respective genes [P. C. Zamecnik, M. L. Stephenson, Proc. Natl. Acad. Sci. USA, 75, (1) 280 (1978) and P. C. Zamecnik, J. Goodchild, Y. Taguchi, Sarin, Proc. Natl. Acad. Sci. USA, 83, (6) 4143 (1986)].

It has previously been thought that, in order that an anti-sense oligodeoxyribonucleotide should exhibit the desired activity, the oligodeoxyribonucleotide should be capable of forming a stable hybrid with the target RNA or DNA in vivo and that, accordingly, it should have a chain length of 15 or more nucleotides. In general, however, synthesize such oligodeoxyribonucleotides in yields and purities which enable them to be put to practical use. Moreover the anti-sense oligodeoxyribonucleotides do not have sufficient activity to inhibit the replication of the virus or to inhibit the multiplication of the cells to enable them to be used for treatment; moreover, the toxicity of these compounds towards the normal cells of a host is relatively high.

Although oligodeoxynucleotides having a short chain length are known, it has previously been considered that they would have poor inhibitory activity. As a result, most researchers have concentrated on the investigation of oligodeoxyribonucleotides having longer chains than those of the present invention. Thus, for example, although PCT Application No. WO 88/07544 (which is thought to represent the closest prior art to the present invention) includes within its scope oligonucleotides having as few as 4 base units, in practice, it is clear that the only materials tested are those having significantly greater numbers of units, larger than those of the present invention. We have now found that certain modified oligodeoxyribonucleotides consisting of various base sequences and prepared by introducing various substituents into the 5'-and/or 3'-terminals exhibit excellent anti-AIDS virus activity, and that the toxicity of the nucleotide toward the normal cells of a host animal is low. Moreover, and important practical consideration is that the modified oligodeoxyribonucleotides of the present invention can readily be synthesized using simple known techniques.

BRIEF SUMMARY OF INVENTION

It is, therefore, an object of the present invention to provide a series of new modified oligodeoxyribonucleotides.

It is a further and more specific object of the invention to provide such modified oligodeoxyribonucleotides which have the ability to inhibit the replication of foreign nucleic acids in normal cells and which can therefore be used for the treatment and prophylaxis of viral infections, including AIDS, and tumors.

A related object of the present invention is to provide processes for preparing the new olgodexyribonucleotide compounds, and intermediates for use in the preparative processes.

Other objects and advantages of the invention will become apparent as the description proceeds.

SUMMARY OF THE INVENTION

The compounds of the present invention are those modified oligodeoxyribonucleotides of formula (1):

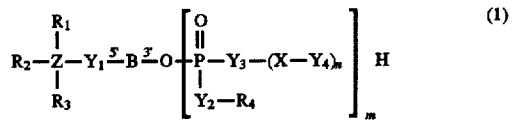

wherein:

$R_1$, $R_2$ and $R_3$ are independently selected from the group consisting of hydrogen atoms, alkyl groups having from 1 to 4 carbon atoms, aryl groups as defined below, and anthraquinonyl groups which are unsubstituted or are substituted by at least one substituent preferably selected from the group consisting of substituents 1 defined below;

Z represents a carbon atom or a silicon atom; or $R_2$, $R_3$ and Z together represent a fluorenyl or xanthenyl group;

$R_4$ represents a hydrogen atom, an unsubstituted alkyl group having from 1 to 4 carbon atoms, a substituted alkyl group which has from 1 to 4 carbon atoms and which is substituted by at least one substituent preferably selected from the group consisting of substituents 2 defined below, an aryl group as defined below, or an aralkyl group as defined below;

$Y_1$, $Y_3$ and $Y_4$ are independently selected from the group consisting of oxygen atoms, sulfur atoms and groups of formula >NH;

$Y_2$ represents an oxygen atom, a sulfur atom, a group of formula >NH, an alkylene group having from 1 to 4 carbon atoms, or a phenylene group;

X represents an unsubstituted alkylene group having from 1 to 10 carbon atoms, or an alkylene group which has from 1 to 10 carbon atoms and which is substituted by at least one hydroxy group;

m and n is each independently 0 or an integer from 1 to 10; and

B represents an oligodeoxyribonucleotide having a chain length of from 3 to 9;

said aryl group is an aromatic carbocyclic group which has from 6 to 20 ring carbon atoms and which is unsubstituted or is substituted by at least one substituent selected from the group consisting of substituents 1 defined below;

said aralkyl group is an alkyl group which has from 1 to 4 carbon atoms and which is substituted by at least one aryl group as defined above;

said substituents 1 are selected from the group consisting of alkyl groups having from 1 to 4 carbon atoms, haloalkyl groups having from 1 to 4 carbon atoms, halogen atoms, nitro groups, cyano groups, amino groups, alkoxy groups having from 1 to 4 carbon atoms, alkylthio groups having from 1 to 4 carbon atoms, aryl groups as defined above, aryloxy groups in which the aryl part is as defined above, and aralkyloxy groups in which the aralkyl part is as defined above, provided that, where said substituent 1 represents an aryl group or a group containing an aryl group which is substituted by a further aryl group or group or group containing an aryl group, that further group is not itself substituted by an aryl group or a group containing an aryl group; and said substituents 2 are selected from the group consisting of amino groups, alkoxy groups having from 1 to 4 carbon atoms, and halogen atoms.

The invention also provides a composition for the treatment or prophylaxis of viral infections, which comprises an effective amount of at least one oligodeoxyribonucleotide, wherein said oligodeoxyribonucleotide is a compound of formula (1) as defined above.

The invention also provides a method for the treatment or prophylaxis of a viral infection in a mammal, which may be human, which method comprises administering to said mammal an effective amount of at least one oligodeoxyribonucleotide, wherein said oligodeoxyribonucleotide is a compound of formula (1) as defined above.

The invention also provides processes and intermediates for preparing the compounds of the present invention, which processes are described in greater detail hereafter.

DETAILED DESCRIPTION OF INVENTION

The new modified oligodeoxyribonucleotides of the present invention are normally provided in a form free from reaction by-products.

In the compounds of the present invention, where $R_1$, $R_2$ or $R_3$ represents an alkyl group, this may be a straight or branched chain alkyl group having from 1 to 4 carbon atoms, and examples include the methyl, ethyl, propyl, isopropyl, butyl, isobutyl, sec-butyl and t-butyl groups. Of these, we prefer the t-butyl group.

Where $R_1$, $R_2$ or $R_3$ represents an aryl group, this may be an aromatic carbocyclic group which has from 6 to 20 ring carbon atoms, more preferably from 6 to 16 ring carbon atoms, still more preferably from 6 to 10 ring carbon atoms and most preferably 6 or 10 carbon atoms, and which is unsubstituted or is substituted by at least one substituent selected from the group consisting of substituents 1 defined and exemplified below. Examples of the unsubstituted groups include the phenyl, 1-naphthyl, 2-naphthyl, phenanthren-4-yl, anthracen-9-yl, anthracen-2-yl and pyrenyl groups. Of these, the more preferred groups are the naphthyl and phenyl groups, the phenyl group being most preferred. The substituted groups may be any of these groups and may be substituted by one or more of substituents 1, defined above and exemplified below. There is no particular restriction on the number of substituents, except such as may be imposed by the number of substitutable positions (for example, 5 in the case of the phenyl group or 7 in the case of the naphthyl groups) and possibly by steric constraints. Most commonly, however, we prefer from 1 to 5 such substituents, more preferably from 1 to 3 and most preferably 1 or 2, substituents. Specific examples of substituents 1 include:

alkyl groups having from 1 to 4 carbon atoms, such as the methyl, ethyl, propyl, isopropyl, butyl, isobutyl, sec-butyl and t-butyl groups, of which we prefer the methyl and t-butyl groups;

haloalkyl groups having from 1 to 4 carbon atoms, such as the fluoromethyl, trifluoromethyl, trichloromethyl, 2,2,2-trifluoroethyl, 2,2,2-trichloroethyl, 2-fluoroethyl, 2-chloroethyl, 2-iodoethyl, 3-chloropropyl and 4-fluorobutyl and 6-iodohexyl groups, of which we prefer the 2,2,2-trichloroethyl and trifluoromethyl groups;

halogen atoms, such as the fluorine, chlorine, bromine and iodine atoms, of which the chlorine and fluorine atoms are preferred;

nitro groups, cyano groups, amino groups;

alkoxy groups having from 1 to 4 carbon atoms, such as the methoxy, ethoxy, propoxy, isopropoxy, butoxy, isobutoxy, sec-butoxy and t-butoxy groups, of which we prefer the methoxy and t-butoxy groups;

alkylthio groups having from 1 to 4 carbon atoms, such as the methylthio, ethylthio, propylthio, isopropylthio, butylthio, isobutylthio, sec-butylthio and t-butylthio groups, of which we prefer the methylthio and t-butylthio groups;

aryl groups as defined and exemplified above, and most preferably the phenyl group;

aryloxy groups in which the aryl part is as defined and exemplified above, and most preferably the phenoxy group;

and aralkyloxy groups in which the aralkyl part is as defined above, such as the benzyloxy and dibenzyloxybenzyloxy [particularly the 3,5-dibenzyloxybenzyloxy group].

It should be observed that, whilst an aryl group (or a group containing an aryl group) may itself be substituted by a further such group, a limit is imposed herein on such further substitution, in that, where said substituent 1 represents an aryl group or a group containing an aryl group which is substituted by a further aryl group or group or group containing an aryl group, that further group is not itself substituted by an aryl group or a group containing an aryl group.

Specific examples of such substituted aryl groups include the 4-methylphenyl, 4-t-butylphenyl, 2-phenylphenyl, 4-phenylphenyl, 4-fluorophenyl, 2-chlorophenyl, 4-chlorophenyl, 4-bromophenyl, 4-iodophenyl, 2,4-difluorophenyl, 4-nitrophenyl, 4-t-butoxyphenyl, 4-methoxyphenyl, 4-ethoxyphenyl, 3-phenoxyphenyl, 4-phenoxyphenyl, 2-benzyloxyphenyl, 4-benzyloxyphenyl, 3,4-dibenzyloxyphenyl, 3,5-dibenzyloxyphenyl and 3,5-bis(3,5-dibenzyloxybenzyloxy)phenyl groups. Of the substituted and unsubstituted aryl groups, we prefer the phenyl, 4-methoxyphenyl, 3,4-dibenzyloxyphenyl, 3,5-dibenzyloxyphenyl group and 3,5-bis(3,5-dibenzyloxybenzyloxy)phenyl groups.

Where $R_1$, $R_2$ or $R_3$ represents an anthraquinonyl group, this may be unsubstituted or it may be substituted by one or more of substituents 1, defined and exemplified above. Where the group is substituted, it may be substituted by at least one substituent selected from the group consisting of substituents 1 defined and exemplified above. There is no particular restriction on the number of substituents, except such as may be imposed by the number of substitutable positions and possibly by steric constraints. We prefer from 1 to 5 such substituents, more preferably from 1 to 3 and most preferably 1, substituents. Examples of such groups include the 9,10-anthraquinon-1-yl, 9,10-anthraquinon-2-yl, 4-methyl-9,10-anthraquinon-1-yl, 5-methoxy-9,10-anthraquinon-1-yl, 7-chloro-9,10-anthraquinon-1-yl, 8-fluoro-9,10-anthraquinon-2-yl, 6-ethyl-9,10- anthraquinon-2-yl, 8-ethoxy-9,10-anthraquinon-2-yl and 6-hydroxy-9,10-anthraquinon-1-yl groups. Of these, we prefer the unsubstituted anthraquinonyl groups.

Alternatively, R2, R3, and Z may together represent a fluorenyl or xanthenyl group, in which case this is preferably a fluoren-9-yl or xanthen-9-yl group.

Where $R_4$ represents an alkyl group, this may be any of those exemplified above in relation to $R_1$ etc., but may be unsubstituted or substituted. If substituted, it is substituted by at least one of substituents 2, defined above. Examples of such substituents 2 include amino groups, alkoxy groups having from 1 to 4 carbon atoms and halogen atoms, which may be as exemplified above in relation to substituents 1, above. Specific examples of such substituted and unsubtituted alkyl groups include the methyl, ethyl, 2-aminoethyl, 2-methoxyethyl, propyl, isopropyl, butyl, isobutyl, sec-butyl and t-butyl group. Of these, we prefer the methyl, ethyl, 2aminoethyl, 2-methoxyethyl and propyl groups.

Where $R_4$ represents an aryl group, this may be any of the aryl groups exemplified above in relation to $R_1$ etc., and may be a substituted or unsubstituted group. Examples of such groups include: the phenyl group; alkylphenyl groups, such as the 2-methylphenyl or 3-ethylphenyl group; halogenated phenyl groups, such as the 2-fluorophenyl, 2-chlorophenyl, 4-chlorophenyl, 2-bromophenyl or 2-iodophenyl group; nitrophenyl groups, such as the 2-nitrophenyl or 4-nitrophenyl group; alkoxyphenyl groups, such as the 4-methoxyphenyl or 4-ethoxyphenyl group; alkylthiophenyl groups, such as the 4-methylthiophenyl or 4-ethylthiophenyl group; and the naphthyl, phenanthrenyl, anthracenyl and pyrenyl groups. Of these, we prefer then unsubstituted phenyl, halogenated phenyl and nitrophenyl groups.

Where $R_4$ represents an aralkyl group, this is an alkyl group which has from 1 to 4 carbon atoms and which is substituted by at least one (and preferably 1, 2 or 3, more preferably 1) aryl groups which may be as defined and exemplified above. Examples of such groups include the benzyl, methylbenzyl, ethylbenzyl, methoxybenzyl, ethoxybenzyl, fluorobenzyl, chlorobenzyl, bromobenzyl, chloronaphthylmethyl, indenylmethyl, phenanthrenylmethyl, anthracenylmethyl, diphenylmethyl, triphenylmethyl, 1-phenethyl, 2-phenethyl, 2,2-diphenylethyl, 2,2,2-triphenylethyl, 3,3,3-triphenylpropyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl and 6-naphthylhexyl groups. Of these, we prefer an unsubstituted benzyl or 2-phenethyl group.

Where $Y_2$ represents a alkylene group, this may be a methylene, ethylene, propylene, tetramethylene or pentamethylene group. Of these, we prefer a methylene group.

$Y_1$, $Y_3$ and $Y_4$ each preferably represents an oxygen atom.

$Y_2$ represents preferably an oxygen or sulfur atom.

Z preferably represents a carbon atom.

Where X represents a straight or branched chain optionally substituted with a hydroxy group, examples include a methylene, methylmethylene, ethylene, propylene, tetramethylene, methylethylene, 1-methyltrimethylene, 2-methyltrimethylene, 2-methyltetramethylene, 3-methyltrimethylene, pentamethylene, hexamethylene, heptamethylene, octamethylene, nonamethylene, decamethylene, 2-hydroxytrimethylene or 2-hydroxytetramethylene group. Of these, we prefer a methylene, methylmethylene, ethylene, or methylethylene group.

The preferred values for each of m and n is an integer of 0 to 6. We particularly prefer that m is an integer of 0 to 4.

The oligodeoxyribonucleotide represented by B preferably has a chain length of 4 to 8; more preferably a chain length of 5 or 6. Moreover, it is preferred that the fourth deoxyribonucleotide from the 5'-terminal end is guaninedeoxyribonucleotide.

The typical preferred illustrative oligodeoxyribonucleotides are those in the following "α group" and the more preferred ones are those in the following "β group", where the abbreviations used in the following α and β groups have the following significance:

A: adeninedeoxyribonucleotide;

G: guaninedeoxyribonucleotide;

C: cytosinedeoxyribonucleotide;

T: thyminedeoxyribonucleotide;

mC: 5-methylcytosinedeoxyribonucleotide; and mG: $O^6$-methylguaninedeoxyribonucleotide. The term "left end" signifies a 5'-terminal end and the term "right end" signifies a 3'-terminal end, subject to the proviso that there is no hydroxy group at both the 5'-and 3'-terminal ends of each oligodeoxyribonucleotide. "α group": TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, GGGCGGGGC, TAGGAGG, TGGGAGGT, TGGGCGCAG, CCG, TCGGAGG, TGmCGAGG, CTGGGAGG, TGG, TGGGAmGG, TGGGAGA, AATGGGAGG, TTGGGG, TGGGGG, CGGGG, CGCGG, CGGGT, TGGGC, TGGGT. "β group": TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, TTGGGG, TGGGGG, CGGGG, CGCGG.

A preferred group of formula: $R_1R_2R_3Z-Y_1$, at the 5'-terminal end is exemplified by a triphenylmethyloxy, 3,4-(dibenzyloxy)benzyloxy, 3,5-(dibenzyloxy)benzyloxy, 3,5-bis[3,5-(dibenzyloxy)benzyloxy]benzyloxy, tert-butyldiphenylsilyloxy, phenylfluorenyloxy or phenylxanthenyloxy group; more preferably a triphenylmethyloxy, 3,4-(dibenzyloxy)benzyloxy or 3,5-(dibenzyloxy)benzyloxy group.

A preferred group of formula: $[P(O)(Y_2R_4)-Y_3-(X-Y_4)_n]_mH$ at the 3'-terminal end is exemplified by a hydrogen atom, a methylphosphoryl, 2-chlorophenylphosphoryl,-O-methylthiophosphoryl, methylphosphonyl, methylthiophosphonyl, phenylphosphonyl, 2-hydroxyethylphosphoryl,-O-(2-hydroxyethyl) thiophosphoryl, phenylphosphoryl, 4-chlorophenylphosphoryl, 2-nitrophenylphosphoryl, 4-nitrophenylphosphoryl, ethylphosphoryl or-O-ethylthiophosphoryl group; more preferably a hydrogen atom, a methylphosphoryl, 2-chlorophenylphosphoryl,-O-methylthiophosphoryl, methylphosphonyl, methylthiophosphonyl, phenylphosphonyl, 2-hydroxyethylphosphoryl or-O-(2-hydroxyethyl) thiophosphoryl group.

Collectively, the preferred compounds of the present invention are those in which:

(1) the chain length of B is 4 to 8;

(2) the chain length of B is 5 or 6;

(3) the chain length of B is 4 to 8, and the fourth deoxyribonucleotide from the 5'-terminal of B is guaninedeoxyribonucleotide;

(4) the group of formula: $R_1R_2R_3Z-Y_1$, at the 5'-terminal end is a triphenylmethyloxy, 3,4-(dibenzyloxy) benzyloxy, 3,5-(dibenzyloxy)benzyloxy, 3,5-bis[3,5-(dibenzyloxy)benzyloxy]benzyloxy, tert-butyldiphenylsilyloxy, phenylfluorenyloxy or phenylxanthenyloxy group; a group of formula: $[P(O)(Y_2R_4) Y_3-(X-Y_4)_n]_mH$, at the 3'-terminal end is a hydrogen atom, a methylphosphoryl, 2-chlorophenylphosphoryl, -O-methylthiophosphoryl, methylphosphonyl, methylthiophosphonyl, phenylphosphonyl, 2-hydroxyethylphosphoryl,-O-(2-hydroxyethyl)thiophosphoryl, phenylphosphoryl, 4-chlorophenylphosphoryl, 2-nitrophenylphosphoryl, 4-nitrophenylphosphoryl, ethylphosphoryl or-O-ethylthiophosphoryl group; and B is TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, GGGCGGGGC, TAGGAGG, TGGGAGGT, TGGGCGCAG, CCG, TCGGAGG, TGmCGAGG, CTGGGAGG, TGG, TGGGAmGG, TGGGAGA, AATGGAGG, TTGGGG, TGGGGG, CGGGG, CGCGG, CGGGT, TGGGC or TGGGT;

(5) the group of formula: $R_1R_2R_3Z-Y_1$, at the 5'-terminal end is a triphenylmethyloxy, 3,4-(dibenzyloxy) benzyloxy, 3,5-(dibenzyloxy)benzyloxy, 3,5-bis[3,5-(dibenzyloxy)benzyloxy]benzyloxy, tert-butyldiphenylsilyloxy, phenylfluorenyloxy or phenylxanthenyloxy group; a group of formula: $[p(O)(Y_2R_4)-Y_3-(X-Y_4)_n]_mH$ at the 3'-terminal end is a hydrogen atom, a methylphosphoryl, 2-chlorophenylphosphoryl, -O-methylthiophosphoryl, methylphosphonyl, methylthiophosphonyl, phenylphosphonyl, 2-hydroxyethylphosphoryl,-O-(2-hydroxyethyl)thiophosphoryl, phenylphosphoryl, 4-chlorophenylphosphoryl, 2-nitrophenylphosphoryl, 4-nitrophenylphosphoryl, ethylphosphoryl or-O-ethylthiophosphoryl group; and B is TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, TTGGGG, TGGGGG, CGGGG or CGCGG;

(6) the group of formula: $R_1R_2R_3Z-Y_1$, at the 5'-terminal end is a triphenylmethyloxy, 3,4-(dibenzyloxy) benzyloxy, 3,5-(dibenzyloxy)benzyloxy, 3,5-bis[3,5-(dibenzyloxy)benzyloxy]benzyloxy, tert-butyldiphenylsilyloxy, phenylfluorenyloxy or phenylxanthenyloxy group; a group of formula: $[P(O)(Y_2R_4)-Y_3-(X-Y_4)_n]_mH$ at the 3'-terminal end is a hydrogen atom, a methylphosphoryl, 2-chlorophenylphosphoryl, -O-methylthiophosphoryl, methylphosphonyl, methylthiophosphonyl, phenylphosphonyl, 2-hydroxyethylphosphoryl or-O-(2-hydroxyethyl)thiophosphoryl group; and B is TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, TTGGGG, TGGGG, CGGGG or CGCGG;

(7) the group of formula: $R_1R_2R_3Z-Y_1$ at the 5'-terminal end is a triphenylmethyloxy, 3,4-(dibenzyloxy) benzyloxy or 3,5-(dibenzyloxy)benzyloxy group; a group of formula: $[(P(O)(Y_2R_4) Y_3-(X-Y_4)_n]_mH$ at the 3'-terminal end is a hydrogen atom, a methylphosphoryl, 2-chlorophenylphosphoryl, -O-methylthiophosphoryl, methylphosphonyl, methylthiophosphonyl, phenylphosphonyl, 2-hydroxyethylphosphoryl,-O-(2-hydroxyethyl)thiophosphoryl, phenylphosphoryl, 4-chlorophenylphosphoryl, 2-nitrophenylphosphoryl, 4-nitrophenylphosphoryl, ethylphosphoryl or-O-ethylthiophosphoryl group; and B is TGGGAG, TGGGA, TGGGG, TGGG, TGGG, CGGGAGG, TTGGAGG, TTGGGAGG TGCGAGG, GGGGAGG, mCGGGAGG, mCGmCGAGG, CTGGGAGG, TTGGGG, TGGGGG, CGGGG or CGCGG;

(8) the group of formula: $R_1R_2R_3Z-Y_1$, at the 5'-terminal end is a triphenylmethyloxy, 3,4-(dibenzyloxy) benzyloxy or 3,5-(dibenzyloxy)benzyloxy group; a group of formula: $[P(O)(Y_2R_4)-Y_3-(X-Y_4)_n]_mH$ at the 3'-terminal end is a hydrogen atom, a methylphosphoryl, 2-chlorophenylphosphoryl, -O-methylthiophosphoryl, methylphosphonyl, methylthiophosphonyl, phenylphosphonyl, 2-hydroxyethylphosphoryl or-O-(2-hydroxyethyl) thiophosphoryl group; and B is TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, TTGGGG, TGGGGG, CGGGG or CGCGG.

Examples of the compounds of the present invention are listed in Table 1. Such examples are not to be construed as being limitative of the invention.

In the Table, the following abbreviations are used to denote certain groups:

| | |
|---|---|
| 2-Anq | anthraquinon-2-yl |
| 2-Ant | anthracen-2-yl |
| 9-Ant | anthracen-9-yl |
| Bdbbp | 3,5-bis[3,5-(dibenzyloxy)benzyloxy]phenyl |
| Bu | butyl |
| tBu | t-butyl |
| Bz | benzyl |
| 3,4-Dbp | 3,4-(dibenzyloxy)phenyl |
| 3,5-Dbp | 3,5-(dibenzyloxy)phenyl |
| Decm | decamethylene [—(CH$_2$)$_{10}$—] |
| Et | ethyl |
| Ete | ethylene [—CH$_2$CH$_2$—] |
| Hepm | heptamethylene [—(CH$_2$)$_7$—] |
| Hexm | hexamethylene [—(CH$_2$)$_6$—] |
| Hpr | 2-hydroxypropylene [—CH$_2$C(OH) (CH$_3$)—] |
| Me | methyl |
| Mee | methylene [—CH$_2$—] |
| Nonm | nonamethylene [—(CH$_2$)$_9$—] |
| Npe | naphthalenyl [e.g. 2-Npe is naphthalen-2-yl or 1-Npe is naphthalen-1-yl] |
| Octm | octamethylene [—(CH$_2$)$_8$—] |
| Penm | pentamethylene [—(CH$_2$)$_5$—] |
| Ph | phenyl |
| Pha | phenanthrenyl [e.g. 4-Pha is phenanthren-4-yl] |
| Phe | 1,4-phenylene |
| Pr | propyl |
| Pre | propylene [—CH$_2$CH(CH$_3$)—] |
| 1-Pyr | pyren-1-yl |
| Tetm | tetramethylene [—(CH$_2$)$_4$—] |
| Trim | trimethylene [—(CH$_2$)$_3$—] |

In addition, the sequence represented by "B" in formula (1) is identified by the following code numbers:

| | |
|---|---|
| 1 | TGGGAG |
| 2 | TGGGA |
| 3 | TGGGG |
| 4 | TGGG |
| 5 | TGGGAGG |
| 6 | CGGGAGG |
| 7 | TTGGAGG |
| 8 | TTGGGAGG |
| 9 | TGCGAGG |
| 10 | GGGGAGG |
| 11 | mCGGGAGG |
| 12 | mCGmCGAGG |
| 13 | CTGGGAGG |
| 14 | GGGCGGGC |
| 15 | TAGGAGG |
| 16 | TGGGAGGT |
| 17 | TGGGCGCAG |
| 18 | CCG |
| 19 | TCGGAGG |
| 20 | TGmCGAGG |
| 21 | GTGGGAGG |
| 22 | TGG |
| 23 | TGGGAmGG |
| 24 | TGGGAGA |
| 25 | AATGGGAGG |
| 26 | TTGGGG |
| 27 | TGGGGG |
| 28 | CGGGG |
| 29 | CGCGG |
| 30 | CGGGT |
| 31 | TGGGC |
| 32 | TGGGT. |

Also, where a fluorenyl or xanthenyl group is shown in the Table, this is represented by $R_2$, $R_3$ and Z together.

TABLE 1

| Cpd. No. | $R_1$ | $R_2$ | $R_3$ | Z | $Y_1$ | $Y_2$ | $R_4$ | $Y_3$ | X | $Y_4$ | n | m | B |
|---|---|---|---|---|---|---|---|---|---|---|---|---|---|
| 1 | 3,4-Dbp | H | H | C | O | O | H | O | Ete | O | 1 | 1 | T |
| 2 | 3,4-Dbp | H | H | C | O | S | H | O | Ete | O | 1 | 1 | T |
| 3 | 3,4-Dbp | H | H | C | O | — | — | — | — | — | 0 | 0 | T |
| 4 | 3,4-Dbp | H | H | C | O | O | Me | O | — | — | 0 | 1 | T |
| 5 | 3,4-Dbp | H | H | C | O | O | Me | S | — | — | 0 | 1 | T |
| 6 | 3,4-Dbp | H | H | C | O | O | 2-ClPh | O | — | — | 0 | 1 | T |
| 7 | 3,4-Dbp | H | H | C | O | Mee | H | O | — | — | 0 | 1 | T |
| 8 | 3,4-Dbp | H | H | C | O | Mee | H | S | — | — | 0 | 1 | T |
| 9 | 3,4-Dbp | H | H | C | O | Phe | H | O | — | — | 0 | 1 | T |
| 10 | 3,4-Dbp | H | H | C | O | NH | Pr | O | Ete | O | 1 | 1 | T |
| 11 | 3,4-Dbp | H | H | C | O | O | Me | NH | Trim | — | 1 | 1 | T |
| 12 | Ph | Ph | Ph | C | O | O | H | O | Ete | O | 1 | 1 | T |
| 13 | Ph | Ph | Ph | C | O | S | H | O | Ete | O | 1 | 1 | T |
| 14 | Ph | Ph | Ph | C | O | — | — | — | — | — | 0 | 0 | T |
| 15 | Ph | Ph | Ph | C | O | O | Me | O | — | — | 0 | 1 | T |
| 16 | Ph | Ph | Ph | C | O | O | Me | S | — | — | 0 | 1 | T |
| 17 | Ph | Ph | Ph | C | O | O | 2-ClPh | O | — | — | 0 | 1 | T |
| 18 | Ph | Ph | Ph | C | O | Mee | H | O | — | — | 0 | 1 | T |
| 19 | Ph | Ph | Ph | C | O | Mee | H | S | — | — | 0 | 1 | T |
| 20 | Ph | Ph | Ph | C | O | Phe | H | O | — | — | 0 | 1 | T |
| 21 | Ph | Ph | Ph | C | O | NH | Pr | O | Ete | O | 1 | 1 | T |
| 22 | Ph | Ph | Ph | C | O | O | me | NH | Trim | — | 1 | 1 | T |
| 23 | 3,5-Dbp | H | H | C | O | O | H | O | Ete | O | 1 | 1 | T |
| 24 | 3,5-Dbp | H | H | C | O | S | H | O | Ete | O | 1 | 1 | T |
| 25 | 3,5-Dbp | H | H | C | O | — | — | — | — | — | 0 | 0 | T |
| 26 | 3,5-Dbp | H | H | C | O | O | Me | O | — | — | 0 | 1 | T |
| 27 | 3,5-Dbp | H | H | C | O | O | Me | S | — | — | 0 | 1 | T |
| 28 | 3,5-Dbp | H | H | C | O | O | 2-ClPh | O | — | — | 0 | 1 | T |
| 29 | 3,5-Dbp | H | H | C | O | Mee | H | O | — | — | 0 | 1 | T |
| 30 | 3,5-Dbp | H | H | C | O | Mee | H | S | — | — | 0 | 1 | T |
| 31 | 3,5-Dbp | H | H | C | O | Phe | H | O | — | — | 0 | 1 | T |
| 32 | 3,5-Dbp | H | H | C | O | NH | Pr | O | Ete | O | 1 | 1 | T |
| 33 | 3,5-Dbp | H | H | C | O | O | Me | NH | Trim | — | 1 | 1 | T |
| 34 | 4-MeOPh | 4-MeOPh | Ph | C | O | O | H | O | Ete | O | 1 | 1 | T |
| 35 | 4-MeOPh | 4-MeOPh | Ph | C | O | S | H | O | Ete | O | 1 | 1 | T |
| 36 | 4-MeOPh | 4-MeOPh | Ph | C | O | — | — | — | — | — | 0 | 0 | T |
| 37 | 4-MeOPh | 4-MeOPh | Ph | C | O | O | Me | O | — | — | 0 | 1 | T |
| 38 | 4-MeOPh | 4-MeOPh | Ph | C | O | O | Me | S | — | — | 0 | 1 | T |
| 39 | 4-MeOPh | 4-MeOPh | Ph | C | O | O | 2-ClPh | O | — | — | 0 | 1 | T |
| 40 | 4-MeOPh | 4-MeOPh | Ph | C | O | Mee | H | O | — | — | 0 | 1 | T |
| 41 | 4-MeOPh | 4-MeOPh | Ph | C | O | Mee | H | S | — | — | 0 | 1 | T |
| 42 | 4-MeOPh | 4-MeOPh | Ph | C | O | Phe | H | O | — | — | 0 | 1 | T |
| 43 | 4-MeOPh | 4-MeOPh | Ph | C | O | NH | Pr | O | Ete | O | 1 | 1 | T |
| 44 | 4-MeOPh | 4-MeOPh | Ph | C | O | O | Me | NH | Trim | — | 1 | 1 | T |
| 45 | 4-MeOPh | Ph | Ph | C | O | O | H | O | Ete | O | 1 | 1 | Ī |
| 46 | 4-MeOPh | Ph | Ph | C | O | S | H | O | Ete | O | 1 | 1 | T |
| 47 | 4-MeOPh | Ph | Ph | C | O | — | — | — | — | — | 0 | 0 | T |
| 48 | 4-MeOPh | Ph | Ph | C | O | O | Me | O | — | — | 0 | 1 | Ī |
| 49 | 4-MeOPh | Ph | Ph | C | O | O | Me | S | — | — | 0 | 1 | T |
| 50 | 4-MeOPh | Ph | Ph | C | O | O | 2-ClPh | O | — | — | 0 | 1 | Ī |
| 51 | 4-MeOPh | Ph | Ph | C | O | Mee | H | O | — | — | 0 | 1 | Ī |
| 52 | 4-MeOPh | Ph | Ph | C | O | Mee | H | S | — | — | 0 | 1 | T |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 53 | 4-MeOPh | Ph | Ph | C | O | Phe | H | O | — | — | 0 | 1 | 1 |
| 54 | 4-MeOPh | Ph | Ph | C | O | NH | Pr | O | Ete | O | 1 | 1 | 1 |
| 55 | 4-MeOPh | Ph | Ph | C | O | O | Me | NH | Trim | — | 1 | 1 | 1 |
| 56 | tBu | Ph | Ph | Si | O | O | H | O | Ete | O | 1 | 1 | 1 |
| 57 | tBu | Ph | Ph | Si | O | S | H | O | Ete | O | 1 | 1 | 1 |
| 58 | tBu | Ph | Ph | Si | O | — | — | — | — | — | 0 | 0 | 1 |
| 59 | tBu | Ph | Ph | Si | O | O | Me | O | — | — | 0 | 1 | 1 |
| 60 | tBu | Ph | Ph | Si | O | O | Me | S | — | — | 0 | 1 | 1 |
| 61 | tBu | Ph | Ph | Si | O | O | 2-ClPh | O | — | — | 0 | 1 | 1 |
| 62 | tBu | Ph | Ph | Si | O | Mee | H | O | — | — | 0 | 1 | 1 |
| 63 | tBu | Ph | Ph | Si | O | Mee | H | S | — | — | 0 | 1 | 1 |
| 64 | tBu | Ph | Ph | Si | O | Phe | H | O | — | — | 0 | 1 | 1 |
| 65 | tBu | Ph | Ph | Si | O | NH | Pr | O | Ete | O | 1 | 1 | 1 |
| 66 | tBu | Ph | Ph | Si | O | O | Me | NH | Trim | — | 1 | 1 | 1 |
| 67 | Ph | Ph | Ph | C | S | O | H | O | Ete | O | 1 | 1 | 1 |
| 68 | Ph | Ph | Ph | C | S | S | H | O | Ete | O | 1 | 1 | 1 |
| 69 | Ph | Ph | Ph | C | S | — | — | — | — | — | 0 | 0 | 1 |
| 70 | Ph | Ph | Ph | C | S | O | Me | O | — | — | 0 | 1 | 1 |
| 71 | Ph | Ph | Ph | C | S | O | Me | S | — | — | 0 | 1 | 1 |
| 72 | Ph | Ph | Ph | C | S | O | 2-ClPh | O | — | — | 0 | 1 | 1 |
| 73 | Ph | Ph | Ph | C | S | Mee | H | O | — | — | 0 | 1 | 1 |
| 74 | Ph | Ph | Ph | C | S | Mee | H | S | — | — | 0 | 1 | 1 |
| 75 | Ph | Ph | Ph | C | S | Phe | H | O | — | — | 0 | 1 | 1 |
| 76 | Ph | Ph | Ph | C | S | NH | Pr | O | Ete | O | 1 | 1 | 1 |
| 77 | Ph | Ph | Ph | C | S | O | Me | NH | Trim | — | 1 | 1 | 1 |
| 78 | 4-BzOPh | H | H | C | O | O | H | O | Ete | O | 1 | 1 | 1 |
| 79 | 4-BzOPh | H | H | C | O | S | H | O | Ete | O | 1 | 1 | 1 |
| 80 | 4-BzOPh | H | H | C | O | — | — | — | — | — | 0 | 0 | 1 |
| 81 | 4-BzOPh | H | H | C | O | O | Me | O | — | — | 0 | 1 | 1 |
| 82 | 4-BzOPh | H | H | C | O | O | Me | S | — | — | 0 | 1 | 1 |
| 83 | 4-BzOPh | H | H | C | O | O | 2-ClPh | O | — | — | 0 | 1 | 1 |
| 84 | 4-BzOPh | H | H | C | O | Mee | H | O | — | — | 0 | 1 | 1 |
| 85 | 4-BzOPh | H | H | C | O | Mee | H | S | — | — | 0 | 1 | 1 |
| 86 | 4-BzOPh | H | H | C | O | Phe | H | O | — | — | 0 | 1 | 1 |
| 87 | 4-BzOPh | H | H | C | O | NH | Pr | O | Ete | O | 1 | 1 | 1 |
| 88 | 4-BzOPh | H | H | C | O | O | Me | NH | Trim | — | 1 | 1 | 1 |
| 89 | Ph | Xanthen-9-yl | | | O | O | H | O | Ete | O | 0 | 1 | 1 |
| 90 | Ph | Xanthen-9-yl | | | O | S | H | O | Ete | O | 0 | 1 | 1 |
| 91 | Ph | Xanthen-9-yl | | | O | — | — | — | — | — | 0 | 0 | 1 |
| 92 | Ph | Xanthen-9-yl | | | O | O | Me | O | — | — | 0 | 1 | 1 |
| 93 | Ph | Xanthen-9-yl | | | O | O | Me | S | — | — | 0 | 0 | 1 |
| 94 | Ph | Xanthen-9-yl | | | O | O | 2-ClPh | O | — | — | 0 | 1 | 1 |
| 95 | Ph | Xanthen-9-yl | | | O | Mee | H | O | — | — | 0 | 1 | 1 |
| 96 | Ph | Xanthen-9-yl | | | O | Mee | H | S | — | — | 0 | 1 | 1 |
| 97 | Ph | Xanthen-9-yl | | | O | Phe | H | O | — | — | 0 | 1 | 1 |
| 98 | Ph | Xanthen-9-yl | | | O | NH | Pr | O | Ete | O | 1 | 1 | 1 |
| 99 | Ph | Xanthen-9-yl | | | O | O | Me | NH | Trim | — | 1 | 1 | 1 |
| 100 | Ph | Fluoren-9-yl | | | O | O | H | O | Ete | O | 1 | 1 | 1 |
| 101 | Ph | Fluoren-9-yl | | | O | S | H | O | Ete | O | 1 | 1 | 1 |
| 102 | Ph | Fluoren-9-yl | | | O | — | — | — | — | — | 0 | 0 | 1 |
| 103 | Ph | Fluoren-9-yl | | | O | O | Me | O | — | — | 0 | 1 | 1 |
| 104 | Ph | Fluoren-9-yl | | | O | O | Me | S | — | — | 0 | 1 | 1 |
| 105 | Ph | Fluoren-9-yl | | | O | O | 2-ClPh | O | — | — | 0 | 1 | 1 |
| 106 | Ph | Fluoren-9-yl | | | O | Mee | H | O | — | — | 0 | 1 | 1 |
| 107 | Ph | Fluoren-9-yl | | | O | Mee | H | S | — | — | 0 | 1 | 1 |
| 108 | Ph | Fluoren-9-yl | | | O | Phe | H | O | — | — | 0 | 1 | 1 |
| 109 | Ph | Fluoren-9-yl | | | O | NH | Pr | O | Ete | O | 1 | 1 | 1 |
| 110 | Ph | Fluoren-9-yl | | | O | O | Me | NH | Trim | — | 1 | 1 | 1 |
| 111 | 3,4-Dbp | H | H | C | O | O | H | O | Ete | O | 1 | 1 | 2 |
| 112 | 3,4-Dbp | H | H | C | O | S | H | O | Ete | O | 1 | 1 | 2 |
| 113 | 3,4-Dbp | H | H | C | O | — | — | — | — | — | 0 | 0 | 2 |
| 114 | 3,4-Dbp | H | H | C | O | O | Me | O | — | — | 0 | 1 | 2 |
| 115 | 3,4-Dbp | H | H | C | O | O | Me | S | — | — | 0 | 1 | 2 |
| 116 | 3,4-Dbp | H | H | C | O | O | 2-ClPh | O | — | — | 0 | 1 | 2 |
| 117 | 3,4-Dbp | H | H | C | O | Mee | H | O | — | — | 0 | 1 | 2 |
| 118 | 3,4-Dbp | H | H | C | O | Mee | H | S | — | — | 0 | 1 | 2 |
| 119 | 3,4-Dbp | H | H | C | O | Phe | H | O | — | — | 0 | 1 | 2 |
| 120 | 3,4-Dbp | H | H | C | O | NH | Pr | O | Ete | O | 1 | 1 | 2 |
| 121 | 3,4-Dbp | H | H | C | O | O | Me | NH | Trim | — | 1 | 1 | 2 |
| 122 | Ph | Ph | Ph | C | O | O | H | O | Ete | O | 1 | 1 | 2 |
| 123 | Ph | Ph | Ph | C | O | S | H | O | Ete | O | 1 | 1 | 2 |
| 124 | Ph | Ph | Ph | C | O | — | — | — | — | — | 0 | 0 | 2 |
| 125 | Ph | Ph | Ph | C | O | O | Me | O | — | — | 0 | 1 | 2 |
| 126 | Ph | Ph | Ph | C | O | O | Me | S | — | — | 0 | 1 | 2 |
| 127 | Ph | Ph | Ph | C | O | O | 2-ClPh | O | — | — | 0 | 1 | 2 |
| 128 | Ph | Ph | Ph | C | O | Mee | H | O | — | — | 0 | 1 | 2 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 129 | Ph | Ph | Ph | C | O | Mee | H | S | — | — | 0 | 1 | 2 |
| 130 | Ph | Ph | Ph | C | O | Phe | H | O | — | — | 0 | 1 | 2 |
| 131 | Ph | Ph | Ph | C | O | NH | Pr | O | Ete | O | 1 | 1 | 2 |
| 132 | Ph | Ph | Ph | C | O | O | Me | NH | Trim | — | 1 | 1 | 2 |
| 133 | 3,5-Dbp | H | H | C | O | O | H | O | Ete | O | 1 | 1 | 2 |
| 134 | 3,5-Dbp | H | H | C | O | S | H | O | Ete | O | 1 | 1 | 2 |
| 135 | 3,5-Dbp | H | H | C | O | — | — | — | — | — | 0 | 0 | 2 |
| 136 | 3,5-Dbp | H | H | C | O | O | Me | O | — | — | 0 | 1 | 2 |
| 137 | 3,5-Dbp | H | H | C | O | O | Me | S | — | — | 0 | 1 | 2 |
| 138 | 3,5-Dbp | H | H | C | O | O | 2-ClPh | O | — | — | 0 | 1 | 2 |
| 139 | 3,5-Dbp | H | H | C | O | Mee | H | O | — | — | 0 | 1 | 2 |
| 140 | 3,5-Dbp | H | H | C | O | Mee | H | S | — | — | 0 | 1 | 2 |
| 141 | 3,5-Dbp | H | H | C | O | Phe | H | O | — | — | 0 | 1 | 2 |
| 142 | 3,5-Dbp | H | H | C | O | NH | Pr | O | Ete | O | 1 | 1 | 2 |
| 143 | 3,5-Dbp | H | H | C | O | O | Me | NH | Trim | — | 1 | 1 | 2 |
| 144 | 4-MeOPh | 4-MeOPh | Ph | C | O | O | H | O | Ete | O | 1 | 1 | 2 |
| 145 | 4-MeOPh | 4-MeOPh | Ph | C | O | S | H | O | Ete | O | 1 | 1 | 2 |
| 146 | 4-MeOPh | 4-MeOPh | Ph | C | O | — | — | — | — | — | 0 | 0 | 2 |
| 147 | 4-MeOPh | 4-MeOPh | Ph | C | O | O | Me | O | — | — | 0 | 1 | 2 |
| 148 | 4-MeOPh | 4-MeOPh | Ph | C | O | O | Me | S | — | — | 0 | 1 | 2 |
| 149 | 4-MeOPh | 4-MeOPh | Ph | C | O | O | 2-ClPh | O | — | — | 0 | 1 | 2 |
| 150 | 4-MeOPh | 4-MeOPh | Ph | C | O | Mee | H | O | — | — | 0 | 1 | 2 |
| 151 | 4-MeOPh | 4-MeOPh | Ph | C | O | Mee | H | S | — | — | 0 | 1 | 2 |
| 152 | 4-MeOPh | 4-MeOPh | Ph | C | O | Phe | H | O | — | — | 0 | 1 | 2 |
| 153 | 4-MeOPh | 4-MeOPh | Ph | C | O | NH | Pr | O | Ete | O | 1 | 1 | 2 |
| 154 | 4-MeOPh | 4-MeOPh | Ph | C | O | O | Me | NH | Trim | — | 1 | 1 | 2 |
| 155 | 4-MeOPh | Ph | Ph | C | O | O | H | O | Ete | O | 1 | 1 | 2 |
| 156 | 4-MeOPh | Ph | Ph | C | O | S | H | O | Ete | O | 1 | 1 | 2 |
| 157 | 4-MeOPh | Ph | Ph | C | O | — | — | — | — | — | 0 | 0 | 2 |
| 158 | 4-MeOPh | Ph | Ph | C | O | O | Me | O | — | — | 0 | 1 | 2 |
| 159 | 4-MeOPh | Ph | Ph | C | O | O | Me | S | — | — | 0 | 1 | 2 |
| 160 | 4-MeOPh | Ph | Ph | C | O | O | 2-ClPh | O | — | — | 0 | 1 | 2 |
| 161 | 4-MeOPh | Ph | Ph | C | O | Mee | H | O | — | — | 0 | 1 | 2 |
| 162 | 4-MeOPh | Ph | Ph | C | O | Mee | H | S | — | — | 0 | 1 | 2 |
| 163 | 4-MeOPh | Ph | Ph | C | O | Phe | H | O | — | — | 0 | 1 | 2 |
| 164 | 4-MeOPh | Ph | Ph | C | O | NH | Pr | O | Ete | O | 1 | 1 | 2 |
| 165 | 4-MeOPh | Ph | Ph | C | O | O | Me | NH | Trim | — | 1 | 1 | 2 |
| 166 | tBu | Ph | Ph | Si | O | O | H | O | Ete | O | 1 | 1 | 2 |
| 167 | tBu | Ph | Ph | Si | O | S | H | O | Ete | O | 1 | 1 | 2 |
| 168 | tBu | Ph | Ph | Si | O | — | — | — | — | — | 0 | 0 | 2 |
| 169 | tBu | Ph | Ph | Si | O | O | Me | O | — | — | 0 | 1 | 2 |
| 170 | tBu | Ph | Ph | Si | O | O | Me | S | — | — | 0 | 1 | 2 |
| 171 | tBu | Ph | Ph | Si | O | O | 2-ClPh | O | — | — | 0 | 1 | 2 |
| 172 | tBu | Ph | Ph | Si | O | Mee | H | O | — | — | 0 | 1 | 2 |
| 173 | tBu | Ph | Ph | Si | O | Mee | H | S | — | — | 0 | 1 | 2 |
| 174 | tBu | Ph | Ph | Si | O | Phe | H | O | — | — | 0 | 1 | 2 |
| 175 | tBu | Ph | Ph | Si | O | NH | Pr | O | Ete | O | 1 | 1 | 2 |
| 176 | tBu | Ph | Ph | Si | O | O | Me | NH | Trim | — | 1 | 1 | 2 |
| 177 | Ph | Ph | Ph | C | S | O | H | O | Ete | O | 1 | 1 | 2 |
| 178 | Ph | Ph | Ph | C | S | S | H | O | Ete | O | 1 | 1 | 2 |
| 179 | Ph | Ph | Ph | C | S | — | — | — | — | — | 0 | 0 | 2 |
| 180 | Ph | Ph | Ph | C | S | O | Me | O | — | — | 0 | 1 | 2 |
| 181 | Ph | Ph | Ph | C | S | O | Me | S | — | — | 0 | 1 | 2 |
| 182 | Ph | Ph | Ph | C | S | O | 2-ClPh | O | — | — | 0 | 1 | 2 |
| 183 | Ph | Ph | Ph | C | S | Mee | H | O | — | — | 0 | 1 | 2 |
| 184 | Ph | Ph | Ph | C | S | Mee | H | S | — | — | 0 | 1 | 2 |
| 185 | Ph | Ph | Ph | C | S | Phe | H | O | — | — | 0 | 1 | 2 |
| 186 | Ph | Ph | Ph | C | S | NH | Pr | O | Ete | O | 1 | 1 | 2 |
| 187 | Ph | Ph | Ph | C | S | O | Me | NH | Trim | — | 1 | 1 | 2 |
| 188 | 4-BzOPh | H | H | C | O | O | H | O | Ete | O | 1 | 1 | 2 |
| 189 | 4-BzOPh | H | H | C | O | S | H | O | Ete | O | 1 | 1 | 2 |
| 190 | 4-BzOPh | H | H | C | O | — | — | — | — | — | 0 | 0 | 2 |
| 191 | 4-BzOPh | H | H | C | O | O | Me | O | — | — | 0 | 1 | 2 |
| 192 | 4-BzOPh | H | H | C | O | O | Me | S | — | — | 0 | 1 | 2 |
| 193 | 4-BzOPh | H | H | C | O | O | 2-ClPh | O | — | — | 0 | 1 | 2 |
| 194 | 4-BzOPh | H | H | C | O | Mee | H | O | — | — | 0 | 1 | 2 |
| 195 | 4-BzOPh | H | H | C | O | Mee | H | S | — | — | 0 | 1 | 2 |
| 196 | 4-BzOPh | H | H | C | O | Phe | H | O | — | — | 0 | 1 | 2 |
| 197 | 4-BzOPh | H | H | C | O | NH | Pr | O | Ete | O | 1 | 1 | 2 |
| 198 | 4-BzOPh | H | H | C | O | O | Me | NH | Trim | — | 1 | 1 | 2 |
| 199 | Ph | Xanthen-9-yl | | | O | O | H | O | Ete | O | 1 | 1 | 2 |
| 200 | Ph | Xanthen-9-yl | | | O | S | H | O | Ete | O | 1 | 1 | 2 |
| 201 | Ph | Xanthen-9-yl | | | O | — | — | — | — | — | 0 | 0 | 2 |
| 202 | Ph | Xanthen-9-yl | | | O | O | Me | O | — | — | 0 | 1 | 2 |
| 203 | Ph | Xanthen-9-yl | | | O | O | Me | S | — | — | 0 | 1 | 2 |
| 204 | Ph | Xanthen-9-yl | | | O | O | 2-ClPh | O | — | — | 0 | 1 | 2 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 205 | Ph | Xanthen-9-yl | | | O | Mee | H | O | — | — | 0 | 1 | 2 |
| 206 | Ph | Xanthen-9-yl | | | O | Mee | H | S | — | — | 0 | 1 | 2 |
| 207 | Ph | Xanthen-9-yl | | | O | Phe | H | O | — | — | 0 | 1 | 2 |
| 208 | Ph | Xanthen-9-yl | | | O | NH | Pr | O | Ete | O | 1 | 1 | 2 |
| 209 | Ph | Xanthen-9-yl | | | O | O | Me | NH | Trim | — | 1 | 1 | 2 |
| 210 | Ph | Fluoren-9-yl | | | O | O | H | O | Ete | O | 1 | 1 | 2 |
| 211 | Ph | Fluoren-9-yl | | | O | S | H | O | Ete | O | 1 | 1 | 2 |
| 212 | Ph | Fluoren-9-yl | | | O | — | — | — | — | — | 0 | 0 | 2 |
| 213 | Ph | Fluoren-9-yl | | | O | O | Me | O | — | — | 0 | 1 | 2 |
| 214 | Ph | Fluoren-9-yl | | | O | O | Me | S | — | — | 0 | 1 | 2 |
| 215 | Ph | Fluoren-9-yl | | | O | O | 2-ClPh | O | — | — | 0 | 1 | 2 |
| 216 | Ph | Fluoren-9-yl | | | O | Mee | H | O | — | — | 0 | 1 | 2 |
| 217 | Ph | Fluoren-9-yl | | | O | Mee | H | S | — | — | 0 | 1 | 2 |
| 218 | Ph | Fluoren-9-yl | | | O | Phe | H | O | — | — | 0 | 1 | 2 |
| 219 | Ph | Fluoren-9-yl | | | O | NH | Pr | O | Ete | O | 1 | 1 | 2 |
| 220 | Ph | Fluoren-9-yl | | | O | O | Me | NH | Trim | — | 1 | 1 | 2 |
| 221 | 3,4-Dbp | H | H | C | O | O | H | O | Ete | O | 1 | 1 | 3 |
| 222 | 3,4-Dbp | H | H | C | O | S | H | O | Ete | O | 1 | 1 | 3 |
| 223 | 3,4-Dbp | H | H | C | O | — | — | — | — | — | 0 | 0 | 3 |
| 224 | 3,4-Dbp | H | H | C | O | O | Me | O | — | — | 0 | 1 | 3 |
| 225 | 3,4-Dbp | H | H | C | O | O | Me | S | — | — | 0 | 1 | 3 |
| 226 | 3,4-Dbp | H | H | C | O | O | 2-ClPh | O | — | — | 0 | 1 | 3 |
| 227 | 3,4-Dbp | H | H | C | O | Mee | H | O | — | — | 0 | 1 | 3 |
| 228 | 3,4-Dbp | H | H | C | O | Mee | H | S | — | — | 0 | 1 | 3 |
| 229 | 3,4-Dbp | H | H | C | O | Phe | H | O | — | — | 0 | 1 | 3 |
| 230 | 3,4-Dbp | H | H | C | O | NH | Pr | O | Ete | O | 1 | 1 | 3 |
| 231 | 3,4-Dbp | H | H | C | O | O | Me | NH | Trim | — | 1 | 1 | 3 |
| 232 | Ph | Ph | Ph | C | O | O | H | O | Ete | O | 1 | 1 | 3 |
| 233 | Ph | Ph | Ph | C | O | S | H | O | Ete | O | 1 | 1 | 3 |
| 234 | Ph | Ph | Ph | C | O | — | — | — | — | — | 0 | 0 | 3 |
| 235 | Ph | Ph | Ph | C | O | O | Me | O | — | — | 0 | 1 | 3 |
| 236 | Ph | Ph | Ph | C | O | O | Me | S | — | — | 0 | 1 | 3 |
| 237 | Ph | Ph | Ph | C | O | O | 2-ClPh | O | — | — | 0 | 1 | 3 |
| 238 | Ph | Ph | Ph | C | O | Mee | H | O | — | — | 0 | 1 | 3 |
| 239 | Ph | Ph | Ph | C | O | Mee | H | S | — | — | 0 | 1 | 3 |
| 240 | Ph | Ph | Ph | C | O | Phe | H | O | — | — | 0 | 1 | 3 |
| 241 | Ph | Ph | Ph | C | O | NH | Pr | O | Ete | O | 1 | 1 | 3 |
| 242 | Ph | Ph | Ph | C | O | O | Me | NH | Trim | — | 1 | 1 | 3 |
| 243 | 3,5-Dbp | H | H | C | O | O | H | O | Ete | O | 1 | 1 | 3 |
| 244 | 3,5-Dbp | H | H | C | O | S | H | O | Ete | O | 1 | 1 | 3 |
| 245 | 3,5-Dbp | H | H | C | O | — | — | — | — | — | 0 | 0 | 3 |
| 246 | 3,5-Dbp | H | H | C | O | O | Me | O | — | — | 0 | 1 | 3 |
| 247 | 3,5-Dbp | H | H | C | O | O | Me | S | — | — | 0 | 1 | 3 |
| 248 | 3,5-Dbp | H | H | C | O | O | 2-ClPh | O | — | — | 0 | 1 | 3 |
| 249 | 3,5-Dbp | H | H | C | O | Mee | H | O | — | — | 0 | 1 | 3 |
| 250 | 3,5-Dbp | H | H | C | O | Mee | H | S | — | — | 0 | 1 | 3 |
| 251 | 3,5-Dbp | H | H | C | O | Phe | H | O | — | — | 0 | 1 | 3 |
| 252 | 3,5-Dbp | H | H | C | O | NH | Pr | O | Ete | O | 1 | 1 | 3 |
| 253 | 3,5-Dbp | H | H | C | O | O | Me | NH | Trim | — | 1 | 1 | 3 |
| 254 | 4-MeOPh | 4-MeOPh | Ph | C | O | O | H | O | Ete | O | 1 | 1 | 3 |
| 255 | 4-MeOPh | 4-MeOPh | Ph | C | O | S | H | O | Ete | O | 1 | 1 | 3 |
| 256 | 4-MeOPh | 4-MeOPh | Ph | C | O | — | — | — | — | — | 0 | 0 | 3 |
| 257 | 4-MeOPh | 4-MeOPh | Ph | C | O | O | Me | O | — | — | 0 | 1 | 3 |
| 258 | 4-MeOPh | 4-MeOPh | Ph | C | O | O | Me | S | — | — | 0 | 1 | 3 |
| 259 | 4-MeOPh | 4-MeOPh | Ph | C | O | O | 2-ClPh | O | — | — | 0 | 1 | 3 |
| 260 | 4-MeOPh | 4-MeOPh | Ph | C | O | Mee | H | O | — | — | 0 | 1 | 3 |
| 261 | 4-MeOPh | 4-MeOPh | Ph | C | O | Mee | H | S | — | — | 0 | 1 | 3 |
| 262 | 4-MeOPh | 4-MeOPh | Ph | C | O | Phe | H | O | — | — | 0 | 1 | 1 |
| 263 | 4-MeOPh | 4-MeOPh | Ph | C | O | NH | Pr | O | Ete | O | 1 | 1 | 3 |
| 264 | 4-MeOPh | 4-MeOPh | Ph | C | O | O | Me | NH | Trim | — | 1 | 1 | 3 |
| 265 | 4-MeOPh | Ph | Ph | C | O | O | H | O | Ete | O | 1 | 1 | 3 |
| 266 | 4-MeOPh | Ph | Ph | C | O | S | H | O | Ete | O | 1 | 1 | 3 |
| 267 | 4-MeOPh | Ph | Ph | C | O | — | — | — | — | — | 0 | 0 | 3 |
| 268 | 4-MeOPh | Ph | Ph | C | O | O | Me | O | — | — | 0 | 1 | 3 |
| 269 | 4-MeOPh | Ph | Ph | C | O | O | Me | S | — | — | 0 | 1 | 3 |
| 270 | 4-MeOPh | Ph | Ph | C | O | O | 2-ClPh | O | — | — | 0 | 1 | 3 |
| 271 | 4-MeOPh | Ph | Ph | C | O | Mee | H | O | — | — | 0 | 1 | 3 |
| 272 | 4-MeOPh | Ph | Ph | C | O | Mee | H | S | — | — | 0 | 1 | 3 |
| 273 | 4-MeOPh | Ph | Ph | C | O | Phe | H | O | — | — | 0 | 1 | 3 |
| 274 | 4-MeOPh | Ph | Ph | C | O | NH | Pr | O | Ete | O | 1 | 1 | 3 |
| 275 | 4-MeOPh | Ph | Ph | C | O | O | Me | NH | Trim | — | 1 | 1 | 3 |
| 276 | tBu | Ph | Ph | Si | O | O | H | O | Ete | O | 1 | 1 | 3 |
| 277 | tBu | Ph | Ph | Si | O | S | H | O | Ete | O | 1 | 1 | 3 |
| 278 | tBu | Ph | Ph | Si | O | — | — | — | — | — | 0 | 0 | 3 |
| 279 | tBu | Ph | Ph | Si | O | O | Me | O | — | — | 0 | 1 | 3 |
| 280 | tBu | Ph | Ph | Si | O | O | Me | S | — | — | 0 | 1 | 3 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 281 | tBu | Ph | Ph | Si | O | O | 2-ClPh | O | — | — | 0 | 1 | 3 |
| 282 | tBu | Ph | Ph | Si | O | Mee | H | O | — | — | 0 | 1 | 3 |
| 283 | tBu | Ph | Ph | Si | O | Mee | H | S | — | — | 0 | 1 | 3 |
| 284 | tBu | Ph | Ph | Si | O | Phe | H | O | — | — | 0 | 1 | 3 |
| 285 | tBu | Ph | Ph | Si | O | NH | Pr | O | Ete | O | 1 | 1 | 3 |
| 286 | tBu | Ph | Ph | Si | O | O | Me | NH | Trim | — | 1 | 1 | 3 |
| 287 | Ph | Ph | Ph | C | S | O | H | O | Ete | O | 1 | 1 | 3 |
| 288 | Ph | Ph | Ph | C | S | S | H | O | Ete | O | 1 | 1 | 3 |
| 289 | Ph | Ph | Ph | C | S | — | — | — | — | — | 0 | 0 | 3 |
| 290 | Ph | Ph | Ph | C | S | O | Me | O | — | — | 0 | 1 | 3 |
| 291 | Ph | Ph | Ph | C | S | O | Me | S | — | — | 0 | 1 | 3 |
| 292 | Ph | Ph | Ph | C | S | O | 2-ClPh | O | — | — | 0 | 1 | 3 |
| 293 | Ph | Ph | Ph | C | S | Mee | H | O | — | — | 0 | 1 | 3 |
| 294 | Ph | Ph | Ph | C | S | Mee | H | S | — | — | 0 | 1 | 3 |
| 295 | Ph | Ph | Ph | C | S | Phe | H | O | — | — | 0 | 1 | 3 |
| 296 | Ph | Ph | Ph | C | S | NH | Pr | O | Ete | O | 1 | 1 | 3 |
| 297 | Ph | Ph | Ph | C | S | O | Me | NH | Trim | — | 1 | 1 | 3 |
| 298 | 4-BzOPh | H | H | C | O | O | H | O | Ete | O | 1 | 1 | 3 |
| 299 | 4-BzOPh | H | H | C | O | S | H | O | Ete | O | 1 | 1 | 3 |
| 300 | 4-BzOPh | H | H | C | O | — | — | — | — | — | 0 | 0 | 3 |
| 301 | 4-BzOPh | H | H | C | O | O | Me | O | — | — | 0 | 1 | 3 |
| 302 | 4-BzOPh | H | H | C | O | O | Me | S | — | — | 0 | 1 | 3 |
| 303 | 4-BzOPh | H | H | C | O | O | 2-ClPh | O | — | — | 0 | 1 | 3 |
| 304 | 4-BzOPh | H | H | C | O | Mee | H | O | — | — | 0 | 1 | 3 |
| 305 | 4-BzOPh | H | H | C | O | Mee | H | S | — | — | 0 | 1 | 3 |
| 306 | 4-BzOPh | H | H | C | O | Phe | H | O | — | — | 0 | 1 | 3 |
| 307 | 4-BzOPh | H | H | C | O | NH | Pr | O | Ete | O | 1 | 1 | 3 |
| 308 | 4-BzOPh | H | H | C | O | O | Me | NH | Trim | — | 1 | 1 | 3 |
| 309 | Ph | Xanthen-9-yl | | | O | O | H | O | Ete | O | 1 | 1 | 3 |
| 310 | Ph | Xanthen-9-yl | | | O | S | H | O | Ete | O | 1 | 1 | 3 |
| 311 | Ph | Xanthen-9-yl | | | O | — | — | — | — | — | 0 | 0 | 3 |
| 312 | Ph | Xanthen-9-yl | | | O | O | Me | O | — | — | 0 | 1 | 3 |
| 313 | Ph | Xanthen-9-yl | | | O | O | Me | S | — | — | 0 | 1 | 3 |
| 314 | Ph | Xanthen-9-yl | | | O | O | 2-ClPh | O | — | — | 0 | 1 | 3 |
| 315 | Ph | Xanthen-9-yl | | | O | Mee | H | O | — | — | 0 | 1 | 3 |
| 316 | Ph | Xanthen-9-yl | | | O | Mee | H | S | — | — | 0 | 1 | 3 |
| 317 | Ph | Xanthen-9-yl | | | O | Phe | H | O | — | — | 0 | 1 | 3 |
| 318 | Ph | Xanthen-9-yl | | | O | NH | Pr | O | Ete | O | 1 | 1 | 3 |
| 319 | Ph | Xanthen-9-yl | | | O | O | Me | NH | Trim | — | 1 | 1 | 3 |
| 320 | Ph | Fluoren-9-yl | | | O | O | H | O | Ete | O | 1 | 1 | 3 |
| 321 | Ph | Fluoren-9-yl | | | O | S | H | O | Ete | O | 1 | 1 | 3 |
| 322 | Ph | Fluoren-9-yl | | | O | — | — | — | — | — | 0 | 0 | 3 |
| 323 | Ph | Fluoren-9-yl | | | O | O | Me | O | — | — | 0 | 1 | 3 |
| 324 | Ph | Fluoren-9-yl | | | O | O | Me | S | — | — | 0 | 1 | 3 |
| 325 | Ph | Fluoren-9-yl | | | O | O | 2-ClPh | O | — | — | 0 | 1 | 3 |
| 326 | Ph | Fluoren-9-yl | | | O | Mee | H | O | — | — | 0 | 1 | 3 |
| 327 | Ph | Fluoren-9-yl | | | O | Mee | H | S | — | — | 0 | 1 | 3 |
| 328 | Ph | Fluoren-9-yl | | | O | Phe | H | O | — | — | 0 | 1 | 3 |
| 329 | Ph | Fluoren-9-yl | | | O | NH | Pr | O | Ete | O | 1 | 1 | 3 |
| 330 | Ph | Fluoren-9-yl | | | O | O | Me | NH | Trim | — | 1 | 1 | 3 |
| 331 | 3,4-Dbp | H | H | C | O | O | H | O | Ete | O | 1 | 1 | 4 |
| 332 | 3,4-Dbp | H | H | C | O | S | H | O | Ete | O | 1 | 1 | 4 |
| 333 | 3,4-Dbp | H | H | C | O | — | — | — | — | — | 0 | 0 | 4 |
| 334 | 3,4-Dbp | H | H | C | O | O | Me | O | — | — | 0 | 1 | 4 |
| 335 | 3,4-Dbp | H | H | C | O | O | Me | S | — | — | 0 | 1 | 4 |
| 336 | 3,4-Dbp | H | H | C | O | O | 2-ClPh | O | — | — | 0 | 1 | 4 |
| 337 | 3,4-Dbp | H | H | C | O | Mee | H | O | — | — | 0 | 1 | 4 |
| 338 | 3,4-Dbp | H | H | C | O | Mee | H | S | — | — | 0 | 1 | 4 |
| 339 | 3,4-Dbp | H | H | C | O | Phe | H | O | — | — | 0 | 1 | 4 |
| 340 | 3,4-Dbp | H | H | C | O | NH | Pr | O | Ete | O | 1 | 1 | 4 |
| 341 | 3,4-Dbp | H | H | C | O | O | Me | NH | Trim | — | 1 | 1 | 4 |
| 342 | Ph | Ph | Ph | C | O | O | H | O | Ete | O | 1 | 1 | 4 |
| 343 | Ph | Ph | Ph | C | O | S | H | O | Ete | O | 1 | 1 | 4 |
| 344 | Ph | Ph | Ph | C | O | — | — | — | — | — | 0 | 0 | 4 |
| 345 | Ph | Ph | Ph | C | O | O | Me | O | — | — | 0 | 1 | 4 |
| 346 | Ph | Ph | Ph | C | O | O | Me | S | — | — | 0 | 1 | 4 |
| 347 | Ph | Ph | Ph | C | O | O | 2-ClPh | O | — | — | 0 | 1 | 4 |
| 348 | Ph | Ph | Ph | C | O | Mee | H | O | — | — | 0 | 1 | 4 |
| 349 | Ph | Ph | Ph | C | O | Mee | H | S | — | — | 0 | 1 | 4 |
| 350 | Ph | Ph | Ph | C | O | Phe | H | O | — | — | 0 | 1 | 4 |
| 351 | Ph | Ph | Ph | C | O | NH | Pr | O | Ete | O | 1 | 1 | 4 |
| 352 | Ph | Ph | Ph | C | O | O | Me | NH | Trim | — | 1 | 1 | 4 |
| 353 | 3,5-Dbp | H | H | C | O | O | H | O | Ete | O | 1 | 1 | 4 |
| 354 | 3,5-Dbp | H | H | C | O | S | H | O | Ete | O | 1 | 1 | 4 |
| 355 | 3,5-Dbp | H | H | C | O | — | — | — | — | — | 0 | 0 | 4 |
| 356 | 3,5-Dbp | H | H | C | O | O | Me | O | — | — | 0 | 1 | 4 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 357 | 3,5-Dbp | H | H | C | O | O | Me | S | — | — | 0 | 1 | 4 |
| 358 | 3,5-Dbp | H | H | C | O | O | 2-ClPh | O | — | — | 0 | 1 | 4 |
| 359 | 3,5-Dbp | H | H | C | O | Mee | H | O | — | — | 0 | 1 | 4 |
| 360 | 3,5-Dbp | H | H | C | O | Mee | H | S | — | — | 0 | 1 | 4 |
| 361 | 3,5-Dbp | H | H | C | O | Phe | H | O | — | — | 0 | 1 | 4 |
| 362 | 3,5-Dbp | H | H | C | O | NH | Pr | O | Ete | O | 1 | 1 | 4 |
| 363 | 3,5-Dbp | H | H | C | O | O | Me | NH | Trim | — | 1 | 1 | 4 |
| 364 | 4-MeOPh | 4-MeOPh | Ph | C | O | O | H | O | Ete | O | 1 | 1 | 4 |
| 365 | 4-MeOPh | 4-MeOPh | Ph | C | O | S | H | O | Ete | O | 1 | 1 | 4 |
| 366 | 4-MeOPh | 4-MeOPh | Ph | C | O | — | — | — | — | — | 0 | 0 | 4 |
| 367 | 4-MeOPh | 4-MeOPh | Ph | C | O | O | Me | O | — | — | 0 | 1 | 4 |
| 368 | 4-MeOPh | 4-MeOPh | Ph | C | O | O | Me | S | — | — | 0 | 1 | 4 |
| 369 | 4-MeOPh | 4-MeOPh | Ph | C | O | O | 2-ClPh | O | — | — | 0 | 1 | 4 |
| 370 | 4-MeOPh | 4-MeOPh | Ph | C | O | Mee | H | O | — | — | 0 | 1 | 4 |
| 371 | 4-MeOPh | 4-MeOPh | Ph | C | O | Mee | H | S | — | — | 0 | 1 | 4 |
| 372 | 4-MeOPh | 4-MeOPh | Ph | C | O | Phe | H | O | — | — | 0 | 1 | 4 |
| 373 | 4-MeOPh | 4-MeOPh | Ph | C | O | NH | Pr | O | Ete | O | 1 | 1 | 4 |
| 374 | 4-MeOPh | 4-MeOPh | Ph | C | O | O | Me | NH | Trim | — | 1 | 1 | 4 |
| 375 | 4-MeOPh | Ph | Ph | C | O | O | H | O | Ete | O | 1 | 1 | 4 |
| 376 | 4-MeOPh | Ph | Ph | C | O | S | H | O | Ete | O | 1 | 1 | 4 |
| 377 | 4-MeOPh | Ph | Ph | C | O | — | — | — | — | — | 0 | 0 | 4 |
| 378 | 4-MeOPh | Ph | Ph | C | O | O | Me | O | — | — | 0 | 1 | 4 |
| 379 | 4-MeOPh | Ph | Ph | C | O | O | Me | S | — | — | 0 | 1 | 4 |
| 380 | 4-MeOPh | Ph | Ph | C | O | O | 2-ClPh | O | — | — | 0 | 1 | 4 |
| 381 | 4-MeOPh | Ph | Ph | C | O | Mee | H | O | — | — | 0 | 1 | 4 |
| 382 | 4-MeOPh | Ph | Ph | C | O | Mee | H | S | — | — | 0 | 1 | 4 |
| 383 | 4-MeOPh | Ph | Ph | C | O | Phe | H | O | — | — | 0 | 1 | 4 |
| 384 | 4-MeOPh | Ph | Ph | C | O | NH | Pr | O | Ete | O | 1 | 1 | 4 |
| 385 | 4-MeOPh | Ph | Ph | C | O | O | Me | NH | Trim | — | 1 | 1 | 4 |
| 386 | tBu | Ph | Ph | Si | O | O | H | O | Ete | O | 1 | 1 | 4 |
| 387 | tBu | Ph | Ph | Si | O | S | H | O | Ete | O | 1 | 1 | 4 |
| 388 | tBu | Ph | Ph | Si | O | — | — | — | — | — | 0 | 0 | 4 |
| 389 | tBu | Ph | Ph | Si | O | O | Me | O | — | — | 0 | 1 | 4 |
| 390 | tBu | Ph | Ph | Si | O | O | Me | S | — | — | 0 | 1 | 4 |
| 391 | tBu | Ph | Ph | Si | O | O | 2-ClPh | O | — | — | 0 | 1 | 4 |
| 392 | tBu | Ph | Ph | Si | O | Mee | H | O | — | — | 0 | 1 | 4 |
| 393 | tBu | Ph | Ph | Si | O | Mee | H | S | — | — | 0 | 1 | 4 |
| 394 | tBu | Ph | Ph | Si | O | Phe | H | O | — | — | 0 | 1 | 4 |
| 395 | tBu | Ph | Ph | Si | O | NH | Pr | O | Ete | O | 1 | 1 | 4 |
| 396 | tBu | Ph | Ph | Si | O | O | Me | NH | Trim | — | 1 | 1 | 4 |
| 397 | Ph | Ph | Ph | C | S | O | H | O | Ete | O | 1 | 1 | 4 |
| 398 | Ph | Ph | Ph | C | S | S | H | O | Ete | O | 1 | 1 | 4 |
| 399 | Ph | Ph | Ph | C | S | — | — | — | — | — | 0 | 0 | 4 |
| 400 | Ph | Ph | Ph | C | S | O | Me | O | — | — | 0 | 1 | 4 |
| 401 | Ph | Ph | Ph | C | S | O | Me | S | — | — | 0 | 1 | 4 |
| 402 | Ph | Ph | Ph | C | S | O | 2-ClPh | O | — | — | 0 | 1 | 4 |
| 403 | Ph | Ph | Ph | C | S | Mee | H | O | — | — | 0 | 1 | 4 |
| 404 | Ph | Ph | Ph | C | S | Mee | H | S | — | — | 0 | 1 | 4 |
| 405 | Ph | Ph | Ph | C | S | Phe | H | O | — | — | 0 | 1 | 4 |
| 406 | Ph | Ph | Ph | C | S | NH | Pr | O | Ete | O | 1 | 1 | 4 |
| 407 | Ph | Ph | Ph | C | S | O | Me | NH | Trim | — | 1 | 1 | 4 |
| 408 | 4-BzOPh | H | H | C | O | O | H | O | Ete | O | 1 | 1 | 4 |
| 409 | 4-BzOPh | H | H | C | O | S | H | O | Ete | O | 1 | 1 | 4 |
| 410 | 4-BzOPh | H | H | C | O | — | — | — | — | — | 0 | 0 | 4 |
| 411 | 4-BzOPh | H | H | C | O | O | Me | O | — | — | 0 | 1 | 4 |
| 412 | 4-BzOPh | H | H | C | O | O | Me | S | — | — | 0 | 1 | 4 |
| 413 | 4-BzOPh | H | H | C | O | O | 2-ClPh | O | — | — | 0 | 1 | 4 |
| 414 | 4-BzOPh | H | H | C | O | Mee | H | O | — | — | 0 | 1 | 4 |
| 415 | 4-BzOPh | H | H | C | O | Mee | H | S | — | — | 0 | 1 | 4 |
| 416 | 4-BzOPh | H | H | C | O | Phe | H | O | — | — | 0 | 1 | 4 |
| 417 | 4-BzOPh | H | H | C | O | NH | Pr | O | Ete | O | 1 | 1 | 4 |
| 418 | 4-BzOPh | H | H | C | O | O | Me | NH | Trim | — | 1 | 1 | 4 |
| 419 | Ph | Xanthen-9-yl | | | O | O | H | O | Ete | O | 1 | 1 | 4 |
| 420 | Ph | Xanthen-9-yl | | | O | S | H | O | Ete | O | 1 | 1 | 4 |
| 421 | Ph | Xanthen-9-yl | | | O | — | — | — | — | — | 0 | 0 | 4 |
| 422 | Ph | Xanthen-9-yl | | | O | O | Me | O | — | — | 0 | 1 | 4 |
| 423 | Ph | Xanthen-9-yl | | | O | O | Me | S | — | — | 0 | 1 | 4 |
| 424 | Ph | Xanthen-9-yl | | | O | O | 2-ClPh | O | — | — | 0 | 1 | 4 |
| 425 | Ph | Xanthen-9-yl | | | O | Mee | H | O | — | — | 0 | 1 | 4 |
| 426 | Ph | Xanthen-9-yl | | | O | Mee | H | S | — | — | 0 | 1 | 4 |
| 427 | Ph | Xanthen-9-yl | | | O | Phe | H | O | — | — | 0 | 1 | 4 |
| 428 | Ph | Xanthen-9-yl | | | O | NH | Pr | O | Ete | O | 1 | 1 | 4 |
| 429 | Ph | Xanthen-9-yl | | | O | O | Me | NH | Trim | — | 1 | 1 | 4 |
| 430 | Ph | Fluoren-9-yl | | | O | O | H | O | Ete | O | 1 | 1 | 4 |
| 431 | Ph | Fluoren-9-yl | | | O | S | H | O | Ete | O | 1 | 1 | 4 |
| 432 | Ph | Fluoren-9-yl | | | O | — | — | — | — | — | 0 | 0 | 4 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 433 | Ph | Fluoren-9-yl | | | O | O | Me | O | — | — | 0 | 1 | 4 |
| 434 | Ph | Fluoren-9-yl | | | O | O | Me | S | — | — | 0 | 1 | 4 |
| 435 | Ph | Fluoren-9-yl | | | O | O | 2-ClPh | O | — | — | 0 | 1 | 4 |
| 436 | Ph | Fluoren-9-yl | | | O | Mee | H | O | — | — | 0 | 1 | 4 |
| 437 | Ph | Fluoren-9-yl | | | O | Mee | H | S | — | — | 0 | 1 | 4 |
| 438 | Ph | Fluoren-9-yl | | | O | Phe | H | O | — | — | 0 | 1 | 4 |
| 439 | Ph | Fluoren-9-yl | | | O | NH | Pr | O | Ete | O | 1 | 1 | 4 |
| 440 | Ph | Fluoren-9-yl | | | O | O | Me | NH | Trim | — | 1 | 1 | 4 |
| 441 | 3,4-Dbp | H | H | C | O | O | H | O | Ete | O | 1 | 1 | 5 |
| 442 | 3,4-Dbp | H | H | C | O | S | H | O | Ete | O | 1 | 1 | 5 |
| 443 | 3,4-Dbp | H | H | C | O | — | — | — | — | — | 0 | 0 | 5 |
| 444 | 3,4-Dbp | H | H | C | O | O | Me | O | — | — | 0 | 1 | 5 |
| 445 | 3,4-Dbp | H | H | C | O | O | Me | S | — | — | 0 | 1 | 5 |
| 446 | 3,4-Dbp | H | H | C | O | O | 2-ClPh | O | — | — | 0 | 1 | 5 |
| 447 | 3,4-Dbp | H | H | C | O | Mee | H | O | — | — | 0 | 1 | 5 |
| 448 | 3,4-Dbp | H | H | C | O | Mee | H | S | — | — | 0 | 1 | 5 |
| 449 | 3,4-Dbp | H | H | C | O | Phe | H | O | — | — | 0 | 1 | 5 |
| 450 | 3,4-Dbp | H | H | C | O | NH | Pr | O | Ete | O | 1 | 1 | 5 |
| 451 | 3,4-Dbp | H | H | C | O | O | Me | NH | Trim | — | 1 | 1 | 5 |
| 452 | Ph | Ph | Ph | C | O | O | H | O | Ete | O | 1 | 1 | 5 |
| 453 | Ph | Ph | Ph | C | O | S | H | O | Ete | O | 1 | 1 | 5 |
| 454 | Ph | Ph | Ph | C | O | — | — | — | — | — | 0 | 0 | 5 |
| 455 | Ph | Ph | Ph | C | O | O | Me | O | — | — | 0 | 1 | 5 |
| 456 | Ph | Ph | Ph | C | O | O | Me | S | — | — | 0 | 1 | 5 |
| 457 | Ph | Ph | Ph | C | O | O | 2-ClPh | O | — | — | 0 | 1 | 5 |
| 458 | Ph | Ph | Ph | C | O | Mee | H | O | — | — | 0 | 1 | 5 |
| 459 | Ph | Ph | Ph | C | O | Mee | H | S | — | — | 0 | 1 | 5 |
| 460 | Ph | Ph | Ph | C | O | Phe | H | O | — | — | 0 | 1 | 5 |
| 461 | Ph | Ph | Ph | C | O | NH | Pr | O | Ete | O | 1 | 1 | 5 |
| 462 | Ph | Ph | Ph | C | O | O | Me | NH | Trim | — | 1 | 1 | 5 |
| 463 | 3,5-Dbp | H | H | C | O | O | H | O | Ete | O | 1 | 1 | 5 |
| 464 | 3,5-Dbp | H | H | C | O | S | H | O | Ete | O | 1 | 1 | 5 |
| 465 | 3,5-Dbp | H | H | C | O | — | — | — | — | — | 0 | 0 | 5 |
| 466 | 3,5-Dbp | H | H | C | O | O | Me | O | — | — | 0 | 1 | 5 |
| 467 | 3,5-Dbp | H | H | C | O | O | Me | S | — | — | 0 | 1 | 5 |
| 468 | 3,5-Dbp | H | H | C | O | O | 2-ClPh | O | — | — | 0 | 1 | 5 |
| 469 | 3,5-Dbp | H | H | C | O | Mee | H | O | — | — | 0 | 1 | 5 |
| 470 | 3,5-Dbp | H | H | C | O | Mee | H | S | — | — | 0 | 1 | 5 |
| 471 | 3,5-Dbp | H | H | C | O | Phe | H | O | — | — | 0 | 1 | 5 |
| 472 | 3,5-Dbp | H | H | C | O | NH | Pr | O | Ete | O | 1 | 1 | 5 |
| 473 | 3,5-Dbp | H | H | C | O | O | Me | NH | Trim | — | 1 | 1 | 5 |
| 474 | 4-MeOPh | 4-MeOPh | Ph | C | O | O | H | O | Ete | O | 1 | 1 | 5 |
| 475 | 4-MeOPh | 4-MeOPh | Ph | C | O | S | H | O | Ete | O | 1 | 1 | 5 |
| 476 | 4-MeOPh | 4-MeOPh | Ph | C | O | — | — | — | — | — | 0 | 0 | 5 |
| 477 | 4-MeOPh | 4-MeOPh | Ph | C | O | O | Me | O | — | — | 0 | 1 | 5 |
| 478 | 4-MeOPh | 4-MeOPh | Ph | C | O | O | Me | S | — | — | 0 | 1 | 5 |
| 479 | 4-MeOPh | 4-MeOPh | Ph | C | O | O | 2-ClPh | O | — | — | 0 | 1 | 5 |
| 480 | 4-MeOPh | 4-MeOPh | Ph | C | O | Mee | H | O | — | — | 0 | 1 | 5 |
| 481 | 4-MeOPh | 4-MeOPh | Ph | C | O | Mee | H | S | — | — | 0 | 1 | 5 |
| 482 | 4-MeOPh | 4-MeOPh | Ph | C | O | Phe | H | O | — | — | 0 | 1 | 5 |
| 483 | 4-MeOPh | 4-MeOPh | Ph | C | O | NH | Pr | O | Ete | O | 1 | 1 | 5 |
| 484 | 4-MeOPh | 4-MeOPh | Ph | C | O | O | Me | NH | Trim | — | 1 | 1 | 5 |
| 485 | 4-MeOPh | Ph | Ph | C | O | O | H | O | Ete | O | 1 | 1 | 5 |
| 486 | 4-MeOPh | Ph | Ph | C | O | S | H | O | Ete | O | 1 | 1 | 5 |
| 487 | 4-MeOPh | Ph | Ph | C | O | — | — | — | — | — | 0 | 0 | 5 |
| 488 | 4-MeOPh | Ph | Ph | C | O | O | Me | O | — | — | 0 | 1 | 5 |
| 489 | 4-MeOPh | Ph | Ph | C | O | O | Me | S | — | — | 0 | 1 | 5 |
| 490 | 4-MeOPh | Ph | Ph | C | O | O | 2-ClPh | O | — | — | 0 | 1 | 5 |
| 491 | 4-MeOPh | Ph | Ph | C | O | Mee | H | O | — | — | 0 | 1 | 5 |
| 492 | 4-MeOPh | Ph | Ph | C | O | Mee | H | S | — | — | 0 | 1 | 5 |
| 493 | 4-MeOPh | Ph | Ph | C | O | Phe | H | O | — | — | 0 | 1 | 5 |
| 494 | 4-MeOPh | Ph | Ph | C | O | NH | Pr | O | Ete | O | 1 | 1 | 5 |
| 495 | 4-MeOPh | Ph | Ph | C | O | O | Me | NH | Trim | — | 1 | 1 | 5 |
| 496 | tBu | Ph | Ph | Si | O | O | H | O | Ete | O | 1 | 1 | 5 |
| 497 | tBu | Ph | Ph | Si | O | S | H | O | Ete | O | 1 | 1 | 5 |
| 498 | tBu | Ph | Ph | Si | O | — | — | — | — | — | 0 | 0 | 5 |
| 499 | tBu | Ph | Ph | Si | O | O | Me | O | — | — | 0 | 1 | 5 |
| 500 | tBu | Ph | Ph | Si | O | O | Me | S | — | — | 0 | 1 | 5 |
| 501 | tBu | Ph | Ph | Si | O | O | 2-ClPh | O | — | — | 0 | 1 | 5 |
| 502 | tBu | Ph | Ph | Si | O | Mee | H | O | — | — | 0 | 1 | 5 |
| 503 | tBu | Ph | Ph | Si | O | Mee | H | S | — | — | 0 | 1 | 5 |
| 504 | tBu | Ph | Ph | Si | O | Phe | H | O | — | — | 0 | 1 | 5 |
| 505 | tBu | Ph | Ph | Si | O | NH | Pr | O | Ete | O | 1 | 1 | 5 |
| 506 | tBu | Ph | Ph | Si | O | O | Me | NH | Trim | — | 1 | 1 | 5 |
| 507 | Ph | Ph | Ph | C | S | O | H | O | Ete | O | 1 | 1 | 5 |
| 508 | Ph | Ph | Ph | C | S | S | H | O | Ete | O | 1 | 1 | 5 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 509 | Ph | Ph | Ph | C | S | — | — | — | — | — | 0 | 0 | 5 |
| 510 | Ph | Ph | Ph | C | S | O | Me | O | — | — | 0 | 1 | 5 |
| 511 | Ph | Ph | Ph | C | S | O | Me | S | — | — | 0 | 1 | 5 |
| 512 | Ph | Ph | Ph | C | S | O | 2-ClPh | O | — | — | 0 | 1 | 5 |
| 513 | Ph | Ph | Ph | C | S | Mee | H | O | — | — | 0 | 1 | 5 |
| 514 | Ph | Ph | Ph | C | S | Mee | H | S | — | — | 0 | 1 | 5 |
| 515 | Ph | Ph | Ph | C | S | Phe | H | O | — | — | 0 | 1 | 5 |
| 516 | Ph | Ph | Ph | C | S | NH | Pr | O | Ete | O | 1 | 1 | 5 |
| 517 | Ph | Ph | Ph | C | S | O | Me | NH | Trim | — | 1 | 1 | 5 |
| 518 | 4-BzOPh | H | H | C | O | O | H | O | Ete | O | 1 | 1 | 5 |
| 519 | 4-BzOPh | H | H | C | O | S | H | O | Ete | O | 1 | 1 | 5 |
| 520 | 4-BzOPh | H | H | C | O | — | — | — | — | — | 0 | 0 | 5 |
| 521 | 4-BzOPh | H | H | C | O | O | Me | O | — | — | 0 | 1 | 5 |
| 522 | 4-BzOPh | H | H | C | O | O | Me | S | — | — | 0 | 1 | 5 |
| 523 | 4-BzOPh | H | H | C | O | O | 2-ClPh | O | — | — | 0 | 1 | 5 |
| 524 | 4-BzOPh | H | H | C | O | Mee | H | O | — | — | 0 | 1 | 5 |
| 525 | 4-BzOPh | H | H | C | O | Mee | H | S | — | — | 0 | 1 | 5 |
| 526 | 4-BzOPh | H | H | C | O | Phe | H | O | — | — | 0 | 1 | 5 |
| 527 | 4-BzOPh | H | H | C | O | NH | Pr | O | Ete | O | 1 | 1 | 5 |
| 528 | 4-BzOPh | H | H | C | O | O | Me | NH | Trim | — | 1 | 1 | 5 |
| 529 | Ph | Xanthen-9-yl | | | O | O | H | O | Ete | O | 1 | 1 | 5 |
| 530 | Ph | Xanthen-9-yl | | | O | S | H | O | Ete | O | 1 | 1 | 5 |
| 531 | Ph | Xanthen-9-yl | | | O | — | — | — | — | — | 0 | 0 | 5 |
| 532 | Ph | Xanthen-9-yl | | | O | O | Me | O | — | — | 0 | 1 | 5 |
| 533 | Ph | Xanthen-9-yl | | | O | O | Me | S | — | — | 0 | 1 | 5 |
| 534 | Ph | Xanthen-9-yl | | | O | O | 2-ClPh | O | — | — | 0 | 1 | 5 |
| 535 | Ph | Xanthen-9-yl | | | O | Mee | H | O | — | — | 0 | 1 | 5 |
| 536 | Ph | Xanthen-9-yl | | | O | Mee | H | S | — | — | 0 | 1 | 5 |
| 537 | Ph | Xanthen-9-yl | | | O | Phe | H | O | — | — | 0 | 1 | 5 |
| 538 | Ph | Xanthen-9-yl | | | O | NH | Pr | O | Ete | O | 1 | 1 | 5 |
| 539 | Ph | Xanthen-9-yl | | | O | O | Me | NH | Trim | — | 1 | 1 | 5 |
| 540 | Ph | Fluoren-9-yl | | | O | O | H | O | Ete | O | 1 | 1 | 5 |
| 541 | Ph | Fluoren-9-yl | | | O | S | H | O | Ete | O | 1 | 1 | 5 |
| 542 | Ph | Fluoren-9-yl | | | O | — | — | — | — | — | 0 | 0 | 5 |
| 543 | Ph | Fluoren-9-yl | | | O | O | Me | O | — | — | 0 | 1 | 5 |
| 544 | Ph | Fluoren-9-yl | | | O | O | Me | S | — | — | 0 | 1 | 5 |
| 545 | Ph | Fluoren-9-yl | | | O | O | 2-ClPh | O | — | — | 0 | 1 | 5 |
| 546 | Ph | Fluoren-9-yl | | | O | Mee | H | O | — | — | 0 | 1 | 5 |
| 547 | Ph | Fluoren-9-yl | | | O | Mee | H | S | — | — | 0 | 1 | 5 |
| 548 | Ph | Fluoren-9-yl | | | O | Phe | H | O | — | — | 0 | 1 | 5 |
| 549 | Ph | Fluoren-9-yl | | | O | NH | Pr | O | Ete | O | 1 | 1 | 5 |
| 550 | Ph | Fluoren-9-yl | | | O | O | Me | NH | Trim | — | 1 | 1 | 5 |
| 551 | 3,4-Dbp | H | H | C | O | O | H | O | Ete | O | 1 | 1 | 6 |
| 552 | 3,4-Dbp | H | H | C | O | S | H | O | Ete | O | 1 | 1 | 6 |
| 553 | 3,4-Dbp | H | H | C | O | — | — | — | — | — | 0 | 0 | 6 |
| 554 | 3,4-Dbp | H | H | C | O | O | Me | O | — | — | 0 | 1 | 6 |
| 555 | 3,4-Dbp | H | H | C | O | O | Me | S | — | — | 0 | 1 | 6 |
| 556 | 3,4-Dbp | H | H | C | O | O | 2-ClPh | O | — | — | 0 | 1 | 6 |
| 557 | 3,4-Dbp | H | H | C | O | Mee | H | O | — | — | 0 | 1 | 6 |
| 558 | 3,4-Dbp | H | H | C | O | Mee | H | S | — | — | 0 | 1 | 6 |
| 559 | 3,4-Dbp | H | H | C | O | Phe | H | O | — | — | 0 | 1 | 6 |
| 560 | 3,4-Dbp | H | H | C | O | NH | Pr | O | Ete | O | 1 | 1 | 6 |
| 561 | 3,4-Dbp | H | H | C | O | O | Me | NH | Trim | — | 1 | 1 | 6 |
| 562 | Ph | Ph | Ph | C | O | O | H | O | Ete | O | 1 | 1 | 6 |
| 563 | Ph | Ph | Ph | C | O | S | H | O | Ete | O | 1 | 1 | 6 |
| 564 | Ph | Ph | Ph | C | O | — | — | — | — | — | 0 | 0 | 6 |
| 565 | Ph | Ph | Ph | C | O | O | Me | O | — | — | 0 | 1 | 6 |
| 566 | Ph | Ph | Ph | C | O | O | Me | S | — | — | 0 | 1 | 6 |
| 567 | Ph | Ph | Ph | C | O | O | 2-ClPh | O | — | — | 0 | 1 | 6 |
| 568 | Ph | Ph | Ph | C | O | Mee | H | O | — | — | 0 | 1 | 6 |
| 569 | Ph | Ph | Ph | C | O | Mee | H | S | — | — | 0 | 1 | 6 |
| 570 | Ph | Ph | Ph | C | O | Phe | H | O | — | — | 0 | 1 | 6 |
| 571 | Ph | Ph | Ph | C | O | NH | Pr | O | Ete | O | 1 | 1 | 6 |
| 572 | Ph | Ph | Ph | C | O | O | Me | NH | Trim | — | 1 | 1 | 6 |
| 573 | 3,5-Dbp | H | H | C | O | O | H | O | Ete | O | 1 | 1 | 6 |
| 574 | 3,5-Dbp | H | H | C | O | S | H | O | Ete | O | 1 | 1 | 6 |
| 575 | 3,5-Dbp | H | H | C | O | — | — | — | — | — | 0 | 0 | 6 |
| 576 | 3,5-Dbp | H | H | C | O | O | Me | O | — | — | 0 | 1 | 6 |
| 577 | 3,5-Dbp | H | H | C | O | O | Me | S | — | — | 0 | 1 | 6 |
| 578 | 3,5-Dbp | H | H | C | O | O | 2ClPh | O | — | — | 0 | 1 | 6 |
| 579 | 3,5-Dbp | H | H | C | O | Mee | H | O | — | — | 0 | 1 | 6 |
| 580 | 3,5-Dbp | H | H | C | O | Mee | H | S | — | — | 0 | 1 | 6 |
| 581 | 3,5-Dbp | H | H | C | O | Phe | H | O | — | — | 0 | 1 | 6 |
| 582 | 3,5-Dbp | H | H | C | O | NH | Pr | O | Ete | O | 1 | 1 | 6 |
| 583 | 3,5-Dbp | H | H | C | O | O | Me | NH | Trim | — | 1 | 1 | 6 |
| 584 | 4-MeOPh | 4-MeOPh | Ph | C | O | O | H | O | Ete | O | 1 | 1 | 6 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 585 | 4-MeOPh | 4-MeOPh | Ph | C | O | S | H | O | Ete | O | 1 | 1 | 6 |
| 586 | 4-MeOPh | 4-MeOPh | Ph | C | O | — | — | — | — | — | 0 | 0 | 5 |
| 587 | 4-MeOPh | 4-MeOPh | Ph | C | O | O | Me | O | — | — | 0 | 1 | 5 |
| 588 | 4-MeOPh | 4-MeOPh | Ph | C | O | O | Me | S | — | — | 0 | 1 | 5 |
| 589 | 4-MeOPh | 4-MeOPh | Ph | C | O | O | 2-ClPh | O | — | — | 0 | 1 | 5 |
| 590 | 4-MeOPh | 4-MeOPh | Ph | C | O | Mee | H | O | — | — | 0 | 1 | 5 |
| 591 | 4-MeOPh | 4-MeOPh | Ph | C | O | Mee | H | S | — | — | 0 | 1 | 5 |
| 592 | 4-MeOPh | 4-MeOPh | Ph | C | O | Phe | H | O | — | — | 0 | 1 | 5 |
| 593 | 4-MeOPh | 4-MeOPh | Ph | C | O | NH | Pr | O | Ete | O | 1 | 1 | 5 |
| 594 | 4-MeOPh | 4-MeOPh | Ph | C | O | O | Me | NH | Trim | — | 1 | 1 | 5 |
| 595 | 4-MeOPh | Ph | Ph | C | O | O | H | O | Ete | O | 1 | 1 | 5 |
| 596 | 4-MeOPh | Ph | Ph | C | O | S | H | O | Ete | O | 1 | 1 | 5 |
| 597 | 4-MeOPh | Ph | Ph | C | O | — | — | — | — | — | 0 | 0 | 5 |
| 598 | 4-MeOPh | Ph | Ph | C | O | O | Me | O | — | — | 0 | 1 | 5 |
| 599 | 4-MeOPh | Ph | Ph | C | O | O | Me | S | — | — | 0 | 1 | 5 |
| 600 | 4-MeOPh | Ph | Ph | C | O | O | 2-ClPh | O | — | — | 0 | 1 | 5 |
| 601 | 4-MeOPh | Ph | Ph | C | O | Mee | H | O | — | — | 0 | 1 | 5 |
| 602 | 4-MeOPh | Ph | Ph | C | O | Mee | H | S | — | — | 0 | 1 | 5 |
| 603 | 4-MeOPh | Ph | Ph | C | O | Phe | H | O | — | — | 0 | 1 | 5 |
| 604 | 4-MeOPh | Ph | Ph | C | O | NH | Pr | O | Ete | O | 1 | 1 | 5 |
| 605 | 4-MeOPh | Ph | Ph | C | O | O | Me | NH | Trim | — | 1 | 1 | 5 |
| 606 | tBu | Ph | Ph | Si | O | O | H | O | Ete | O | 1 | 1 | 6 |
| 607 | tBu | Ph | Ph | Si | O | S | H | O | Ete | O | 1 | 1 | 6 |
| 608 | tBu | Ph | Ph | Si | O | — | — | — | — | — | 0 | 0 | 6 |
| 609 | tBu | Ph | Ph | Si | O | O | Me | O | — | — | 0 | 1 | 6 |
| 610 | tBu | Ph | Ph | Si | O | O | Me | S | — | — | 0 | 1 | 6 |
| 611 | tBu | Ph | Ph | Si | O | O | 2-ClPh | O | — | — | 0 | 1 | 6 |
| 612 | tBu | Ph | Ph | Si | O | Mee | H | O | — | — | 0 | 1 | 6 |
| 613 | tBu | Ph | Ph | Si | O | Mee | H | S | — | — | 0 | 1 | 6 |
| 614 | tBu | Ph | Ph | Si | O | Phe | H | O | — | — | 0 | 1 | 6 |
| 615 | tBu | Ph | Ph | Si | O | NH | Pr | O | Ete | O | 1 | 1 | 6 |
| 616 | tBu | Ph | Ph | Si | O | O | Me | NH | Trim | — | 1 | 1 | 6 |
| 617 | Ph | Ph | Ph | C | S | O | H | O | Ete | O | 1 | 1 | 6 |
| 618 | Ph | Ph | Ph | C | S | S | H | O | Ete | O | 1 | 1 | 5 |
| 619 | Ph | Ph | Ph | C | S | — | — | — | — | — | 0 | 0 | 5 |
| 620 | Ph | Ph | Ph | C | S | O | Me | O | — | — | 0 | 1 | 5 |
| 621 | Ph | Ph | Ph | C | S | O | Me | S | — | — | 0 | 1 | 5 |
| 622 | Ph | Ph | Ph | C | S | O | 2-ClPh | O | — | — | 0 | 1 | 5 |
| 623 | Ph | Ph | Ph | C | S | Mee | H | O | — | — | 0 | 1 | 5 |
| 624 | Ph | Ph | Ph | C | S | Mee | H | S | — | — | 0 | 1 | 5 |
| 625 | Ph | Ph | Ph | C | S | Phe | H | O | — | — | 0 | 1 | 5 |
| 626 | Ph | Ph | Ph | C | S | NH | Pr | O | Ete | O | 1 | 1 | 5 |
| 627 | Ph | Ph | Ph | C | S | O | Me | NH | Trim | — | 1 | 1 | 5 |
| 628 | 4-BzOPh | H | H | C | O | O | H | O | Ete | O | 1 | 1 | 5 |
| 629 | 4-BzOPh | H | H | C | O | S | H | O | Ete | O | 1 | 1 | 5 |
| 630 | 4-BzOPh | H | H | C | O | — | — | — | — | — | 0 | 0 | 5 |
| 631 | 4-BzOPh | H | H | C | O | O | Me | O | — | — | 0 | 1 | 5 |
| 632 | 4-BzOPh | H | H | C | O | O | Me | S | — | — | 0 | 1 | 5 |
| 633 | 4-BzOPh | H | H | C | O | O | 2-ClPh | O | — | — | 0 | 1 | 5 |
| 634 | 4-BzOPh | H | H | C | O | Mee | H | O | — | — | 0 | 1 | 5 |
| 635 | 4-BzOPh | H | H | C | O | Mee | H | S | — | — | 0 | 1 | 5 |
| 636 | 4-BzOPh | H | H | C | O | Phe | H | O | — | — | 0 | 1 | 5 |
| 637 | 4-BzOPh | H | H | C | O | NH | Pr | O | Ete | O | 1 | 1 | 5 |
| 638 | 4-BzOPh | H | H | C | O | O | Me | NH | Trim | — | 1 | 1 | 5 |
| 639 | Ph | Xanthen-9-yl | | | O | O | H | O | Ete | O | 1 | 1 | 5 |
| 640 | Ph | Xanthen-9-yl | | | O | S | H | O | Ete | O | 1 | 1 | 5 |
| 641 | Ph | Xanthen-9-yl | | | O | — | — | — | — | — | 0 | 0 | 5 |
| 642 | Ph | Xanthen-9-yl | | | O | O | Me | O | — | — | 0 | 1 | 5 |
| 643 | Ph | Xanthen-9-yl | | | O | O | Me | S | — | — | 0 | 1 | 5 |
| 644 | Ph | Xanthen-9-yl | | | O | O | 2-ClPh | O | — | — | 0 | 1 | 5 |
| 645 | Ph | Xanthen-9-yl | | | O | Mee | H | O | — | — | 0 | 1 | 5 |
| 646 | Ph | Xanthen-9-yl | | | O | Mee | H | S | — | — | 0 | 1 | 5 |
| 647 | Ph | Xanthen-9-yl | | | O | Phe | H | O | — | — | 0 | 1 | 5 |
| 648 | Ph | Xanthen-9-yl | | | O | NH | Pr | O | Ete | O | 1 | 1 | 5 |
| 649 | Ph | Xanthen-9-yl | | | O | O | Me | NH | Trim | — | 1 | 1 | 5 |
| 650 | Ph | Fluoren-9-yl | | | O | O | H | O | Ete | O | 1 | 1 | 5 |
| 651 | Ph | Fluoren-9-yl | | | O | S | H | O | Ete | O | 1 | 1 | 5 |
| 652 | Ph | Fluoren-9-yl | | | O | — | — | — | — | — | 0 | 0 | 5 |
| 653 | Ph | Fluoren-9-yl | | | O | O | Me | O | — | — | 0 | 1 | 5 |
| 654 | Ph | Fluoren-9-yl | | | O | O | Me | S | — | — | 0 | 1 | 5 |
| 655 | Ph | Fluoren-9-yl | | | O | O | 2-ClPh | O | — | — | 0 | 1 | 5 |
| 656 | Ph | Fluoren-9-yl | | | O | Mee | H | O | — | — | 0 | 1 | 5 |
| 657 | Ph | Fluoren-9-yl | | | O | Mee | H | S | — | — | 0 | 1 | 5 |
| 658 | Ph | Fluoren-9-yl | | | O | Phe | H | O | — | — | 0 | 1 | 5 |
| 659 | Ph | Fluoren-9-yl | | | O | NH | Pr | O | Ete | O | 1 | 1 | 5 |
| 660 | Ph | Fluoren-9-yl | | | O | O | Me | NH | Trim | — | 1 | 1 | 5 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 661 | 3,4-Dbp | H | H | C | O | O | H | O | Ete | O | 1 | 1 | 7 |
| 662 | 3,4-Dbp | H | H | C | O | S | H | O | Ete | O | 1 | 1 | 7 |
| 663 | 3,4-Dbp | H | H | C | O | — | — | — | — | — | 0 | 0 | 7 |
| 664 | 3,4-Dbp | H | H | C | O | O | Me | O | — | — | 0 | 1 | 7 |
| 665 | 3,4-Dbp | H | H | C | O | O | Me | S | — | — | 0 | 1 | 7 |
| 666 | 3,4-Dbp | H | H | C | O | O | 2-ClPh | O | — | — | 0 | 1 | 7 |
| 667 | 3,4-Dbp | H | H | C | O | Mee | H | O | — | — | 0 | 1 | 7 |
| 668 | 3,4-Dbp | H | H | C | O | Mee | H | S | — | — | 0 | 1 | 7 |
| 669 | 3,4-Dbp | H | H | C | O | Phe | H | O | — | — | 0 | 1 | 7 |
| 670 | 3,4-Dbp | H | H | C | O | NH | Pr | O | Ete | O | 1 | 1 | 7 |
| 671 | 3,4-Dbp | H | H | C | O | O | Me | NH | Trim | — | 1 | 1 | 7 |
| 672 | Ph | Ph | Ph | C | O | O | H | O | Ete | O | 1 | 1 | 7 |
| 673 | Ph | Ph | Ph | C | O | S | H | O | Ete | O | 1 | 1 | 7 |
| 674 | Ph | Ph | Ph | C | O | — | — | — | — | — | 0 | 0 | 7 |
| 675 | Ph | Ph | Ph | C | O | O | Me | O | — | — | 0 | 1 | 7 |
| 676 | Ph | Ph | Ph | C | O | O | Me | S | — | — | 0 | 1 | 7 |
| 677 | Ph | Ph | Ph | C | O | O | 2-ClPh | O | — | — | 0 | 1 | 7 |
| 678 | Ph | Ph | Ph | C | O | Mee | H | O | — | — | 0 | 1 | 7 |
| 679 | Ph | Ph | Ph | C | O | Mee | H | S | — | — | 0 | 1 | 7 |
| 680 | Ph | Ph | Ph | C | O | Phe | H | O | — | — | 0 | 1 | 7 |
| 681 | Ph | Ph | Ph | C | O | NH | Pr | O | Ete | O | 1 | 1 | 7 |
| 682 | Ph | Ph | Ph | C | O | O | Me | NH | Trim | — | 1 | 1 | 7 |
| 683 | 3,5-Dbp | H | H | C | O | O | H | O | Ete | O | 1 | 1 | 7 |
| 684 | 3,5-Dbp | H | H | C | O | S | H | O | Ete | O | 1 | 1 | 7 |
| 685 | 3,5-Dbp | H | H | C | O | — | — | — | — | — | 0 | 0 | 7 |
| 686 | 3,5-Dbp | H | H | C | O | O | Me | O | — | — | 0 | 1 | 7 |
| 687 | 3,5-Dbp | H | H | C | O | O | Me | S | — | — | 0 | 1 | 7 |
| 688 | 3,5-Dbp | H | H | C | O | O | 2-ClPh | O | — | — | 0 | 1 | 7 |
| 689 | 3,5-Dbp | H | H | C | O | Mee | H | O | — | — | 0 | 1 | 7 |
| 690 | 3,5-Dbp | H | H | C | O | Mee | H | S | — | — | 0 | 1 | 7 |
| 691 | 3,5-Dbp | H | H | C | O | Phe | H | O | — | — | 0 | 1 | 7 |
| 692 | 3,5-Dbp | H | H | C | O | NH | Pr | O | Ete | O | 1 | 1 | 7 |
| 693 | 3,5-Dbp | H | H | C | O | O | Me | NH | Trim | — | 1 | 1 | 7 |
| 694 | 4-MeOPh | 4-MeOPh | Ph | C | O | O | H | O | Ete | O | 1 | 1 | 7 |
| 695 | 4-MeOPh | 4-MeOPh | Ph | C | O | S | H | O | Ete | O | 1 | 1 | 7 |
| 696 | 4-MeOPh | 4-MeOPh | Ph | C | O | — | — | — | — | — | 0 | 0 | 7 |
| 697 | 4-MeOPh | 4-MeOPh | Ph | C | O | O | Me | O | — | — | 0 | 1 | 7 |
| 698 | 4-MeOPh | 4-MeOPh | Ph | C | O | O | Me | S | — | — | 0 | 1 | 7 |
| 699 | 4-MeOPh | 4-MeOPh | Ph | C | O | O | 2-ClPh | O | — | — | 0 | 1 | 7 |
| 700 | 4-MeOPh | 4-MeOPh | Ph | C | O | Mee | H | O | — | — | 0 | 1 | 7 |
| 701 | 4-MeOPh | 4-MeOPh | Ph | C | O | Mee | H | S | — | — | 0 | 1 | 7 |
| 702 | 4-MeOPh | 4-MeOPh | Ph | C | O | Phe | H | O | — | — | 0 | 1 | 7 |
| 703 | 4-MeOPh | 4-MeOPh | Ph | C | O | NH | Pr | O | Ete | O | 1 | 1 | 7 |
| 704 | 4-MeOPh | 4-MeOPh | Ph | C | O | O | Me | NH | Trim | — | 1 | 1 | 7 |
| 705 | 4-MeOPh | Ph | Ph | C | O | O | H | O | Ete | O | 1 | 1 | 7 |
| 706 | 4-MeOPh | Ph | Ph | C | O | S | H | O | Ete | O | 1 | 1 | 7 |
| 707 | 4-MeOPh | Ph | Ph | C | O | — | — | — | — | — | 0 | 0 | 7 |
| 708 | 4-MeOPh | Ph | Ph | C | O | O | Me | O | — | — | 0 | 1 | 7 |
| 709 | 4-MeOPh | Ph | Ph | C | O | O | Me | S | — | — | 0 | 1 | 7 |
| 710 | 4-MeOPh | Ph | Ph | C | O | O | 2-ClPh | O | — | — | 0 | 1 | 7 |
| 711 | 4-MeOPh | Ph | Ph | C | O | Mee | H | O | — | — | 0 | 1 | 7 |
| 712 | 4-MeOPh | Ph | Ph | C | O | Mee | H | S | — | — | 0 | 1 | 7 |
| 713 | 4-MeOPh | Ph | Ph | C | O | Phe | H | O | — | — | 0 | 1 | 7 |
| 714 | 4-MeOPh | Ph | Ph | C | O | NH | Pr | O | Ete | O | 1 | 1 | 7 |
| 715 | 4-MeOPh | Ph | Ph | C | O | O | Me | NH | Trim | — | 1 | 1 | 7 |
| 716 | tBu | Ph | Ph | Si | O | O | H | O | Ete | O | 1 | 1 | 7 |
| 717 | tBu | Ph | Ph | Si | O | S | H | O | Ete | O | 1 | 1 | 7 |
| 718 | tBu | Ph | Ph | Si | O | — | — | — | — | — | 0 | 0 | 7 |
| 719 | tBu | Ph | Ph | Si | O | O | Me | O | — | — | 0 | 1 | 7 |
| 720 | tBu | Ph | Ph | Si | O | O | Me | S | — | — | 0 | 1 | 7 |
| 721 | tBu | Ph | Ph | Si | O | O | 2-ClPh | O | — | — | 0 | 1 | 7 |
| 722 | tBu | Ph | Ph | Si | O | Mee | H | O | — | — | 0 | 1 | 7 |
| 723 | tBu | Ph | Ph | Si | O | Mee | H | S | — | — | 0 | 1 | 7 |
| 724 | tBu | Ph | Ph | Si | O | Phe | H | O | — | — | 0 | 1 | 7 |
| 725 | tBu | Ph | Ph | Si | O | NH | Pr | O | Ete | O | 1 | 1 | 7 |
| 726 | tBu | Ph | Ph | Si | O | O | Me | NH | Trim | — | 1 | 1 | 7 |
| 727 | Ph | Ph | Ph | C | S | O | H | O | Ete | O | 1 | 1 | 7 |
| 728 | Ph | Ph | Ph | C | S | S | H | O | Ete | O | 1 | 1 | 7 |
| 729 | Ph | Ph | Ph | C | S | — | — | — | — | — | 0 | 0 | 7 |
| 730 | Ph | Ph | Ph | C | S | O | Me | O | — | — | 0 | 1 | 7 |
| 731 | Ph | Ph | Ph | C | S | O | Me | S | — | — | 0 | 1 | 7 |
| 732 | Ph | Ph | Ph | C | S | O | 2-ClPh | O | — | — | 0 | 1 | 7 |
| 733 | Ph | Ph | Ph | C | S | Mee | H | O | — | — | 0 | 1 | 7 |
| 734 | Ph | Ph | Ph | C | S | Mee | H | S | — | — | 0 | 1 | 7 |
| 735 | Ph | Ph | Ph | C | S | Phe | H | O | — | — | 0 | 1 | 7 |
| 736 | Ph | Ph | Ph | C | S | NH | Pr | O | Ete | O | 1 | 1 | 7 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 737 | Ph | Ph | Ph | C | S | O | Me | NH | Trim | — | 1 | 1 | 7 |
| 738 | 4-BzOPh | H | H | C | O | O | H | O | Ete | O | 1 | 1 | 7 |
| 739 | 4-BzOPh | H | H | C | O | S | H | O | Ete | O | 1 | 1 | 7 |
| 740 | 4-BzOPh | H | H | C | O | — | — | — | — | — | 0 | 0 | 7 |
| 741 | 4-BzOPh | H | H | C | O | O | Me | O | — | — | 0 | 1 | 7 |
| 742 | 4-BzOPh | H | H | C | O | O | Me | S | — | — | 0 | 1 | 7 |
| 743 | 4-BzOPh | H | H | C | O | O | 2-ClPh | O | — | — | 0 | 1 | 7 |
| 744 | 4-BzOPh | H | H | C | O | Mee | H | O | — | — | 0 | 1 | 7 |
| 745 | 4-BzOPh | H | H | C | O | Mee | H | S | — | — | 0 | 1 | 7 |
| 746 | 4-BzOPh | H | H | C | O | Phe | H | O | — | — | 0 | 1 | 7 |
| 747 | 4-BzOPh | H | H | C | O | NH | Pr | O | Ete | O | 1 | 1 | 7 |
| 748 | 4-BzOPh | H | H | C | O | O | Me | NH | Trim | — | 1 | 1 | 7 |
| 749 | Ph | Xanthen-9-yl | | | O | O | H | O | Ete | O | 1 | 1 | 7 |
| 750 | Ph | Xanthen-9-yl | | | O | S | H | O | Ete | O | 1 | 1 | 7 |
| 751 | Ph | Xanthen-9-yl | | | O | — | — | — | — | — | 0 | 0 | 7 |
| 752 | Ph | Xanthen-9-yl | | | O | O | Me | O | — | — | 0 | 1 | 7 |
| 753 | Ph | Xanthen-9-yl | | | O | O | Me | S | — | — | 0 | 1 | 7 |
| 754 | Ph | Xanthen-9-yl | | | O | O | 2-ClPh | O | — | — | 0 | 1 | 7 |
| 755 | Ph | Xanthen-9-yl | | | O | Mee | H | O | — | — | 0 | 1 | 7 |
| 756 | Ph | Xanthen-9-yl | | | O | Mee | H | S | — | — | 0 | 1 | 7 |
| 757 | Ph | Xanthen-9-yl | | | O | Phe | H | O | — | — | 0 | 1 | 7 |
| 758 | Ph | Xanthen-9-yl | | | O | NH | Pr | O | Ete | O | 1 | 1 | 7 |
| 759 | Ph | Xanthen-9-yl | | | O | O | Me | NH | Trim | — | 1 | 1 | 7 |
| 760 | Ph | Fluoren-9-yl | | | O | O | H | O | Ete | O | 1 | 1 | 7 |
| 761 | Ph | Fluoren-9-yl | | | O | S | H | O | Ete | O | 1 | 1 | 7 |
| 762 | Ph | Fluoren-9-yl | | | O | — | — | — | — | — | 0 | 0 | 7 |
| 763 | Ph | Fluoren-9-yl | | | O | O | Me | O | — | — | 0 | 1 | 7 |
| 764 | Ph | Fluoren-9-yl | | | O | O | Me | S | — | — | 0 | 1 | 7 |
| 765 | Ph | Fluoren-9-yl | | | O | O | 2-ClPh | O | — | — | 0 | 1 | 7 |
| 766 | Ph | Fluoren-9-yl | | | O | Mee | H | O | — | — | 0 | 1 | 7 |
| 767 | Ph | Fluoren-9-yl | | | O | Mee | H | S | — | — | 0 | 1 | 7 |
| 768 | Ph | Fluoren-9-yl | | | O | Phe | H | O | — | — | 0 | 1 | 7 |
| 769 | Ph | Fluoren-9-yl | | | O | NH | Pr | O | Ete | O | 1 | 1 | 7 |
| 770 | Ph | Fluoren-9-yl | | | O | O | Me | NH | Trim | — | 1 | 1 | 7 |
| 771 | 3,4-Dbp | H | H | C | O | O | H | O | Ete | O | 1 | 1 | 8 |
| 772 | 3,4-Dbp | H | H | C | O | S | H | O | Ete | O | 1 | 1 | 8 |
| 773 | 3,4-Dbp | H | H | C | O | — | — | — | — | — | 0 | 0 | 8 |
| 774 | 3,4-Dbp | H | H | C | O | O | Me | O | — | — | 0 | 1 | 8 |
| 775 | 3,4-Dbp | H | H | C | O | O | Me | S | — | — | 0 | 1 | 8 |
| 776 | 3,4-Dbp | H | H | C | O | O | 2-ClPh | O | — | — | 0 | 1 | 8 |
| 777 | 3,4-Dbp | H | H | C | O | Mee | H | O | — | — | 0 | 1 | 8 |
| 778 | 3,4-Dbp | H | H | C | O | Mee | H | S | — | — | 0 | 1 | 8 |
| 779 | 3,4-Dbp | H | H | C | O | Phe | H | O | — | — | 0 | 1 | 8 |
| 780 | 3,4-Dbp | H | H | C | O | NH | Pr | O | Ete | O | 1 | 1 | 8 |
| 781 | 3,4-Dbp | H | H | C | O | O | Me | NH | Trim | — | 1 | 1 | 8 |
| 782 | Ph | Ph | Ph | C | O | O | H | O | Ete | O | 1 | 1 | 8 |
| 783 | Ph | Ph | Ph | C | O | S | H | O | Ete | O | 1 | 1 | 8 |
| 784 | Ph | Ph | Ph | C | O | — | — | — | — | — | 0 | 0 | 8 |
| 785 | Ph | Ph | Ph | C | O | O | Me | O | — | — | 0 | 1 | 8 |
| 786 | Ph | Ph | Ph | C | O | O | Me | S | — | — | 0 | 1 | 8 |
| 787 | Ph | Ph | Ph | C | O | O | 2-ClPh | O | — | — | 0 | 1 | 8 |
| 788 | Ph | Ph | Ph | C | O | Mee | H | O | — | — | 0 | 1 | 8 |
| 789 | Ph | Ph | Ph | C | O | Mee | H | S | — | — | 0 | 1 | 8 |
| 790 | Ph | Ph | Ph | C | O | Phe | H | O | — | — | 0 | 1 | 8 |
| 791 | Ph | Ph | Ph | C | O | NH | Pr | O | Ete | O | 1 | 1 | 8 |
| 792 | Ph | Ph | Ph | C | O | O | Me | NH | Trim | — | 1 | 1 | 8 |
| 793 | 3,5-Dbp | H | H | C | O | O | H | O | Ete | O | 1 | 1 | 8 |
| 794 | 3,5-Dbp | H | H | C | O | S | H | O | Ete | O | 1 | 1 | 8 |
| 795 | 3,5-Dbp | H | H | C | O | — | — | — | — | — | 0 | 0 | 8 |
| 796 | 3,5-Dbp | H | H | C | O | O | Me | O | — | — | 0 | 1 | 8 |
| 797 | 3,5-Dbp | H | H | C | O | O | Me | S | — | — | 0 | 1 | 8 |
| 798 | 3,5-Dbp | H | H | C | O | O | 2-ClPh | O | — | — | 0 | 1 | 8 |
| 799 | 3,5-Dbp | H | H | C | O | Mee | H | O | — | — | 0 | 1 | 8 |
| 800 | 3,5-Dbp | H | H | C | O | Mee | H | S | — | — | 0 | 1 | 8 |
| 801 | 3,5-Dbp | H | H | C | O | Phe | H | O | — | — | 0 | 1 | 8 |
| 802 | 3,5-Dbp | H | H | C | O | NH | Pr | O | Ete | O | 1 | 1 | 8 |
| 803 | 3,5-Dbp | H | H | C | O | O | Me | NH | Trim | — | 1 | 1 | 8 |
| 804 | 4-MeOPh | 4-MeOPh | Ph | C | O | O | H | O | Ete | O | 1 | 1 | 8 |
| 805 | 4-MeOPh | 4-MeOPh | Ph | C | O | S | H | O | Ete | O | 1 | 1 | 8 |
| 806 | 4-MeOPh | 4-MeOPh | Ph | C | O | — | — | — | — | — | 0 | 0 | 8 |
| 807 | 4-MeOPh | 4-MeOPh | Ph | C | O | O | Me | O | — | — | 0 | 1 | 8 |
| 808 | 4-MeOPh | 4-MeOPh | Ph | C | O | O | Me | S | — | — | 0 | 1 | 8 |
| 809 | 4-MeOPh | 4-MeOPh | Ph | C | O | O | 2-ClPh | O | — | — | 0 | 1 | 8 |
| 810 | 4-MeOPh | 4-MeOPh | Ph | C | O | Mee | H | O | — | — | 0 | 1 | 8 |
| 811 | 4-MeOPh | 4-MeOPh | Ph | C | O | Mee | H | S | — | — | 0 | 1 | 8 |
| 812 | 4-MeOPh | 4-MeOPh | Ph | C | O | Phe | H | O | — | — | 0 | 1 | 8 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 813 | 4-MeOPh | 4-MeOPh | Ph | C | O | NH | Pr | O | Ete | O | 1 | 1 | 8 |
| 814 | 4-MeOPh | 4-MeOPh | Ph | C | O | O | Me | NH | Trim | — | 1 | 1 | 8 |
| 815 | 4-MeOPh | Ph | Ph | C | O | O | H | O | Ete | O | 1 | 1 | 8 |
| 816 | 4-MeOPh | Ph | Ph | C | O | S | H | O | Ete | O | 1 | 1 | 8 |
| 817 | 4-MeOPh | Ph | Ph | C | O | — | — | — | — | — | 0 | 0 | 8 |
| 818 | 4-MeOPh | Ph | Ph | C | O | O | Me | O | — | — | 0 | 1 | 8 |
| 819 | 4-MeOPh | Ph | Ph | C | O | O | Me | S | — | — | 0 | 1 | 8 |
| 820 | 4-MeOPh | Ph | Ph | C | O | O | 2-ClPh | O | — | — | 0 | 1 | 8 |
| 821 | 4-MeOPh | Ph | Ph | C | O | Mee | H | O | — | — | 0 | 1 | 8 |
| 822 | 4-MeOPh | Ph | Ph | C | O | Mee | H | S | — | — | 0 | 1 | 8 |
| 823 | 4-MeOPh | Ph | Ph | C | O | Phe | H | O | — | — | 0 | 1 | 8 |
| 824 | 4-MeOPh | Ph | Ph | C | O | NH | Pr | O | Ete | O | 1 | 1 | 8 |
| 825 | 4-MeOPh | Ph | Ph | C | O | O | Me | NH | Trim | — | 1 | 1 | 8 |
| 826 | tBu | Ph | Ph | Si | O | O | H | O | Ete | O | 1 | 1 | 8 |
| 827 | tBu | Ph | Ph | Si | O | S | H | O | Ete | O | 1 | 1 | 8 |
| 828 | tBu | Ph | Ph | Si | O | — | — | — | — | — | 0 | 0 | 8 |
| 829 | tBu | Ph | Ph | Si | O | O | Me | O | — | — | 0 | 1 | 8 |
| 830 | tBu | Ph | Ph | Si | O | O | Me | S | — | — | 0 | 1 | 8 |
| 831 | tBu | Ph | Ph | Si | O | O | 2-ClPh | O | — | — | 0 | 1 | 8 |
| 832 | tBu | Ph | Ph | Si | O | Mee | H | O | — | — | 0 | 1 | 8 |
| 833 | tBu | Ph | Ph | Si | O | Mee | H | S | — | — | 0 | 1 | 8 |
| 834 | tBu | Ph | Ph | Si | O | Phe | H | O | — | — | 0 | 1 | 8 |
| 835 | tBu | Ph | Ph | Si | O | NH | Pr | O | Ete | O | 1 | 1 | 8 |
| 836 | tBu | Ph | Ph | Si | O | O | Me | NH | Trim | — | 1 | 1 | 8 |
| 837 | Ph | Ph | Ph | C | S | O | H | O | Ete | O | 1 | 1 | 8 |
| 838 | Ph | Ph | Ph | C | S | S | H | O | Ete | O | 1 | 1 | 8 |
| 839 | Ph | Ph | Ph | C | S | — | — | — | — | — | 0 | 0 | 8 |
| 840 | Ph | Ph | Ph | C | S | O | Me | O | — | — | 0 | 1 | 8 |
| 841 | Ph | Ph | Ph | C | S | O | Me | S | — | — | 0 | 1 | 8 |
| 842 | Ph | Ph | Ph | C | S | O | 2-ClPh | O | — | — | 0 | 1 | 8 |
| 843 | Ph | Ph | Ph | C | S | Mee | H | O | — | — | 0 | 1 | 8 |
| 844 | Ph | Ph | Ph | C | S | Mee | H | S | — | — | 0 | 1 | 8 |
| 845 | Ph | Ph | Ph | C | S | Phe | H | O | — | — | 0 | 1 | 8 |
| 846 | Ph | Ph | Ph | C | S | NH | Pr | O | Ete | O | 1 | 1 | 8 |
| 847 | Ph | Ph | Ph | C | S | O | Me | NH | Trim | — | 1 | 1 | 8 |
| 848 | 4-BzOPh | H | H | C | O | O | H | O | Ete | O | 1 | 1 | 8 |
| 849 | 4-BzOPh | H | H | C | O | S | H | O | Ete | O | 1 | 1 | 8 |
| 850 | 4-BzOPh | H | H | C | O | — | — | — | — | — | 0 | 0 | 8 |
| 851 | 4-BzOPh | H | H | C | O | O | Me | O | — | — | 0 | 1 | 8 |
| 852 | 4-BzOPh | H | H | C | O | O | Me | S | — | — | 0 | 1 | 8 |
| 853 | 4-BzOPh | H | H | C | O | O | 2-ClPh | O | — | — | 0 | 1 | 8 |
| 854 | 4-BzOPh | H | H | C | O | Mee | H | O | — | — | 0 | 1 | 8 |
| 855 | 4-BzOPh | H | H | C | O | Mee | H | S | — | — | 0 | 1 | 8 |
| 856 | 4-BzOPh | H | H | C | O | Phe | H | O | — | — | 0 | 1 | 8 |
| 857 | 4-BzOPh | H | H | C | O | NH | Pr | O | Ete | O | 1 | 1 | 8 |
| 858 | 4-BzOPh | H | H | C | O | O | Me | NH | Trim | — | 1 | 1 | 8 |
| 859 | Ph | Xanthen-9-yl | | | O | O | H | O | Ete | O | 1 | 1 | 8 |
| 860 | Ph | Xanthen-9-yl | | | O | S | H | O | Ete | O | 1 | 1 | 8 |
| 861 | Ph | Xanthen-9-yl | | | O | — | — | — | — | — | 0 | 0 | 8 |
| 862 | Ph | Xanthen-9-yl | | | O | O | Me | O | — | — | 0 | 1 | 8 |
| 863 | Ph | Xanthen-9-yl | | | O | O | Me | S | — | — | 0 | 1 | 8 |
| 864 | Ph | Xanthen-9-yl | | | O | O | 2-ClPh | O | — | — | 0 | 1 | 8 |
| 865 | Ph | Xanthen-9-yl | | | O | Mee | H | O | — | — | 0 | 1 | 8 |
| 866 | Ph | Xanthen-9-yl | | | O | Mee | H | S | — | — | 0 | 1 | 8 |
| 867 | Ph | Xanthen-9-yl | | | O | Phe | H | O | — | — | 0 | 1 | 8 |
| 868 | Ph | Xanthen-9-yl | | | O | NH | Pr | O | Ete | O | 1 | 1 | 8 |
| 869 | Ph | Xanthen-9-yl | | | O | O | Me | NH | Trim | — | 1 | 1 | 8 |
| 870 | Ph | Fluoren-9-yl | | | O | O | H | O | Ete | O | 1 | 1 | 8 |
| 871 | Ph | Fluoren-9-yl | | | O | S | H | O | Ete | O | 1 | 1 | 8 |
| 872 | Ph | Fluoren-9-yl | | | O | — | — | — | — | — | 0 | 0 | 8 |
| 873 | Ph | Fluoren-9-yl | | | O | O | Me | O | — | — | 0 | 1 | 8 |
| 874 | Ph | Fluoren-9-yl | | | O | O | Me | S | — | — | 0 | 1 | 8 |
| 875 | Ph | Fluoren-9-yl | | | O | O | 2-ClPh | O | — | — | 0 | 1 | 8 |
| 876 | Ph | Fluoren-9-yl | | | O | Mee | H | O | — | — | 0 | 1 | 8 |
| 877 | Ph | Fluoren-9-yl | | | O | Mee | H | S | — | — | 0 | 1 | 8 |
| 878 | Ph | Fluoren-9-yl | | | O | Phe | H | O | — | — | 0 | 1 | 8 |
| 879 | Ph | Fluoren-9-yl | | | O | NH | Pr | O | Ete | O | 1 | 1 | 8 |
| 880 | Ph | Fluoren-9-yl | | | O | O | Me | NH | Trim | — | 1 | 1 | 8 |
| 881 | 3,4-Dbp | H | H | C | O | O | H | O | Ete | O | 1 | 1 | 9 |
| 882 | 3,4-Dbp | H | H | C | O | S | H | O | Ete | O | 1 | 1 | 9 |
| 883 | 3,4-Dbp | H | H | C | O | — | — | — | — | — | 0 | 0 | 9 |
| 884 | 3,4-Dbp | H | H | C | O | O | Me | O | — | — | 0 | 1 | 9 |
| 885 | 3,4-Dbp | H | H | C | O | O | Me | S | — | — | 0 | 1 | 9 |
| 886 | 3,4-Dbp | H | H | C | O | O | 2-ClPh | O | — | — | 0 | 1 | 9 |
| 887 | 3,4-Dbp | H | H | C | O | Mee | H | O | — | — | 0 | 1 | 9 |
| 888 | 3,4-Dbp | H | H | C | O | Mee | H | S | — | — | 0 | 1 | 9 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 889 | 3,4-Dbp | H | H | C | O | Phe | H | O | — | — | 0 | 1 | 9 |
| 890 | 3,4-Dbp | H | H | C | O | NH | Pr | O | Ete | O | 1 | 1 | 9 |
| 891 | 3,4-Dbp | H | H | C | O | O | Me | NH | Trim | — | 1 | 1 | 9 |
| 892 | Ph | Ph | Ph | C | O | O | H | O | Ete | O | 1 | 1 | 9 |
| 893 | Ph | Ph | Ph | C | O | S | H | O | Ete | O | 1 | 1 | 9 |
| 894 | Ph | Ph | Ph | C | O | — | — | — | — | — | 0 | 0 | 9 |
| 895 | Ph | Ph | Ph | C | O | O | Me | O | — | — | 0 | 1 | 9 |
| 896 | Ph | Ph | Ph | C | O | O | Me | S | — | — | 0 | 1 | 9 |
| 897 | Ph | Ph | Ph | C | O | O | 2-ClPh | O | — | — | 0 | 1 | 9 |
| 898 | Ph | Ph | Ph | C | O | Mee | H | O | — | — | 0 | 1 | 9 |
| 899 | Ph | Ph | Ph | C | O | Mee | H | S | — | — | 0 | 1 | 9 |
| 900 | Ph | Ph | Ph | C | O | Phe | H | O | — | — | 0 | 1 | 9 |
| 901 | Ph | Ph | Ph | C | O | NH | Pr | O | Ete | O | 1 | 1 | 9 |
| 902 | Ph | Ph | Ph | C | O | O | Me | NH | Trim | — | 1 | 1 | 9 |
| 903 | 3,5-Dbp | H | H | C | O | O | H | O | Ete | O | 1 | 1 | 9 |
| 904 | 3,5-Dbp | H | H | C | O | S | H | O | Ete | O | 1 | 1 | 9 |
| 905 | 3,5-Dbp | H | H | C | O | — | — | — | — | — | 0 | 0 | 9 |
| 906 | 3,5-Dbp | H | H | C | O | O | Me | O | — | — | 0 | 1 | 9 |
| 907 | 3,5-Dbp | H | H | C | O | O | Me | S | — | — | 0 | 1 | 9 |
| 908 | 3,5-Dbp | H | H | C | O | O | 2-ClPh | O | — | — | 0 | 1 | 9 |
| 909 | 3,5-Dbp | H | H | C | O | Mee | H | O | — | — | 0 | 1 | 9 |
| 910 | 3,5-Dbp | H | H | C | O | Mee | H | S | — | — | 0 | 1 | 9 |
| 911 | 3,5-Dbp | H | H | C | O | Phe | H | O | — | — | 0 | 1 | 9 |
| 912 | 3,5-Dbp | H | H | C | O | NH | Pr | O | Ete | O | 0 | 1 | 9 |
| 913 | 3,5-Dbp | H | H | C | O | O | Me | NH | Trim | — | 1 | 1 | 9 |
| 914 | 4-MeOPh | 4-MeOPh | Ph | C | O | O | H | O | Ete | O | 1 | 1 | 9 |
| 915 | 4-MeOPh | 4-MeOPh | Ph | C | O | S | H | O | Ete | O | 1 | 1 | 9 |
| 916 | 4-MeOPh | 4-MeOPh | Ph | C | O | — | — | — | — | — | 0 | 0 | 9 |
| 917 | 4-MeOPh | 4-MeOPh | Ph | C | O | O | Me | O | — | — | 0 | 1 | 9 |
| 918 | 4-MeOPh | 4-MeOPh | Ph | C | O | O | Me | S | — | — | 0 | 1 | 9 |
| 919 | 4-MeOPh | 4-MeOPh | Ph | C | O | O | 2-ClPh | O | — | — | 0 | 1 | 9 |
| 920 | 4-MeOPh | 4-MeOPh | Ph | C | O | Mee | H | O | — | — | 0 | 1 | 9 |
| 921 | 4-MeOPh | 4-MeOPh | Ph | C | O | Mee | H | S | — | — | 0 | 1 | 9 |
| 922 | 4-MeOPh | 4-MeOPh | Ph | C | O | Phe | H | O | — | — | 0 | 1 | 9 |
| 923 | 4-MeOPh | 4-MeOPh | Ph | C | O | NH | Pr | O | Ete | O | 1 | 1 | 9 |
| 924 | 4-MeOPh | 4-MeOPh | Ph | C | O | O | Me | NH | Trim | — | 1 | 1 | 9 |
| 925 | 4-MeOPh | Ph | Ph | C | O | O | H | O | Ete | O | 1 | 1 | 9 |
| 926 | 4-MeOPh | Ph | Ph | C | O | S | H | O | Ete | O | 1 | 1 | 9 |
| 927 | 4-MeOPh | Ph | Ph | C | O | — | — | — | — | — | 0 | 0 | 9 |
| 928 | 4-MeOPh | Ph | Ph | C | O | O | Me | O | — | — | 0 | 1 | 9 |
| 929 | 4-MeOPh | Ph | Ph | C | O | O | Me | S | — | — | 0 | 1 | 9 |
| 930 | 4-MeOPh | Ph | Ph | C | O | O | 2-ClPh | O | — | — | 0 | 1 | 9 |
| 931 | 4-MeOPh | Ph | Ph | C | O | Mee | H | O | — | — | 0 | 1 | 9 |
| 932 | 4-MeOPh | Ph | Ph | C | O | Mee | H | S | — | — | 0 | 1 | 9 |
| 933 | 4-MeOPh | Ph | Ph | C | O | Phe | H | O | — | — | 0 | 1 | 9 |
| 934 | 4-MeOPh | Ph | Ph | C | O | NH | Pr | O | Ete | O | 1 | 1 | 9 |
| 935 | 4-MeOPh | Ph | Ph | C | O | O | Me | NH | Trim | — | 1 | 1 | 9 |
| 936 | tBu | Ph | Ph | Si | O | O | H | O | Ete | O | 1 | 1 | 9 |
| 937 | tBu | Ph | Ph | Si | O | S | H | O | Ete | O | 1 | 1 | 9 |
| 938 | tBu | Ph | Ph | Si | O | — | — | — | — | — | 0 | 0 | 9 |
| 939 | tBu | Ph | Ph | Si | O | O | Me | O | — | — | 0 | 1 | 9 |
| 940 | tBu | Ph | Ph | Si | O | O | Me | S | — | — | 0 | 1 | 9 |
| 941 | tBu | Ph | Ph | Si | O | O | 2-ClPh | O | — | — | 0 | 1 | 9 |
| 942 | tBu | Ph | Ph | Si | O | Mee | H | O | — | — | 0 | 1 | 9 |
| 943 | tBu | Ph | Ph | Si | O | Mee | H | S | — | — | 0 | 1 | 9 |
| 944 | tBu | Ph | Ph | Si | O | Phe | H | O | — | — | 0 | 1 | 9 |
| 945 | tBu | Ph | Ph | Si | O | NH | Pr | O | Ete | O | 1 | 1 | 9 |
| 946 | tBu | Ph | Ph | Si | O | O | Me | NH | Trim | — | 1 | 1 | 9 |
| 947 | Ph | Ph | Ph | C | S | O | H | O | Ete | O | 1 | 1 | 9 |
| 948 | Ph | Ph | Ph | C | S | S | H | O | Ete | O | 1 | 1 | 9 |
| 949 | Ph | Ph | Ph | C | S | — | — | — | — | — | 0 | 0 | 9 |
| 950 | Ph | Ph | Ph | C | S | O | Me | O | — | — | 0 | 1 | 9 |
| 951 | Ph | Ph | Ph | C | S | O | Me | S | — | — | 0 | 1 | 9 |
| 952 | Ph | Ph | Ph | C | S | O | 2-ClPh | O | — | — | 0 | 1 | 9 |
| 953 | Ph | Ph | Ph | C | S | Mee | H | O | — | — | 0 | 1 | 9 |
| 954 | Ph | Ph | Ph | C | S | Mee | H | S | — | — | 0 | 1 | 9 |
| 955 | Ph | Ph | Ph | C | S | Phe | H | O | — | — | 0 | 1 | 9 |
| 956 | Ph | Ph | Ph | C | S | NH | Pr | O | Ete | O | 1 | 1 | 9 |
| 957 | Ph | Ph | Ph | C | S | O | Me | NH | Trim | — | 1 | 1 | 9 |
| 958 | 4-BzOPh | H | H | C | O | O | H | O | Ete | O | 1 | 1 | 9 |
| 959 | 4-BzOPh | H | H | C | O | S | H | O | Ete | O | 1 | 1 | 9 |
| 960 | 4-BzOPh | H | H | C | O | — | — | — | — | — | 0 | 0 | 9 |
| 961 | 4-BzOPh | H | H | C | O | O | Me | O | — | — | 0 | 1 | 9 |
| 962 | 4-BzOPh | H | H | C | O | O | Me | S | — | — | 0 | 1 | 9 |
| 963 | 4-BzOPh | H | H | C | O | O | 2-ClPh | O | — | — | 0 | 1 | 9 |
| 964 | 4-BzOPh | H | H | C | O | Mee | H | O | — | — | 0 | 1 | 9 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 965 | 4-BzOPh | H | H | C | O | Mee | H | S | — | — | 0 | 1 | 9 |
| 966 | 4-BzOPh | H | H | C | O | Phe | H | O | — | — | 0 | 1 | 9 |
| 967 | 4-BzOPh | H | H | C | O | NH | Pr | O | Ete | O | 1 | 1 | 9 |
| 968 | 4-BzOPh | H | H | C | O | O | Me | NH | Trim | — | 1 | 1 | 9 |
| 969 | Ph | Xanthen-9-yl | | | O | O | H | O | Ete | O | 1 | 1 | 9 |
| 970 | Ph | Xanthen-9-yl | | | O | S | H | O | Ete | O | 1 | 1 | 9 |
| 971 | Ph | Xanthen-9-yl | | | O | — | — | — | — | — | 0 | 0 | 9 |
| 972 | Ph | Xanthen-9-yl | | | O | O | Me | O | — | — | 0 | 1 | 9 |
| 973 | Ph | Xanthen-9-yl | | | O | O | Me | S | — | — | 0 | 1 | 9 |
| 974 | Ph | Xanthen-9-yl | | | O | O | 2-ClPh | O | — | — | 0 | 1 | 9 |
| 975 | Ph | Xanthen-9-yl | | | O | Mee | H | O | — | — | 0 | 1 | 9 |
| 976 | Ph | Xanthen-9-yl | | | O | Mee | H | S | — | — | 0 | 1 | 9 |
| 977 | Ph | Xanthen-9-yl | | | O | Phe | H | O | — | — | 0 | 1 | 9 |
| 978 | Ph | Xanthen-9-yl | | | O | NH | Pr | O | Ete | O | 1 | 1 | 9 |
| 979 | Ph | Xanthen-9-yl | | | O | O | Me | NH | Trim | — | 1 | 1 | 9 |
| 980 | Ph | Fluoren-9-yl | | | O | O | H | O | Ete | O | 1 | 1 | 9 |
| 981 | Ph | Fluoren-9-yl | | | O | S | H | O | Ete | O | 1 | 1 | 9 |
| 982 | Ph | Fluoren-9-yl | | | O | — | — | — | — | — | 0 | 0 | 9 |
| 983 | Ph | Fluoren-9-yl | | | O | O | Me | O | — | — | 0 | 1 | 9 |
| 984 | Ph | Fluoren-9-yl | | | O | O | Me | S | — | — | 0 | 1 | 9 |
| 985 | Ph | Fluoren-9-yl | | | O | O | 2-ClPh | O | — | — | 0 | 1 | 9 |
| 986 | Ph | Fluoren-9-yl | | | O | Mee | H | O | — | — | 0 | 1 | 9 |
| 987 | Ph | Fluoren-9-yl | | | O | Mee | H | S | — | — | 0 | 1 | 9 |
| 988 | Ph | Fluoren-9-yl | | | O | Phe | H | O | — | — | 0 | 1 | 9 |
| 989 | Ph | Fluoren-9-yl | | | O | NH | Pr | O | Ete | O | 1 | 1 | 9 |
| 990 | Ph | Fluoren-9-yl | | | O | O | Me | NH | Trim | — | 1 | 1 | 9 |
| 991 | 3,4-Dbp | H | H | C | O | O | H | O | Ete | O | 1 | 1 | 10 |
| 992 | 3,4-Dbp | H | H | C | O | S | H | O | Ete | O | 1 | 1 | 10 |
| 993 | 3,4-Dbp | H | H | C | O | — | — | — | — | — | 0 | 0 | 10 |
| 994 | 3,4-Dbp | H | H | C | O | O | Me | O | — | — | 0 | 1 | 10 |
| 995 | 3,4-Dbp | H | H | C | O | O | Me | S | — | — | 0 | 1 | 10 |
| 996 | 3,4-Dbp | H | H | C | O | O | 2-ClPh | O | — | — | 0 | 1 | 10 |
| 997 | 3,4-Dbp | H | H | C | O | Mee | H | O | — | — | 0 | 1 | 10 |
| 998 | 3,4-Dbp | H | H | C | O | Mee | H | S | — | — | 0 | 1 | 10 |
| 999 | 3,4-Dbp | H | H | C | O | Phe | H | O | — | — | 0 | 1 | 10 |
| 1000 | 3,4-Dbp | H | H | C | O | NH | Pr | O | Ete | O | 1 | 1 | 10 |
| 1001 | 3,4-Dbp | H | H | C | O | O | Me | NH | Trim | — | 1 | 1 | 10 |
| 1002 | Ph | Ph | Ph | C | O | O | H | O | Ete | O | 1 | 1 | 10 |
| 1003 | Ph | Ph | Ph | C | O | S | H | O | Ete | O | 1 | 1 | 10 |
| 1004 | Ph | Ph | Ph | C | O | — | — | — | — | — | 0 | 0 | 10 |
| 1005 | Ph | Ph | Ph | C | O | O | Me | O | — | — | 0 | 1 | 10 |
| 1006 | Ph | Ph | Ph | C | O | O | Me | S | — | — | 0 | 1 | 10 |
| 1007 | Ph | Ph | Ph | C | O | O | 2-ClPh | O | — | — | 0 | 1 | 10 |
| 1008 | Ph | Ph | Ph | C | O | Mee | H | O | — | — | 0 | 1 | 10 |
| 1009 | Ph | Ph | Ph | C | O | Mee | H | S | — | — | 0 | 1 | 10 |
| 1010 | Ph | Ph | Ph | C | O | Phe | H | O | — | — | 0 | 1 | 10 |
| 1011 | Ph | Ph | Ph | C | O | NH | Pr | O | Ete | O | 1 | 1 | 10 |
| 1012 | Ph | Ph | Ph | C | O | O | Me | NH | Trim | — | 1 | 1 | 10 |
| 1013 | 3,5-Dbp | H | H | C | O | O | H | O | Ete | O | 1 | 1 | 10 |
| 1014 | 3,5-Dbp | H | H | C | O | S | H | O | Ete | O | 1 | 1 | 10 |
| 1015 | 3,5-Dbp | H | H | C | O | — | — | — | — | — | 0 | 0 | 10 |
| 1016 | 3,5-Dbp | H | H | C | O | O | Me | O | — | — | 0 | 1 | 10 |
| 1017 | 3,5-Dbp | H | H | C | O | O | Me | S | — | — | 0 | 1 | 10 |
| 1018 | 3,5-Dbp | H | H | C | O | O | 2-ClPh | O | — | — | 0 | 1 | 10 |
| 1019 | 3,5-Dbp | H | H | C | O | Mee | H | O | — | — | 0 | 1 | 10 |
| 1020 | 3,5-Dbp | H | H | C | O | Mee | H | S | — | — | 0 | 1 | 10 |
| 1021 | 3,5-Dbp | H | H | C | O | Phe | H | O | — | — | 0 | 1 | 10 |
| 1022 | 3,5-Dbp | H | H | C | O | NH | Pr | O | Ete | O | 1 | 1 | 10 |
| 1023 | 3,5-Dbp | H | H | C | O | O | Me | NH | Trim | — | 1 | 1 | 10 |
| 1024 | 4-MeOPh | 4-MeOPh | Ph | C | O | O | H | O | Ete | O | 1 | 1 | 10 |
| 1025 | 4-MeOPh | 4-MeOPh | Ph | C | O | S | H | O | Ete | O | 1 | 1 | 10 |
| 1026 | 4-MeOPh | 4-MeOPh | Ph | C | O | — | — | — | — | — | 0 | 0 | 10 |
| 1027 | 4-MeOPh | 4-MeOPh | Ph | C | O | O | Me | O | — | — | 0 | 1 | 10 |
| 1028 | 4-MeOPh | 4-MeOPh | Ph | C | O | O | Me | S | — | — | 0 | 1 | 10 |
| 1029 | 4-MeOPh | 4-MeOPh | Ph | C | O | O | 2-ClPh | O | — | — | 0 | 1 | 10 |
| 1030 | 4-MeOPh | 4-MeOPh | Ph | C | O | Mee | H | O | — | — | 0 | 1 | 10 |
| 1031 | 4-MeOPh | 4-MeOPh | Ph | C | O | Mee | H | S | — | — | 0 | 1 | 10 |
| 1032 | 4-MeOPh | 4-MeOPh | Ph | C | O | Phe | H | O | — | — | 0 | 1 | 10 |
| 1033 | 4-MeOPh | 4-MeOPh | Ph | C | O | NH | Pr | O | Ete | O | 1 | 1 | 10 |
| 1034 | 4-MeOPh | 4-MeOPh | Ph | C | O | O | Me | NH | Trim | — | 1 | 1 | 10 |
| 1035 | 4-MeOPh | Ph | Ph | C | O | O | H | O | Ete | O | 1 | 1 | 10 |
| 1036 | 4-MeOPh | Ph | Ph | C | O | S | H | O | Ete | O | 1 | 1 | 10 |
| 1037 | 4-MeOPh | Ph | Ph | C | O | — | — | — | — | — | 0 | 0 | 10 |
| 1038 | 4-MeOPh | Ph | Ph | C | O | O | Me | O | — | — | 0 | 1 | 10 |
| 1039 | 4-MeOPh | Ph | Ph | C | O | O | Me | S | — | — | 0 | 1 | 10 |
| 1040 | 4-MeOPh | Ph | Ph | C | O | O | 2-ClPh | O | — | — | 0 | 1 | 10 |

TABLE 1-continued

| Cpd. No. | $R_1$ | $R_2$ | $R_3$ | Z | $Y_1$ | $Y_2$ | $R_4$ | $Y_3$ | X | $Y_4$ | n | m | B |
|---|---|---|---|---|---|---|---|---|---|---|---|---|---|
| 1041 | 4-MeOPh | Ph | Ph | C | O | Mee | H | O | — | — | 0 | 1 | 10 |
| 1042 | 4-MeOPh | Ph | Ph | C | O | Mee | H | S | — | — | 0 | 1 | 10 |
| 1043 | 4-MeOPh | Ph | Ph | C | O | Phe | H | O | — | — | 0 | 1 | 10 |
| 1044 | 4-MeOPh | Ph | Ph | C | O | NH | Pr | O | Ete | O | 1 | 1 | 10 |
| 1045 | 4-MeOPh | Ph | Ph | C | O | O | Me | NH | Trim | — | 1 | 1 | 10 |
| 1046 | tBu | Ph | Ph | Si | O | O | H | O | Ete | O | 1 | 1 | 10 |
| 1047 | tBu | Ph | Ph | Si | O | S | H | O | Ete | O | 1 | 1 | 10 |
| 1048 | tBu | Ph | Ph | Si | O | — | — | — | — | — | 0 | 0 | 10 |
| 1049 | tBu | Ph | Ph | Si | O | O | Me | O | — | — | 0 | 1 | 10 |
| 1050 | tBu | Ph | Ph | Si | O | O | Me | S | — | — | 0 | 1 | 10 |
| 1051 | tBu | Ph | Ph | Si | O | O | 2-ClPh | O | — | — | 0 | 1 | 10 |
| 1052 | tBu | Ph | Ph | Si | O | Mee | H | O | — | — | 0 | 1 | 10 |
| 1053 | tBu | Ph | Ph | Si | O | Mee | H | S | — | — | 0 | 1 | 10 |
| 1054 | tBu | Ph | Ph | Si | O | Phe | H | O | — | — | 0 | 1 | 10 |
| 1055 | tBu | Ph | Ph | Si | O | NH | Pr | O | Ete | O | 1 | 1 | 10 |
| 1056 | tBu | Ph | Ph | Si | O | O | Me | NH | Trim | — | 1 | 1 | 10 |
| 1057 | Ph | Ph | Ph | C | S | O | H | O | Ete | O | 1 | 1 | 10 |
| 1058 | Ph | Ph | Ph | C | S | S | H | O | Ete | O | 1 | 1 | 10 |
| 1059 | Ph | Ph | Ph | C | S | — | — | — | — | — | 0 | 0 | 10 |
| 1060 | Ph | Ph | Ph | C | S | O | Me | O | — | — | 0 | 1 | 10 |
| 1061 | Ph | Ph | Ph | C | S | O | Me | S | — | — | 0 | 1 | 10 |
| 1062 | Ph | Ph | Ph | C | S | O | 2-ClPh | O | — | — | 0 | 1 | 10 |
| 1063 | Ph | Ph | Ph | C | S | Mee | H | O | — | — | 0 | 1 | 10 |
| 1064 | Ph | Ph | Ph | C | S | Mee | H | S | — | — | 0 | 1 | 10 |
| 1065 | Ph | Ph | Ph | C | S | Phe | H | O | — | — | 0 | 1 | 10 |
| 1066 | Ph | Ph | Ph | C | S | NH | Pr | O | Ete | O | 1 | 1 | 10 |
| 1067 | Ph | Ph | Ph | C | S | O | Me | NH | Trim | — | 1 | 1 | 10 |
| 1068 | 4-BzOPh | H | H | C | O | O | H | O | Ete | O | 1 | 1 | 10 |
| 1069 | 4-BzOPh | H | H | C | O | S | H | O | Ete | O | 1 | 1 | 10 |
| 1070 | 4-BzOPh | H | H | C | O | — | — | — | — | — | 0 | 0 | 10 |
| 1071 | 4-BzOPh | H | H | C | O | O | Me | O | — | — | 0 | 1 | 10 |
| 1072 | 4-BzOPh | H | H | C | O | O | Me | S | — | — | 0 | 1 | 10 |
| 1073 | 4-BzOPh | H | H | C | O | O | 2-ClPh | O | — | — | 0 | 1 | 10 |
| 1074 | 4-BzOPh | H | H | C | O | Meg | H | O | — | — | 0 | 1 | 10 |
| 1075 | 4-BzOPh | H | H | C | O | Mee | H | S | — | — | 0 | 1 | 10 |
| 1076 | 4-BzOPh | H | H | C | O | Phe | H | O | — | — | 0 | 1 | 10 |
| 1077 | 4-BzOPh | H | H | C | O | NH | Pr | O | Ete | O | 1 | 1 | 10 |
| 1078 | 4-BzOPh | H | H | C | O | O | Me | NH | Trim | — | 1 | 1 | 10 |
| 1079 | Ph | Xanthen-9-yl | | | O | O | H | O | Ete | O | 1 | 1 | 10 |
| 1080 | Ph | Xanthen-9-yl | | | O | S | H | O | Ete | O | 1 | 1 | 10 |
| 1081 | Ph | Xanthen-9-yl | | | O | — | — | — | — | — | 0 | 0 | 10 |
| 1082 | Ph | Xanthen-9-yl | | | O | O | Me | O | — | — | 0 | 1 | 10 |
| 1083 | Ph | Xanthen-9-yl | | | O | O | Me | S | — | — | 0 | 1 | 10 |
| 1084 | Ph | Xanthen-9-yl | | | O | O | 2-ClPh | O | — | — | 0 | 1 | 10 |
| 1085 | Ph | Xanthen-9-yl | | | O | Mee | H | O | — | — | 0 | 1 | 10 |
| 1086 | Ph | Xanthen-9-yl | | | O | Mee | H | S | — | — | 0 | 1 | 10 |
| 1087 | Ph | Xanthen-9-yl | | | O | Phe | H | O | — | — | 0 | 1 | 10 |
| 1088 | Ph | Xanthen-9-yl | | | O | NH | Pr | O | Ete | O | 1 | 1 | 10 |
| 1089 | Ph | Xanthen-9-yl | | | O | O | Me | NH | Trim | — | 1 | 1 | 10 |
| 1090 | Ph | Fluoren-9-yl | | | O | O | H | O | Ete | O | 1 | 1 | 10 |
| 1091 | Ph | Fluoren-9-yl | | | O | S | H | O | Ete | O | 1 | 1 | 10 |
| 1092 | Ph | Fluoren-9-yl | | | O | — | — | — | — | — | 0 | 0 | 10 |
| 1093 | Ph | Fluoren-9-yl | | | O | O | Me | O | — | — | 0 | 1 | 10 |
| 1094 | Ph | Fluoren-9-yl | | | O | O | Me | S | — | — | 0 | 1 | 10 |
| 1095 | Ph | Fluoren-9-yl | | | O | O | 2-ClPh | O | — | — | 0 | 1 | 10 |
| 1096 | Ph | Fluoren-9-yl | | | O | Mee | H | O | — | — | 0 | 1 | 10 |
| 1097 | Ph | Fluoren-9-yl | | | O | Mee | H | S | — | — | 0 | 1 | 10 |
| 1098 | Ph | Fluoren-9-yl | | | O | Phe | H | O | — | — | 0 | 1 | 10 |
| 1099 | Ph | Fluoren-9-yl | | | O | NH | Pr | O | Ete | O | 1 | 1 | 10 |
| 1100 | Ph | Fluoren-9-yl | | | O | O | Me | NH | Trim | — | 1 | 1 | 10 |
| 1101 | 3,4-Dbp | H | H | C | O | O | H | O | Ete | O | 1 | 1 | 11 |
| 1102 | 3,4-Dbp | H | H | C | O | S | H | O | Ete | O | 1 | 1 | 11 |
| 1103 | 3,4-Dbp | H | H | C | O | — | — | — | — | — | 0 | 0 | 11 |
| 1104 | 3,4-Dbp | H | H | C | O | O | Me | O | — | — | 0 | 1 | 11 |
| 1105 | 3,4-Dbp | H | H | C | O | O | Me | S | — | — | 0 | 1 | 11 |
| 1106 | 3,4-Dbp | H | H | C | O | O | 2-ClPh | O | — | — | 0 | 1 | 11 |
| 1107 | 3,4-Dbp | H | H | C | O | Mee | H | O | — | — | 0 | 1 | 11 |
| 1108 | 3,4-Dbp | H | H | C | O | Mee | H | S | — | — | 0 | 1 | 11 |
| 1109 | 3,4-Dbp | H | H | C | O | Phe | H | O | — | — | 0 | 1 | 11 |
| 1110 | 3,4-Dbp | H | H | C | O | NH | Pr | O | Ete | O | 1 | 1 | 11 |
| 1111 | 3,4-Dbp | H | H | C | O | O | Me | NH | Trim | — | 1 | 1 | 11 |
| 1112 | Ph | Ph | Ph | C | O | O | H | O | Ete | O | 1 | 1 | 11 |
| 1113 | Ph | Ph | Ph | C | O | S | H | O | Ete | O | 1 | 1 | 11 |
| 1114 | Ph | Ph | Ph | C | O | — | — | — | — | — | 0 | 0 | 11 |
| 1115 | Ph | Ph | Ph | C | O | O | Me | O | — | — | 0 | 1 | 11 |
| 1116 | Ph | Ph | Ph | C | O | O | Me | S | — | — | 0 | 1 | 11 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1117 | Ph | Ph | Ph | C | O | O | 2-ClPh | O | — | — | 0 | 1 | II |
| 1118 | Ph | Ph | Ph | C | O | Mee | H | O | — | — | 0 | 1 | II |
| 1119 | Ph | Ph | Ph | C | O | Mee | H | S | — | — | 0 | 1 | II |
| 1120 | Ph | Ph | Ph | C | O | Phe | H | O | — | — | 0 | 1 | II |
| 1121 | Ph | Ph | Ph | C | O | NH | Pr | O | Ete | O | 1 | 1 | II |
| 1122 | Ph | Ph | Ph | C | O | O | Me | NH | Trim | — | 1 | 1 | II |
| 1123 | 3,5-Dbp | H | H | C | O | O | H | O | Ete | O | 1 | 1 | II |
| 1124 | 3,5-Dbp | H | H | C | O | S | H | O | Ete | O | 1 | 1 | II |
| 1125 | 3,5-Dbp | H | H | C | O | — | — | — | — | — | 0 | 0 | II |
| 1126 | 3,5-Dbp | H | H | C | O | O | Me | O | — | — | 0 | 1 | II |
| 1127 | 3,5-Dbp | H | H | C | O | O | Me | S | — | — | 0 | 1 | II |
| 1128 | 3,5-Dbp | H | H | C | O | O | 2-ClPh | O | — | — | 0 | 1 | II |
| 1129 | 3,5-Dbp | H | H | C | O | Mee | H | O | — | — | 0 | 1 | II |
| 1130 | 3,5-Dbp | H | H | C | O | Mee | H | S | — | — | 0 | 1 | II |
| 1131 | 3,5-Dbp | H | H | C | O | Phe | H | O | — | — | 0 | 1 | II |
| 1132 | 3,5-Dbp | H | H | C | O | NH | Pr | O | Ete | O | 1 | 1 | II |
| 1133 | 3,5-Dbp | H | H | C | O | O | Me | NH | Trim | — | 1 | 1 | II |
| 1134 | 4-MeOPh | 4-MeOPh | Ph | C | O | O | H | O | Ete | O | 1 | 1 | II |
| 1135 | 4-MeOPh | 4-MeOPh | Ph | C | O | S | H | O | Ete | O | 1 | 1 | II |
| 1136 | 4-MeOPh | 4-MeOPh | Ph | C | O | — | — | — | — | — | 0 | 0 | II |
| 1137 | 4-MeOPh | 4-MeOPh | Ph | C | O | O | Me | O | — | — | 0 | 1 | II |
| 1138 | 4-MeOPh | 4-MeOPh | Ph | C | O | O | Me | S | — | — | 0 | 1 | II |
| 1139 | 4-MeOPh | 4-MeOPh | Ph | C | O | O | 2-ClPh | O | — | — | 0 | 1 | II |
| 1140 | 4-MeOPh | 4-MeOPh | Ph | C | O | Mee | H | O | — | — | 0 | 1 | II |
| 1141 | 4-MeOPh | 4-MeOPh | Ph | C | O | Mee | H | S | — | — | 0 | 1 | II |
| 1142 | 4-MeOPh | 4-MeOPh | Ph | C | O | Phe | H | O | — | — | 0 | 1 | II |
| 1143 | 4-MeOPh | 4-MeOPh | Ph | C | O | NH | Pr | O | Ete | O | 1 | 1 | II |
| 1144 | 4-MeOPh | 4-MeOPh | Ph | C | O | O | Me | NH | Trim | — | 1 | 1 | II |
| 1145 | 4-MeOPh | Ph | Ph | C | O | O | H | O | Ete | O | 1 | 1 | II |
| 1146 | 4-MeOPh | Ph | Ph | C | O | S | H | O | Ete | O | 1 | 1 | II |
| 1147 | 4-MeOPh | Ph | Ph | C | O | — | — | — | — | — | 0 | 0 | II |
| 1148 | 4-MeOPh | Ph | Ph | C | O | O | Me | O | — | — | 0 | 1 | II |
| 1149 | 4-MeOPh | Ph | Ph | C | O | O | Me | S | — | — | 0 | 1 | II |
| 1150 | 4-MeOPh | Ph | Ph | C | O | O | 2-ClPh | O | — | — | 0 | 1 | II |
| 1151 | 4-MeOPh | Ph | Ph | C | O | Mee | H | O | — | — | 0 | 1 | II |
| 1152 | 4-MeOPh | Ph | Ph | C | O | Mee | H | S | — | — | 0 | 1 | II |
| 1153 | 4-MeOPh | Ph | Ph | C | O | Phe | H | O | — | — | 0 | 1 | II |
| 1154 | 4-MeOPh | Ph | Ph | C | O | NH | Pr | O | Ete | O | 1 | 1 | II |
| 1155 | 4-MeOPh | Ph | Ph | C | O | O | Me | NH | Trim | — | 1 | 1 | II |
| 1156 | tBu | Ph | Ph | Si | O | O | H | O | Ete | O | 1 | 1 | 11 |
| 1157 | tBu | Ph | Ph | Si | O | S | H | O | Ete | O | 1 | 1 | 11 |
| 1158 | tBu | Ph | Ph | Si | O | — | — | — | — | — | 0 | 0 | 11 |
| 1159 | tBu | Ph | Ph | Si | O | O | Me | O | — | — | 0 | 1 | 11 |
| 1160 | tBu | Ph | Ph | Si | O | O | Me | S | — | — | 0 | 1 | 11 |
| 1161 | tBu | Ph | Ph | Si | O | O | 2-ClPh | O | — | — | 0 | 1 | 11 |
| 1162 | tBu | Ph | Ph | Si | O | Mee | H | O | — | — | 0 | 1 | 11 |
| 1163 | tBu | Ph | Ph | Si | O | Mee | H | S | — | — | 0 | 1 | 11 |
| 1164 | tBu | Ph | Ph | Si | O | Phe | H | O | — | — | 0 | 1 | 11 |
| 1165 | tBu | Ph | Ph | Si | O | NH | Pr | O | Ete | O | 1 | 1 | 11 |
| 1166 | tBu | Ph | Ph | Si | O | O | Me | NH | Trim | — | 1 | 1 | 11 |
| 1167 | Ph | Ph | Ph | C | S | O | H | O | Ete | O | 1 | 1 | 11 |
| 1168 | Ph | Ph | Ph | C | S | S | H | O | Ete | O | 1 | 1 | II |
| 1169 | Ph | Ph | Ph | C | S | — | — | — | — | — | 0 | 0 | II |
| 1170 | Ph | Ph | Ph | C | S | O | Me | O | — | — | 0 | 1 | II |
| 1171 | Ph | Ph | Ph | C | S | O | Me | S | — | — | 0 | 1 | II |
| 1172 | Ph | Ph | Ph | C | S | O | 2-ClPh | O | — | — | 0 | 1 | II |
| 1173 | Ph | Ph | Ph | C | S | Mee | H | O | — | — | 0 | 1 | II |
| 1174 | Ph | Ph | Ph | C | S | Mee | H | S | — | — | 0 | 1 | II |
| 1175 | Ph | Ph | Ph | C | S | Phe | H | O | — | — | 0 | 1 | II |
| 1176 | Ph | Ph | Ph | C | S | NH | Pr | O | Ete | O | 1 | 1 | II |
| 1177 | Ph | Ph | Ph | C | S | O | Me | NH | Trim | — | 1 | 1 | II |
| 1178 | 4-BzOPh | H | H | C | O | O | H | O | Ete | O | 1 | 1 | II |
| 1179 | 4-BzOPh | H | H | C | O | S | H | O | Ete | O | 1 | 1 | II |
| 1180 | 4-BzOPh | H | H | C | O | — | — | — | — | — | 0 | 0 | II |
| 1181 | 4-BzOPh | H | H | C | O | O | Me | O | — | — | 0 | 1 | II |
| 1182 | 4-BzOPh | H | H | C | O | O | Me | S | — | — | 0 | 1 | II |
| 1183 | 4-BzOPh | H | H | C | O | O | 2-ClPh | O | — | — | 0 | 1 | II |
| 1184 | 4-BzOPh | H | H | C | O | Mee | H | O | — | — | 0 | 1 | II |
| 1185 | 4-BzOPh | H | H | C | O | Mee | H | S | — | — | 0 | 1 | II |
| 1186 | 4-BzOPh | H | H | C | O | Phe | H | O | — | — | 0 | 1 | II |
| 1187 | 4-BzOPh | H | H | C | O | NH | Pr | O | Ete | O | 1 | 1 | II |
| 1188 | 4-BzOPh | H | H | C | O | O | Me | NH | Trim | — | 1 | 1 | II |
| 1189 | Ph | Xanthen-9-yl | | | O | O | H | O | Ete | O | 1 | 1 | II |
| 1190 | Ph | Xanthen-9-yl | | | O | S | H | O | Ete | O | 1 | 1 | II |
| 1191 | Ph | Xanthen-9-yl | | | O | — | — | — | — | — | 0 | 0 | II |
| 1192 | Ph | Xanthen-9-yl | | | O | O | Me | O | — | — | 0 | 1 | II |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1193 | Ph | Xanthen-9-yl | | | O | O | Me | S | — | — | 0 | 1 | T1 |
| 1194 | Ph | Xanthen-9-yl | | | O | O | 2-ClPh | O | — | — | 0 | 1 | T1 |
| 1195 | Ph | Xanthen-9-yl | | | O | Mee | H | O | — | — | 0 | 1 | T1 |
| 1196 | Ph | Xanthen-9-yl | | | O | Mee | H | S | — | — | 0 | 1 | T1 |
| 1197 | Ph | Xanthen-9-yl | | | O | Phe | H | O | — | — | 0 | 1 | T1 |
| 1198 | Ph | Xanthen-9-yl | | | O | NH | Pr | O | Ete | O | 1 | 1 | T1 |
| 1199 | Ph | Xanthen-9-yl | | | O | O | Me | NH | Trim | — | 1 | 1 | T1 |
| 1200 | Ph | Fluoren-9-yl | | | O | O | H | O | Ete | O | 1 | 1 | T1 |
| 1201 | Ph | Fluoren-9-yl | | | O | S | H | O | Ete | O | 1 | 1 | T1 |
| 1202 | Ph | Fluoren-9-yl | | | O | — | — | — | — | — | 0 | 0 | T1 |
| 1203 | Ph | Fluoren-9-yl | | | O | O | Me | O | — | — | 0 | 1 | T1 |
| 1204 | Ph | Fluoren-9-yl | | | O | O | Me | S | — | — | 0 | 1 | T1 |
| 1205 | Ph | Fluoren-9-yl | | | O | O | 2-ClPh | O | — | — | 0 | 1 | T1 |
| 1206 | Ph | Fluoren-9-yl | | | O | Mee | H | O | — | — | 0 | 1 | T1 |
| 1207 | Ph | Fluoren-9-yl | | | O | Mee | H | S | — | — | 0 | 1 | T1 |
| 1208 | Ph | Fluoren-9-yl | | | O | Phe | H | O | — | — | 0 | 1 | T1 |
| 1209 | Ph | Fluoren-9-yl | | | O | NH | Pr | O | Ete | O | 1 | 1 | T1 |
| 1210 | Ph | Fluoren-9-yl | | | O | O | Me | NH | Trim | — | 1 | 1 | T1 |
| 1211 | 3,4-Dbp | H | H | C | O | O | H | O | Ete | O | 1 | 1 | T2 |
| 1212 | 3,4-Dbp | H | H | C | O | S | H | O | Ete | O | 1 | 1 | T2 |
| 1213 | 3,4-Dbp | H | H | C | O | — | — | — | — | — | 0 | 0 | T2 |
| 1214 | 3,4-Dbp | H | H | C | O | O | Me | O | — | — | 0 | 1 | T2 |
| 1215 | 3,4-Dbp | H | H | C | O | O | Me | S | — | — | 0 | 1 | T2 |
| 1216 | 3,4-Dbp | H | H | C | O | O | 2-ClPh | O | — | — | 0 | 1 | T2 |
| 1217 | 3,4-Dbp | H | H | C | O | Mee | H | O | — | — | 0 | 1 | T2 |
| 1218 | 3,4-Dbp | H | H | C | O | Mee | H | S | — | — | 0 | 1 | T2 |
| 1219 | 3,4-Dbp | H | H | C | O | Phe | H | O | — | — | 0 | 1 | T2 |
| 1220 | 3,4-Dbp | H | H | C | O | NH | Pr | O | Ete | O | 1 | 1 | T2 |
| 1221 | 3,4-Dbp | H | H | C | O | O | Me | NH | Trim | — | 1 | 1 | T2 |
| 1222 | Ph | Ph | Ph | C | O | O | H | O | Ete | O | 1 | 1 | T2 |
| 1223 | Ph | Ph | Ph | C | O | S | H | O | Ete | O | 1 | 1 | T2 |
| 1224 | Ph | Ph | Ph | C | O | — | — | — | — | — | 0 | 0 | T2 |
| 1225 | Ph | Ph | Ph | C | O | O | Me | O | — | — | 0 | 1 | T2 |
| 1226 | Ph | Ph | Ph | C | O | O | Me | S | — | — | 0 | 1 | T2 |
| 1227 | Ph | Ph | Ph | C | O | O | 2-ClPh | O | — | — | 0 | 1 | T2 |
| 1228 | Ph | Ph | Ph | C | O | Mee | H | O | — | — | 0 | 1 | T2 |
| 1229 | Ph | Ph | Ph | C | O | Mee | H | S | — | — | 0 | 1 | T2 |
| 1230 | Ph | Ph | Ph | C | O | Phe | H | O | — | — | 0 | 1 | T2 |
| 1231 | Ph | Ph | Ph | C | O | NH | Pr | O | Ete | O | 1 | 1 | T2 |
| 1232 | Ph | Ph | Ph | C | O | O | Me | NH | Trim | — | 1 | 1 | T2 |
| 1233 | 3,5-Dbp | H | H | C | O | O | H | O | Ete | O | 1 | 1 | T2 |
| 1234 | 3,5-Dbp | H | H | C | O | S | H | O | Ete | O | 1 | 1 | T2 |
| 1235 | 3,5-Dbp | H | H | C | O | — | — | — | — | — | 0 | 0 | T2 |
| 1236 | 3,5-Dbp | H | H | C | O | O | Me | O | — | — | 0 | 1 | T2 |
| 1237 | 3,5-Dbp | H | H | C | O | O | Me | S | — | — | 0 | 1 | T2 |
| 1238 | 3,5-Dbp | H | H | C | O | O | 2-ClPh | O | — | — | 0 | 1 | T2 |
| 1239 | 3,5-Dbp | H | H | C | O | Mee | H | O | — | — | 0 | 1 | T2 |
| 1240 | 3,5-Dbp | H | H | C | O | Mee | H | S | — | — | 0 | 1 | T2 |
| 1241 | 3,5-Dbp | H | H | C | O | Phe | H | O | — | — | 0 | 1 | T2 |
| 1242 | 3,5-Dbp | H | H | C | O | NH | Pr | O | Ete | O | 1 | 1 | T2 |
| 1243 | 3,5-Dbp | H | H | C | O | O | Me | NH | Trim | — | 1 | 1 | T2 |
| 1244 | 4-MeOPh | 4-MeOPh | Ph | C | O | O | H | O | Ete | O | 1 | 1 | T2 |
| 1245 | 4-MeOPh | 4-MeOPh | Ph | C | O | S | H | O | Ete | O | 1 | 1 | T2 |
| 1246 | 4-MeOPh | 4-MeOPh | Ph | C | O | — | — | — | — | — | 0 | 0 | T2 |
| 1247 | 4-MeOPh | 4-MeOPh | Ph | C | O | O | Me | O | — | — | 0 | 1 | T2 |
| 1248 | 4-MeOPh | 4-MeOPh | Ph | C | O | O | Me | S | — | — | 0 | 1 | T2 |
| 1249 | 4-MeOPh | 4-MeOPh | Ph | C | O | O | 2-ClPh | O | — | — | 0 | 1 | T2 |
| 1250 | 4-MeOPh | 4-MeOPh | Ph | C | O | Mee | H | O | — | — | 0 | 1 | T2 |
| 1251 | 4-MeOPh | 4-MeOPh | Ph | C | O | Mee | H | S | — | — | 0 | 1 | T2 |
| 1252 | 4-MeOPh | 4-MeOPh | Ph | C | O | Phe | H | O | — | — | 0 | 1 | T2 |
| 1253 | 4-MeOPh | 4-MeOPh | Ph | C | O | NH | Pr | O | Ete | O | 1 | 1 | T2 |
| 1254 | 4-MeOPh | 4-MeOPh | Ph | C | O | O | Me | NH | Trim | — | 1 | 1 | T2 |
| 1255 | 4-MeOPh | Ph | Ph | C | O | O | H | O | Ete | O | 1 | 1 | T2 |
| 1256 | 4-MeOPh | Ph | Ph | C | O | S | H | O | Ete | O | 1 | 1 | T2 |
| 1257 | 4-MeOPh | Ph | Ph | C | O | — | — | — | — | — | 0 | 0 | T2 |
| 1258 | 4-MeOPh | Ph | Ph | C | O | O | Me | O | — | — | 0 | 1 | T2 |
| 1259 | 4-MeOPh | Ph | Ph | C | O | O | Me | S | — | — | 0 | 1 | T2 |
| 1260 | 4-MeOPh | Ph | Ph | C | O | O | 2-ClPh | O | — | — | 0 | 1 | T2 |
| 1261 | 4-MeOPh | Ph | Ph | C | O | Mee | H | O | — | — | 0 | 1 | T2 |
| 1262 | 4-MeOPh | Ph | Ph | C | O | Mee | H | S | — | — | 0 | 1 | T2 |
| 1263 | 4-MeOPh | Ph | Ph | C | O | Phe | H | O | — | — | 0 | 1 | T2 |
| 1264 | 4-MeOPh | Ph | Ph | C | O | NH | Pr | O | Ete | O | 1 | 1 | T2 |
| 1265 | 4-MeOPh | Ph | Ph | C | O | O | Me | NH | Trim | — | 1 | 1 | T2 |
| 1266 | tBu | Ph | Ph | Si | O | O | H | O | Ete | O | 1 | 1 | 12 |
| 1267 | tBu | Ph | Ph | Si | O | S | H | O | Ete | O | 1 | 1 | 12 |
| 1268 | tBu | Ph | Ph | Si | O | — | — | — | — | — | 0 | 0 | 12 |

TABLE 1-continued

| Cpd. No. | $R_1$ | $R_2$ | $R_3$ | Z | $Y_1$ | $Y_2$ | $R_4$ | $Y_3$ | X | $Y_4$ | n | m | B |
|---|---|---|---|---|---|---|---|---|---|---|---|---|---|
| 1269 | tBu | Ph | Ph | Si | O | O | Me | O | — | — | 0 | 1 | 12 |
| 1270 | tBu | Ph | Ph | Si | O | O | Me | S | — | — | 0 | 1 | 12 |
| 1271 | tBu | Ph | Ph | Si | O | O | 2-ClPh | O | — | — | 0 | 1 | 12 |
| 1272 | tBu | Ph | Ph | Si | O | Mee | H | O | — | — | 0 | 1 | 12 |
| 1273 | tBu | Ph | Ph | Si | O | Mee | H | S | — | — | 0 | 1 | 12 |
| 1274 | tBu | Ph | Ph | Si | O | Phe | H | O | — | — | 0 | 1 | 12 |
| 1275 | tBu | Ph | Ph | Si | O | NH | Pr | O | Ete | O | 1 | 1 | 12 |
| 1276 | tBu | Ph | Ph | Si | O | O | Me | NH | Trim | — | 1 | 1 | 12 |
| 1277 | Ph | Ph | Ph | C | S | O | H | O | Ete | O | 1 | 1 | 12 |
| 1278 | Ph | Ph | Ph | C | S | S | H | O | Ete | O | 1 | 1 | 12 |
| 1279 | Ph | Ph | Ph | C | S | — | — | — | — | — | 0 | 0 | 12 |
| 1280 | Ph | Ph | Ph | C | S | O | Me | O | — | — | 0 | 1 | 12 |
| 1281 | Ph | Ph | Ph | C | S | O | Me | S | — | — | 0 | 1 | 12 |
| 1282 | Ph | Ph | Ph | C | S | O | 2-ClPh | O | — | — | 0 | 1 | 12 |
| 1283 | Ph | Ph | Ph | C | S | Mee | H | O | — | — | 0 | 1 | 12 |
| 1284 | Ph | Ph | Ph | C | S | Mee | H | S | — | — | 0 | 1 | 12 |
| 1285 | Ph | Ph | Ph | C | S | Phe | H | O | — | — | 0 | 1 | 12 |
| 1286 | Ph | Ph | Ph | C | S | NH | Pr | O | Ete | O | 1 | 1 | 12 |
| 1287 | Ph | Ph | Ph | C | S | O | Me | NH | Trim | — | 1 | 1 | 12 |
| 1288 | 4-BzOPh | H | H | C | O | O | H | O | Ete | O | 1 | 1 | 12 |
| 1289 | 4-BzOPh | H | H | C | O | S | H | O | Ete | O | 1 | 1 | 12 |
| 1290 | 4-BzOPh | H | H | C | O | — | — | — | — | — | 0 | 0 | 12 |
| 1291 | 4-BzOPh | H | H | C | O | O | Me | O | — | — | 0 | 1 | 12 |
| 1292 | 4-BzOPh | H | H | C | O | O | Me | S | — | — | 0 | 1 | 12 |
| 1293 | 4-BzOPh | H | H | C | O | O | 2-ClPh | O | — | — | 0 | 1 | 12 |
| 1294 | 4-BzOPh | H | H | C | O | Mee | H | O | — | — | 0 | 1 | 12 |
| 1295 | 4-BzOPh | H | H | C | O | Mee | H | S | — | — | 0 | 1 | 12 |
| 1296 | 4-BzOPh | H | H | C | O | Phe | H | O | — | — | 0 | 1 | 12 |
| 1297 | 4-BzOPh | H | H | C | O | NH | Pr | O | Ete | O | 1 | 1 | 12 |
| 1298 | 4-BzOPh | H | H | C | O | O | Me | NH | Trim | — | 1 | 1 | 12 |
| 1299 | Ph | Xanthen-9-yl | | | O | O | H | O | Ete | O | 1 | 1 | 12 |
| 1300 | Ph | Xanthen-9-yl | | | O | S | H | O | Ete | O | 1 | 1 | 12 |
| 1301 | Ph | Xanthen-9-yl | | | O | — | — | — | — | — | 0 | 0 | 12 |
| 1302 | Ph | Xanthen-9-yl | | | O | O | Me | O | — | — | 0 | 1 | 12 |
| 1303 | Ph | Xanthen-9-yl | | | O | O | Me | S | — | — | 0 | 1 | 12 |
| 1304 | Ph | Xanthen-9-yl | | | O | O | 2-ClPh | O | — | — | 0 | 1 | 12 |
| 1305 | Ph | Xanthen-9-yl | | | O | Mee | H | O | — | — | 0 | 1 | 12 |
| 1306 | Ph | Xanthen-9-yl | | | O | Mee | H | S | — | — | 0 | 1 | 12 |
| 1307 | Ph | Xanthen-9-yl | | | O | Phe | H | O | — | — | 0 | 1 | 12 |
| 1308 | Ph | Xanthen-9-yl | | | O | NH | Pr | O | Ete | O | 1 | 1 | 12 |
| 1309 | Ph | Xanthen-9-yl | | | O | O | Me | NH | Trim | — | 1 | 1 | 12 |
| 1310 | Ph | Fluoren-9-yl | | | O | O | H | O | Ete | O | 1 | 1 | 12 |
| 1311 | Ph | Fluoren-9-yl | | | O | S | H | O | Ete | O | 1 | 1 | 12 |
| 1312 | Ph | Fluoren-9-yl | | | O | — | — | — | — | — | 0 | 0 | 12 |
| 1313 | Ph | Fluoren-9-yl | | | O | O | Me | O | — | — | 0 | 1 | 12 |
| 1314 | Ph | Fluoren-9-yl | | | O | O | Me | S | — | — | 0 | 1 | 12 |
| 1315 | Ph | Fluoren-9-yl | | | O | O | 2-ClPh | O | — | — | 0 | 1 | 12 |
| 1316 | Ph | Fluoren-9-yl | | | O | Mee | H | O | — | — | 0 | 1 | 12 |
| 1317 | Ph | Fluoren-9-yl | | | O | Mee | H | S | — | — | 0 | 1 | 12 |
| 1318 | Ph | Fluoren-9-yl | | | O | Phe | H | O | — | — | 0 | 1 | 12 |
| 1319 | Ph | Fluoren-9-yl | | | O | NH | Pr | O | Ete | O | 1 | 1 | 12 |
| 1320 | Ph | Fluoren-9-yl | | | O | O | Me | NH | Trim | — | 1 | 1 | 12 |
| 1321 | 3,4-Dbp | H | H | C | O | O | H | O | Ete | O | 1 | 1 | 13 |
| 1322 | 3,4-Dbp | H | H | C | O | S | H | O | Ete | O | 1 | 1 | 13 |
| 1323 | 3,4-Dbp | H | H | C | O | — | — | — | — | — | 0 | 0 | 13 |
| 1324 | 3,4-Dbp | H | H | C | O | O | Me | O | — | — | 0 | 1 | 13 |
| 1325 | 3,4-Dbp | H | H | C | O | O | Me | S | — | — | 0 | 1 | 13 |
| 1326 | 3,4-Dbp | H | H | C | O | O | 2-ClPh | O | — | — | 0 | 1 | 13 |
| 1327 | 3,4-Dbp | H | H | C | O | Mee | H | O | — | — | 0 | 1 | 13 |
| 1328 | 3,4-Dbp | H | H | C | O | Mee | H | S | — | — | 0 | 1 | 13 |
| 1329 | 3,4-Dbp | H | H | C | O | Phe | H | O | — | — | 0 | 1 | 13 |
| 1330 | 3,4-Dbp | H | H | C | O | NH | Pr | O | Ete | O | 1 | 1 | 13 |
| 1331 | 3,4-Dbp | H | H | C | O | O | Me | NH | Trim | — | 1 | 1 | 13 |
| 1332 | Ph | Ph | Ph | C | O | O | H | O | Ete | O | 1 | 1 | 13 |
| 1333 | Ph | Ph | Ph | C | O | S | H | O | Ete | O | 1 | 1 | 13 |
| 1334 | Ph | Ph | Ph | C | O | — | — | — | — | — | 0 | 0 | 13 |
| 1335 | Ph | Ph | Ph | C | O | O | Me | O | — | — | 0 | 1 | 13 |
| 1336 | Ph | Ph | Ph | C | O | O | Me | S | — | — | 0 | 1 | 13 |
| 1337 | Ph | Ph | Ph | C | O | O | 2-ClPh | O | — | — | 0 | 1 | 13 |
| 1338 | Ph | Ph | Ph | C | O | Mee | H | O | — | — | 0 | 1 | 13 |
| 1339 | Ph | Ph | Ph | C | O | Mee | H | S | — | — | 0 | 1 | 13 |
| 1340 | Ph | Ph | Ph | C | O | Phe | H | O | — | — | 0 | 1 | 13 |
| 1341 | Ph | Ph | Ph | C | O | NH | Pr | O | Ete | O | 1 | 1 | 13 |
| 1342 | Ph | Ph | Ph | C | O | O | Me | NH | Trim | — | 1 | 1 | 13 |
| 1343 | 3,5-Dbp | H | H | C | O | O | H | O | Ete | O | 1 | 1 | 13 |
| 1344 | 3,5-Dbp | H | H | C | O | S | H | O | Ete | O | 1 | 1 | 13 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1345 | 3,5-Dbp | H | H | C | O | — | — | — | — | — | 0 | 0 | 13 |
| 1346 | 3,5-Dbp | H | H | C | O | O | Me | O | — | — | 0 | 1 | 13 |
| 1347 | 3,5-Dbp | H | H | C | O | O | Me | S | — | — | 0 | 1 | 13 |
| 1348 | 3,5-Dbp | H | H | C | O | O | 2-ClPh | O | — | — | 0 | 1 | 13 |
| 1349 | 3,5-Dbp | H | H | C | O | Mee | H | O | — | — | 0 | 1 | 13 |
| 1350 | 3,5-Dbp | H | H | C | O | Mee | H | S | — | — | 0 | 1 | 13 |
| 1351 | 3,5-Dbp | H | H | C | O | Phe | H | O | — | — | 0 | 1 | 13 |
| 1352 | 3,5-Dbp | H | H | C | O | NH | Pr | O | Ete | O | 1 | 1 | 13 |
| 1353 | 3,5-Dbp | H | H | C | O | O | Me | NH | Trim | — | 1 | 1 | 13 |
| 1354 | 4-MeOPh | 4-MeOPh | Ph | C | O | O | H | O | Ete | O | 1 | 1 | 13 |
| 1355 | 4-MeOPh | 4-MeOPh | Ph | C | O | S | H | O | Ete | O | 1 | 1 | 13 |
| 1356 | 4-MeOPh | 4-MeOPh | Ph | C | O | — | — | — | — | — | 0 | 0 | 13 |
| 1357 | 4-MeOPh | 4-MeOPh | Ph | C | O | O | Me | O | — | — | 0 | 1 | 13 |
| 1358 | 4-MeOPh | 4-MeOPh | Ph | C | O | O | Me | S | — | — | 0 | 1 | 13 |
| 1359 | 4-MeOPh | 4-MeOPh | Ph | C | O | O | 2-ClPh | O | — | — | 0 | 1 | 13 |
| 1360 | 4-MeOPh | 4-MeOPh | Ph | C | O | Mee | H | O | — | — | 0 | 1 | 13 |
| 1361 | 4-MeOPh | 4-MeOPh | Ph | C | O | Mee | H | S | — | — | 0 | 1 | 13 |
| 1362 | 4-MeOPh | 4-MeOPh | Ph | C | O | Phe | H | O | — | — | 0 | 1 | 13 |
| 1363 | 4-MeOPh | 4-MeOPh | Ph | C | O | NH | Pr | O | Ete | O | 1 | 1 | 13 |
| 1364 | 4-MeOPh | 4-MeOPh | Ph | C | O | O | Me | NH | Trim | — | 1 | 1 | 13 |
| 1365 | 4-MeOPh | Ph | Ph | C | O | O | H | O | Ete | O | 1 | 1 | 13 |
| 1366 | 4-MeOPh | Ph | Ph | C | O | S | H | O | Ete | O | 1 | 1 | 13 |
| 1367 | 4-MeOPh | Ph | Ph | C | O | — | — | — | — | — | 0 | 0 | 13 |
| 1368 | 4-MeOPh | Ph | Ph | C | O | O | Me | O | — | — | 0 | 1 | 13 |
| 1369 | 4-MeOPh | Ph | Ph | C | O | O | Me | S | — | — | 0 | 1 | 13 |
| 1370 | 4-MeOPh | Ph | Ph | C | O | O | 2-ClPh | O | — | — | 0 | 1 | 13 |
| 1371 | 4-MeOPh | Ph | Ph | C | O | Mee | H | O | — | — | 0 | 1 | 13 |
| 1372 | 4-MeOPh | Ph | Ph | C | O | Mee | H | S | — | — | 0 | 1 | 13 |
| 1373 | 4-MeOPh | Ph | Ph | C | O | Phe | H | O | — | — | 0 | 1 | 13 |
| 1374 | 4-MeOPh | Ph | Ph | C | O | NH | Pr | O | Ete | O | 1 | 1 | 13 |
| 1375 | 4-MeOPh | Ph | Ph | C | O | O | Me | NH | Trim | — | 1 | 1 | 13 |
| 1376 | tBu | Ph | Ph | Si | O | O | H | O | Ete | O | 1 | 1 | 13 |
| 1377 | tBu | Ph | Ph | Si | O | S | H | O | Ete | O | 1 | 1 | 13 |
| 1378 | tBu | Ph | Ph | Si | O | — | — | — | — | — | 0 | 0 | 13 |
| 1379 | tBu | Ph | Ph | Si | O | O | Me | O | — | — | 0 | 1 | 13 |
| 1380 | tBu | Ph | Ph | Si | O | O | Me | S | — | — | 0 | 1 | 13 |
| 1381 | tBu | Ph | Ph | Si | O | O | 2-ClPh | O | — | — | 0 | 1 | 13 |
| 1382 | tBu | Ph | Ph | Si | O | Mee | H, | O | — | — | 0 | 1 | 13 |
| 1383 | tBu | Ph | Ph | Si | O | Mee | H | S | — | — | 0 | 1 | 13 |
| 1384 | tBu | Ph | Ph | Si | O | Phe | H | O | — | — | 0 | 1 | 13 |
| 1385 | tBu | Ph | Ph | Si | O | NH | Pr | O | Ete | O | 1 | 1 | 13 |
| 1386 | tBu | Ph | Ph | Si | O | O | Me | NH | Trim | — | 1 | 1 | 13 |
| 1387 | Ph | Ph | Ph | C | S | O | H | O | Ete | O | 1 | 1 | 13 |
| 1388 | Ph | Ph | Ph | C | S | S | H | O | Ete | O | 1 | 1 | 13 |
| 1389 | Ph | Ph | Ph | C | S | — | — | — | — | — | 0 | 0 | 13 |
| 1390 | Ph | Ph | Ph | C | S | O | Me | O | — | — | 0 | 1 | 13 |
| 1391 | Ph | Ph | Ph | C | S | O | Me | S | — | — | 0 | 1 | 13 |
| 1392 | Ph | Ph | Ph | C | S | O | 2-ClPh | O | — | — | 0 | 1 | 13 |
| 1393 | Ph | Ph | Ph | C | S | Mee | H | O | — | — | 0 | 1 | 13 |
| 1394 | Ph | Ph | Ph | C | S | Mee | H | S | — | — | 0 | 1 | 13 |
| 1395 | Ph | Ph | Ph | C | S | Phe | H | O | — | — | 0 | 1 | 13 |
| 1396 | Ph | Ph | Ph | C | S | NH | Pr | O | Ete | O | 1 | 1 | 13 |
| 1397 | Ph | Ph | Ph | C | S | O | Me | NH | Trim | — | 1 | 1 | 13 |
| 1398 | 4-BzOPh | H | H | C | O | O | H | O | Ete | O | 1 | 1 | 13 |
| 1399 | 4-BzOPh | H | H | C | O | S | H | O | Ete | O | 1 | 1 | 13 |
| 1400 | 4-BzOPh | H | H | C | O | — | — | — | — | — | 0 | 0 | 13 |
| 1401 | 4-BzOPh | H | H | C | O | O | Me | O | — | — | 0 | 1 | 13 |
| 1402 | 4-BzOPh | H | H | C | O | O | Me | S | — | — | 0 | 1 | 13 |
| 1403 | 4-BzOPh | H | H | C | O | O | 2-ClPh | O | — | — | 0 | 1 | 13 |
| 1404 | 4-BzOPh | H | H | C | O | Mee | H | O | — | — | 0 | 1 | 13 |
| 1405 | 4-BzOPh | H | H | C | O | Mee | H | S | — | — | 0 | 1 | 13 |
| 1406 | 4-BzOPh | H | H | C | O | Phe | H | O | — | — | 0 | 1 | 13 |
| 1407 | 4-BzOPh | H | H | C | O | NH | Pr | O | Ete | O | 1 | 1 | 13 |
| 1408 | 4-BzOPh | H | H | C | O | O | Me | NH | Trim | — | 1 | 1 | 13 |
| 1409 | Ph | Xanthen-9-yl | | | O | O | H | O | Ete | O | 1 | 1 | 13 |
| 1410 | Ph | Xanthen-9-yl | | | O | S | H | O | Ete | O | 1 | 1 | 13 |
| 1411 | Ph | Xanthen-9-yl | | | O | — | — | — | — | — | 0 | 0 | 13 |
| 1412 | Ph | Xanthen-9-yl | | | O | O | Me | O | — | — | 0 | 1 | 13 |
| 1413 | Ph | Xanthen-9-yl | | | O | O | Me | S | — | — | 0 | 1 | 13 |
| 1414 | Ph | Xanthen-9-yl | | | O | O | 2-ClPh | O | — | — | 0 | 1 | 13 |
| 1415 | Ph | Xanthen-9-yl | | | O | Mee | H | O | — | — | 0 | 1 | 13 |
| 1416 | Ph | Xanthen-9-yl | | | O | Mee | H | S | — | — | 0 | 1 | 13 |
| 1417 | Ph | Xanthen-9-yl | | | O | Phe | H | O | — | — | 0 | 1 | 13 |
| 1418 | Ph | Xanthen-9-yl | | | O | NH | Pr | O | Ete | O | 1 | 1 | 13 |
| 1419 | Ph | Xanthen-9-yl | | | O | O | Me | NH | Trim | — | 1 | 1 | 13 |
| 1420 | Ph | Fluoren-9-yl | | | O | O | H | O | Ete | O | 1 | 1 | 13 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1421 | Ph | Fluoren-9-yl | | | O | S | H | O | Ete | O | 1 | 1 | 13 |
| 1422 | Ph | Fluoren-9-yl | | | O | — | — | — | — | — | 0 | 0 | 13 |
| 1423 | Ph | Fluoren-9-yl | | | O | O | Me | O | — | — | 0 | 1 | 13 |
| 1424 | Ph | Fluoren-9-yl | | | O | O | Me | S | — | — | 0 | 1 | 13 |
| 1425 | Ph | Fluoren-9-yl | | | O | O | 2-ClPh | O | — | — | 0 | 1 | 13 |
| 1426 | Ph | Fluoren-9-yl | | | O | Mee | H | O | — | — | 0 | 1 | 13 |
| 1427 | Ph | Fluoren-9-yl | | | O | Mee | H | S | — | — | 0 | 1 | 13 |
| 1428 | Ph | Fluoren-9-yl | | | O | Phe | H | O | — | — | 0 | 1 | 13 |
| 1429 | Ph | Fluoren-9-yl | | | O | NH | Pr | O | Ete | O | 1 | 1 | 13 |
| 1430 | Ph | Fluoren-9-yl | | | O | O | Me | NH | Trim | — | 1 | 1 | 13 |
| 1431 | 3,4-Dbp | H | H | C | O | O | H | O | Ete | O | 1 | 1 | 14 |
| 1432 | 3,4-Dbp | H | H | C | O | S | H | O | Ete | O | 1 | 1 | 14 |
| 1433 | 3,4-Dbp | H | H | C | O | — | — | — | — | — | 0 | 0 | 14 |
| 1434 | 3,4-Dbp | H | H | C | O | O | Me | O | — | — | 0 | 1 | 14 |
| 1435 | 3,4-Dbp | H | H | C | O | O | Me | S | — | — | 0 | 1 | 14 |
| 1436 | 3,4-Dbp | H | H | C | O | O | 2-ClPh | O | — | — | 0 | 1 | 14 |
| 1437 | 3,4-Dbp | H | H | C | O | Mee | H | O | — | — | 0 | 1 | 14 |
| 1438 | 3,4-Dbp | H | H | C | O | Mee | H | S | — | — | 0 | 1 | 14 |
| 1439 | 3,4-Dbp | H | H | C | O | Phe | H | O | — | — | 0 | 1 | 14 |
| 1440 | 3,4-Dbp | H | H | C | O | NH | Pr | O | Ete | O | 1 | 1 | 14 |
| 1441 | 3,4-Dbp | H | H | C | O | O | Me | NH | Trim | — | 1 | 1 | 14 |
| 1442 | Ph | Ph | Ph | C | O | O | H | O | Ete | O | 1 | 1 | 14 |
| 1443 | Ph | Ph | Ph | C | O | S | H | O | Ete | O | 1 | 1 | 14 |
| 1444 | Ph | Ph | Ph | C | O | — | — | — | — | — | 0 | 0 | 14 |
| 1445 | Ph | Ph | Ph | C | O | O | Me | O | — | — | 0 | 1 | 14 |
| 1446 | Ph | Ph | Ph | C | O | O | Me | S | — | — | 0 | 1 | 14 |
| 1447 | Ph | Ph | Ph | C | O | O | 2-ClPh | O | — | — | 0 | 1 | 14 |
| 1448 | Ph | Ph | Ph | C | O | Mee | H | O | — | — | 0 | 1 | 14 |
| 1449 | Ph | Ph | Ph | C | O | Mee | H | S | — | — | 0 | 1 | 14 |
| 1450 | Ph | Ph | Ph | C | O | Phe | H | O | — | — | 0 | 1 | 14 |
| 1451 | Ph | Ph | Ph | C | O | NH | Pr | O | Ete | O | 1 | 1 | 14 |
| 1452 | Ph | Ph | Ph | C | O | O | Me | NH | Trim | — | 1 | 1 | 14 |
| 1453 | 3,5-Dbp | H | H | C | O | O | H | O | Ete | O | 1 | 1 | 14 |
| 1454 | 3,5-Dbp | H | H | C | O | S | H | O | Ete | O | 1 | 1 | 14 |
| 1455 | 3,5-Dbp | H | H | C | O | — | — | — | — | — | 0 | 0 | 14 |
| 1456 | 3,5-Dbp | H | H | C | O | O | Me | O | — | — | 0 | 1 | 14 |
| 1457 | 3,5-Dbp | H | H | C | O | O | Me | S | — | — | 0 | 1 | 14 |
| 1458 | 3,5-Dbp | H | H | C | O | O | 2-ClPh | O | — | — | 0 | 1 | 14 |
| 1459 | 3,5-Dbp | H | H | C | O | Mee | H | C | — | — | 0 | 1 | 14 |
| 1460 | 3,5-Dbp | H | H | C | O | Mee | H | S | — | — | 0 | 1 | 14 |
| 1461 | 3,5-Dbp | H | H | C | O | Phe | H | O | — | — | 0 | 1 | 14 |
| 1462 | 3,5-Dbp | H | H | C | O | NH | Pr | O | Ete | O | 1 | 1 | 14 |
| 1463 | 3,5-Dbp | H | H | C | O | O | Me | NH | Trim | — | 1 | 1 | 14 |
| 1464 | 4-MeOPh | 4-MeOPh | Ph | C | O | O | H | O | Ete | O | 1 | 1 | 14 |
| 1465 | 4-MeOPh | 4-MeOPh | Ph | C | O | S | H | O | Ete | O | 1 | 1 | 14 |
| 1466 | 4-MeOPh | 4-MeOPh | Ph | C | O | — | — | — | — | — | 0 | 0 | 14 |
| 1467 | 4-MeOPh | 4-MeOPh | Ph | C | O | O | Me | O | — | — | 0 | 1 | 14 |
| 1468 | 4-MeOPh | 4-MeOPh | Ph | C | O | O | Me | S | — | — | 0 | 1 | 14 |
| 1469 | 4-MeOPh | 4-MeOPh | Ph | C | O | O | 2-ClPh | O | — | — | 0 | 1 | 14 |
| 1470 | 4-MeOPh | 4-MeOPh | Ph | C | O | Mee | H | O | — | — | 0 | 1 | 14 |
| 1471 | 4-MeOPh | 4-MeOPh | Ph | C | O | Mee | H | S | — | — | 0 | 1 | 14 |
| 1472 | 4-MeOPh | 4-MeOPh | Ph | C | O | Phe | H | O | — | — | 0 | 1 | 14 |
| 1473 | 4-MeOPh | 4-MeOPh | Ph | C | O | NH | Pr | O | Ete | O | 1 | 1 | 14 |
| 1474 | 4-MeOPh | 4-MeOPh | Ph | C | O | O | Me | NH | Trim | — | 1 | 1 | 14 |
| 1475 | 4-MeOPh | Ph | Ph | C | O | O | H | O | Ete | O | 1 | 1 | 14 |
| 1476 | 4-MeOPh | Ph | Ph | C | O | S | H | O | Ete | O | 1 | 1 | 14 |
| 1477 | 4-MeOPh | Ph | Ph | C | O | — | — | — | — | — | 0 | 0 | 14 |
| 1478 | 4-MeOPh | Ph | Ph | C | O | O | Me | O | — | — | 0 | 1 | 14 |
| 1479 | 4-MeOPh | Ph | Ph | C | O | O | Me | S | — | — | 0 | 1 | 14 |
| 1480 | 4-MeOPh | Ph | Ph | C | O | O | 2-ClPh | O | — | — | 0 | 1 | 14 |
| 1481 | 4-MeOPh | Ph | Ph | C | O | Mee | H | O | — | — | 0 | 1 | 14 |
| 1482 | 4-MeOPh | Ph | Ph | C | O | Mee | H | S | — | — | 0 | 1 | 14 |
| 1483 | 4-MeOPh | Ph | Ph | C | O | Phe | H | O | — | — | 0 | 1 | 14 |
| 1484 | 4-MeOPh | Ph | Ph | C | O | NH | Pr | O | Ete | O | 1 | 1 | 14 |
| 1485 | 4-MeOPh | Ph | Ph | C | O | O | Me | NH | Trim | — | 1 | 1 | 14 |
| 1486 | tBu | Ph | Ph | Si | O | O | H | O | Ete | O | 1 | 1 | 14 |
| 1487 | tBu | Ph | Ph | Si | O | S | H | O | Ete | O | 1 | 1 | 14 |
| 1488 | tBu | Ph | Ph | Si | O | — | — | — | — | — | 0 | 0 | 14 |
| 1489 | tBu | Ph | Ph | Si | O | O | Me | O | — | — | 0 | 1 | 14 |
| 1490 | tBu | Ph | Ph | Si | O | O | Me | S | — | — | 0 | 1 | 14 |
| 1491 | tBu | Ph | Ph | Si | O | O | 2-ClPh | O | — | — | 0 | 1 | 14 |
| 1492 | tBu | Ph | Ph | Si | O | Mee | H | O | — | — | 0 | 1 | 14 |
| 1493 | tBu | Ph | Ph | Si | O | Mee | H | S | — | — | 0 | 1 | 14 |
| 1494 | tBu | Ph | Ph | Si | O | Phe | H | O | — | — | 0 | 1 | 14 |
| 1495 | tBu | Ph | Ph | Si | O | NH | Pr | O | Ete | O | 1 | 1 | 14 |
| 1496 | tBu | Ph | Ph | Si | O | O | Me | NH | Trim | — | 1 | 1 | 14 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1497 | Ph | Ph | Ph | C | S | O | H | O | Ete | O | 1 | 1 | 14 |
| 1498 | Ph | Ph | Ph | C | S | S | H | O | Ete | O | 1 | 1 | 14 |
| 1499 | Ph | Ph | Ph | C | S | — | — | — | — | — | 0 | 0 | 14 |
| 1500 | Ph | Ph | Ph | C | S | O | Me | O | — | — | 0 | 1 | 14 |
| 1501 | Ph | Ph | Ph | C | S | O | Me | S | — | — | 0 | 1 | 14 |
| 1502 | Ph | Ph | Ph | C | S | O | 2-ClPh | O | — | — | 0 | 1 | 14 |
| 1503 | Ph | Ph | Ph | C | S | Mee | H | O | — | — | 0 | 1 | 14 |
| 1504 | Ph | Ph | Ph | C | S | Mee | H | S | — | — | 0 | 1 | 14 |
| 1505 | Ph | Ph | Ph | C | S | Phe | H | O | — | — | 0 | 1 | 14 |
| 1506 | Ph | Ph | Ph | C | S | NH | Pr | O | Ete | O | 1 | 1 | 14 |
| 1507 | Ph | Ph | Ph | C | S | O | Me | NH | Trim | — | 1 | 1 | 14 |
| 1508 | 4-BzOPh | H | H | C | O | O | H | O | Ete | O | 1 | 1 | 14 |
| 1509 | 4-BzOPh | H | H | C | O | S | H | O | Ete | O | 1 | 1 | 14 |
| 1510 | 4-BzOPh | H | H | C | O | — | — | — | — | — | 0 | 0 | 14 |
| 1511 | 4-BzOPh | H | H | C | O | O | Me | O | — | — | 0 | 1 | 14 |
| 1512 | 4-BzOPh | H | H | C | O | O | Me | S | — | — | 0 | 1 | 14 |
| 1513 | 4-BzOPh | H | H | C | O | O | 2-ClPh | O | — | — | 0 | 1 | 14 |
| 1514 | 4-BzOPh | H | H | C | O | Mee | H | O | — | — | 0 | 1 | 14 |
| 1515 | 4-BzOPh | H | H | C | O | Mee | H | S | — | — | 0 | 1 | 14 |
| 1516 | 4-BzOPh | H | H | C | O | Phe | H | O | — | — | 0 | 1 | 14 |
| 1517 | 4-BzOPh | H | H | C | O | NH | Pr | O | Ete | O | 1 | 1 | 14 |
| 1518 | 4-BzOPh | H | H | C | O | O | Me | NH | Trim | — | 1 | 1 | 14 |
| 1519 | Ph | Xanthen-9-yl | | | O | O | H | O | Ete | O | 1 | 1 | 14 |
| 1520 | Ph | Xanthen-9-yl | | | O | S | H | O | Ete | O | 1 | 1 | 14 |
| 1521 | Ph | Xanthen-9-yl | | | O | — | — | — | — | — | 0 | 0 | 14 |
| 1522 | Ph | Xanthen-9-yl | | | O | O | Me | O | — | — | 0 | 1 | 14 |
| 1523 | Ph | Xanthen-9-yl | | | O | O | Me | S | — | — | 0 | 1 | 14 |
| 1524 | Ph | Xanthen-9-yl | | | O | O | 2-ClPh | O | — | — | 0 | 1 | 14 |
| 1525 | Ph | Xanthen-9-yl | | | O | Mee | H | O | — | — | 0 | 1 | 14 |
| 1526 | Ph | Xanthen-9-yl | | | O | Mee | H | S | — | — | 0 | 1 | 14 |
| 1527 | Ph | Xanthen-9-yl | | | O | Phe | H | O | — | — | 0 | 1 | 14 |
| 1528 | Ph | Xanthen-9-yl | | | O | NH | Pr | O | Ete | O | 1 | 1 | 14 |
| 1529 | Ph | Xanthen-9-yl | | | O | O | Me | NH | Trim | — | 1 | 1 | 14 |
| 1530 | Ph | Fluoren-9-yl | | | O | O | H | O | Ete | O | 1 | 1 | 14 |
| 1531 | Ph | Fluoren-9-yl | | | O | S | H | O | Ete | O | 1 | 1 | 14 |
| 1532 | Ph | Fluoren-9-yl | | | O | — | — | — | — | — | 0 | 0 | 14 |
| 1533 | Ph | Fluoren-9-yl | | | O | O | Me | O | — | — | 0 | 1 | 14 |
| 1534 | Ph | Fluoren-9-yl | | | O | O | Me | S | — | — | 0 | 1 | 14 |
| 1535 | Ph | Fluoren-9-yl | | | O | O | 2-ClPh | O | — | — | 0 | 1 | 14 |
| 1536 | Ph | Fluoren-9-yl | | | O | Mee | H | O | — | — | 0 | 1 | 14 |
| 1537 | Ph | Fluoren-9-yl | | | O | Mee | H | S | — | — | 0 | 1 | 14 |
| 1538 | Ph | Fluoren-9-yl | | | O | Phe | H | O | — | — | 0 | 1 | 14 |
| 1539 | Ph | Fluoren-9-yl | | | O | NH | Pr | O | Ete | O | 1 | 1 | 14 |
| 1540 | Ph | Fluoren-9-yl | | | O | O | Me | NH | Trim | — | 1 | 1 | 14 |
| 1541 | 3,4-Dbp | H | H | C | O | O | H | O | Ete | O | 1 | 1 | 15 |
| 1542 | 3,4-Dbp | H | H | C | O | S | H | O | Ete | O | 1 | 1 | 15 |
| 1543 | 3,4-Dbp | H | H | C | O | — | — | — | — | — | 0 | 0 | 15 |
| 1544 | 3,4-Dbp | H | H | C | O | O | Me | O | — | — | 0 | 1 | 15 |
| 1545 | 3,4-Dbp | H | H | C | O | O | Me | S | — | — | 0 | 1 | 15 |
| 1546 | 3,4-Dbp | H | H | C | O | O | 2-ClPh | O | — | — | 0 | 1 | 15 |
| 1547 | 3,4-Dbp | H | H | C | O | Mee | H | O | — | — | 0 | 1 | 15 |
| 1548 | 3,4-Dbp | H | H | C | O | Mee | H | S | — | — | 0 | 1 | 15 |
| 1549 | 3,4-Dbp | H | H | C | O | Phe | H | O | — | — | 0 | 1 | 15 |
| 1550 | 3,4-Dbp | H | H | C | O | NH | Pr | O | Ete | O | 1 | 1 | 15 |
| 1551 | 3,4-Dbp | H | H | C | O | O | Me | NH | Trim | — | 1 | 1 | 15 |
| 1552 | Ph | Ph | Ph | C | O | O | H | O | Ete | O | 1 | 1 | 15 |
| 1553 | Ph | Ph | Ph | C | O | S | H | O | Ete | O | 1 | 1 | 15 |
| 1554 | Ph | Ph | Ph | C | O | — | — | — | — | — | 0 | 0 | 15 |
| 1555 | Ph | Ph | Ph | C | O | O | Me | O | — | — | 0 | 1 | 15 |
| 1556 | Ph | Ph | Ph | C | O | O | Me | S | — | — | 0 | 1 | 15 |
| 1557 | Ph | Ph | Ph | C | O | O | 2-ClPh | O | — | — | 0 | 1 | 15 |
| 1558 | Ph | Ph | Ph | C | O | Mee | H | O | — | — | 0 | 1 | 15 |
| 1559 | Ph | Ph | Ph | C | O | Mee | H | S | — | — | 0 | 1 | 15 |
| 1560 | Ph | Ph | Ph | C | O | Phe | H | O | — | — | 0 | 1 | 15 |
| 1561 | Ph | Ph | Ph | C | O | NH | Pr | O | Ete | O | 1 | 1 | 15 |
| 1562 | Ph | Ph | Ph | C | O | O | Me | NH | Trim | — | 1 | 1 | 15 |
| 1563 | 3,5-Dbp | H | H | C | O | O | H | O | Ete | O | 1 | 1 | 15 |
| 1564 | 3,5-Dbp | H | H | C | O | S | H | O | Ete | O | 1 | 1 | 15 |
| 1565 | 3,5-Dbp | H | H | C | O | — | — | — | — | — | 0 | 0 | 15 |
| 1566 | 3,5-Dbp | H | H | C | O | O | Me | O | — | — | 0 | 1 | 15 |
| 1567 | 3,5-Dbp | H | H | C | O | O | Me | S | — | — | 0 | 1 | 15 |
| 1568 | 3,5-Dbp | H | H | C | O | O | 2-ClPh | O | — | — | 0 | 1 | 15 |
| 1569 | 3,5-Dbp | H | H | C | O | Mee | H | O | — | — | 0 | 1 | 15 |
| 1570 | 3,5-Dbp | H | H | C | O | Mee | H | S | — | — | 0 | 1 | 15 |
| 1571 | 3,5-Dbp | H | H | C | O | Phe | H | O | — | — | 0 | 1 | 15 |
| 1572 | 3,5-Dbp | H | H | C | O | NH | Pr | O | Ete | O | 1 | 1 | 15 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1573 | 3,5-Dbp | H | H | C | O | O | Me | NH | Trim | — | 1 | 1 | 15 |
| 1574 | 4-MeOPh | 4-MeOPh | Ph | C | O | O | H | O | Ete | O | 1 | 1 | 15 |
| 1575 | 4-MeOPh | 4-MeOPh | Ph | C | O | S | H | O | Ete | O | 1 | 1 | 15 |
| 1576 | 4-MeOPh | 4-MeOPh | Ph | C | O | — | — | — | — | — | 0 | 0 | 15 |
| 1577 | 4-MeOPh | 4-MeOPh | Ph | C | O | O | Me | O | — | — | 0 | 1 | 15 |
| 1578 | 4-MeOPh | 4-MeOPh | Ph | C | O | O | Me | S | — | — | 0 | 1 | 15 |
| 1579 | 4-MeOPh | 4-MeOPh | Ph | C | O | O | 2-ClPh | O | — | — | 0 | 1 | 15 |
| 1580 | 4-MeOPh | 4-MeOPh | Ph | C | O | Mee | H | O | — | — | 0 | 1 | 15 |
| 1581 | 4-MeOPh | 4-MeOPh | Ph | C | O | Mee | H | S | — | — | 0 | 1 | 15 |
| 1582 | 4-MeOPh | 4-MeOPh | Ph | C | O | Phe | H | O | — | — | 0 | 1 | 15 |
| 1583 | 4-MeOPh | 4-MeOPh | Ph | C | O | NH | Pr | O | Ete | O | 1 | 1 | 15 |
| 1584 | 4-MeOPh | 4-MeOPh | Ph | C | O | O | Me | NH | Trim | — | 1 | 1 | 15 |
| 1585 | 4-MeOPh | Ph | Ph | C | O | O | H | O | Ete | O | 1 | 1 | 15 |
| 1586 | 4-MeOPh | Ph | Ph | C | O | S | H | O | Ete | O | 1 | 1 | 15 |
| 1587 | 4-MeOPh | Ph | Ph | C | O | — | — | — | — | — | 0 | 0 | 15 |
| 1588 | 4-MeOPh | Ph | Ph | C | O | O | Me | O | — | — | 0 | 1 | 15 |
| 1589 | 4-MeOPh | Ph | Ph | C | O | O | Me | S | — | — | 0 | 1 | 15 |
| 1590 | 4-MeOPh | Ph | Ph | C | O | O | 2-ClPh | O | — | — | 0 | 1 | 15 |
| 1591 | 4-MeOPh | Ph | Ph | C | O | Mee | H | O | — | — | 0 | 1 | 15 |
| 1592 | 4-MeOPh | Ph | Ph | C | O | Mee | H | S | — | — | 0 | 1 | 15 |
| 1593 | 4-MeOPh | Ph | Ph | C | O | Phe | H | O | — | — | 0 | 1 | 15 |
| 1594 | 4-MeOPh | Ph | Ph | C | O | NH | Pr | O | Ete | O | 1 | 1 | 15 |
| 1595 | 4-MeOPh | Ph | Ph | C | O | O | Me | NH | Trim | — | 1 | 1 | 15 |
| 1596 | tBu | Ph | Ph | Si | O | O | H | O | Ete | O | 1 | 1 | 15 |
| 1597 | tBu | Ph | Ph | Si | O | S | H | O | Ete | O | 1 | 1 | 15 |
| 1598 | tBu | Ph | Ph | Si | O | — | — | — | — | — | 0 | 0 | 15 |
| 1599 | tBu | Ph | Ph | Si | O | O | Me | O | — | — | 0 | 1 | 15 |
| 1600 | tBu | Ph | Ph | Si | O | O | Me | S | — | — | 0 | 1 | 15 |
| 1601 | tBu | Ph | Ph | Si | O | O | 2-ClPh | O | — | — | 0 | 1 | 15 |
| 1602 | tBu | Ph | Ph | Si | O | Mee | H | O | — | — | 0 | 1 | 15 |
| 1603 | tBu | Ph | Ph | Si | O | Mee | H | S | — | — | 0 | 1 | 15 |
| 1604 | tBu | Ph | Ph | Si | O | Phe | H | O | — | — | 0 | 1 | 15 |
| 1605 | tBu | Ph | Ph | Si | O | NH | Pr | O | Ete | O | 1 | 1 | 15 |
| 1606 | tBu | Ph | Ph | Si | O | O | Me | NH | Trim | — | 1 | 1 | 15 |
| 1607 | Ph | Ph | Ph | C | S | O | H | O | Ete | O | 1 | 1 | 15 |
| 1608 | Ph | Ph | Ph | C | S | S | H | O | Ete | O | 1 | 1 | 15 |
| 1609 | Ph | Ph | Ph | C | S | — | — | — | — | — | 0 | 0 | 15 |
| 1610 | Ph | Ph | Ph | C | S | O | Me | O | — | — | 0 | 1 | 15 |
| 1611 | Ph | Ph | Ph | C | S | O | Me | S | — | — | 0 | 1 | 15 |
| 1612 | Ph | Ph | Ph | C | S | O | 2-ClPh | O | — | — | 0 | 1 | 15 |
| 1613 | Ph | Ph | Ph | C | S | Mee | H | O | — | — | 0 | 1 | 15 |
| 1614 | Ph | Ph | Ph | C | S | Mee | H | S | — | — | 0 | 1 | 15 |
| 1615 | Ph | Ph | Ph | C | S | Phe | H | O | — | — | 0 | 1 | 15 |
| 1616 | Ph | Ph | Ph | C | S | NH | Pr | O | Ete | O | 1 | 1 | 15 |
| 1617 | Ph | Ph | Ph | C | S | O | Me | NH | Trim | — | 1 | 1 | 15 |
| 1618 | 4-BzOPh | H | H | C | O | O | H | O | Ete | O | 1 | 1 | 15 |
| 1619 | 4-BzOPh | H | H | C | O | S | H | O | Ete | O | 1 | 1 | 15 |
| 1620 | 4-BzOPh | H | H | C | O | — | — | — | — | — | 0 | 0 | 15 |
| 1621 | 4-BzOPh | H | H | C | O | O | Me | O | — | — | 0 | 1 | 15 |
| 1622 | 4-BzOPh | H | H | C | O | O | Me | S | — | — | 0 | 1 | 15 |
| 1623 | 4-BzOPh | H | H | C | O | O | 2-ClPh | O | — | — | 0 | 1 | 15 |
| 1624 | 4-BzOPh | H | H | C | O | Mee | H | O | — | — | 0 | 1 | 15 |
| 1625 | 4-BzOPh | H | H | C | O | Mee | H | S | — | — | 0 | 1 | 15 |
| 1626 | 4-BzOPh | H | H | C | O | Phe | H | O | — | — | 0 | 1 | 15 |
| 1627 | 4-BzOPh | H | H | C | O | NH | Pr | O | Ete | O | 1 | 1 | 15 |
| 1628 | 4-BzOPh | H | H | C | O | O | Me | NH | Trim | — | 1 | 1 | 15 |
| 1629 | Ph | Xanthen-9-yl | | | O | O | H | O | Ete | O | 1 | 1 | 15 |
| 1630 | Ph | Xanthen-9-yl | | | O | S | H | O | Ete | O | 1 | 1 | 15 |
| 1631 | Ph | Xanthen-9-yl | | | O | — | — | — | — | — | 0 | 0 | 15 |
| 1632 | Ph | Xanthen-9-yl | | | O | O | Me | O | — | — | 0 | 1 | 15 |
| 1633 | Ph | Xanthen-9-yl | | | O | O | Me | S | — | — | 0 | 1 | 15 |
| 1634 | Ph | Xanthen-9-yl | | | O | O | 2-ClPh | O | — | — | 0 | 1 | 15 |
| 1635 | Ph | Xanthen-9-yl | | | O | Mee | H | O | — | — | 0 | 1 | 15 |
| 1636 | Ph | Xanthen-9-yl | | | O | Mee | H | S | — | — | 0 | 1 | 15 |
| 1637 | Ph | Xanthen-9-yl | | | O | Phe | H | O | — | — | 0 | 1 | 15 |
| 1638 | Ph | Xanthen-9-yl | | | O | NH | Pr | O | Ete | O | 1 | 1 | 15 |
| 1639 | Ph | Xanthen-9-yl | | | O | O | Me | NH | Trim | — | 1 | 1 | 15 |
| 1640 | Ph | Fluoren-9-yl | | | O | O | H | O | Ete | O | 1 | 1 | 15 |
| 1641 | Ph | Fluoren-9-yl | | | O | S | H | O | Ete | O | 1 | 1 | 15 |
| 1642 | Ph | Fluoren-9-yl | | | O | — | — | — | — | — | 0 | 0 | 15 |
| 1643 | Ph | Fluoren-9-yl | | | O | O | Me | O | — | — | 0 | 1 | 15 |
| 1644 | Ph | Fluoren-9-yl | | | O | O | Me | S | — | — | 0 | 1 | 15 |
| 1645 | Ph | Fluoren-9-yl | | | O | O | 2-ClPh | O | — | — | 0 | 1 | 15 |
| 1646 | Ph | Fluoren-9-yl | | | O | Mee | H | O | — | — | 0 | 1 | 15 |
| 1647 | Ph | Fluoren-9-yl | | | O | Mee | H | S | — | — | 0 | 1 | 15 |
| 1648 | Ph | Fluoren-9-yl | | | O | Phe | H | O | — | — | 0 | 1 | 15 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1649 | Ph | Fluoren-9-yl | | | O | NH | Pr | O | Ete | O | 1 | 1 | 15 |
| 1650 | Ph | Fluoren-9-yl | | | O | O | Me | NH | Trim | — | 1 | 1 | 15 |
| 1651 | 3,4-Dbp | H | H | C | O | O | H | O | Ete | O | 1 | 1 | 16 |
| 1652 | 3,4-Dbp | H | H | C | O | S | H | O | Ete | O | 1 | 1 | 16 |
| 1653 | 3,4-Dbp | H | H | C | O | — | — | — | — | — | 0 | 0 | 16 |
| 1654 | 3,4-Dbp | H | H | C | O | O | Me | O | — | — | 0 | 1 | 16 |
| 1655 | 3,4-Dbp | H | H | C | O | O | Me | S | — | — | 0 | 1 | 16 |
| 1656 | 3,4-Dbp | H | H | C | O | O | 2-ClPh | O | — | — | 0 | 1 | 16 |
| 1657 | 3,4-Dbp | H | H | C | O | Mee | H | O | — | — | 0 | 1 | 16 |
| 1658 | 3,4-Dbp | H | H | C | O | Mee | H | S | — | — | 0 | 1 | 16 |
| 1659 | 3,4-Dbp | H | H | C | O | Phe | H | O | — | — | 0 | 1 | 16 |
| 1660 | 3,4-Dbp | H | H | C | O | NH | Pr | O | Ete | O | 1 | 1 | 16 |
| 1661 | 3,4-Dbp | H | H | C | O | O | Me | NH | Trim | — | 1 | 1 | 16 |
| 1662 | Ph | Ph | Ph | C | O | O | H | O | Ete | O | 1 | 1 | 16 |
| 1663 | Ph | Ph | Ph | C | O | S | H | O | Ete | O | 1 | 1 | 16 |
| 1664 | Ph | Ph | Ph | C | O | — | — | — | — | — | 0 | 0 | 16 |
| 1665 | Ph | Ph | Ph | C | O | O | Me | O | — | — | 0 | 1 | 16 |
| 1666 | Ph | Ph | Ph | C | O | O | Me | S | — | — | 0 | 1 | 16 |
| 1667 | Ph | Ph | Ph | C | O | O | 2-ClPh | O | — | — | 0 | 1 | 16 |
| 1668 | Ph | Ph | Ph | C | O | Mee | H | O | — | — | 0 | 1 | 16 |
| 1669 | Ph | Ph | Ph | C | O | Mee | H | S | — | — | 0 | 1 | 16 |
| 1670 | Ph | Ph | Ph | C | O | Phe | H | O | — | — | 0 | 1 | 16 |
| 1671 | Ph | Ph | Ph | C | O | NH | Pr | O | Ete | O | 1 | 1 | 16 |
| 1672 | Ph | Ph | Ph | C | O | O | Me | NH | Trim | — | 1 | 1 | 16 |
| 1673 | 3,5-Dbp | H | H | C | O | 6 | H | O | Ete | O | 1 | 1 | 16 |
| 1674 | 3,5-Dbp | H | H | C | O | S | H | O | Ete | O | 1 | 1 | 16 |
| 1675 | 3,5-Dbp | H | H | C | O | — | — | — | — | — | 0 | 0 | 16 |
| 1676 | 3,5-Dbp | H | H | C | O | O | Me | O | — | — | 0 | 1 | 16 |
| 1677 | 3,5-Dbp | H | H | C | O | O | Me | S | — | — | 0 | 1 | 16 |
| 1678 | 3,5-Dbp | H | H | C | O | O | 2-ClPh | O | — | — | 0 | 1 | 16 |
| 1679 | 3,5-Dbp | H | H | C | O | Mee | H | O | — | — | 0 | 1 | 16 |
| 1680 | 3,5-Dbp | H | H | C | O | Mee | H | S | — | — | 0 | 1 | 16 |
| 1681 | 3,5-Dbp | H | H | C | O | Phe | H | O | — | — | 0 | 1 | 16 |
| 1682 | 3,5-Dbp | H | H | C | O | NH | Pr | O | Ete | O | 1 | 1 | 16 |
| 1683 | 3,5-Dbp | H | H | C | O | O | Me | NH | Trim | — | 1 | 1 | 16 |
| 1684 | 4-MeOPh | 4-MeOPh | Ph | C | O | O | H | O | Ete | O | 1 | 1 | 16 |
| 1685 | 4-MeOPh | 4-MeOPh | Ph | C | O | S | H | O | Ete | O | 1 | 1 | 16 |
| 1686 | 4-MeOPh | 4-MeOPh | Ph | C | O | — | — | — | — | — | 0 | 0 | 16 |
| 1687 | 4-MeOPh | 4-MeOPh | Ph | C | O | O | Me | O | — | — | 0 | 1 | 16 |
| 1688 | 4-MeOPh | 4-MeOPh | Ph | C | O | O | Me | S | — | — | 0 | 1 | 16 |
| 1689 | 4-MeOPh | 4-MeOPh | Ph | C | O | O | 2-ClPh | O | — | — | 0 | 1 | 16 |
| 1690 | 4-MeOPh | 4-MeOPh | Ph | C | O | Mee | H | O | — | — | 0 | 1 | 16 |
| 1691 | 4-MeOPh | 4-MeOPh | Ph | C | O | Mee | H | S | — | — | 0 | 1 | 16 |
| 1692 | 4-MeOPh | 4-MeOPh | Ph | C | O | Phe | H | O | — | — | 0 | 1 | 16 |
| 1693 | 4-MeOPh | 4-MeOPh | Ph | C | O | NH | Pr | O | Ete | O | 1 | 1 | 16 |
| 1694 | 4-MeOPh | 4-MeOPh | Ph | C | O | O | Me | NH | Trim | — | 1 | 1 | 16 |
| 1695 | 4-MeOPh | Ph | Ph | C | O | O | H | O | Ete | O | 1 | 1 | 16 |
| 1696 | 4-MeOPh | Ph | Ph | C | O | S | H | O | Ete | O | 1 | 1 | 16 |
| 1697 | 4-MeOPh | Ph | Ph | C | O | — | — | — | — | — | 0 | 0 | 16 |
| 1698 | 4-MeOPh | Ph | Ph | C | O | O | Me | O | — | — | 0 | 1 | 16 |
| 1699 | 4-MeOPh | Ph | Ph | C | O | O | Me | S | — | — | 0 | 1 | 16 |
| 1700 | 4-MeOPh | Ph | Ph | C | O | O | 2-ClPh | O | — | — | 0 | 1 | 16 |
| 1701 | 4-MeOPh | Ph | Ph | C | O | Mee | H | O | — | — | 0 | 1 | 16 |
| 1702 | 4-MeOPh | Ph | Ph | C | O | Mee | H | S | — | — | 0 | 1 | 16 |
| 1703 | 4-MeOPh | Ph | Ph | C | O | Phe | H | O | — | — | 0 | 1 | 16 |
| 1704 | 4-MeOPh | Ph | Ph | C | O | NH | Pr | O | Ete | O | 1 | 1 | 16 |
| 1705 | 4-MeOPh | Ph | Ph | C | O | O | Me | NH | Trim | — | 1 | 1 | 16 |
| 1706 | tBu | Ph | Ph | Si | O | O | H | O | Ete | O | 1 | 1 | 16 |
| 1707 | tBu | Ph | Ph | Si | O | S | H | O | Ete | O | 1 | 1 | 16 |
| 1708 | tBu | Ph | Ph | Si | O | — | — | — | — | — | 0 | 0 | 16 |
| 1709 | tBu | Ph | Ph | Si | O | O | Me | O | — | — | 0 | 1 | 16 |
| 1710 | tBu | Ph | Ph | Si | O | O | Me | S | — | — | 0 | 1 | 16 |
| 1711 | tBu | Ph | Ph | Si | O | O | 2-ClPh | O | — | — | 0 | 1 | 16 |
| 1712 | tBu | Ph | Ph | Si | O | Mee | H | O | — | — | 0 | 1 | 16 |
| 1713 | tBu | Ph | Ph | Si | O | Mee | H | S | — | — | 0 | 1 | 16 |
| 1714 | tBu | Ph | Ph | Si | O | Phe | H | O | — | — | 0 | 1 | 16 |
| 1715 | tBu | Ph | Ph | Si | O | NH | Pr | O | Ete | O | 1 | 1 | 16 |
| 1716 | tBu | Ph | Ph | Si | O | O | Me | NH | Trim | — | 1 | 1 | 16 |
| 1717 | Ph | Ph | Ph | C | S | O | H | O | Ete | O | 1 | 1 | 16 |
| 1718 | Ph | Ph | Ph | C | S | S | H | O | Ete | O | 1 | 1 | 16 |
| 1719 | Ph | Ph | Ph | C | S | — | — | — | — | — | 0 | 0 | 16 |
| 1720 | Ph | Ph | Ph | C | S | O | Me | O | — | — | 0 | 1 | 16 |
| 1721 | Ph | Ph | Ph | C | S | O | Me | S | — | — | 0 | 1 | 16 |
| 1722 | Ph | Ph | Ph | C | S | O | 2-ClPh | O | — | — | 0 | 1 | 16 |
| 1723 | Ph | Ph | Ph | C | S | Mee | H | O | — | — | 0 | 1 | 16 |
| 1724 | Ph | Ph | Ph | C | S | Mee | H | S | — | — | 0 | 1 | 16 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1725 | Ph | Ph | Ph | C | S | Phe | H | O | — | — | 0 | 1 | 16 |
| 1726 | Ph | Ph | Ph | C | S | NH | Pr | O | Ete | O | 1 | 1 | 16 |
| 1727 | Ph | Ph | Ph | C | S | O | Me | NH | Trim | — | 1 | 1 | 16 |
| 1728 | 4-BzOPh | H | H | C | O | O | H | O | Ete | O | 1 | 1 | 16 |
| 1729 | 4-BzOPh | H | H | C | O | S | H | O | Ete | O | 1 | 1 | 16 |
| 1730 | 4-BzOPh | H | H | C | O | — | — | — | — | — | 0 | 0 | 16 |
| 1731 | 4-BzOPh | H | H | C | O | O | Me | O | — | — | 0 | 1 | 16 |
| 1732 | 4-BzOPh | H | H | C | O | O | Me | S | — | — | 0 | 1 | 16 |
| 1733 | 4-BzOPh | H | H | C | O | O | 2-ClPh | O | — | — | 0 | 1 | 16 |
| 1734 | 4-BzOPh | H | H | C | O | Mee | H | O | — | — | 0 | 1 | 16 |
| 1735 | 4-BzOPh | H | H | C | O | Mee | H | S | — | — | 0 | 1 | 16 |
| 1736 | 4-BzOPh | H | H | C | O | Phe | H | O | — | — | 0 | 1 | 16 |
| 1737 | 4-BzOPh | H | H | C | O | NH | Pr | O | Ete | O | 1 | 1 | 16 |
| 1738 | 4-BzOPh | H | H | C | O | O | Me | NH | Trim | — | 1 | 1 | 16 |
| 1739 | Ph | Xanthen-9-yl | | O | O | H | O | Ete | O | 1 | 1 | 16 |
| 1740 | Ph | Xanthen-9-yl | | O | S | H | O | Ete | O | 1 | 1 | 16 |
| 1741 | Ph | Xanthen-9-yl | | O | — | — | — | — | — | 0 | 0 | 16 |
| 1742 | Ph | Xanthen-9-yl | | O | O | Me | O | — | — | 0 | 1 | 16 |
| 1743 | Ph | Xanthen-9-yl | | O | O | Me | S | — | — | 0 | 1 | 16 |
| 1744 | Ph | Xanthen-9-yl | | O | O | 2-ClPh | O | — | — | 0 | 1 | 16 |
| 1745 | Ph | Xanthen-9-yl | | O | Mee | H | O | — | — | 0 | 1 | 16 |
| 1746 | Ph | Xanthen-9-yl | | O | Mee | H | S | — | — | 0 | 1 | 16 |
| 1747 | Ph | Xanthen-9-yl | | O | Phe | H | O | — | — | 0 | 1 | 16 |
| 1748 | Ph | Xanthen-9-yl | | O | NH | Pr | O | Ete | O | 1 | 1 | 16 |
| 1749 | Ph | Xanthen-9-yl | | O | O | Me | NH | Trim | — | 1 | 1 | 16 |
| 1750 | Ph | Fluoren-9-yl | | O | O | H | O | Ete | O | 1 | 1 | 16 |
| 1751 | Ph | Fluoren-9-yl | | O | S | H | O | Ete | O | 1 | 1 | 16 |
| 1752 | Ph | Fluoren-9-yl | | O | — | — | — | — | — | 0 | 0 | 16 |
| 1753 | Ph | Fluoren-9-yl | | O | O | Me | O | — | — | 0 | 1 | 16 |
| 1754 | Ph | Fluoren-9-yl | | O | O | Me | S | — | — | 0 | 1 | 16 |
| 1755 | Ph | Fluoren-9-yl | | O | O | 2-ClPh | O | — | — | 0 | 1 | 16 |
| 1756 | Ph | Fluoren-9-yl | | O | Mee | H | O | — | — | 0 | 1 | 16 |
| 1757 | Ph | Fluoren-9-yl | | O | Mee | H | S | — | — | 0 | 1 | 16 |
| 1758 | Ph | Fluoren-9-yl | | O | Phe | H | O | — | — | 0 | 1 | 16 |
| 1759 | Ph | Fluoren-9-yl | | O | NH | Pr | O | Ete | O | 1 | 1 | 16 |
| 1760 | Ph | Fluoren-9-yl | | O | O | Me | NH | Trim | — | 1 | 1 | 16 |
| 1761 | 1-Pyr | H | H | C | O | O | H | O | Ete | O | 1 | 1 | 1 |
| 1762 | 1-Pyr | H | H | C | O | S | H | O | Ete | O | 1 | 1 | 1 |
| 1763 | 1-Pyr | H | H | C | O | — | — | — | — | — | 0 | 0 | 1 |
| 1764 | 1-Pyr | H | H | C | O | O | Me | O | — | — | 0 | 1 | 1 |
| 1765 | 1-Pyr | H | H | C | O | O | Me | S | — | — | 0 | 1 | 1 |
| 1766 | 2-Npe | H | H | C | O | O | H | O | Ete | O | 1 | 1 | 1 |
| 1767 | 2-Npe | H | H | C | O | S | H | O | Ete | O | 1 | 1 | 1 |
| 1768 | 2-Npe | H | H | C | O | — | — | — | — | — | 0 | 0 | 1 |
| 1769 | 2-Npe | H | H | C | O | O | Me | O | — | — | 0 | 1 | 1 |
| 1770 | 2-Npe | H | H | C | O | O | Me | S | — | — | 0 | 1 | 1 |
| 1771 | Ph | Ph | H | C | O | O | H | O | Ete | O | 1 | 1 | 1 |
| 1772 | Ph | Ph | H | C | O | S | H | O | Ete | O | 1 | 1 | 1 |
| 1773 | Ph | Ph | H | C | O | — | — | — | — | — | 0 | 0 | 1 |
| 1774 | Ph | Ph | H | C | O | O | Me | O | — | — | 0 | 1 | 1 |
| 1775 | Ph | Ph | H | C | O | O | Me | S | — | — | 0 | 1 | 1 |
| 1776 | 4-PhPh | H | H | C | O | O | H | O | Ete | O | 1 | 1 | 1 |
| 1777 | 4-PhPh | H | H | C | O | S | H | O | Ete | O | 1 | 1 | 1 |
| 1778 | 4-PhPh | H | H | C | O | — | — | — | — | — | 0 | 0 | 1 |
| 1779 | 4-PhPh | H | H | C | O | O | Me | O | — | — | 0 | 1 | 1 |
| 1780 | 4-PhPh | H | H | C | O | O | Me | S | — | — | 0 | 1 | 1 |
| 1781 | 2-PhPh | H | H | C | O | O | H | O | Ete | O | 1 | 1 | 1 |
| 1782 | 2-PhPh | H | H | C | O | S | H | O | Ete | O | 1 | 1 | 1 |
| 1783 | 2-PhPh | H | H | C | O | — | — | — | — | — | 0 | 0 | 1 |
| 1784 | 2-PhPh | H | H | C | O | O | Me | O | — | — | 0 | 1 | 1 |
| 1785 | 2-PhPh | H | H | C | O | O | Me | S | — | — | 0 | 1 | 1 |
| 1786 | Ph | Ph | H | C | S | O | H | O | Ete | O | 1 | 1 | 1 |
| 1787 | Ph | Ph | H | C | S | S | H | O | Ete | O | 1 | 1 | 1 |
| 1788 | Ph | Ph | H | C | S | — | — | — | — | — | 0 | 0 | 1 |
| 1789 | Ph | Ph | H | C | S | O | Me | O | — | — | 0 | 1 | 1 |
| 1790 | Ph | Ph | H | C | S | O | Me | S | — | — | 0 | 1 | 1 |
| 1791 | Ph | Ph | Ph | C | NH | O | H | O | Ete | O | 1 | 1 | 1 |
| 1792 | Ph | Ph | Ph | C | NH | S | H | O | Ete | O | 1 | 1 | 1 |
| 1793 | Ph | Ph | Ph | C | NH | — | — | — | — | — | 0 | 0 | 1 |
| 1794 | Ph | Ph | Ph | C | NH | O | Me | O | — | — | 0 | 1 | 1 |
| 1795 | Ph | Ph | Ph | C | NH | O | Me | S | — | — | 0 | 1 | 1 |
| 1796 | 1-Pyr | H | H | C | O | O | H | O | Ete | O | 1 | 1 | 2 |
| 1797 | 1-Pyr | H | H | C | O | S | H | O | Ete | O | 1 | 1 | 2 |
| 1798 | 1-Pyr | H | H | C | O | — | — | — | — | — | 0 | 0 | 2 |
| 1799 | 1-Pyr | H | H | C | O | O | Me | O | — | — | 0 | 1 | 2 |
| 1800 | 1-Pyr | H | H | C | O | O | Me | S | — | — | 0 | 1 | 2 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1801 | 2-Npe | H | H | C | O | O | H | O | Ete | O | 1 | 1 | 2 |
| 1802 | 2-Npe | H | H | C | O | S | H | O | Ete | O | 1 | 1 | 2 |
| 1803 | 2-Npe | H | H | C | O | — | — | — | — | — | 0 | 0 | 2 |
| 1804 | 2-Npe | H | H | C | O | O | Me | O | — | — | 0 | 1 | 2 |
| 1805 | 2-Npe | H | H | C | O | O | Me | S | — | — | 0 | 1 | 2 |
| 1806 | Ph | Ph | H | C | O | O | H | O | Ete | O | 1 | 1 | 2 |
| 1807 | Ph | Ph | H | C | O | S | H | O | Ete | O | 1 | 1 | 2 |
| 1808 | Ph | Ph | H | C | O | — | — | — | — | — | 0 | 0 | 2 |
| 1809 | Ph | Ph | H | C | O | O | Me | O | — | — | 0 | 1 | 2 |
| 1810 | Ph | Ph | H | C | O | O | Me | S | — | — | 0 | 1 | 2 |
| 1811 | 4-PhPh | H | H | C | O | O | H | O | Ete | O | 1 | 1 | 2 |
| 1812 | 4-PhPh | H | H | C | O | S | H | O | Ete | O | 1 | 1 | 2 |
| 1813 | 4-PhPh | H | H | C | O | — | — | — | — | — | 0 | 0 | 7 |
| 1814 | 4-PhPh | H | H | C | O | O | Me | O | — | — | 0 | 1 | 2 |
| 1815 | 4-PhPh | H | H | C | O | O | Me | S | — | — | 0 | 1 | 2 |
| 1816 | 4-PhPh | H | H | C | O | O | H | O | Ete | O | 1 | 1 | 2 |
| 1817 | 4-PhPh | H | H | C | O | S | H | O | Ete | O | 1 | 1 | 2 |
| 1818 | 4-PhPh | H | H | C | O | — | — | — | — | — | 0 | 0 | 2 |
| 1819 | 4-PhPh | H | H | C | O | O | Me | O | — | — | 0 | 1 | 2 |
| 1820 | 4-PhPh | H | H | C | O | O | Me | S | — | — | 0 | 1 | 2 |
| 1821 | Ph | Ph | H | C | S | O | H | O | Ete | O | 1 | 1 | 2 |
| 1822 | Ph | Ph | H | C | S | S | H | O | Ete | O | 1 | 1 | 2 |
| 1823 | Ph | Ph | H | C | S | — | — | — | — | — | 0 | 0 | 2 |
| 1824 | Ph | Ph | H | C | S | O | Me | O | — | — | 0 | 1 | 2 |
| 1825 | Ph | Ph | H | C | S | O | Me | S | — | — | 0 | 1 | 2 |
| 1826 | Ph | Ph | Ph | C | NH | O | H | O | Ete | O | 1 | 1 | 2 |
| 1827 | Ph | Ph | Ph | C | NH | S | H | O | Ete | O | 1 | 1 | 2 |
| 1828 | Ph | Ph | Ph | C | NH | — | — | — | — | — | 0 | 0 | 2 |
| 1829 | Ph | Ph | Ph | C | NH | O | Me | O | — | — | 0 | 1 | 2 |
| 1830 | Ph | Ph | Ph | C | NH | O | Me | S | — | — | 0 | 1 | 2 |
| 1831 | 1-Pyr | H | H | C | O | O | H | O | Ete | O | 1 | 1 | 3 |
| 1832 | 1-Pyr | H | H | C | O | S | H | O | Ete | O | 1 | 1 | 3 |
| 1833 | 1-Pyr | H | H | C | O | — | — | — | — | — | 0 | 0 | 3 |
| 1834 | 1-Pyr | H | H | C | O | O | Me | O | — | — | 0 | 1 | 3 |
| 1835 | 1-Pyr | H | H | C | O | O | Me | S | — | — | 0 | 1 | 3 |
| 1836 | 2-Npe | H | H | C | O | O | H | O | Ete | O | 1 | 1 | 3 |
| 1837 | 2-Npe | H | H | C | O | S | H | O | Ete | O | 1 | 1 | 3 |
| 1838 | 2-Npe | H | H | C | O | — | — | — | — | — | 0 | 0 | 3 |
| 1839 | 2-Npe | H | H | C | O | O | Me | O | — | — | 0 | 1 | 3 |
| 1840 | 2-Npe | H | H | C | O | O | Me | S | — | — | 0 | 1 | 3 |
| 1841 | Ph | Ph | H | C | O | O | H | O | Ete | O | 1 | 1 | 3 |
| 1842 | Ph | Ph | H | C | O | S | H | O | Ete | O | 1 | 1 | 3 |
| 1843 | Ph | Ph | H | C | O | — | — | — | — | — | 0 | 0 | 3 |
| 1844 | Ph | Ph | H | C | O | O | Me | O | — | — | 0 | 1 | 3 |
| 1845 | Ph | Ph | H | C | O | O | Me | S | — | — | 0 | 1 | 3 |
| 1846 | 4-PhPh | H | H | C | O | O | H | O | Ete | O | 1 | 1 | 3 |
| 1847 | 4-PhPh | H | H | C | O | S | H | O | Ete | O | 1 | 1 | 3 |
| 1848 | 4-PhPh | H | H | C | O | — | — | — | — | — | 0 | 0 | 3 |
| 1849 | 4-PhPh | H | H | C | O | O | Me | O | — | — | 0 | 1 | 3 |
| 1850 | 4-PhPh | H | H | C | O | O | Me | S | — | — | 0 | 1 | 3 |
| 1851 | 2-PhPh | H | H | C | O | O | H | O | Ete | O | 1 | 1 | 3 |
| 1852 | 2-PhPh | H | H | C | O | S | H | O | Ete | O | 1 | 1 | 3 |
| 1853 | 2-PhPh | H | H | C | O | — | — | — | — | — | 0 | 0 | 3 |
| 1854 | 2-PhPh | H | H | C | O | O | Me | O | — | — | 0 | 1 | 3 |
| 1855 | 2-PhPh | H | H | C | O | O | Me | S | — | — | 0 | 1 | 3 |
| 1856 | Ph | Ph | H | C | S | O | H | O | Ete | O | 1 | 1 | 3 |
| 1857 | Ph | Ph | H | C | S | S | H | O | Ete | O | 1 | 1 | 3 |
| 1858 | Ph | Ph | H | C | S | — | — | — | — | — | 0 | 0 | 3 |
| 1859 | Ph | Ph | H | C | S | O | Me | O | — | — | 0 | 1 | 3 |
| 1860 | Ph | Ph | H | C | S | O | Me | S | — | — | 0 | 1 | 3 |
| 1861 | Ph | Ph | Ph | C | NH | O | H | O | Ete | O | 1 | 1 | 3 |
| 1862 | Ph | Ph | Ph | C | NH | S | H | O | Ete | O | 1 | 1 | 3 |
| 1863 | Ph | Ph | Ph | C | NH | — | — | — | — | — | 0 | 0 | 3 |
| 1864 | Ph | Ph | Ph | C | NH | O | Me | O | — | — | 0 | 1 | 3 |
| 1865 | Ph | Ph | Ph | C | NH | O | Me | S | — | — | 0 | 1 | 3 |
| 1866 | 1-Pyr | H | H | C | O | O | H | O | Ete | O | 1 | 1 | 4 |
| 1867 | 1-Pyr | H | H | C | O | S | H | O | Ete | O | 1 | 1 | 4 |
| 1868 | 1-Pyr | H | H | C | O | — | — | — | — | — | 0 | 0 | 4 |
| 1869 | 1-Pyr | H | H | C | O | O | Me | O | — | — | 0 | 1 | 4 |
| 1870 | 1-Pyr | H | H | C | O | O | Me | S | — | — | 0 | 1 | 4 |
| 1871 | 2-Npe | H | H | C | O | O | H | O | Ete | O | 1 | 1 | 4 |
| 1872 | 2-Npe | H | H | C | O | S | H | O | Ete | O | 1 | 1 | 4 |
| 1873 | 2-Npe | H | H | C | O | — | — | — | — | — | 0 | 0 | 4 |
| 1874 | 2-Npe | H | H | C | O | O | Me | O | — | — | 0 | 1 | 4 |
| 1875 | 2-Npe | H | H | C | O | O | Me | S | — | — | 0 | 1 | 4 |
| 1876 | Ph | Ph | H | C | O | O | H | O | Ete | O | 1 | 1 | 4 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1877 | Ph | Ph | H | C | O | S | H | O | Ete | O | 1 | 1 | 4 |
| 1878 | Ph | Ph | H | C | O | — | — | — | — | — | 0 | 0 | 4 |
| 1879 | Ph | Ph | H | C | O | O | Me | O | — | — | 0 | 1 | 4 |
| 1880 | Ph | Ph | H | C | O | O | Me | S | — | — | 0 | 1 | 4 |
| 1881 | 4-PhPh | H | H | C | O | O | H | O | Ete | O | 1 | 1 | 4 |
| 1882 | 4-PhPh | H | H | C | O | S | H | O | Ete | O | 1 | 1 | 4 |
| 1883 | 4-PhPh | H | H | C | O | — | — | — | — | — | 0 | 0 | 4 |
| 1884 | 4-PhPh | H | H | C | O | O | Me | O | — | — | 0 | 1 | 4 |
| 1885 | 4-PhPh | H | H | C | O | O | Me | S | — | — | 0 | 1 | 4 |
| 1886 | 2-PhPh | H | H | C | O | O | H | O | Ete | O | 1 | 1 | 4 |
| 1887 | 2-PhPh | H | H | C | O | S | H | O | Ete | O | 1 | 1 | 4 |
| 1888 | 2-PhPh | H | H | C | O | — | — | — | — | — | 0 | 0 | 4 |
| 1889 | 2-PhPh | H | H | C | O | O | Me | O | — | — | 0 | 1 | 4 |
| 1890 | 2-PhPh | H | H | C | O | O | Me | S | — | — | 0 | 1 | 4 |
| 1891 | Ph | Ph | H | C | S | O | H | O | Ete | O | 1 | 1 | 4 |
| 1892 | Ph | Ph | H | C | S | S | H | O | Ete | O | 1 | 1 | 4 |
| 1893 | Ph | Ph | H | C | S | — | — | — | — | — | 0 | 0 | 4 |
| 1894 | Ph | Ph | H | C | S | O | Me | O | — | — | 0 | 1 | 4 |
| 1895 | Ph | Ph | H | C | S | O | Me | S | Ete | — | 0 | 1 | 4 |
| 1896 | Ph | Ph | Ph | C | NH | O | H | O | Ete | O | 1 | 1 | 4 |
| 1897 | Ph | Ph | Ph | C | NH | S | H | O | Ete | O | 1 | 1 | 4 |
| 1898 | Ph | Ph | Ph | C | NH | — | — | — | — | — | 0 | 0 | 4 |
| 1899 | Ph | Ph | Ph | C | NH | O | Me | O | — | — | 0 | 1 | 4 |
| 1900 | Ph | Ph | Ph | C | NH | O | Me | S | — | — | 0 | 1 | 4 |
| 1901 | 3,4-Dbp | H | H | C | O | O | H | O | Ete | O | 1 | 1 | 17 |
| 1902 | 3,4-Dbp | H | H | C | O | S | H | O | Ete | O | 1 | 1 | 17 |
| 1903 | 3,4-Dbp | H | H | C | O | — | — | — | — | — | 0 | 0 | 17 |
| 1904 | 3,4-Dbp | H | H | C | O | O | Me | O | — | — | 0 | 1 | 17 |
| 1905 | 3,4-Dbp | H | H | C | O | O | Me | S | — | — | 0 | 1 | 17 |
| 1906 | Ph | Ph | Ph | C | O | O | H | O | Ete | O | 1 | 1 | 17 |
| 1907 | Ph | Ph | Ph | C | O | S | H | O | Ete | O | 1 | 1 | 17 |
| 1908 | Ph | Ph | Ph | C | O | — | — | — | — | — | 0 | 0 | 17 |
| 1909 | Ph | Ph | Ph | C | O | O | Me | O | — | — | 0 | 1 | 17 |
| 1910 | Ph | Ph | Ph | C | O | O | Me | S | — | — | 0 | 1 | 17 |
| 1911 | 3,5-Dbp | H | H | C | O | O | H | O | Ete | O | 1 | 1 | 17 |
| 1912 | 3,5-Dbp | H | H | C | O | S | H | O | Ete | O | 1 | 1 | 17 |
| 1913 | 3,5-Dbp | H | H | C | O | — | — | — | — | — | 0 | 0 | 17 |
| 1914 | 3,5-Dbp | H | H | C | O | O | Me | O | — | — | 0 | 1 | 17 |
| 1915 | 3,5-Dbp | H | H | C | O | O | Me | S | — | — | 0 | 1 | 17 |
| 1916 | 3,4-Dbp | H | H | C | O | O | H | O | Ete | O | 1 | 1 | 17 |
| 1917 | 3,4-Dbp | H | H | C | O | S | H | O | Ete | O | 1 | 1 | 17 |
| 1918 | 3,4-Dbp | H | H | C | O | — | — | — | — | — | 0 | 0 | 18 |
| 1919 | 3,4-Dbp | H | H | C | O | O | Me | O | — | — | 0 | 1 | 18 |
| 1920 | 3,4-Dbp | H | H | C | O | O | Me | S | — | — | 0 | 1 | 18 |
| 1921 | Ph | Ph | Ph | C | O | O | H | O | Ete | O | 1 | 1 | 18 |
| 1922 | Ph | Ph | Ph | C | O | S | H | O | Ete | O | 1 | 1 | 18 |
| 1923 | Ph | Ph | Ph | C | O | — | — | — | — | — | 0 | 0 | 18 |
| 1924 | Ph | Ph | Ph | C | O | O | Me | O | — | — | 0 | 1 | 18 |
| 1925 | Ph | Ph | Ph | C | O | O | Me | S | — | — | 0 | 1 | 18 |
| 1926 | 3,5-Dbp | H | H | C | O | O | H | O | Ete | O | 1 | 1 | 18 |
| 1927 | 3,5-Dbp | H | H | C | O | S | H | O | Ete | O | 1 | 1 | 18 |
| 1928 | 3,5-Dbp | H | H | C | O | — | — | — | — | — | 0 | 0 | 18 |
| 1929 | 3,5-Dbp | H | H | C | O | O | Me | O | — | — | 0 | 1 | 18 |
| 1930 | 3,5-Dbp | H | H | C | O | O | Me | S | — | — | 0 | 1 | 18 |
| 1931 | 3,4-Dbp | H | H | C | O | O | H | O | Ete | O | 1 | 1 | 19 |
| 1932 | 3,4-Dbp | H | H | C | O | S | H | O | Ete | O | 1 | 1 | 19 |
| 1933 | 3,4-Dbp | H | H | C | O | — | — | — | — | — | 0 | 0 | 19 |
| 1934 | 3,4-Dbp | H | H | C | O | O | Me | O | — | — | 0 | 1 | 19 |
| 1935 | 3,4-Dbp | H | H | C | O | O | Me | S | — | — | 0 | 1 | 19 |
| 1936 | Ph | Ph | Ph | C | O | O | H | O | Ete | O | 1 | 1 | 19 |
| 1937 | Ph | Ph | Ph | C | O | S | H | O | Ete | O | 1 | 1 | 19 |
| 1938 | Ph | Ph | Ph | C | O | — | — | — | — | — | 0 | 0 | 19 |
| 1939 | Ph | Ph | Ph | C | O | O | Me | O | — | — | 0 | 1 | 19 |
| 1940 | Ph | Ph | Ph | C | O | O | Me | S | — | — | 0 | 1 | 19 |
| 1941 | 3,5-Dbp | H | H | C | O | O | H | O | Ete | O | 1 | 1 | 19 |
| 1942 | 3,5-Dbp | H | H | C | O | S | H | O | Ete | O | 1 | 1 | 19 |
| 1943 | 3,5-Dbp | H | H | C | O | — | — | — | — | — | 0 | 0 | 19 |
| 1944 | 3,5-Dbp | H | H | C | O | O | Me | O | — | — | 0 | 1 | 19 |
| 1945 | 3,5-Dbp | H | H | C | O | O | Me | S | — | — | 0 | 1 | 19 |
| 1946 | 3,4-Dbp | H | H | C | O | O | H | O | Ete | O | 1 | 1 | 20 |
| 1947 | 3,4-Dbp | H | H | C | O | S | H | O | Ete | O | 1 | 1 | 20 |
| 1948 | 3,4-Dbp | H | H | C | O | — | — | — | — | — | 0 | 0 | 20 |
| 1949 | 3,4-Dbp | H | H | C | O | O | Me | O | — | — | 0 | 1 | 20 |
| 1950 | 3,4-Dbp | H | H | C | O | O | Me | S | — | — | 0 | 1 | 20 |
| 1951 | Ph | Ph | Ph | C | O | O | H | O | Ete | O | 1 | 1 | 20 |
| 1952 | Ph | Ph | Ph | C | O | S | H | O | Ete | O | 1 | 1 | 20 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 1953 | Ph | Ph | Ph | C | O | — | — | — | — | — | 0 | 0 | 20 |
| 1954 | Ph | Ph | Ph | C | O | O | Me | O | — | — | 0 | 1 | 20 |
| 1955 | Ph | Ph | Ph | C | O | O | Me | S | — | — | 0 | 1 | 20 |
| 1956 | 3,5-Dbp | H | H | C | O | O | H | O | Ete | O | 1 | 1 | 20 |
| 1957 | 3,5-Dbp | H | H | C | O | S | H | O | Ete | O | 1 | 1 | 20 |
| 1958 | 3,5-Dbp | H | H | C | O | — | — | — | — | — | 0 | 0 | 20 |
| 1959 | 3,5-Dbp | H | H | C | O | O | Me | O | — | — | 0 | 1 | 20 |
| 1960 | 3,5-Dbp | H | H | C | O | O | Me | S | — | — | 0 | 1 | 20 |
| 1961 | 3,4-Dbp | H | H | C | O | NH | Me | O | Ete | O | 1 | 1 | 1 |
| 1962 | 3,4-Dbp | H | H | C | O | O | Ph | O | — | — | 0 | 1 | 1 |
| 1963 | 3,4-Dbp | H | H | C | O | O | 4-ClPh | O | — | — | 0 | 1 | 1 |
| 1964 | 3,4-Dbp | H | H | C | O | NH | 2-NH₂Et | O | Ete | O | 1 | 1 | 1 |
| 1965 | 3,4-Dbp | H | H | C | O | NH | 2-MeOEt | O | Ete | O | 1 | 1 | 1 |
| 1966 | 3,4-Dbp | H | H | C | O | S | Me | O | — | — | 0 | 1 | 1 |
| 1967 | 3,4-Dbp | H | H | C | O | S | H | O | — | — | 0 | 1 | 1 |
| 1968 | 3,4-Dbp | H | H | C | O | O | H | S | Ete | O | 1 | 1 | 1 |
| 1969 | 3,4-Dbp | H | H | C | O | O | Et | O | — | — | 0 | 1 | 1 |
| 1970 | 3,4-Dbp | H | H | C | O | O | Et | S | — | — | 0 | 1 | 1 |
| 1971 | 3,4-Dbp | H | H | C | O | O | Bu | O | — | — | 0 | 1 | 1 |
| 1972 | 3,4-Dbp | H | H | C | O | O | Bu | S | — | — | 0 | 1 | 1 |
| 1973 | 3,4-Dbp | H | H | C | O | O | H | O | Ete | O | 6 | 1 | 1 |
| 1974 | 3,4-Dbp | H | H | C | O | O | H | O | Ete | O | 6 | 2 | 1 |
| 1975 | 3,4-Dbp | H | H | C | O | O | H | O | Ete | O | 6 | 3 | 1 |
| 1976 | 3,4-Dbp | H | H | C | O | O | H | O | Ete | O | 6 | 4 | 1 |
| 1977 | 3,4-Dbp | H | H | C | O | O | H | O | 2-Hpr | NH | 1 | 1 | 1 |
| 1978 | Ph | Ph | Ph | C | O | NH | Me | O | Ete | O | 1 | 1 | 1 |
| 1979 | Ph | Ph | Ph | C | O | O | Ph | O | — | — | 0 | 1 | 1 |
| 1980 | Ph | Ph | Ph | C | O | O | 4-ClPh | O | — | — | 0 | 1 | 1 |
| 1981 | Ph | Ph | Ph | C | O | NH | 2-NH₂Et | O | Ete | O | 1 | 1 | 1 |
| 1982 | Ph | Ph | Ph | C | O | NH | 2-MeOEt | O | Ete | O | 1 | 1 | 1 |
| 1983 | Ph | Ph | Ph | C | O | S | Me | O | — | — | 0 | 1 | 1 |
| 1984 | Ph | Ph | Ph | C | O | S | H | O | — | — | 0 | 1 | 1 |
| 1985 | Ph | Ph | Ph | C | O | O | H | S | Ete | O | 1 | 1 | 1 |
| 1986 | Ph | Ph | Ph | C | O | O | Et | O | — | — | 0 | 1 | 1 |
| 1987 | Ph | Ph | Ph | C | O | O | Et | S | — | — | 0 | 1 | 1 |
| 1988 | Ph | Ph | Ph | C | O | O | Bu | O | — | — | 0 | 1 | 1 |
| 1989 | Ph | Ph | Ph | C | O | O | Bu | S | — | — | 0 | 1 | 1 |
| 1990 | Ph | Ph | Ph | C | O | O | H | O | Ete | O | 6 | 1 | 1 |
| 1991 | Ph | Ph | Ph | C | O | O | H | O | Ete | O | 6 | 2 | 1 |
| 1992 | Ph | Ph | Ph | C | O | O | H | O | Ete | O | 6 | 3 | 1 |
| 1993 | Ph | Ph | Ph | C | O | O | H | O | Ete | O | 6 | 4 | 1 |
| 1994 | Ph | Ph | Ph | C | O | O | H | O | 2-Hpr | NH | 1 | 1 | 1 |
| 1995 | 3,5-Dbp | H | H | C | O | NH | Me | O | Ete | O | 1 | 1 | 1 |
| 1996 | 3,5-Dbp | H | H | C | O | O | Ph | O | — | — | 0 | 1 | 1 |
| 1997 | 3,5-Dbp | H | H | C | O | O | 4-ClPh | O | — | — | 0 | 1 | 1 |
| 1998 | 3,5-Dbp | H | H | C | O | NH | 2-NH₂Et | O | Ete | O | 1 | 1 | 1 |
| 1999 | 3,5-Dbp | H | H | C | O | NH | 2-MeOEt | O | Ete | O | 1 | 1 | 1 |
| 2000 | 3,5-Dbp | H | H | C | O | S | Me | O | — | — | 0 | 1 | 1 |
| 2001 | 3,5-Dbp | H | H | C | O | S | H | O | — | — | 0 | 1 | 1 |
| 2002 | 3,5-Dbp | H | H | C | O | O | H | S | Ete | O | 1 | 1 | 1 |
| 2003 | 3,5-Dbp | H | H | C | O | O | Et | O | — | — | 0 | 1 | 1 |
| 2004 | 3,5-Dbp | H | H | C | O | O | Et | S | — | — | 0 | 1 | 1 |
| 2005 | 3,5-Dbp | H | H | C | O | O | Bu | O | — | — | 0 | 1 | 1 |
| 2006 | 3,5-Dbp | H | H | C | O | O | Bu | S | — | — | 0 | 1 | 1 |
| 2007 | 3,5-Dbp | H | H | C | O | O | H | O | Ete | O | 6 | 1 | 1 |
| 2008 | 3,5-Dbp | H | H | C | O | O | H | O | Ete | O | 6 | 2 | 1 |
| 2009 | 3,5-Dbp | H | H | C | O | O | H | O | Ete | O | 6 | 3 | 1 |
| 2010 | 3,5-Dbp | H | H | C | O | O | H | O | Ete | O | 6 | 4 | 1 |
| 2011 | 3,5-Dbp | H | H | C | O | O | H | O | 2-Hpr | NH | 1 | 1 | 1 |
| 2012 | 3,4-Dbp | H | H | C | O | NH | Me | O | Ete | O | 1 | 1 | 2 |
| 2013 | 3,4-Dbp | H | H | C | O | O | Ph | O | — | — | 0 | 1 | 2 |
| 2014 | 3,4-Dbp | H | H | C | O | O | 4-ClPh | O | — | — | 0 | 1 | 2 |
| 2015 | 3,4-Dbp | H | H | C | O | NH | 2-NH₂Et | O | Ete | O | 1 | 1 | 2 |
| 2016 | 3,4-Dbp | H | H | C | O | NH | 2-MeOEt | O | Ete | O | 1 | 1 | 2 |
| 2017 | 3,4-Dbp | H | H | C | O | S | Me | O | — | — | 0 | 1 | 2 |
| 2018 | 3,4-Dbp | H | H | C | O | S | H | O | — | — | 0 | 1 | 2 |
| 2019 | 3,4-Dbp | H | H | C | O | O | H | S | Ete | O | 1 | 1 | 2 |
| 2020 | 3,4-Dbp | H | H | C | O | O | Et | O | — | — | 0 | 1 | 2 |
| 2021 | 3,4-Dbp | H | H | C | O | O | Et | S | — | — | 0 | 1 | 2 |
| 2022 | 3,4-Dbp | H | H | C | O | O | Bu | O | — | — | 0 | 1 | 2 |
| 2023 | 3,4-Dbp | H | H | C | O | O | Bu | S | — | — | 0 | 1 | 2 |
| 2024 | 3,4-Dbp | H | H | C | O | O | H | O | Ete | O | 6 | 1 | 2 |
| 2025 | 3,4-Dbp | H | H | C | O | O | H | O | Ete | O | 6 | 2 | 2 |
| 2026 | 3,4-Dbp | H | H | C | O | O | H | O | Ete | O | 6 | 3 | 2 |
| 2027 | 3,4-Dbp | H | H | C | O | O | H | O | Ete | O | 6 | 4 | 2 |
| 2028 | 3,4-Dbp | H | H | C | O | O | H | O | 2-Hpr | NH | 1 | 1 | 2 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2029 | Ph | Ph | Ph | C | O | NH | Me | O | Ete | O | 1 | 1 | 2 |
| 2030 | Ph | Ph | Ph | C | O | O | Ph | O | — | — | 0 | 1 | 2 |
| 2031 | Ph | Ph | Ph | C | O | O | 4-ClPh | O | — | — | 0 | 1 | 2 |
| 2032 | Ph | Ph | Ph | C | O | NH | 2-NH₂Et | O | Ete | O | 1 | 1 | 2 |
| 2033 | Ph | Ph | Ph | C | O | NH | 2-MeOEt | O | Ete | O | 1 | 1 | 2 |
| 2034 | Ph | Ph | Ph | C | O | S | Me | O | — | — | 0 | 1 | 2 |
| 2035 | Ph | Ph | Ph | C | O | S | H | O | — | — | 0 | 1 | 2 |
| 2036 | Ph | Ph | Ph | C | O | O | H | S | Ete | O | 1 | 1 | 2 |
| 2037 | Ph | Ph | Ph | C | O | O | Et | O | — | — | 0 | 1 | 2 |
| 2038 | Ph | Ph | Ph | C | O | O | Et | S | — | — | 0 | 1 | 2 |
| 2039 | Ph | Ph | Ph | C | O | O | Bu | O | — | — | 0 | 1 | 2 |
| 2040 | Ph | Ph | Ph | C | O | O | Bu | S | — | — | 0 | 1 | 2 |
| 2041 | Ph | Ph | Ph | C | O | O | H | O | Ete | O | 6 | 1 | 2 |
| 2042 | Ph | Ph | Ph | C | O | O | H | O | Ete | O | 6 | 2 | 2 |
| 2043 | Ph | Ph | Ph | C | O | O | H | O | Ete | O | 6 | 3 | 2 |
| 2044 | Ph | Ph | Ph | C | O | O | H | O | Ete | O | 6 | 4 | 2 |
| 2045 | Ph | Ph | Ph | C | O | O | H | O | 2-Hpr | NH | 1 | 1 | 2 |
| 2046 | 3,5-Dbp | H | H | C | O | NH | Me | O | Ete | O | 1 | 1 | 2 |
| 2047 | 3,5-Dbp | H | H | C | O | O | Ph | O | — | — | 0 | 1 | 2 |
| 2048 | 3,5-Dbp | H | H | C | O | O | 4-ClPh | O | — | — | 0 | 1 | 2 |
| 2049 | 3,5-Dbp | H | H | C | O | NH | 2-NH₂Et | O | Ete | O | 1 | 1 | 2 |
| 2050 | 3,5-Dbp | H | H | C | O | NH | 2-MeOEt | O | Ete | O | 1 | 1 | 2 |
| 2051 | 3,5-Dbp | H | H | C | O | S | Me | O | — | — | 0 | 1 | 2 |
| 2052 | 3,5-Dbp | H | H | C | O | S | H | O | — | — | 0 | 1 | 2 |
| 2053 | 3,5-Dbp | H | H | C | O | O | H | S | Ete | O | 1 | 1 | 2 |
| 2054 | 3,5-Dbp | H | H | C | O | O | Et | O | — | — | 0 | 1 | 2 |
| 2055 | 3,5-Dbp | H | H | C | O | O | Et | S | — | — | 0 | 1 | 2 |
| 2056 | 3,5-Dbp | H | H | C | O | O | Bu | O | — | — | 0 | 1 | 2 |
| 2057 | 3,5-Dbp | H | H | C | O | O | Bu | S | — | — | 0 | 1 | 2 |
| 2058 | 3,5-Dbp | H | H | C | O | O | H | O | Ete | O | 6 | 1 | 2 |
| 2059 | 3,5-Dbp | H | H | C | O | O | H | O | Ete | O | 6 | 2 | 2 |
| 2060 | 3,5-Dbp | H | H | C | O | O | H | O | Ete | O | 6 | 3 | 2 |
| 2061 | 3,5-Dbp | H | H | C | O | O | H | O | Ete | O | 6 | 4 | 2 |
| 2062 | 3,5-Dbp | H | H | C | O | O | H | O | 2-Hpr | NH | 1 | 1 | 2 |
| 2063 | 3,4-Dbp | H | H | C | O | NH | Me | O | Ete | O | 1 | 1 | 3 |
| 2064 | 3,4-Dbp | H | H | C | O | O | Ph | O | — | — | 0 | 1 | 3 |
| 2065 | 3,4-Dbp | H | H | C | O | O | 4-ClPh | O | — | — | 0 | 1 | 3 |
| 2066 | 3,4-Dbp | H | H | C | O | NH | 2-NH₂Et | O | Ete | O | 1 | 1 | 3 |
| 2067 | 3,4-Dbp | H | H | C | O | NH | 2-MeOEt | O | Ete | O | 1 | 1 | 3 |
| 2068 | 3,4-Dbp | H | H | C | O | S | Me | O | — | — | 0 | 1 | 3 |
| 2069 | 3,4-Dbp | H | H | C | O | S | H | O | — | — | 0 | 1 | 3 |
| 2070 | 3,4-Dbp | H | H | C | O | O | H | S | Ete | O | 1 | 1 | 3 |
| 2071 | 3,4-Dbp | H | H | C | O | O | Et | O | — | — | 0 | 1 | 3 |
| 2072 | 3,4-Dbp | H | H | C | O | O | Et | S | — | — | 0 | 1 | 3 |
| 2073 | 3,4-Dbp | H | H | C | O | O | Bu | O | — | — | 0 | 1 | 3 |
| 2074 | 3,4-Dbp | H | H | C | O | O | Bu | S | — | — | 0 | 1 | 3 |
| 2075 | 3,4-Dbp | H | H | C | O | O | H | O | Ete | O | 6 | 1 | 3 |
| 2076 | 3,4-Dbp | H | H | C | O | O | H | O | Ete | O | 6 | 2 | 3 |
| 2077 | 3,4-Dbp | H | H | C | O | O | H | O | Ete | O | 6 | 3 | 3 |
| 2078 | 3,4-Dbp | H | H | C | O | O | H | O | Ete | O | 6 | 4 | 3 |
| 2079 | 3,4-Dbp | H | H | C | O | O | H | O | 2-Hpr | NH | 1 | 1 | 3 |
| 2080 | Ph | Ph | Ph | C | O | NH | Me | O | Ete | O | 1 | 1 | 3 |
| 2081 | Ph | Ph | Ph | C | O | O | Ph | O | — | — | 0 | 1 | 3 |
| 2082 | Ph | Ph | Ph | C | O | O | 4-ClPh | O | — | — | 0 | 1 | 3 |
| 2083 | Ph | Ph | Ph | C | O | NH | 2-NH₂Et | O | Ete | O | 1 | 1 | 3 |
| 2084 | Ph | Ph | Ph | C | O | NH | 2-MeOEt | O | Ete | O | 1 | 1 | 3 |
| 2085 | Ph | Ph | Ph | C | O | S | Me | O | — | — | 0 | 1 | 3 |
| 2086 | Ph | Ph | Ph | C | O | S | H | O | — | — | 0 | 1 | 3 |
| 2087 | Ph | Ph | Ph | C | O | O | H | S | Ete | O | 1 | 1 | 3 |
| 2088 | Ph | Ph | Ph | C | O | O | Et | O | — | — | 0 | 1 | 3 |
| 2089 | Ph | Ph | Ph | C | O | O | Et | S | — | — | 0 | 1 | 3 |
| 2090 | Ph | Ph | Ph | C | O | O | Bu | O | — | — | 0 | 1 | 3 |
| 2091 | Ph | Ph | Ph | C | O | O | Bu | S | — | — | 0 | 1 | 3 |
| 2092 | Ph | Ph | Ph | C | O | O | H | O | Ete | O | 6 | 1 | 3 |
| 2093 | Ph | Ph | Ph | C | O | O | H | O | Ete | O | 6 | 2 | 3 |
| 2094 | Ph | Ph | Ph | C | O | O | H | O | Ete | O | 6 | 3 | 3 |
| 2095 | Ph | Ph | Ph | C | O | O | H | O | Ete | O | 6 | 4 | 3 |
| 2096 | Ph | Ph | Ph | C | O | O | H | O | 2-Hpr | NH | 1 | 1 | 3 |
| 2097 | 3,5-Dbp | H | H | C | O | NH | Me | O | Ete | O | 1 | 1 | 3 |
| 2098 | 3,5-Dbp | H | H | C | O | O | Ph | O | — | — | 0 | 1 | 3 |
| 2099 | 3,5-Dbp | H | H | C | O | O | 4-ClPh | O | — | — | 0 | 1 | 3 |
| 2100 | 3,5-Dbp | H | H | C | O | NH | 2-NH₂Et | O | Ete | O | 1 | 1 | 3 |
| 2101 | 3,5-Dbp | H | H | C | O | NH | 2-MeOEt | O | Ete | O | 1 | 1 | 3 |
| 2102 | 3,5-Dbp | H | H | C | O | S | Me | O | — | — | 0 | 1 | 3 |
| 2103 | 3,5-Dbp | H | H | C | O | S | H | O | — | — | 0 | 1 | 3 |
| 2104 | 3,5-Dbp | H | H | C | O | O | H | S | Ete | O | 1 | 1 | 3 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2105 | 3,5-Dbp | H | H | C | O | O | Et | O | — | — | 0 | 1 | 3̄ |
| 2106 | 3,5-Dbp | H | H | C | O | O | Et | S | — | — | 0 | 1 | 3̄ |
| 2107 | 3,5-Dbp | H | H | C | O | O | Bu | O | — | — | 0 | 1 | 3̄ |
| 2108 | 3,5-Dbp | H | H | C | O | O | Bu | S | — | — | 0 | 1 | 3̄ |
| 2109 | 3,5-Dbp | H | H | C | O | O | H | O | Ete | O | 6 | 1 | 3̄ |
| 2110 | 3,5-Dbp | H | H | C | O | O | H | O | Ete | O | 6 | 2 | 3̄ |
| 2111 | 3,5-Dbp | H | H | C | O | O | H | O | Ete | O | 6 | 3 | 3̄ |
| 2112 | 3,5-Dbp | H | H | C | O | O | H | O | Ete | O | 6 | 4 | 3̄ |
| 2113 | 3,5-Dbp | H | H | C | O | O | H | O | 2-Hpr | NH | 1 | 1 | 3̄ |
| 2114 | 3,4-Dbp | H | H | C | O | NH | Me | O | Ete | O | 1 | 1 | 4̄ |
| 2115 | 3,4-Dbp | H | H | C | O | O | Ph | O | — | — | 0 | 1 | 4̄ |
| 2116 | 3,4-Dbp | H | H | C | O | O | 4-ClPh | O | — | — | 0 | 1 | 4̄ |
| 2117 | 3,4-Dbp | H | H | C | O | NH | 2-NH₂Et | O | Ete | O | 1 | 1 | 4̄ |
| 2118 | 3,4-Dbp | H | H | C | O | NH | 2-MeOEt | O | Ete | O | 1 | 1 | 4̄ |
| 2119 | 3,4-Dbp | H | H | C | O | S | Me | O | — | — | 0 | 1 | 4̄ |
| 2120 | 3,4-Dbp | H | H | C | O | S | H | O | — | — | 0 | 1 | 4̄ |
| 2121 | 3,4-Dbp | H | H | C | O | O | H | S | Ete | O | 1 | 1 | 4̄ |
| 2122 | 3,4-Dbp | H | H | C | O | O | Et | O | — | — | 0 | 1 | 4̄ |
| 2123 | 3,4-Dbp | H | H | C | O | O | Et | S | — | — | 0 | 1 | 4̄ |
| 2124 | 3,4-Dbp | H | H | C | O | O | Bu | O | — | — | 0 | 1 | 4̄ |
| 2125 | 3,4-Dbp | H | H | C | O | O | Bu | S | — | — | 0 | 1 | 4̄ |
| 2126 | 3,4-Dbp | H | H | C | O | O | H | O | Ete | O | 6 | 1 | 4̄ |
| 2127 | 3,4-Dbp | H | H | C | O | O | H | O | Ete | O | 6 | 2 | 4̄ |
| 2128 | 3,4-Dbp | H | H | C | O | O | H | O | Ete | O | 6 | 3 | 4̄ |
| 2129 | 3,4-Dbp | H | H | C | O | O | H | O | Ete | O | 6 | 4 | 4̄ |
| 2130 | 3,4-Dbp | H | H | C | O | O | H | O | 2-Hpr | NH | 1 | 1 | 4̄ |
| 2131 | Ph | Ph | Ph | C | O | NH | Me | O | Ete | O | 1 | 1 | 4̄ |
| 2132 | Ph | Ph | Ph | C | O | O | Ph | O | — | — | 0 | 1 | 4̄ |
| 2133 | Ph | Ph | Ph | C | O | O | 4-ClPh | O | — | — | 0 | 1 | 4̄ |
| 2134 | Ph | Ph | Ph | C | O | NH | 2-NH₂Et | O | Ete | O | 1 | 1 | 4̄ |
| 2135 | Ph | Ph | Ph | C | O | NH | 2-MeOEt | O | Ete | O | 1 | 1 | 4̄ |
| 2136 | Ph | Ph | Ph | C | O | S | Me | O | — | — | 0 | 1 | 4̄ |
| 2137 | Ph | Ph | Ph | C | O | S | H | O | — | — | 0 | 1 | 4̄ |
| 2138 | Ph | Ph | Ph | C | O | O | H | S | Ete | O | 1 | 1 | 4̄ |
| 2139 | Ph | Ph | Ph | C | O | O | Et | O | — | — | 0 | 1 | 4̄ |
| 2140 | Ph | Ph | Ph | C | O | O | Et | S | — | — | 0 | 1 | 4̄ |
| 2141 | Ph | Ph | Ph | C | O | O | Bu | O | — | — | 0 | 1 | 4̄ |
| 2142 | Ph | Ph | Ph | C | O | O | Bu | S | — | — | 0 | 1 | 4̄ |
| 2143 | Ph | Ph | Ph | C | O | O | H | O | Ete | O | 6 | 1 | 4̄ |
| 2144 | Ph | Ph | Ph | C | O | O | H | O | Ete | O | 6 | 2 | 4̄ |
| 2145 | Ph | Ph | Ph | C | O | O | H | O | Ete | O | 6 | 3 | 4̄ |
| 2146 | Ph | Ph | Ph | C | O | O | H | O | Ete | O | 6 | 4 | 4̄ |
| 2147 | Ph | Ph | Ph | C | O | O | H | O | 2-Hpr | NH | 1 | 1 | 4̄ |
| 2148 | 3,5-Dbp | H | H | C | O | NH | Me | O | Ete | O | 1 | 1 | 4̄ |
| 2149 | 3,5-Dbp | H | H | C | O | O | Ph | O | — | — | 0 | 1 | 4̄ |
| 2150 | 3,5-Dbp | H | H | C | O | O | 4-ClPh | O | — | — | 0 | 1 | 4̄ |
| 2151 | 3,5-Dbp | H | H | C | O | NH | 2-NH₂Et | O | Ete | O | 1 | 1 | 4̄ |
| 2152 | 3,5-Dbp | H | H | C | O | NH | 2-MeOEt | O | Ete | O | 1 | 1 | 4̄ |
| 2153 | 3,5-Dbp | H | H | C | O | S | Me | O | — | — | 0 | 1 | 4̄ |
| 2154 | 3,5-Dbp | H | H | C | O | S | H | O | — | — | 0 | 1 | 4̄ |
| 2155 | 3,5-Dbp | H | H | C | O | O | H | S | Ete | O | 1 | 1 | 4̄ |
| 2156 | 3,5-Dbp | H | H | C | O | O | Et | O | — | — | 0 | 1 | 4̄ |
| 2157 | 3,5-Dbp | H | H | C | O | O | Et | S | — | — | 0 | 1 | 4̄ |
| 2158 | 3,5-Dbp | H | H | C | O | O | Bu | O | — | — | 0 | 1 | 4̄ |
| 2159 | 3,5-Dbp | H | H | C | O | O | Bu | S | — | — | 0 | 1 | 4̄ |
| 2160 | 3,5-Dbp | H | H | C | O | O | H | O | Ete | O | 6 | 1 | 4̄ |
| 2161 | 3,5-Dbp | H | H | C | O | O | H | O | Ete | O | 6 | 2 | 4̄ |
| 2162 | 3,5-Dbp | H | H | C | O | O | H | O | Ete | O | 6 | 3 | 4̄ |
| 2163 | 3,5-Dbp | H | H | C | O | O | H | O | Ete | O | 6 | 4 | 4̄ |
| 2164 | 3,5-Dbp | H | H | C | O | O | H | O | 2-Hpr | NH | 1 | 1 | 4̄ |
| 2165 | 4-MePh | Ph | Ph | C | O | O | H | O | Ete | O | 1 | 1 | 1̱ |
| 2166 | 4-MePh | 4-MePh | Ph | C | O | O | H | O | Ete | O | 1 | 1 | 1̱ |
| 2167 | 4-MePh | 4-MePh | 4-MePh | C | O | O | H | O | Ete | O | 1 | 1 | 1̱ |
| 2168 | 4-tBuPh | Ph | Ph | C | O | O | H | O | Ete | O | 1 | 1 | 1̱ |
| 2169 | 4-tBuPh | 4-tBuPh | Ph | C | O | O | H | O | Ete | O | 1 | 1 | 1̱ |
| 2170 | 4-tBuPh | 4-tBuPh | 4-tBuPh | C | O | O | H | O | Ete | O | 1 | 1 | 1̱ |
| 2171 | 4-NO2Ph | Ph | Ph | C | O | O | H | O | Ete | O | 1 | 1 | 1̱ |
| 2172 | 4-NO2Ph | 4-NO2Ph | Ph | C | O | O | H | O | Ete | O | 1 | 1 | 1̱ |
| 2173 | 4-FPh | Ph | Ph | C | O | O | H | O | Ete | O | 1 | 1 | 1̱ |
| 2174 | 4-FPh | 4-FPh | Ph | C | O | O | H | O | Ete | O | 1 | 1 | 1̱ |
| 2175 | 2,4-diFPh | Ph | Ph | C | O | O | H | O | Ete | O | 1 | 1 | 1̱ |
| 2176 | 2-ClPh | Ph | Ph | C | O | O | H | O | Ete | O | 1 | 1 | 1̱ |
| 2177 | 4-ClPh | Ph | Ph | C | O | O | H | O | Ete | O | 1 | 1 | 1̱ |
| 2178 | 4-ClPh | 4-ClPh | Ph | C | O | O | H | O | Ete | O | 1 | 1 | 1̱ |
| 2179 | 4-BrPh | Ph | Ph | C | O | O | H | O | Ete | O | 1 | 1 | 1̱ |
| 2180 | 4-BrPh | 4-BrPh | Ph | C | O | O | H | O | Ete | O | 1 | 1 | 1̱ |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2181 | 4-IPh | Ph | Ph | C | O | O | H | O | Ete | O | 1 | 1 | 1 |
| 2182 | 4-tBuOPh | Ph | Ph | C | O | O | H | O | Ete | O | 1 | 1 | 1 |
| 2183 | 4-EtOPh | Ph | Ph | C | O | O | H | O | Ete | O | 1 | 1 | 1 |
| 2184 | 4-EtOPh | 4-EtOPh | Ph | C | O | O | H | O | Ete | O | 1 | 1 | I |
| 2185 | 2-BzOPh | H | H | C | O | O | H | O | Ete | O | 1 | 1 | I |
| 2186 | 4-BzOPh | Ph | Ph | C | O | O | H | O | Ete | O | 1 | 1 | I |
| 2187 | 4-BzOPh | 4-BzOPh | Ph | C | O | O | H | O | Ete | O | 1 | 1 | I |
| 2188 | 4-MeOPh | 4-MeOPh | 4-MeOPh | C | O | O | H | O | Ete | O | 1 | 1 | 1 |
| 2189 | 9-Ant | H | H | C | O | O | H | O | Ete | O | 1 | 1 | I |
| 2190 | 2-Ant | H | H | C | O | O | H | O | Ete | O | 1 | 1 | I |
| 2191 | 1-Npe | H | H | C | O | O | H | O | Ete | O | 1 | 1 | I |
| 2192 | 3-PhOPh | H | H | C | O | O | H | O | Ete | O | 1 | 1 | I |
| 2193 | 4-PhOPh | H | H | C | O | O | H | O | Ete | O | 1 | 1 | I |
| 2194 | 2-Anq | H | H | C | O | O | H | O | Ete | O | 1 | 1 | I |
| 2195 | 4-Pha | H | H | C | O | O | H | O | Ete | O | 1 | 1 | I |
| 2196 | 3,4-Dbp | H | H | C | O | S | H | O | Ete | O | 6 | 1 | I |
| 2197 | 3,4-Dbp | H | H | C | O | NH | Et | O | Ete | O | 6 | 1 | I |
| 2198 | 3,4-Dbp | H | H | C | O | NH | Pr | O | Ete | O | 6 | 1 | I |
| 2199 | 3,4-Dbp | H | H | C | O | NH | 2-NH₂Et | O | Ete | O | 6 | 1 | I |
| 2200 | 3,4-Dbp | H | H | C | O | O | H | O | Ete | O | 2 | 1 | I |
| 2201 | 3,4-Dbp | H | H | C | O | S | H | O | Ete | O | 2 | 1 | I |
| 2202 | 3,4-Dbp | H | H | C | O | O | 2-NO2Ph | O | — | — | 0 | 1 | I |
| 2203 | 3,4-Dbp | H | H | C | O | O | 4-NO2Ph | O | — | — | 0 | 1 | I |
| 2204 | 3,4-Dbp | H | H | C | O | O | 2-FPh | O | — | — | 0 | 1 | I |
| 2205 | 3,4-Dbp | H | H | C | O | O | 2-BrPh | O | — | — | 0 | 1 | I |
| 2206 | 3,4-Dbp | H | H | C | O | O | 2-IPh | O | — | — | 0 | 1 | I |
| 2207 | 3,4-Dbp | H | H | C | O | O | 4-MeOPh | O | — | — | 0 | 1 | I |
| 2208 | 3,4-Dbp | H | H | C | O | O | 4-MeSPh | O | — | — | 0 | 1 | I |
| 2209 | 3,4-Dbp | H | H | C | O | O | 4-EtOPh | O | — | — | 0 | 1 | I |
| 2210 | 3,4-Dbp | H | H | C | O | O | H | O | Trim | O | 1 | 1 | I |
| 2211 | 3,4-Dbp | H | H | C | O | O | H | O | Tetm | C | 1 | 1 | I |
| 2212 | 3,4-Dbp | H | H | C | O | O | H | O | Penm | O | 1 | 1 | I |
| 2213 | 3,4-Dbp | H | H | C | O | O | H | O | Hexm | O | 1 | 1 | I |
| 2214 | 3,4-Dbp | H | H | C | O | O | H | O | Hepm | O | 1 | 1 | I |
| 2215 | 3,4-Dbp | H | H | C | O | O | H | O | Octm | O | 1 | 1 | I |
| 2216 | 3,4-Dbp | H | H | C | O | O | H | O | Nonm | O | 1 | 1 | I |
| 2217 | 3,4-Dbp | H | H | C | O | O | H | O | Decm | O | 1 | 1 | I |
| 2218 | 3,4-Dbp | H | H | C | O | O | H | O | Pre | O | 1 | 1 | I |
| 2219 | 3,4-Dbp | H | H | C | O | O | H | O | 1-Me-Trim | O | 1 | 1 | I |
| 2220 | 3,4-Dbp | H | H | C | O | O | H | O | 2-Me-Tetm | O | 1 | 1 | I |
| 2221 | 3,4-Dbp | H | H | C | O | S | H | O | Trim | O | 1 | 1 | I |
| 2222 | 3,4-Dbp | H | H | C | O | S | H | O | Tetm | O | 1 | 1 | I |
| 2223 | 3,4-Dbp | H | H | C | O | S | H | O | Penm | O | 1 | 1 | I |
| 2224 | 3,4-Dbp | H | H | C | O | S | H | O | Hexm | O | 1 | 1 | I |
| 2225 | 3,4-Dbp | H | H | C | O | S | H | O | Hepm | O | 1 | 1 | I |
| 2226 | 3,4-Dbp | H | H | C | O | S | H | O | Octm | O | 1 | 1 | I |
| 2227 | 3,4-Dbp | H | H | C | O | S | H | O | Nonm | O | 1 | 1 | I |
| 2228 | 3,4-Dbp | H | H | C | O | S | H | O | Decm | O | 1 | 1 | I |
| 2229 | 3,4-Dbp | H | H | C | O | S | H | O | Pre | O | 1 | 1 | I |
| 2230 | 3,4-Dbp | H | H | C | O | S | H | O | 1-Me-Trim | O | 1 | 1 | I |
| 2231 | 3,4-Dbp | H | H | C | O | S | H | O | 2-Me-Tetm | O | 1 | 1 | I |
| 2232 | 3,4-Dbp | H | H | C | O | NH | Ph | O | Ete | O | 1 | 1 | I |
| 2233 | 3,4-Dbp | H | H | C | O | NH | 2-ClPh | O | Ete | O | 1 | 1 | I |
| 2234 | 3,4-Dbp | H | H | C | O | NH | Me | O | Trim | O | 1 | 1 | I |
| 2235 | 3,4-Dbp | H | H | C | O | NH | Pr | O | Trim | O | 1 | 1 | I |
| 2236 | 3,4-Dbp | H | H | C | O | NH | 2-NH₂Et | O | Trim | O | 1 | 1 | I |
| 2237 | 3,4-Dbp | H | H | C | O | NH | 2-MeOEt | O | Trim | O | 1 | 1 | I |
| 2238 | 3,4-Dbp | H | H | C | O | NH | Ph | O | Trim | O | 1 | 1 | I |
| 2239 | 3,4-Dbp | H | H | C | O | NH | 2-ClPh | O | Trim | O | 1 | 1 | I |
| 2240 | 3,4-Dbp | H | H | C | O | NH | Pr | O | Tetm | O | 1 | 1 | I |
| 2241 | 3,4-Dbp | H | H | C | O | NH | Pr | O | Penm | O | 1 | 1 | I |
| 2242 | 3,4-Dbp | H | H | C | O | NH | Pr | O | Hexm | O | 1 | 1 | I |
| 2243 | 3,4-Dbp | H | H | C | O | NH | Pr | O | Hepm | O | 1 | 1 | I |
| 2244 | 3,4-Dbp | H | H | C | O | NH | Pr | O | Octm | O | 1 | 1 | I |
| 2245 | 3,4-Dbp | H | H | C | O | NH | Pr | O | Nonm | O | 1 | 1 | I |
| 2246 | 3,4-Dbp | H | H | C | O | NH | Pr | O | Decm | O | 1 | 1 | I |
| 2247 | 3,4-Dbp | H | H | C | O | NH | Pr | O | Pre | O | 1 | 1 | I |
| 2248 | 3,4-Dbp | H | H | C | O | NH | Pr | O | 1-Me-Trim | O | 1 | 1 | I |
| 2249 | 3,4-Dbp | H | H | C | O | NH | Pr | O | 2-Me-Tetm | O | 1 | 1 | I |
| 2250 | Ph | Ph | Ph | C | NH | O | H | O | Ete | O | 6 | 1 | I |
| 2251 | 3,4-Dbp | H | H | C | O | O | H | O | Ete | O | 1 | 1 | 2I |
| 2252 | 3,4-Dbp | H | H | C | O | S | H | O | Ete | O | 1 | 1 | 2I |
| 2253 | 3,4-Dbp | H | H | C | O | — | — | — | — | — | 0 | 0 | 2I |
| 2254 | 3,4-Dbp | H | H | C | O | O | Me | O | — | — | 0 | 1 | 2I |
| 2255 | 3,4-Dbp | H | H | C | O | O | Me | S | — | — | 0 | 1 | 2I |
| 2256 | Ph | Ph | Ph | C | O | O | H | O | Ete | O | 1 | 1 | 2I |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2257 | Ph | Ph | Ph | C | O | S | H | O | Ete | O | 1 | 1 | 21 |
| 2258 | Ph | Ph | Ph | C | O | — | — | — | — | — | 0 | 0 | 21 |
| 2259 | Ph | Ph | Ph | C | O | O | Me | O | — | — | 0 | 1 | 21 |
| 2260 | Ph | Ph | Ph | C | O | O | Me | S | — | — | 0 | 1 | 21 |
| 2261 | 3,5-Dbp | H | H | C | O | O | H | O | Ete | O | 1 | 1 | 21 |
| 2262 | 3,5-Dbp | H | H | C | O | S | H | O | Ete | O | 1 | 1 | 21 |
| 2263 | 3,5-Dbp | H | H | C | O | — | — | — | — | — | 0 | 0 | 21 |
| 2264 | 3,5-Dbp | H | H | C | O | O | Me | O | — | — | 0 | 1 | 21 |
| 2265 | 3,5-Dbp | H | H | C | O | O | Me | S | — | — | 0 | 1 | 21 |
| 2266 | 3,4-Dbp | H | H | C | O | O | H | O | Ete | O | 1 | 1 | 22 |
| 2267 | 3,4-Dbp | H | H | C | O | S | H | O | Ete | O | 1 | 1 | 22 |
| 2268 | 3,4-Dbp | H | H | C | O | — | — | — | — | — | 0 | 0 | 22 |
| 2269 | 3,4-Dbp | H | H | C | O | O | Me | O | — | — | 0 | 1 | 22 |
| 2270 | 3,4-Dbp | H | H | C | O | O | Me | S | — | — | 0 | 1 | 22 |
| 2271 | Ph | Ph | Ph | C | O | O | H | O | Ete | O | 1 | 1 | 22 |
| 2272 | Ph | Ph | Ph | C | O | S | H | O | Ete | O | 1 | 1 | 22 |
| 2273 | Ph | Ph | Ph | C | O | — | — | — | — | — | 0 | 0 | 22 |
| 2274 | Ph | Ph | Ph | C | O | O | Me | O | — | — | 0 | 1 | 22 |
| 2275 | Ph | Ph | Ph | C | O | O | Me | S | — | — | 0 | 1 | 22 |
| 2276 | 3,5-Dbp | H | H | C | O | O | H | O | Ete | O | 1 | 1 | 22 |
| 2277 | 3,5-Dbp | H | H | C | O | S | H | O | Ete | O | 1 | 1 | 22 |
| 2278 | 3,5-Dbp | H | H | C | O | — | — | — | — | — | 0 | 0 | 22 |
| 2279 | 3,5-Dbp | H | H | C | O | O | Me | O | — | — | 0 | 1 | 22 |
| 2280 | 3,5-Dbp | H | H | C | O | O | Me | S | — | — | 0 | 1 | 22 |
| 2281 | 3,4-Dbp | H | H | C | O | O | H | O | — | — | 1 | 1 | 23 |
| 2282 | 3,4-Dbp | H | H | C | O | S | H | O | Ete | O | 1 | 1 | 23 |
| 2283 | 3,4-Dbp | H | H | C | O | — | — | — | — | — | 0 | 0 | 23 |
| 2284 | 3,4-Dbp | H | H | C | O | O | Me | O | — | — | 0 | 1 | 23 |
| 2285 | 3,4-Dbp | H | H | C | O | O | Me | S | — | — | 0 | 1 | 23 |
| 2286 | Ph | Ph | Ph | C | O | O | H | O | Ete | O | 1 | 1 | 23 |
| 2287 | Ph | Ph | Ph | C | O | S | H | O | Ete | O | 1 | 1 | 23 |
| 2288 | Ph | Ph | Ph | C | O | — | — | — | — | — | 0 | 0 | 23 |
| 2289 | Ph | Ph | Ph | C | O | O | Me | O | — | — | 0 | 1 | 23 |
| 2290 | Ph | Ph | Ph | C | O | O | Me | S | — | — | 0 | 1 | 23 |
| 2291 | 3,5-Dbp | H | H | C | O | O | H | O | Ete | O | 1 | 1 | 23 |
| 2292 | 3,5-Dbp | H | H | C | O | S | H | O | Ete | O | 1 | 1 | 23 |
| 2293 | 3,5-Dbp | H | H | C | O | — | — | — | — | — | 0 | 0 | 23 |
| 2294 | 3,5-Dbp | H | H | C | O | O | Me | O | — | — | 0 | 1 | 23 |
| 2295 | 3,5-Dbp | H | H | C | O | O | Me | S | — | — | 0 | 1 | 23 |
| 2296 | 3,4-Dbp | H | H | C | O | O | H | O | Ete | O | 1 | 1 | 24 |
| 2297 | 3,4-Dbp | H | H | C | O | S | H | O | Ete | O | 1 | 1 | 24 |
| 2298 | 3,4-Dbp | H | H | C | O | — | — | — | — | — | 0 | 0 | 24 |
| 2299 | 3,4-Dbp | H | H | C | O | O | Me | O | — | — | 0 | 1 | 24 |
| 2300 | 3,4-Dbp | H | H | C | O | O | Me | S | — | — | 0 | 1 | 24 |
| 2301 | Ph | Ph | Ph | C | O | O | H | O | Ete | O | 1 | 1 | 24 |
| 2302 | Ph | Ph | Ph | C | O | S | H | O | Ete | O | 1 | 1 | 24 |
| 2303 | Ph | Ph | Ph | C | O | — | — | — | — | — | 0 | 0 | 24 |
| 2304 | Ph | Ph | Ph | C | O | O | Me | O | — | — | 0 | 1 | 24 |
| 2305 | Ph | Ph | Ph | C | O | O | Me | S | — | — | 0 | 1 | 24 |
| 2306 | 3,5-Dbp | H | H | C | O | O | H | O | Ete | O | 1 | 1 | 24 |
| 2307 | 3,5-Dbp | H | H | C | O | S | H | O | Ete | O | 1 | 1 | 24 |
| 2308 | 3,5-Dbp | H | H | C | O | — | — | — | — | — | 0 | 0 | 24 |
| 2309 | 3,5-Dbp | H | H | C | O | O | Me | O | — | — | 0 | 1 | 24 |
| 2310 | 3,5-Dbp | H | H | C | O | O | Me | S | — | — | 0 | 1 | 24 |
| 2311 | 3,4-Dbp | H | H | C | O | O | H | O | Ete | O | 1 | 1 | 25 |
| 2312 | 3,4-Dbp | H | H | C | O | S | H | O | Ete | O | 1 | 1 | 25 |
| 2313 | 3,4-Dbp | H | H | C | O | — | — | — | — | — | 0 | 0 | 25 |
| 2314 | 3,4-Dbp | H | H | C | O | O | Me | O | — | — | 0 | 1 | 25 |
| 2315 | 3,4-Dbp | H | H | C | O | O | Me | S | — | — | 0 | 1 | 25 |
| 2316 | Ph | Ph | Ph | C | O | O | H | O | Ete | O | 1 | 1 | 25 |
| 2317 | Ph | Ph | Ph | C | O | S | H | O | Ete | O | 1 | 1 | 25 |
| 2318 | Ph | Ph | Ph | C | O | — | — | — | — | — | 0 | 0 | 25 |
| 2319 | Ph | Ph | Ph | C | O | O | Me | O | — | — | 0 | 1 | 25 |
| 2320 | Ph | Ph | Ph | C | O | O | Me | S | — | — | 0 | 1 | 25 |
| 2321 | 3,5-Dbp | H | H | C | O | O | H | O | Ete | O | 1 | 1 | 25 |
| 2322 | 3,5-Dbp | H | H | C | O | S | H | O | Ete | O | 1 | 1 | 25 |
| 2323 | 3,5-Dbp | H | H | C | O | — | — | — | — | — | 0 | 0 | 25 |
| 2324 | 3,5-Dbp | H | H | C | O | O | Me | O | — | — | 0 | 1 | 25 |
| 2325 | 3,5-Dbp | H | H | C | O | O | Me | S | — | — | 0 | 1 | 25 |
| 2326 | 4-MeOPh | 4-MeOPh | Ph | C | O | — | — | — | — | — | 0 | 0 | 17 |
| 2327 | 4-MeOPh | 4-MeOPh | Ph | C | O | — | — | — | — | — | 0 | 0 | 18 |
| 2328 | 4-MeOPh | 4-MeOPh | Ph | C | O | — | — | — | — | — | 0 | 0 | 19 |
| 2329 | 4-MeOPh | 4-MeOPh | Ph | C | O | — | — | — | — | — | 0 | 0 | 20 |
| 2330 | 4-MeOPh | 4-MeOPh | Ph | C | O | — | — | — | — | — | 0 | 0 | 21 |
| 2331 | 4-MeOPh | 4-MeOPh | Ph | C | O | — | — | — | — | — | 0 | 0 | 22 |
| 2332 | 4-MeOPh | 4-MeOPh | Ph | C | O | — | — | — | — | — | 0 | 0 | 23 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2333 | 4-MeOPh | 4-MeOPh | Ph | C | O | — | — | — | — | — | 0 | 0 | 24 |
| 2334 | 4-MeOPh | 4-MeOPh | Ph | C | O | — | — | — | — | — | 0 | 0 | 25 |
| 2335 | 3,4-Dbp | H | H | C | O | O | H | O | Ete | O | 1 | 1 | 25 |
| 2336 | 3,4-Dbp | H | H | C | O | S | H | O | Ete | O | 1 | 1 | 25 |
| 2337 | 3,4-Dbp | H | H | C | O | — | — | — | — | — | 0 | 0 | 25 |
| 2338 | 3,4-Dbp | H | H | C | O | O | Me | O | — | — | 0 | 1 | 25 |
| 2339 | 3,4-Dbp | H | H | C | O | O | Me | S | — | — | 0 | 1 | 25 |
| 2340 | 3,4-Dbp | H | H | C | O | O | 2-ClPh | O | — | — | 0 | 1 | 25 |
| 2341 | 3,4-Dbp | H | H | C | O | Mee | H | O | — | — | 0 | 1 | 25 |
| 2342 | 3,4-Dbp | H | H | C | O | Mee | H | S | — | — | 0 | 1 | 25 |
| 2343 | 3,4-Dbp | H | H | C | O | Phe | H | O | — | — | 0 | 1 | 25 |
| 2344 | 3,4-Dbp | H | H | C | O | NH | Pr | O | Ete | O | 1 | 1 | 25 |
| 2345 | 3,4-Dbp | H | H | C | O | O | Me | NH | Trim | — | 1 | 1 | 25 |
| 2346 | Ph | Ph | Ph | C | O | O | H | O | Ete | O | 1 | 1 | 25 |
| 2347 | Ph | Ph | Ph | C | O | S | H | O | Ete | O | 1 | 1 | 25 |
| 2348 | Ph | Ph | Ph | C | O | — | — | — | — | — | 0 | 0 | 25 |
| 2349 | Ph | Ph | Ph | C | O | O | Me | O | — | — | 0 | 1 | 25 |
| 2350 | Ph | Ph | Ph | C | O | O | Me | S | — | — | 0 | 1 | 25 |
| 2351 | Ph | Ph | Ph | C | O | O | 2-ClPh | O | — | — | 0 | 1 | 25 |
| 2352 | Ph | Ph | Ph | C | O | Mee | H | O | — | — | 0 | 1 | 25 |
| 2353 | Ph | Ph | Ph | C | O | Mee | H | S | — | — | 0 | 1 | 25 |
| 2354 | Ph | Ph | Ph | C | O | Phe | H | O | — | — | 0 | 1 | 25 |
| 2355 | Ph | Ph | Ph | C | O | NH | Pr | O | Ete | O | 1 | 1 | 25 |
| 2356 | Ph | Ph | Ph | C | O | O | Me | NH | Trim | — | 1 | 1 | 25 |
| 2357 | 3,5-Dbp | H | H | C | O | O | H | O | Ete | O | 1 | 1 | 25 |
| 2358 | 3,5-Dbp | H | H | C | O | S | H | O | Ete | O | 1 | 1 | 25 |
| 2359 | 3,5-Dbp | H | H | C | O | — | — | — | — | — | 0 | 0 | 25 |
| 2360 | 3,5-Dbp | H | H | C | O | O | Me | O | — | — | 0 | 1 | 25 |
| 2361 | 3,5-Dbp | H | H | C | O | O | Me | S | — | — | 0 | 1 | 25 |
| 2362 | 3,5-Dbp | H | H | C | O | O | 2-ClPh | O | — | — | 0 | 1 | 25 |
| 2363 | 3,5-Dbp | H | H | C | O | Mee | H | O | — | — | 0 | 1 | 25 |
| 2364 | 3,5-Dbp | H | H | C | O | Mee | H | S | — | — | 0 | 1 | 25 |
| 2365 | 3,5-Dbp | H | H | C | O | Phe | H | O | — | — | 0 | 1 | 25 |
| 2366 | 3,5-Dbp | H | H | C | O | NH | Pr | O | Ete | O | 1 | 1 | 25 |
| 2367 | 3,5-Dbp | H | H | C | O | O | Me | NH | Trim | — | 1 | 1 | 25 |
| 2368 | 4-MeOPh | 4-MeOPh | Ph | C | O | O | H | O | Ete | O | 1 | 1 | 25 |
| 2369 | 4-MeOPh | 4-MeOPh | Ph | C | O | S | H | O | Ete | O | 1 | 1 | 25 |
| 2370 | 4-MeOPh | 4-MeOPh | Ph | C | O | — | — | — | — | — | 0 | 0 | 25 |
| 2371 | 4-MeOPh | 4-MeOPh | Ph | C | O | O | Me | O | — | — | 0 | 1 | 25 |
| 2372 | 4-MeOPh | 4-MeOPh | Ph | C | O | O | Me | S | — | — | 0 | 1 | 25 |
| 2373 | 4-MeOPh | 4-MeOPh | Ph | C | O | O | 2-ClPh | O | — | — | 0 | 1 | 25 |
| 2374 | 4-MeOPh | 4-MeOPh | Ph | C | O | Mee | H | O | — | — | 0 | 1 | 25 |
| 2375 | 4-MeOPh | 4-MeOPh | Ph | C | O | Mee | H | S | — | — | 0 | 1 | 25 |
| 2376 | 4-MeOPh | 4-MeOPh | Ph | C | O | Phe | H | O | — | — | 0 | 1 | 25 |
| 2377 | 4-MeOPh | 4-MeOPh | Ph | C | O | NH | Pr | O | Ete | O | 1 | 1 | 25 |
| 2378 | 4-MeOPh | 4-MeOPh | Ph | C | O | O | Me | NH | Trim | — | 1 | 1 | 25 |
| 2379 | 4-MeOPh | Ph | Ph | C | O | O | H | O | Ete | O | 1 | 1 | 25 |
| 2380 | 4-MeOPh | Ph | Ph | C | O | S | H | O | Ete | O | 1 | 1 | 25 |
| 2381 | 4-MeOPh | Ph | Ph | C | O | — | — | — | — | — | 0 | 0 | 25 |
| 2382 | 4-MeOPh | Ph | Ph | C | O | O | Me | O | — | — | 0 | 1 | 25 |
| 2383 | 4-MeOPh | Ph | Ph | C | O | O | Me | S | — | — | 0 | 1 | 25 |
| 2384 | 4-MeOPh | Ph | Ph | C | O | O | 2-ClPh | O | — | — | 0 | 1 | 25 |
| 2385 | 4-MeOPh | Ph | Ph | C | O | Mee | H | O | — | — | 0 | 1 | 25 |
| 2386 | 4-MeOPh | Ph | Ph | C | O | Mee | H | S | — | — | 0 | 1 | 25 |
| 2387 | 4-MeOPh | Ph | Ph | C | O | Phe | H | O | — | — | 0 | 1 | 25 |
| 2388 | 4-MeOPh | Ph | Ph | C | O | NH | Pr | O | Ete | O | 1 | 1 | 25 |
| 2389 | 4-MeOPh | Ph | Ph | C | O | O | Me | NH | Trim | — | 1 | 1 | 26 |
| 2390 | tBu | Ph | Ph | Si | O | O | H | O | Ete | O | 1 | 1 | 26 |
| 2391 | tBu | Ph | Ph | Si | O | S | H | O | Ete | O | 1 | 1 | 26 |
| 2392 | tBu | Ph | Ph | Si | O | — | — | — | — | — | 0 | 0 | 26 |
| 2393 | tBu | Ph | Ph | Si | O | O | Me | O | — | — | 0 | 1 | 26 |
| 2394 | tBu | Ph | Ph | Si | O | O | Me | S | — | — | 0 | 1 | 26 |
| 2395 | tBu | Ph | Ph | Si | O | O | 2-ClPh | O | — | — | 0 | 1 | 26 |
| 2396 | tBu | Ph | Ph | Si | O | Mee | H | O | — | — | 0 | 1 | 26 |
| 2397 | tBu | Ph | Ph | Si | O | Mee | H | S | — | — | 0 | 1 | 26 |
| 2398 | tBu | Ph | Ph | Si | O | Phe | H | O | — | — | 0 | 1 | 26 |
| 2399 | tBu | Ph | Ph | Si | O | NH | Pr | O | Ete | O | 1 | 1 | 26 |
| 2400 | tBu | Ph | Ph | Si | O | O | Me | NH | Trim | — | 1 | 1 | 26 |
| 2401 | Ph | Ph | Ph | C | S | O | H | O | Ete | O | 1 | 1 | 26 |
| 2402 | Ph | Ph | Ph | C | S | S | H | O | Ete | O | 1 | 1 | 25 |
| 2403 | Ph | Ph | Ph | C | S | — | — | — | — | — | 0 | 0 | 25 |
| 2404 | Ph | Ph | Ph | C | S | O | Me | O | — | — | 0 | 1 | 25 |
| 2405 | Ph | Ph | Ph | C | S | O | Me | S | — | — | 0 | 1 | 25 |
| 2406 | Ph | Ph | Ph | C | S | O | 2-ClPh | O | — | — | 0 | 1 | 25 |
| 2407 | Ph | Ph | Ph | C | S | Mee | H | O | — | — | 0 | 1 | 25 |
| 2408 | Ph | Ph | Ph | C | S | Mee | H | S | — | — | 0 | 1 | 25 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2409 | Ph | Ph | Ph | C | S | Phe | H | O | — | — | 0 | 1 | 26 |
| 2410 | Ph | Ph | Ph | C | S | NH | Pr | O | Ete | O | 1 | 1 | 26 |
| 2411 | Ph | Ph | Ph | C | S | O | Me | NH | Trim | — | 1 | 1 | 26 |
| 2412 | 4-BzOPh | H | H | C | O | O | H | O | Ete | O | 1 | 1 | 26 |
| 2413 | 4-BzOPh | H | H | C | O | S | H | O | Ete | O | 1 | 1 | 26 |
| 2414 | 4-BzOPh | H | H | C | O | — | — | — | — | — | 0 | 0 | 26 |
| 2415 | 4-BzOPh | H | H | C | O | O | Me | O | — | — | 0 | 1 | 26 |
| 2416 | 4-BzOPh | H | H | C | O | O | Me | S | — | — | 0 | 1 | 26 |
| 2417 | 4-BzOPh | H | H | C | O | O | 2-ClPh | O | — | — | 0 | 1 | 26 |
| 2418 | 4-BzOPh | H | H | C | O | Mee | H | O | — | — | 0 | 1 | 26 |
| 2419 | 4-BzOPh | H | H | C | O | Mee | H | S | — | — | 0 | 1 | 26 |
| 2420 | 4-BzOPh | H | H | C | O | Phe | H | O | — | — | 0 | 1 | 26 |
| 2421 | 4-BzOPh | H | H | C | O | NH | Pr | O | Ete | O | 1 | 1 | 26 |
| 2422 | 4-BzOPh | H | H | C | O | O | Me | NH | Trim | — | 1 | 1 | 26 |
| 2423 | Ph | Xanthen-9-yl | | | O | O | H | O | Ete | O | 1 | 1 | 26 |
| 2424 | Ph | Xanthen-9-yl | | | O | S | H | O | Ete | O | 1 | 1 | 26 |
| 2425 | Ph | Xanthen-9-yl | | | O | — | — | — | — | — | 0 | 0 | 26 |
| 2426 | Ph | Xanthen-9-yl | | | O | O | Me | O | — | — | 0 | 1 | 26 |
| 2427 | Ph | Xanthen-9-yl | | | O | O | Me | S | — | — | 0 | 1 | 26 |
| 2428 | Ph | Xanthen-9-yl | | | O | O | 2-ClPh | O | — | — | 0 | 1 | 26 |
| 2429 | Ph | Xanthen-9-yl | | | O | Mee | H | O | — | — | 0 | 1 | 26 |
| 2430 | Ph | Xanthen-9-yl | | | O | Mee | H | S | — | — | 0 | 1 | 26 |
| 2431 | Ph | Xanthen-9-yl | | | O | Phe | H | O | — | — | 0 | 1 | 26 |
| 2432 | Ph | Xanthen-9-yl | | | O | NH | Pr | O | Ete | O | 1 | 1 | 26 |
| 2433 | Ph | Xanthen-9-yl | | | O | O | Me | NH | Trim | — | 1 | 1 | 26 |
| 2434 | Ph | Fluoren-9-yl | | | O | O | H | O | Ete | O | 1 | 1 | 26 |
| 2435 | Ph | Fluoren-9-yl | | | O | S | H | O | Ete | O | 1 | 1 | 26 |
| 2436 | Ph | Fluoren-9-yl | | | O | — | — | — | — | — | 0 | 0 | 26 |
| 2437 | Ph | Fluoren-9-yl | | | O | O | Me | O | — | — | 0 | 1 | 26 |
| 2438 | Ph | Fluoren-9-yl | | | O | O | Me | S | — | — | 0 | 1 | 26 |
| 2439 | Ph | Fluoren-9-yl | | | O | O | 2-ClPh | O | — | — | 0 | 1 | 26 |
| 2440 | Ph | Fluoren-9-yl | | | O | Mee | H | O | — | — | 0 | 1 | 26 |
| 2441 | Ph | Fluoren-9-yl | | | O | Mee | H | S | — | — | 0 | 1 | 26 |
| 2442 | Ph | Fluoren-9-yl | | | O | Phe | H | O | — | — | 0 | 1 | 26 |
| 2443 | Ph | Fluoren-9-yl | | | O | NH | Pr | O | Ete | O | 1 | 1 | 26 |
| 2444 | Ph | Fluoren-9-yl | | | O | O | Me | NH | Trim | — | 1 | 1 | 26 |
| 2445 | 3,4-Dbp | H | H | C | O | O | H | O | Ete | O | 1 | 1 | 27 |
| 2446 | 3,4-Dbp | H | H | C | O | S | H | O | Ete | O | 1 | 1 | 27 |
| 2447 | 3,4-Dbp | H | H | C | O | — | — | — | — | — | 0 | 0 | 27 |
| 2448 | 3,4-Dbp | H | H | C | O | O | Me | O | — | — | 0 | 1 | 27 |
| 2449 | 3,4-Dbp | H | H | C | O | O | Me | S | — | — | 0 | 1 | 27 |
| 2450 | 3,4-Dbp | H | H | C | O | O | 2-ClPh | O | — | — | 0 | 1 | 27 |
| 2451 | 3,4-Dbp | H | H | C | O | Mee | H | O | — | — | 0 | 1 | 27 |
| 2452 | 3,4-Dbp | H | H | C | O | Mee | H | S | — | — | 0 | 1 | 27 |
| 2453 | 3,4-Dbp | H | H | C | O | Phe | H | O | — | — | 0 | 1 | 27 |
| 2454 | 3,4-Dbp | H | H | C | O | NH | Pr | O | Ete | O | 1 | 1 | 27 |
| 2455 | 3,4-Dbp | H | H | C | O | O | Me | NH | Trim | — | 1 | 1 | 27 |
| 2456 | Ph | Ph | Ph | C | O | O | H | O | Ete | O | 1 | 1 | 27 |
| 2457 | Ph | Ph | Ph | C | O | S | H | O | Ete | O | 1 | 1 | 27 |
| 2458 | Ph | Ph | Ph | C | O | — | — | — | — | — | 0 | 0 | 27 |
| 2459 | Ph | Ph | Ph | C | O | O | Me | O | — | — | 0 | 1 | 27 |
| 2460 | Ph | Ph | Ph | C | O | O | Me | S | — | — | 0 | 1 | 27 |
| 2461 | Ph | Ph | Ph | C | O | O | 2-ClPh | O | — | — | 0 | 1 | 27 |
| 2462 | Ph | Ph | Ph | C | O | Mee | H | O | — | — | 0 | 1 | 27 |
| 2463 | Ph | Ph | Ph | C | O | Mee | H | S | — | — | 0 | 1 | 27 |
| 2464 | Ph | Ph | Ph | C | O | Phe | H | O | — | — | 0 | 1 | 27 |
| 2465 | Ph | Ph | Ph | C | O | NH | Pr | O | Ete | O | 1 | 1 | 27 |
| 2466 | Ph | Ph | Ph | C | O | O | Me | NH | Trim | — | 1 | 1 | 27 |
| 2467 | 3,5-Dbp | H | H | C | O | O | H | O | Ete | O | 1 | 1 | 27 |
| 2468 | 3,5-Dbp | H | H | C | O | S | H | O | Ete | O | 1 | 1 | 27 |
| 2469 | 3,5-Dbp | H | H | C | O | — | — | — | — | — | 0 | 0 | 27 |
| 2470 | 3,5-Dbp | H | H | C | O | O | Me | O | — | — | 0 | 1 | 27 |
| 2471 | 3,5-Dbp | H | H | C | O | O | Me | S | — | — | 0 | 1 | 27 |
| 2472 | 3,5-Dbp | H | H | C | O | O | 2-ClPh | O | — | — | 0 | 1 | 27 |
| 2473 | 3,5-Dbp | H | H | C | O | Mee | H | O | — | — | 0 | 1 | 27 |
| 2474 | 3,5-Dbp | H | H | C | O | Mee | H | S | — | — | 0 | 1 | 27 |
| 2475 | 3,5-Dbp | H | H | C | O | Phe | H | O | — | — | 0 | 1 | 27 |
| 2476 | 3,5-Dbp | H | H | C | O | NH | Pr | O | Ete | O | 1 | 1 | 27 |
| 2477 | 3,5-Dbp | H | H | C | O | O | Me | NH | Trim | — | 1 | 1 | 27 |
| 2478 | 4-MeOPh | 4-MeOPh | Ph | C | O | O | H | O | Ete | O | 1 | 1 | 27 |
| 2479 | 4-MeOPh | 4-MeOPh | Ph | C | O | S | H | O | Ete | O | 1 | 1 | 27 |
| 2480 | 4-MeOPh | 4-MeOPh | Ph | C | O | — | — | — | — | — | 0 | 0 | 27 |
| 2481 | 4-MeOPh | 4-MeOPh | Ph | C | O | O | Me | O | — | — | 0 | 1 | 27 |
| 2482 | 4-MeOPh | 4-MeOPh | Ph | C | O | O | Me | S | — | — | 0 | 1 | 27 |
| 2483 | 4-MeOPh | 4-MeOPh | Ph | C | O | O | 2-ClPh | O | — | — | 0 | 1 | 27 |
| 2484 | 4-MeOPh | 4-MeOPh | Ph | C | O | Mee | H | O | — | — | 0 | 1 | 27 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2485 | 4-MeOPh | 4-MeOPh | Ph | C | O | Mee | H | S | — | — | 0 | 1 | 27 |
| 2486 | 4-MeOPh | 4-MeOPh | Ph | C | O | Phe | H | O | — | — | 0 | 1 | 27 |
| 2487 | 4-MeOPh | 4-MeOPh | Ph | C | O | NH | Pr | O | Ete | O | 1 | 1 | 27 |
| 2488 | 4-MeOPh | 4-MeOPh | Ph | C | O | O | Me | NH | Trim | — | 1 | 1 | 27 |
| 2489 | 4-MeOPh | Ph | Ph | C | O | O | H | O | Ete | O | 1 | 1 | 27 |
| 2490 | 4-MeOPh | Ph | Ph | C | O | S | H | O | Ete | O | 1 | 1 | 27 |
| 2491 | 4-MeOPh | Ph | Ph | C | O | — | — | — | — | — | 0 | 0 | 27 |
| 2492 | 4-MeOPh | Ph | Ph | C | O | O | Me | O | — | — | 0 | 1 | 27 |
| 2493 | 4-MeOPh | Ph | Ph | C | O | O | Me | S | — | — | 0 | 1 | 27 |
| 2494 | 4-MeOPh | Ph | Ph | C | O | O | 2-ClPh | O | — | — | 0 | 1 | 27 |
| 2495 | 4-MeOPh | Ph | Ph | C | O | Mee | H | O | — | — | 0 | 1 | 27 |
| 2496 | 4-MeOPh | Ph | Ph | C | O | Mee | H | S | — | — | 0 | 1 | 27 |
| 2497 | 4-MeOPh | Ph | Ph | C | O | Phe | H | O | — | — | 0 | 1 | 27 |
| 2498 | 4-MeOPh | Ph | Ph | C | O | NH | Pr | O | Ete | O | 1 | 1 | 27 |
| 2499 | 4-MeOPh | Ph | Ph | C | O | O | Me | NH | Trim | — | 1 | 1 | 27 |
| 2500 | tBu | Ph | Ph | Si | O | O | H | O | Ete | O | 1 | 1 | 27 |
| 2501 | tBu | Ph | Ph | Si | O | S | H | O | Ete | O | 1 | 1 | 27 |
| 2502 | tBu | Ph | Ph | Si | O | — | — | — | — | — | 0 | 0 | 27 |
| 2503 | tBu | Ph | Ph | Si | O | O | Me | O | — | — | 0 | 1 | 27 |
| 2504 | tBu | Ph | Ph | Si | O | O | Me | S | — | — | 0 | 1 | 27 |
| 2505 | tBu | Ph | Ph | Si | O | O | 2-ClPh | O | — | — | 0 | 1 | 27 |
| 2506 | tBu | Ph | Ph | Si | O | Mee | H | O | — | — | 0 | 1 | 27 |
| 2507 | tBu | Ph | Ph | Si | O | Mee | H | S | — | — | 0 | 1 | 27 |
| 2508 | tBu | Ph | Ph | Si | O | Phe | H | O | — | — | 0 | 1 | 27 |
| 2509 | tBu | Ph | Ph | Si | O | NH | Pr | O | Ete | O | 1 | 1 | 27 |
| 2510 | tBu | Ph | Ph | Si | O | O | Me | NH | Trim | — | 1 | 1 | 27 |
| 2511 | Ph | Ph | Ph | C | S | O | H | O | Ete | O | 1 | 1 | 27 |
| 2512 | Ph | Ph | Ph | C | S | S | H | O | Ete | O | 1 | 1 | 27 |
| 2513 | Ph | Ph | Ph | C | S | — | — | — | — | — | 0 | 0 | 27 |
| 2514 | Ph | Ph | Ph | C | S | O | Me | O | — | — | 0 | 1 | 27 |
| 2515 | Ph | Ph | Ph | C | S | O | Me | S | — | — | 0 | 1 | 27 |
| 2516 | Ph | Ph | Ph | C | S | O | 2-ClPh | O | — | — | 0 | 1 | 27 |
| 2517 | Ph | Ph | Ph | C | S | Mee | H | O | — | — | 0 | 1 | 27 |
| 2518 | Ph | Ph | Ph | C | S | Mee | H | S | — | — | 0 | 1 | 27 |
| 2519 | Ph | Ph | Ph | C | S | Phe | H | O | — | — | 0 | 1 | 27 |
| 2520 | Ph | Ph | Ph | C | S | NH | Pr | O | Ete | O | 1 | 1 | 27 |
| 2521 | Ph | Ph | Ph | C | S | O | Me | NH | Trim | — | 1 | 1 | 27 |
| 2522 | 4-BzOPh | H | H | C | O | O | H | O | Ete | O | 1 | 1 | 27 |
| 2523 | 4-BzOPh | H | H | C | O | S | H | O | Ete | O | 1 | 1 | 27 |
| 2524 | 4-BzOPh | H | H | C | O | — | — | — | — | — | 0 | 0 | 27 |
| 2525 | 4-BzOPh | H | H | C | O | O | Me | O | — | — | 0 | 1 | 27 |
| 2526 | 4-BzOPh | H | H | C | O | O | Me | S | — | — | 0 | 1 | 27 |
| 2527 | 4-BzOPh | H | H | C | O | O | 2-ClPh | O | — | — | 0 | 1 | 27 |
| 2528 | 4-BzOPh | H | H | C | O | Mee | H | O | — | — | 0 | 1 | 27 |
| 2529 | 4-BzOPh | H | H | C | O | Mee | H | S | — | — | 0 | 1 | 27 |
| 2530 | 4-BzOPh | H | H | C | O | Phe | H | O | — | — | 0 | 1 | 27 |
| 2531 | 4-BzOPh | H | H | C | O | NH | Pr | O | Ete | O | 1 | 1 | 27 |
| 2532 | 4-BzOPh | H | H | C | O | O | Me | NH | Trim | — | 1 | 1 | 27 |
| 2533 | Ph | Xanthen-9-yl | | | O | O | H | O | Ete | O | 1 | 1 | 27 |
| 2534 | Ph | Xanthen-9-yl | | | O | S | H | O | Ete | O | 1 | 1 | 27 |
| 2535 | Ph | Xanthen-9-yl | | | O | — | — | — | — | — | 0 | 0 | 27 |
| 2536 | Ph | Xanthen-9-yl | | | O | O | Me | O | — | — | 0 | 1 | 27 |
| 2537 | Ph | Xanthen-9-yl | | | O | O | Me | S | — | — | 0 | 1 | 27 |
| 2538 | Ph | Xanthen-9-yl | | | O | O | 2-ClPh | O | — | — | 0 | 1 | 27 |
| 2539 | Ph | Xanthen-9-yl | | | O | Mee | H | O | — | — | 0 | 1 | 27 |
| 2540 | Ph | Xanthen-9-yl | | | O | Mee | H | S | — | — | 0 | 1 | 27 |
| 2541 | Ph | Xanthen-9-yl | | | O | Phe | H | O | — | — | 0 | 1 | 27 |
| 2542 | Ph | Xanthen-9-yl | | | O | NH | Pr | O | Ete | O | 1 | 1 | 27 |
| 2543 | Ph | Xanthen-9-yl | | | O | O | Me | NH | Trim | — | 1 | 1 | 27 |
| 2544 | Ph | Fluoren-9-yl | | | O | O | H | O | Ete | O | 1 | 1 | 27 |
| 2545 | Ph | Fluoren-9-yl | | | O | S | H | O | Ete | O | 1 | 1 | 27 |
| 2546 | Ph | Fluoren-9-yl | | | O | — | — | — | — | — | 0 | 0 | 27 |
| 2547 | Ph | Fluoren-9-yl | | | O | O | Me | O | — | — | 0 | 1 | 27 |
| 2548 | Ph | Fluoren-9-yl | | | O | O | Me | S | — | — | 0 | 1 | 27 |
| 2549 | Ph | Fluoren-9-yl | | | O | O | 2-ClPh | O | — | — | 0 | 1 | 27 |
| 2550 | Ph | Fluoren-9-yl | | | O | Mee | H | O | — | — | 0 | 1 | 27 |
| 2551 | Ph | Fluoren-9-yl | | | O | Mee | H | S | — | — | 0 | 1 | 27 |
| 2552 | Ph | Fluoren-9-yl | | | O | Phe | H | O | — | — | 0 | 1 | 27 |
| 2553 | Ph | Fluoren-9-yl | | | O | NH | Pr | O | Ete | O | 1 | 1 | 27 |
| 2554 | Ph | Fluoren-9-yl | | | O | O | Me | NH | Trim | — | 1 | 1 | 27 |
| 2555 | 3,4-Dbp | H | H | C | O | O | H | O | Ete | O | 1 | 1 | 28 |
| 2556 | 3,4-Dbp | H | H | C | O | S | H | O | Ete | O | 1 | 1 | 28 |
| 2557 | 3,4-Dbp | H | H | C | O | — | — | — | — | — | 0 | 0 | 28 |
| 2558 | 3,4-Dbp | H | H | C | O | O | Me | O | — | — | 0 | 1 | 28 |
| 2559 | 3,4-Dbp | H | H | C | O | O | Me | S | — | — | 0 | 1 | 28 |
| 2560 | 3,4-Dbp | H | H | C | O | O | 2-ClPh | O | — | — | 0 | 1 | 28 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2561 | 3,4-Dbp | H | H | C | O | Mee | H | O | — | — | 0 | 1 | 28 |
| 2562 | 3,4-Dbp | H | H | C | O | Mee | H | S | — | — | 0 | 1 | 28 |
| 2563 | 3,4-Dbp | H | H | C | O | Phe | H | O | — | — | 0 | 1 | 28 |
| 2564 | 3,4-Dbp | H | H | C | O | NH | Pr | O | Ete | O | 1 | 1 | 28 |
| 2565 | 3,4-Dbp | H | H | C | O | O | Me | NH | Trim | — | 1 | 1 | 28 |
| 2566 | Ph | Ph | Ph | C | O | O | H | O | Ete | O | 1 | 1 | 28 |
| 2567 | Ph | Ph | Ph | C | O | S | H | O | Ete | O | 1 | 1 | 28 |
| 2568 | Ph | Ph | Ph | C | O | — | — | — | — | — | 0 | 0 | 28 |
| 2569 | Ph | Ph | Ph | C | O | O | Me | O | — | — | 0 | 1 | 28 |
| 2570 | Ph | Ph | Ph | C | O | O | Me | S | — | — | 0 | 1 | 28 |
| 2571 | Ph | Ph | Ph | C | O | O | 2-ClPh | O | — | — | 0 | 1 | 28 |
| 2572 | Ph | Ph | Ph | C | O | Mee | H | O | — | — | 0 | 1 | 28 |
| 2573 | Ph | Ph | Ph | C | O | Mee | H | S | — | — | 0 | 1 | 28 |
| 2574 | Ph | Ph | Ph | C | O | Phe | H | O | — | — | 0 | 1 | 28 |
| 2575 | Ph | Ph | Ph | C | O | NH | Pr | O | Ete | O | 1 | 1 | 28 |
| 2576 | Ph | Ph | Ph | C | O | O | Me | NH | Trim | — | 1 | 1 | 28 |
| 2577 | 3,5-Dbp | H | H | C | O | O | H | O | Ete | O | 1 | 1 | 28 |
| 2578 | 3,5-Dbp | H | H | C | O | S | H | O | Ete | O | 1 | 1 | 28 |
| 2579 | 3,5-Dbp | H | H | C | O | — | — | — | — | — | 0 | 0 | 28 |
| 2580 | 3,5-Dbp | H | H | C | O | O | Me | O | — | — | 0 | 1 | 28 |
| 2581 | 3,5-Dbp | H | H | C | O | O | Me | S | — | — | 0 | 1 | 28 |
| 2582 | 3,5-Dbp | H | H | C | O | O | 2-ClPh | O | — | — | 0 | 1 | 28 |
| 2583 | 3,5-Dbp | H | H | C | O | Mee | H | O | — | — | 0 | 1 | 28 |
| 2584 | 3,5-Dbp | H | H | C | O | Mee | H | S | — | — | 0 | 1 | 28 |
| 2585 | 3,5-Dbp | H | H | C | O | Phe | H | O | — | — | 0 | 1 | 28 |
| 2586 | 3,5-Dbp | H | H | C | O | NH | Pr | O | Ete | O | 1 | 1 | 28 |
| 2587 | 3,5-Dbp | H | H | C | O | O | Me | NH | Trim | — | 1 | 1 | 28 |
| 2588 | 4-MeOPh | 4-MeOPh | Ph | C | O | O | H | O | Ete | O | 1 | 1 | 28 |
| 2589 | 4-MeOPh | 4-MeOPh | Ph | C | O | S | H | O | Ete | O | 1 | 1 | 28 |
| 2590 | 4-MeOPh | 4-MeOPh | Ph | C | O | — | — | — | — | — | 0 | 0 | 28 |
| 2591 | 4-MeOPh | 4-MeOPh | Ph | C | O | O | Me | O | — | — | 0 | 1 | 28 |
| 2592 | 4-MeOPh | 4-MeOPh | Ph | C | O | O | Me | S | — | — | 0 | 1 | 28 |
| 2593 | 4-MeOPh | 4-MeOPh | Ph | C | O | O | 2-ClPh | O | — | — | 0 | 1 | 28 |
| 2594 | 4-MeOPh | 4-MeOPh | Ph | C | O | Mee | H | O | — | — | 0 | 1 | 28 |
| 2595 | 4-MeOPh | 4-MeOPh | Ph | C | O | Mee | H | S | — | — | 0 | 1 | 28 |
| 2596 | 4-MeOPh | 4-MeOPh | Ph | C | O | Phe | H | O | — | — | 0 | 1 | 28 |
| 2597 | 4-MeOPh | 4-MeOPh | Ph | C | O | NH | Pr | O | Ete | O | 1 | 1 | 28 |
| 2598 | 4-MeOPh | 4-MeOPh | Ph | C | O |  | O | Me | NH Trim | — | 1 | 1 | 28 |
| 2599 | 4-MeOPh | Ph | Ph | C | O | O | H | O | Ete | O | 1 | 1 | 28 |
| 2600 | 4-MeOPh | Ph | Ph | C | O | S | H | O | Ete | O | 1 | 1 | 28 |
| 2601 | 4-MeOPh | Ph | Ph | C | O | — | — | — | — | — | 0 | 0 | 28 |
| 2602 | 4-MeOPh | Ph | Ph | C | O | O | Me | O | — | — | 0 | 1 | 28 |
| 2603 | 4-MeOPh | Ph | Ph | C | O | O | Me | S | — | — | 0 | 1 | 28 |
| 2604 | 4-MeOPh | Ph | Ph | C | O | O | 2-ClPh | O | — | — | 0 | 1 | 28 |
| 2605 | 4-MeOPh | Ph | Ph | C | O | Mee | H | O | — | — | 0 | 1 | 28 |
| 2606 | 4-MeOPh | Ph | Ph | C | O | Mee | H | S | — | — | 0 | 1 | 28 |
| 2607 | 4-MeOPh | Ph | Ph | C | O | Phe | H | O | — | — | 0 | 1 | 28 |
| 2608 | 4-MeOPh | Ph | Ph | C | O | NH | Pr | O | Ete | O | 1 | 1 | 28 |
| 2609 | 4-MeOPh | Ph | Ph | C | O | O | Me | NH | Trim | — | 1 | 1 | 28 |
| 2610 | tBu | Ph | Ph | Si | O | O | H | O | Ete | O | 1 | 1 | 28 |
| 2611 | tBu | Ph | Ph | Si | O | S | H | O | Ete | O | 1 | 1 | 28 |
| 2612 | tBu | Ph | Ph | Si | O | — | — | — | — | — | 0 | 0 | 28 |
| 2613 | tBu | Ph | Ph | Si | O | O | Me | O | — | — | 0 | 1 | 28 |
| 2614 | tBu | Ph | Ph | Si | O | O | Me | S | — | — | 0 | 1 | 28 |
| 2615 | tBu | Ph | Ph | Si | O | O | 2-ClPh | O | — | — | 0 | 1 | 28 |
| 2616 | tBu | Ph | Ph | Si | O | Mee | H | O | — | — | 0 | 1 | 28 |
| 2617 | tBu | Ph | Ph | Si | O | Mee | H | S | — | — | 0 | 1 | 28 |
| 2618 | tBu | Ph | Ph | Si | O | Phe | H | O | — | — | 0 | 1 | 28 |
| 2619 | tBu | Ph | Ph | Si | O | NH | Pr | O | Ete | O | 1 | 1 | 28 |
| 2620 | tBu | Ph | Ph | Si | O | O | Me | NH | Trim | — | 1 | 1 | 28 |
| 2621 | Ph | Ph | Ph | C | S | O | H | O | Ete | O | 1 | 1 | 28 |
| 2622 | Ph | Ph | Ph | C | S | S | H | O | Ete | O | 1 | 1 | 28 |
| 2623 | Ph | Ph | Ph | C | S | — | — | — | — | — | 0 | 0 | 28 |
| 2624 | Ph | Ph | Ph | C | S | O | Me | O | — | — | 0 | 1 | 28 |
| 2625 | Ph | Ph | Ph | C | S | O | Me | S | — | — | 0 | 1 | 28 |
| 2626 | Ph | Ph | Ph | C | S | O | 2-ClPh | O | — | — | 0 | 1 | 28 |
| 2627 | Ph | Ph | Ph | C | S | Mee | H | O | — | — | 0 | 1 | 28 |
| 2628 | Ph | Ph | Ph | C | S | Mee | H | S | — | — | 0 | 1 | 28 |
| 2629 | Ph | Ph | Ph | C | S | Phe | H | O | — | — | 0 | 1 | 28 |
| 2630 | Ph | Ph | Ph | C | S | NH | Pr | O | Ete | O | 1 | 1 | 28 |
| 2631 | Ph | Ph | Ph | C | S | O | Me | NH | Trim | — | 1 | 1 | 28 |
| 2632 | 4-BzOPh | H | H | C | O | O | H | O | Ete | O | 1 | 1 | 28 |
| 2633 | 4-BzOPh | H | H | C | O | S | H | O | Ete | O | 1 | 1 | 28 |
| 2634 | 4-BzOPh | H | H | C | O | — | — | — | — | — | 0 | 0 | 28 |
| 2635 | 4-BzOPh | H | H | C | O | O | Me | O | — | — | 0 | 1 | 28 |
| 2636 | 4-BzOPh | H | H | C | O | O | Me | S | — | — | 0 | 1 | 28 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2637 | 4-BzOPh | H | H | C | O | O | 2-ClPh | O | — | — | 0 | 1 | 28 |
| 2638 | 4-BzOPh | H | H | C | O | Mee | H | O | — | — | 0 | 1 | 28 |
| 2639 | 4-BzOPh | H | H | C | O | Mee | H | S | — | — | 0 | 1 | 28 |
| 2640 | 4-BzOPh | H | H | C | O | Phe | H | O | — | — | 0 | 1 | 28 |
| 2641 | 4-BzOPh | H | H | C | O | NH | Pr | O | Ete | O | 1 | 1 | 28 |
| 2642 | 4-BzOPh | H | H | C | O | O | Me | NH | Trim | — | 1 | 1 | 28 |
| 2643 | Ph | Xanthen-9-yl | | | O | O | H | O | Ete | O | 1 | 1 | 28 |
| 2644 | Ph | Xanthen-9-yl | | | O | S | H | O | Ete | O | 1 | 1 | 28 |
| 2645 | Ph | Xanthen-9-yl | | | O | — | — | — | — | — | 0 | 0 | 28 |
| 2646 | Ph | Xanthen-9-yl | | | O | O | Me | O | — | — | 0 | 1 | 28 |
| 2647 | Ph | Xanthen-9-yl | | | O | O | Me | S | — | — | 0 | 1 | 28 |
| 2648 | Ph | Xanthen-9-yl | | | O | O | 2-ClPh | O | — | — | 0 | 1 | 28 |
| 2649 | Ph | Xanthen-9-yl | | | O | Mee | H | O | — | — | 0 | 1 | 28 |
| 2650 | Ph | Xanthen-9-yl | | | O | Mee | H | S | — | — | 0 | 1 | 28 |
| 2651 | Ph | Xanthen-9-yl | | | O | Phe | H | O | — | — | 0 | 1 | 28 |
| 2652 | Ph | Xanthen-9-yl | | | O | NH | Pr | O | Ete | O | 1 | 1 | 28 |
| 2653 | Ph | Xanthen-9-yl | | | O | O | Me | NH | Trim | — | 1 | 1 | 28 |
| 2654 | Ph | Fluoren-9-yl | | | O | O | H | O | Ete | O | 1 | 1 | 28 |
| 2655 | Ph | Fluoren-9-yl | | | O | S | H | O | Ete | O | 1 | 1 | 28 |
| 2656 | Ph | Fluoren-9-yl | | | O | — | — | — | — | — | 0 | 0 | 28 |
| 2657 | Ph | Fluoren-9-yl | | | O | O | Me | O | — | — | 0 | 1 | 28 |
| 2658 | Ph | Fluoren-9-yl | | | O | O | Me | S | — | — | 0 | 1 | 28 |
| 2659 | Ph | Fluoren-9-yl | | | O | O | 2-ClPh | O | — | — | 0 | 1 | 28 |
| 2660 | Ph | Fluoren-9-yl | | | O | Mee | H | O | — | — | 0 | 1 | 28 |
| 2661 | Ph | Fluoren-9-yl | | | O | Mee | H | S | — | — | 0 | 1 | 28 |
| 2662 | Ph | Fluoren-9-yl | | | O | Phe | H | O | — | — | 0 | 1 | 28 |
| 2663 | Ph | Fluoren-9-yl | | | O | NH | Pr | O | Ete | O | 1 | 1 | 28 |
| 2664 | Ph | Fluoren-9-yl | | | O | O | Me | NH | Trim | — | 1 | 1 | 28 |
| 2665 | 3,4-Dbp | H | H | C | O | O | H | O | Ete | O | 1 | 1 | 29 |
| 2666 | 3,4-Dbp | H | H | C | O | S | H | O | Ete | O | 1 | 1 | 29 |
| 2667 | 3,4-Dbp | H | H | C | O | — | — | — | — | — | 0 | 0 | 29 |
| 2668 | 3,4-Dbp | H | H | C | O | O | Me | O | — | — | 0 | 1 | 29 |
| 2669 | 3,4-Dbp | H | H | C | O | O | Me | S | — | — | 0 | 1 | 29 |
| 2670 | 3,4-Dbp | H | H | C | O | O | 2-ClPh | O | — | — | 0 | 1 | 29 |
| 2671 | 3,4-Dbp | H | H | C | O | Mee | H | O | — | — | 0 | 1 | 29 |
| 2672 | 3,4-Dbp | H | H | C | O | Mee | H | S | — | — | 0 | 1 | 29 |
| 2673 | 3,4-Dbp | H | H | C | O | Phe | H | O | — | — | 0 | 1 | 29 |
| 2674 | 3,4-Dbp | H | H | C | O | NH | Pr | O | Ete | O | 1 | 1 | 29 |
| 2675 | 3,4-Dbp | H | H | C | O | O | Me | NH | Trim | — | 1 | 1 | 29 |
| 2676 | Ph | Ph | Ph | C | O | O | H | O | Ete | O | 1 | 1 | 29 |
| 2677 | Ph | Ph | Ph | C | O | S | H | O | Ete | O | 1 | 1 | 29 |
| 2678 | Ph | Ph | Ph | C | O | — | — | — | — | — | 0 | 0 | 29 |
| 2679 | Ph | Ph | Ph | C | O | O | Me | O | — | — | 0 | 1 | 29 |
| 2680 | Ph | Ph | Ph | C | O | O | Me | S | — | — | 0 | 1 | 29 |
| 2681 | Ph | Ph | Ph | C | O | O | 2-ClPh | O | — | — | 0 | 1 | 29 |
| 2682 | Ph | Ph | Ph | C | O | Mee | H | O | — | — | 0 | 1 | 29 |
| 2683 | Ph | Ph | Ph | C | O | Mee | H | S | — | — | 0 | 1 | 29 |
| 2684 | Ph | Ph | Ph | C | O | Phe | H | O | — | — | 0 | 1 | 29 |
| 2685 | Ph | Ph | Ph | C | O | NH | Pr | O | Ete | O | 1 | 1 | 29 |
| 2686 | Ph | Ph | Ph | C | O | O | Me | NH | Trim | — | 1 | 1 | 29 |
| 2687 | 3,5-Dbp | H | H | C | O | O | H | O | Ete | O | 1 | 1 | 29 |
| 2688 | 3,5-Dbp | H | H | C | O | S | H | O | Ete | O | 1 | 1 | 29 |
| 2689 | 3,5-Dbp | H | H | C | O | — | — | — | — | — | 0 | 0 | 29 |
| 2690 | 3,5-Dbp | H | H | C | O | O | Me | O | — | — | 0 | 1 | 29 |
| 2691 | 3,5-Dbp | H | H | C | O | O | Me | S | — | — | 0 | 1 | 29 |
| 2692 | 3,5-Dbp | H | H | C | O | O | 2-ClPh | O | — | — | 0 | 1 | 29 |
| 2693 | 3,5-Dbp | N | H | C | O | Mee | H | O | — | — | 0 | 1 | 29 |
| 2694 | 3,5-Dbp | H | H | C | O | Mee | H | S | — | — | 0 | 1 | 29 |
| 2695 | 3,5-Dbp | H | H | C | O | Phe | H | O | — | — | 0 | 1 | 29 |
| 2696 | 3,5-Dbp | H | H | C | O | NH | Pr | O | Ete | O | 1 | 1 | 29 |
| 2697 | 3,5-Dbp | H | H | C | O | O | Me | NH | Trim | — | 1 | 1 | 29 |
| 2698 | 4-MeOPh | 4-MeOPh | Ph | C | O | O | H | O | Ete | O | 1 | 1 | 29 |
| 2699 | 4-MeOPh | 4-MeOPh | Ph | C | O | S | H | O | Ete | O | 1 | 1 | 29 |
| 2700 | 4-MeOPh | 4-MeOPh | Ph | C | O | — | — | — | — | — | 0 | 0 | 29 |
| 2701 | 4-MeOPh | 4-MeOPh | Ph | C | O | O | Me | O | — | — | 0 | 1 | 29 |
| 2702 | 4-MeOPh | 4-MeOPh | Ph | C | O | O | Me | S | — | — | 0 | 1 | 29 |
| 2703 | 4-MeOPh | 4-MeOPh | Ph | C | O | O | 2-ClPh | O | — | — | 0 | 1 | 29 |
| 2704 | 4-MeOPh | 4-MeOPh | Ph | C | O | Mee | H | O | — | — | 0 | 1 | 29 |
| 2705 | 4-MeOPh | 4-MeOPh | Ph | C | O | Mee | H | S | — | — | 0 | 1 | 29 |
| 2706 | 4-MeOPh | 4-MeOPh | Ph | C | O | Phe | H | O | — | — | 0 | 1 | 29 |
| 2707 | 4-MeOPh | 4-MeOPh | Ph | C | O | NH | Pr | O | Ete | O | 1 | 1 | 29 |
| 2708 | 4-MeOPh | 4-MeOPh | Ph | C | O | O | Me | NH | Trim | — | 1 | 1 | 29 |
| 2709 | 4-MeOPh | Ph | Ph | C | O | O | H | O | Ete | O | 1 | 1 | 29 |
| 2710 | 4-MeOPh | Ph | Ph | C | O | S | H | O | Ete | O | 1 | 1 | 29 |
| 2711 | 4-MeOPh | Ph | Ph | C | O | — | — | — | — | — | 0 | 0 | 29 |
| 2712 | 4-MeOPh | Ph | Ph | C | O | O | Me | O | — | — | 0 | 1 | 29 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2713 | 4-MeOPh | Ph | Ph | C | O | O | Me | S | — | — | 0 | 1 | 29 |
| 2714 | 4-MeOPh | Ph | Ph | C | O | O | 2-ClPh | O | — | — | 0 | 1 | 29 |
| 2715 | 4-MeOPh | Ph | Ph | C | O | Mee | H | O | — | — | 0 | 1 | 29 |
| 2716 | 4-MeOPh | Ph | Ph | C | O | Mee | H | S | — | — | 0 | 1 | 29 |
| 2717 | 4-MeOPh | Ph | Ph | C | O | Phe | H | O | — | — | 0 | 1 | 29 |
| 2718 | 4-MeOPh | Ph | Ph | C | O | NH | Pr | O | Ete | O | 1 | 1 | 29 |
| 2719 | 4-MeOPh | Ph | Ph | C | O | O | Me | NH | Trim | — | 1 | 1 | 29 |
| 2720 | tBu | Ph | Ph | Si | O | O | N | O | Ete | O | 1 | 1 | 29 |
| 2721 | tBu | Ph | Ph | Si | O | S | H | O | Ete | O | 1 | 1 | 29 |
| 2722 | tBu | Ph | Ph | Si | O | — | — | — | — | — | 0 | 0 | 29 |
| 2723 | tBu | Ph | Ph | Si | O | O | Me | O | — | — | 0 | 1 | 29 |
| 2724 | tBu | Ph | Ph | Si | O | O | Me | S | — | — | 0 | 1 | 29 |
| 2725 | tBu | Ph | Ph | Si | O | O | 2-ClPh | O | — | — | 0 | 1 | 29 |
| 2726 | tBu | Ph | Ph | Si | O | Mee | H | O | — | — | 0 | 1 | 29 |
| 2727 | tBu | Ph | Ph | Si | O | Mee | H | S | — | — | 0 | 1 | 29 |
| 2728 | tBu | Ph | Ph | Si | O | Phe | H | O | — | — | 0 | 1 | 29 |
| 2729 | tBu | Ph | Ph | Si | O | NH | Pr | O | Ete | O | 1 | 1 | 29 |
| 2730 | tBu | Ph | Ph | Si | O | O | Me | NH | Trim | — | 1 | 1 | 29 |
| 2731 | Ph | Ph | Ph | C | S | O | H | O | Ete | O | 1 | 1 | 29 |
| 2732 | Ph | Ph | Ph | C | S | S | H | O | Ete | O | 1 | 1 | 29 |
| 2733 | Ph | Ph | Ph | C | S | — | — | — | — | — | 0 | 0 | 29 |
| 2734 | Ph | Ph | Ph | C | S | O | Me | O | — | — | 0 | 1 | 29 |
| 2735 | Ph | Ph | Ph | C | S | O | Me | S | — | — | 0 | 1 | 29 |
| 2736 | Ph | Ph | Ph | C | S | O | 2-ClPh | O | — | — | 0 | 1 | 29 |
| 2737 | Ph | Ph | Ph | C | S | Mee | H | O | — | — | 0 | 1 | 29 |
| 2738 | Ph | Ph | Ph | C | S | Mee | H | S | — | — | 0 | 1 | 29 |
| 2739 | Ph | Ph | Ph | C | S | Phe | H | O | — | — | 0 | 1 | 29 |
| 2740 | Ph | Ph | Ph | C | S | NH | Pr | O | Ete | O | 1 | 1 | 29 |
| 2741 | Ph | Ph | Ph | C | S | O | Me | NH | Trim | — | 1 | 1 | 29 |
| 2742 | 4-BzOPh | H | H | C | O | O | H | O | Ete | O | 1 | 1 | 29 |
| 2743 | 4-BzOPh | H | H | C | O | S | H | O | Ete | O | 1 | 1 | 29 |
| 2744 | 4-BzOPh | H | H | C | O | — | — | — | — | — | 0 | 0 | 29 |
| 2745 | 4-BzOPh | H | H | C | O | O | Me | O | — | — | 0 | 1 | 29 |
| 2746 | 4-BzOPh | H | H | C | O | O | Me | S | — | — | 0 | 1 | 29 |
| 2747 | 4-BzOPh | H | H | C | O | O | 2-ClPh | O | — | — | 0 | 1 | 29 |
| 2748 | 4-BzOPh | H | H | C | O | Mee | H | O | — | — | 0 | 1 | 29 |
| 2749 | 4-BzOPh | H | H | C | O | Mee | H | S | — | — | 0 | 1 | 29 |
| 2750 | 4-BzOPh | H | H | C | O | Phe | H | O | — | — | 0 | 1 | 29 |
| 2751 | 4-BzOPh | H | H | C | O | NH | Pr | O | Ete | O | 1 | 1 | 29 |
| 2752 | 4-BzOPh | H | H | C | O | O | Me | NH | Trim | — | 1 | 1 | 29 |
| 2753 | Ph | Xanthen-9-yl | | | O | O | H | O | Ete | O | 1 | 1 | 29 |
| 2754 | Ph | Xanthen-9-yl | | | O | S | H | O | Ete | O | 1 | 1 | 29 |
| 2755 | Ph | Xanthen-9-yl | | | O | — | — | — | — | — | 0 | 0 | 29 |
| 2756 | Ph | Xanthen-9-yl | | | O | O | Me | O | — | — | 0 | 1 | 29 |
| 2757 | Ph | Xanthen-9-yl | | | O | O | Me | S | — | — | 0 | 1 | 29 |
| 2758 | Ph | Xanthen-9-yl | | | O | O | 2-ClPh | O | — | — | 0 | 1 | 29 |
| 2759 | Ph | Xanthen-9-yl | | | O | Mee | H | O | — | — | 0 | 1 | 29 |
| 2760 | Ph | Xanthen-9-yl | | | O | Mee | H | S | — | — | 0 | 1 | 29 |
| 2761 | Ph | Xanthen-9-yl | | | O | Phe | H | O | — | — | 0 | 1 | 29 |
| 2762 | Ph | Xanthen-9-yl | | | O | NH | Pr | O | Ete | O | 1 | 1 | 29 |
| 2763 | Ph | Xanthen-9-yl | | | O | O | Me | NH | Trim | — | 1 | 1 | 29 |
| 2764 | Ph | Fluoren-9-yl | | | O | O | H | O | Ete | O | 1 | 1 | 29 |
| 2765 | Ph | Fluoren-9-yl | | | O | S | H | O | Ete | O | 1 | 1 | 29 |
| 2766 | Ph | Fluoren-9-yl | | | O | — | — | — | — | — | 0 | 0 | 29 |
| 2767 | Ph | Fluoren-9-yl | | | O | O | Me | O | — | — | 0 | 1 | 29 |
| 2768 | Ph | Fluoren-9-yl | | | O | O | Me | S | — | — | 0 | 1 | 29 |
| 2769 | Ph | Fluoren-9-yl | | | O | O | 2-ClPh | O | — | — | 0 | 1 | 29 |
| 2770 | Ph | Fluoren-9-yl | | | O | Mee | H | O | — | — | 0 | 1 | 29 |
| 2771 | Ph | Fluoren-9-yl | | | O | Mee | H | S | — | — | 0 | 1 | 29 |
| 2772 | Ph | Fluoren-9-yl | | | O | Phe | H | O | — | — | 0 | 1 | 29 |
| 2773 | Ph | Fluoren-9-yl | | | O | NH | Pr | O | Ete | O | 1 | 1 | 29 |
| 2774 | Ph | Fluoren-9-yl | | | O | O | Me | NH | Trim | — | 1 | 1 | 29 |
| 2775 | 3,4-Dbp | H | H | C | S | O | H | O | Ete | O | 1 | 1 | Ţ |
| 2776 | 3,4-Dbp | H | H | C | S | S | H | O | Ete | O | 1 | 1 | Ţ |
| 2777 | 3,4-Dbp | H | H | C | S | — | — | — | — | — | 0 | 0 | Ţ |
| 2778 | 3,4-Dbp | H | H | C | S | O | Me | O | — | — | 0 | 1 | Ţ |
| 2779 | 3,4-Dbp | H | H | C | S | O | Me | S | — | — | 0 | 1 | Ţ |
| 2780 | 3,4-Dbp | H | H | C | S | O | 2-ClPh | O | — | — | 0 | 1 | Ţ |
| 2781 | 3,4-Dbp | H | H | C | S | Mee | H | O | — | — | 0 | 1 | Ţ |
| 2782 | 3,4-Dbp | H | H | C | S | Mee | H | S | — | — | 0 | 1 | Ţ |
| 2783 | 3,4-Dbp | H | H | C | S | Phe | H | O | — | — | 0 | 1 | Ţ |
| 2784 | 3,4-Dbp | H | H | C | S | NH | Pr | O | Ete | O | 1 | 1 | Ţ |
| 2785 | 3,4-Dbp | H | H | C | S | O | Me | NH | Trim | — | 1 | 1 | Ţ |
| 2786 | 9-Ant | H | H | C | S | O | H | O | Ete | O | 1 | 1 | Ţ |
| 2787 | 9-Ant | H | H | C | S | S | H | O | Ete | O | 1 | 1 | Ţ |
| 2788 | 9-Ant | H | H | C | S | — | — | — | — | — | 0 | 0 | Ţ |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2789 | 9-Ant | H | H | C | S | O | Me | O | — | — | 0 | 1 | 1 |
| 2790 | 9-Ant | H | H | C | S | O | Me | S | — | — | 0 | 1 | 1 |
| 2791 | 9-Ant | H | H | C | S | O | 2-ClPh | O | — | — | 0 | 1 | 1 |
| 2792 | 9-Ant | H | H | C | S | Mee | H | O | — | — | 0 | 1 | 1 |
| 2793 | 9-Ant | H | H | C | S | Mee | H | S | — | — | 0 | 1 | 1 |
| 2794 | 9-Ant | H | H | C | S | Phe | H | O | — | — | 0 | 1 | 1 |
| 2795 | 9-Ant | H | H | C | S | NH | Pr | O | Ete | O | 1 | 1 | 1 |
| 2796 | 9-Ant | H | H | C | S | O | Me | NH | Trim | — | 1 | 1 | 1 |
| 2797 | 2-Npe | H | H | C | S | O | H | O | Ete | O | 1 | 1 | 1 |
| 2798 | 2-Npe | H | H | C | S | S | H | O | Ete | O | 1 | 1 | 1 |
| 2799 | 2-Npe | H | H | C | S | — | — | — | — | — | 0 | 0 | 1 |
| 2800 | 2-Npe | H | H | C | S | O | Me | O | — | — | 0 | 1 | 1 |
| 2801 | 2-Npe | H | H | C | S | O | Me | S | — | — | 0 | 1 | 1 |
| 2802 | 2-Npe | H | H | C | S | O | 2-ClPh | O | — | — | 0 | 1 | 1 |
| 2803 | 2-Npe | H | H | C | S | Mee | H | O | — | — | 0 | 1 | 1 |
| 2804 | 2-Npe | H | H | C | S | Mee | H | S | — | — | 0 | 1 | 1 |
| 2805 | 2-Npe | H | H | C | S | Phe | H | O | — | — | 0 | 1 | 1 |
| 2806 | 2-Npe | H | H | C | S | NH | Pr | O | Ete | O | 1 | 1 | 1 |
| 2807 | 2-Npe | H | H | C | S | O | Me | NH | Trim | — | 1 | 1 | 1 |
| 2808 | Bdbbp | H | H | C | S | O | H | O | Ete | O | 1 | 1 | 1 |
| 2809 | Bdbbp | H | H | C | S | S | H | O | Ete | O | 1 | 1 | 1 |
| 2810 | Bdbbp | H | H | C | S | — | — | — | — | — | 0 | 0 | 1 |
| 2811 | Bdbbp | H | H | C | S | O | Me | O | — | — | 0 | 1 | 1 |
| 2812 | Bdbbp | H | H | C | S | O | Me | S | — | — | 0 | 1 | 1 |
| 2813 | Bdbbp | H | H | C | S | O | 2-ClPh | O | — | — | 0 | 1 | 1 |
| 2814 | Bdbbp | H | H | C | S | Mee | H | O | — | — | 0 | 1 | 1 |
| 2815 | Bdbbp | H | H | C | S | Mee | N | S | — | — | 0 | 1 | 1 |
| 2816 | Bdbbp | H | H | C | S | Phe | H | O | — | — | 0 | 1 | 1 |
| 2817 | Bdbbp | H | H | C | S | NH | Pr | O | Ete | O | 1 | 1 | 1 |
| 2818 | Bdbbp | H | H | C | S | O | Me | NH | Trim | — | 1 | 1 | 1 |
| 2819 | 3,4-Dbp | H | H | C | S | O | H | O | Ete | O | 1 | 1 | 28 |
| 2820 | 3,4-Dbp | H | H | C | S | S | H | O | Ete | O | 1 | 1 | 28 |
| 2821 | 3,4-Dbp | H | H | C | S | — | — | — | — | — | 0 | 0 | 28 |
| 2822 | 3,4-Dbp | H | H | C | S | O | Me | O | — | — | 0 | 1 | 28 |
| 2823 | 3,4-Dbp | H | H | C | S | O | Me | S | — | — | 0 | 1 | 28 |
| 2824 | 3,4-Dbp | H | H | C | S | O | 2-ClPh | O | — | — | 0 | 1 | 28 |
| 2825 | 3,4-Dbp | H | H | C | S | Mee | H | O | — | — | 0 | 1 | 28 |
| 2826 | 3,4-Dbp | H | H | C | S | Mee | H | S | — | — | 0 | 1 | 28 |
| 2827 | 3,4-Dbp | H | H | C | S | Phe | H | O | — | — | 0 | 1 | 28 |
| 2828 | 3,4-Dbp | H | H | C | S | NH | Pr | O | Ete | O | 1 | 1 | 28 |
| 2829 | 3,4-Dbp | H | H | C | S | O | Me | NH | Trim | — | 1 | 1 | 28 |
| 2830 | 9-Ant | H | H | C | S | O | H | O | Ete | O | 1 | 1 | 28 |
| 2831 | 9-Ant | H | H | C | S | S | H | O | Ete | O | 1 | 1 | 28 |
| 2832 | 9-Ant | H | H | C | S | — | — | — | — | — | 0 | 0 | 28 |
| 2833 | 9-Ant | H | H | C | S | O | Me | O | — | — | 0 | 1 | 28 |
| 2834 | 9-Ant | H | H | C | S | O | Me | S | — | — | 0 | 1 | 28 |
| 2835 | 9-Ant | H | H | C | S | O | 2-ClPh | O | — | — | 0 | 1 | 28 |
| 2836 | 9-Ant | H | H | C | S | Mee | H | O | — | — | 0 | 1 | 28 |
| 2837 | 9-Ant | H | H | C | S | Mee | H | S | — | — | 0 | 1 | 28 |
| 2838 | 9-Ant | H | H | C | S | Phe | H | O | — | — | 0 | 1 | 28 |
| 2839 | 9-Ant | H | H | C | S | NH | Pr | O | Ete | O | 1 | 1 | 28 |
| 2840 | 9-Ant | H | H | C | S | O | Me | NH | Trim | — | 1 | 1 | 28 |
| 2841 | 2-Npe | H | H | C | S | O | H | O | Ete | O | 1 | 1 | 28 |
| 2842 | 2-Npe | H | H | C | S | S | H | O | Ete | O | 1 | 1 | 28 |
| 2843 | 2-Npe | H | H | C | S | — | — | — | — | — | 0 | 0 | 28 |
| 2844 | 2-Npe | H | H | C | S | O | Me | O | — | — | 0 | 1 | 28 |
| 2845 | 2-Npe | H | H | C | S | O | Me | S | — | — | 0 | 1 | 28 |
| 2846 | 2-Npe | H | H | C | S | O | 2-ClPh | O | — | — | 0 | 1 | 28 |
| 2847 | 2-Npe | H | H | C | S | Mee | H | O | — | — | 0 | 1 | 28 |
| 2848 | 2-Npe | H | H | C | S | Mee | H | S | — | — | 0 | 1 | 28 |
| 2849 | 2-Npe | H | H | C | S | Phe | H | O | — | — | 0 | 1 | 28 |
| 2850 | 2-Npe | H | H | C | S | NH | Pr | O | Ete | O | 1 | 1 | 28 |
| 2851 | 2-Npe | H | H | C | S | O | Me | NH | Trim | — | 1 | 1 | 28 |
| 2852 | Bdbbp | H | H | C | S | O | H | O | Ete | O | 1 | 1 | 28 |
| 2853 | Bdbbp | H | H | C | S | S | H | O | Ete | O | 1 | 1 | 28 |
| 2854 | Bdbbp | H | H | C | S | — | — | — | — | — | 0 | 0 | 28 |
| 2855 | Bdbbp | H | H | C | S | O | Me | O | — | — | 0 | 1 | 28 |
| 2856 | Bdbbp | H | H | C | S | O | Me | S | — | — | 0 | 1 | 28 |
| 2857 | Bdbbp | H | H | C | S | O | 2-ClPh | O | — | — | 0 | 1 | 28 |
| 2858 | Bdbbp | H | H | C | S | Mee | H | O | — | — | 0 | 1 | 28 |
| 2859 | Bdbbp | H | H | C | S | Mee | H | S | — | — | 0 | 1 | 28 |
| 2860 | Bdbbp | H | H | C | S | Phe | H | O | — | — | 0 | 1 | 28 |
| 2861 | Bdbbp | H | H | C | S | NH | Pr | O | Ete | O | 1 | 1 | 28 |
| 2862 | Bdbbp | H | H | C | S | O | Me | NH | Trim | — | 1 | 1 | 28 |
| 2863 | 3,4-Dbp | H | H | C | S | O | H | O | Ete | O | 1 | 1 | 29 |
| 2864 | 3,4-Dbp | H | H | C | S | S | H | O | Ete | O | 1 | 1 | 29 |

TABLE 1-continued

| Cpd. No. | R₁ | R₂ | R₃ | Z | Y₁ | Y₂ | R₄ | Y₃ | X | Y₄ | n | m | B |
|---|---|---|---|---|---|---|---|---|---|---|---|---|---|
| 2865 | 3,4-Dbp | H | H | C | S | — | — | — | — | — | 0 | 0 | 29 |
| 2866 | 3,4-Dbp | H | H | C | S | O | Me | O | — | — | 0 | 1 | 29 |
| 2867 | 3,4-Dbp | H | H | C | S | O | Me | S | — | — | 0 | 1 | 29 |
| 2868 | 3,4-Dbp | H | H | C | S | O | 2-ClPh | O | — | — | 0 | 1 | 29 |
| 2869 | 3,4-Dbp | H | H | C | S | Mee | H | O | — | — | 0 | 1 | 29 |
| 2870 | 3,4-Dbp | H | H | C | S | Mee | H | S | — | — | 0 | 1 | 29 |
| 2871 | 3,4-Dbp | H | H | C | S | Phe | H | O | — | — | 0 | 1 | 29 |
| 2872 | 3,4-Dbp | H | N | C | S | NH | Pr | O | Ete | O | 1 | 1 | 29 |
| 2873 | 3,4-Dbp | H | H | C | S | O | Me | NH | Trim | — | 1 | 1 | 29 |
| 2874 | 9-Ant | H | H | C | S | O | H | O | Ete | O | 1 | 1 | 29 |
| 2875 | 9-Ant | H | H | C | S | S | H | O | Ete | O | 1 | 1 | 29 |
| 2876 | 9-Ant | H | H | C | S | — | — | — | — | — | 0 | 0 | 29 |
| 2877 | 9-Ant | H | H | C | S | O | Me | O | — | — | 0 | 1 | 29 |
| 2878 | 9-Ant | H | H | C | S | O | Me | S | — | — | 0 | 1 | 29 |
| 2879 | 9-Ant | H | H | C | S | O | 2-ClPh | O | — | — | 0 | 1 | 29 |
| 2880 | 9-Ant | H | H | C | S | Mee | H | O | — | — | 0 | 1 | 29 |
| 2881 | 9-Ant | H | H | C | S | Mee | H | S | — | — | 0 | 1 | 29 |
| 2882 | 9-Ant | H | H | C | S | Phe | H | O | — | — | 0 | 1 | 29 |
| 2883 | 9-Ant | H | H | C | S | NH | Pr | O | Ete | O | 1 | 1 | 29 |
| 2884 | 9-Ant | H | H | C | S | O | Me | NH | Trim | — | 1 | 1 | 29 |
| 2885 | 2-Npe | H | H | C | S | O | H | O | Ete | O | 1 | 1 | 29 |
| 2886 | 2-Npe | H | H | C | S | S | H | O | Ete | O | 1 | 1 | 29 |
| 2887 | 2-Npe | H | H | C | S | — | — | — | — | — | 0 | 0 | 29 |
| 2888 | 2-Npe | H | H | C | S | O | Me | O | — | — | 0 | 1 | 29 |
| 2889 | 2-Npe | H | H | C | S | O | Me | S | — | — | 0 | 1 | 29 |
| 2890 | 2-Npe | H | H | C | S | O | 2-ClPh | O | — | — | 0 | 1 | 29 |
| 2891 | 2-Npe | H | H | C | S | Mee | H | O | — | — | 0 | 1 | 29 |
| 2892 | 2-Npe | H | H | C | S | Mee | H | S | — | — | 0 | 1 | 29 |
| 2893 | 2-Npe | H | H | C | S | Phe | H | O | — | — | 0 | 1 | 29 |
| 2894 | 2-Npe | H | H | C | S | NH | Pr | O | Ete | O | 1 | 1 | 29 |
| 2895 | 2-Npe | H | H | C | S | O | Me | NH | Trim | — | 1 | 1 | 29 |
| 2896 | Bdbbp | H | H | C | S | O | H | O | Ete | O | 1 | 1 | 29 |
| 2897 | Bdbbp | H | H | C | S | S | H | O | Ete | O | 1 | 1 | 29 |
| 2898 | Bdbbp | H | H | C | S | — | — | — | — | — | 0 | 0 | 29 |
| 2899 | Bdbbp | H | H | C | S | O | Me | O | — | — | 0 | 1 | 29 |
| 2900 | Bdbbp | H | H | C | S | O | Me | S | — | — | 0 | 1 | 29 |
| 2901 | Bdbbp | H | H | C | S | O | 2-ClPh | O | — | — | 0 | 1 | 29 |
| 2902 | Bdbbp | H | H | C | S | Mee | H | O | — | — | 0 | 1 | 29 |
| 2903 | Bdbbp | H | H | C | S | Mee | H | S | — | — | 0 | 1 | 29 |
| 2904 | Bdbbp | H | H | C | S | Phe | H | O | — | — | 0 | 1 | 29 |
| 2905 | Bdbbp | H | H | C | S | NH | Pr | O | Ete | O | 1 | 1 | 29 |
| 2906 | Bdbbp | H | H | C | S | O | Me | NH | Trim | — | 1 | 1 | 29 |
| 2907 | 3,4-Dbp | H | H | C | O | O | H | O | Ete | O | 1 | 1 | 30 |
| 2908 | 3,4-Dbp | H | H | C | O | S | H | O | Ete | O | 1 | 1 | 30 |
| 2909 | 3,4-Dbp | H | H | C | O | — | — | — | — | — | 0 | 0 | 30 |
| 2910 | 3,4-Dbp | H | H | C | O | O | Me | O | — | — | 0 | 1 | 30 |
| 2911 | 3,4-Dbp | H | H | C | O | O | Me | S | — | — | 0 | 1 | 30 |
| 2912 | 3,4-Dbp | H | H | C | O | O | 2-ClPh | O | — | — | 0 | 1 | 30 |
| 2913 | 3,4-Dbp | H | H | C | O | Mee | H | O | — | — | 0 | 1 | 30 |
| 2914 | 3,4-Dbp | H | H | C | O | Mee | H | S | — | — | 0 | 1 | 30 |
| 2915 | 3,4-Dbp | H | H | C | O | Phe | H | O | — | — | 0 | 1 | 30 |
| 2916 | 3,4-Dbp | H | H | C | O | NH | Pr | O | Ete | O | 1 | 1 | 30 |
| 2917 | 3,4-Dbp | H | H | C | O | O | Me | NH | Trim | — | 1 | 1 | 30 |
| 2918 | 3,4-Dbp | H | H | C | O | O | H | O | Ete | O | 1 | 1 | 31 |
| 2919 | 3,4-Dbp | H | H | C | O | S | H | O | Ete | O | 1 | 1 | 31 |
| 2920 | 3,4-Dbp | H | H | C | O | — | — | — | — | — | 0 | 0 | 31 |
| 2921 | 3,4-Dbp | H | H | C | O | O | Me | O | — | — | 0 | 1 | 31 |
| 2922 | 3,4-Dbp | H | H | C | O | O | Me | S | — | — | 0 | 1 | 31 |
| 2923 | 3,4-Dbp | H | H | C | O | O | 2-ClPh | O | — | — | 0 | 1 | 31 |
| 2924 | 3,4-Dbp | H | H | C | O | Mee | H | O | — | — | 0 | 1 | 31 |
| 2925 | 3,4-Dbp | H | H | C | O | Mee | H | S | — | — | 0 | 1 | 31 |
| 2926 | 3,4-Dbp | H | H | C | O | Phe | H | O | — | — | 0 | 1 | 31 |
| 2927 | 3,4-Dbp | H | H | C | O | NH | Pr | O | Ete | O | 1 | 1 | 31 |
| 2928 | 3,4-Dbp | H | H | C | O | O | Me | NH | Trim | — | 1 | 1 | 31 |
| 2929 | 3,4-Dbp | H | H | C | O | O | H | O | Ete | O | 1 | 1 | 32 |
| 2930 | 3,4-Dbp | H | H | C | O | S | H | O | Ete | O | 1 | 1 | 32 |
| 2931 | 3,4-Dbp | H | H | C | O | — | — | — | — | — | 0 | 0 | 32 |
| 2932 | 3,4-Dbp | H | H | C | O | O | Me | O | — | — | 0 | 1 | 32 |
| 2933 | 3,4-Dbp | H | H | C | O | O | Me | S | — | — | 0 | 1 | 32 |
| 2934 | 3,4-Dbp | H | H | C | O | O | 2-ClPh | O | — | — | 0 | 1 | 32 |
| 2935 | 3,4-Dbp | H | H | C | O | Mee | H | O | — | — | 0 | 1 | 32 |
| 2936 | 3,4-Dbp | H | H | C | O | Mee | H | S | — | — | 0 | 1 | 32 |
| 2937 | 3,4-Dbp | H | H | C | O | Phe | H | O | — | — | 0 | 1 | 32 |
| 2938 | 3,4-Dbp | H | H | C | O | NH | Pr | O | Ete | O | 1 | 1 | 32 |
| 2939 | 3,4-Dbp | H | H | C | O | O | Me | NH | Trim | — | 1 | 1 | 32 |

Of the compounds listed above, preferred compounds are Compound Nos. 1 to 440, 454, 476, 586, 696, 806, 916, 1026, 1136, 1246, 1356, 1466, 1576, 1686, 1763, 1773, 1793, 1979, 1980, 1990 to 1994, 2250 and 2326 to 2906.

The more preferred compounds are Compound Nos. 1 to 110, 113, 221 to 330, 333, 454, 1763, 1773, 1793, 1979, 1980, 1990 to 1994, 2250 and 2334 to 2906.

The most preferred compounds are Compound Nos. 1, 2, 3, 4, 12, 13, 14, 15, 2555, 2556, 2557, 2558, 2566, 2567, 2568, 2569, 2665, 2666, 2667, 2668, 2676, 2677, 2678 and 2679.

The compounds of the present invention can be in the form of salts, especially pharmaceutically acceptable salts with cations. Examples of suitable salts include inorganic or organic salts, for example, those with alkali metals such as sodium or potassium, alkali earth metals such as calcium; ammonia; basic amino acids such as lysine or arginine; and alkylamines such as triethylamine. Preferred salts are the alkali metal salts such as sodium or potassium.

Some methods for the preparation of the compounds of the present invention are illustrated by the following reaction schemes.

In general, the compounds of general formula (1) can be prepared by condensing a suitably derivatized nucleotide, being the nucleotide at the 5'-end of the desired compound, with a protected oligonucleotide lacking a 5'-end nucleotide, the nucleotides of the lacking oligonucleotide giving with the said 5'-end nucleotide the appropriate nucleotide sequence of the desired oligodeoxyribonucleotide compound, the protected lacking nucleotide being linked to a polymer support. Typically the process involves reacting a compound $R^1R^2R^3Z$-Y'-[5'-end nucleotide] with a compound [protector]-[lacking oligonucleotide]-linker-polymer.

More concretely, the present invention provides a process which comprises condensing a compound of the following formula (2) with a compound of the kind [protector]-O-F-W, where F is the lacking oligonucleotide and W is the linker and polymer support. Using DMT as protector, examples of compounds for reacting with compound (2) include compounds of formulae: DMT-O-F-$W_1$ (3), DMT-O-F-$W_{2a}$ (4a), DMT-O-F-$W_{2b}$ (4b), DMT-O-F-$W_3$ (5), DMT-O-F-$W_{4a}$ (6a), DMT-O-F-$W_{4b}$ (6b), DMT-O-F-$W_{4c}$ (6c), DMT-O-F-$W_{4d}$ (6d), DMT-O-F-$W_{5a}$ (7a), and DMT-O-F-$W_{5b}$ (7b), according to Method C-1, C-2 or C-3. The reactant (2) used in this reaction can suitably be prepared by Method A-1 or A-2 and the reactants (3, 4a, 4b, 5, 6a to 6d, 7a and 7b) can suitably be prepared by Method B-1, B-2, B-3, B-4 or B-5.

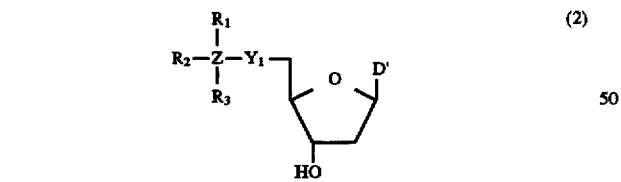

(2)

Method A-1

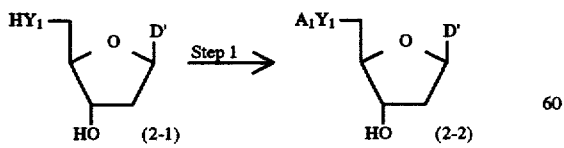

-continued

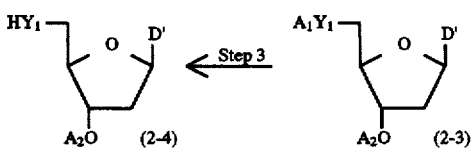

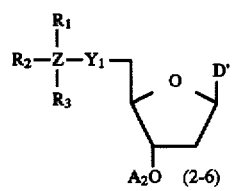

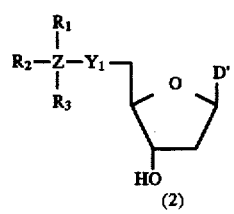

Method A-2

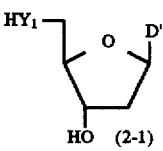

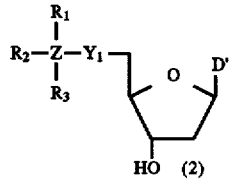

Method B-1
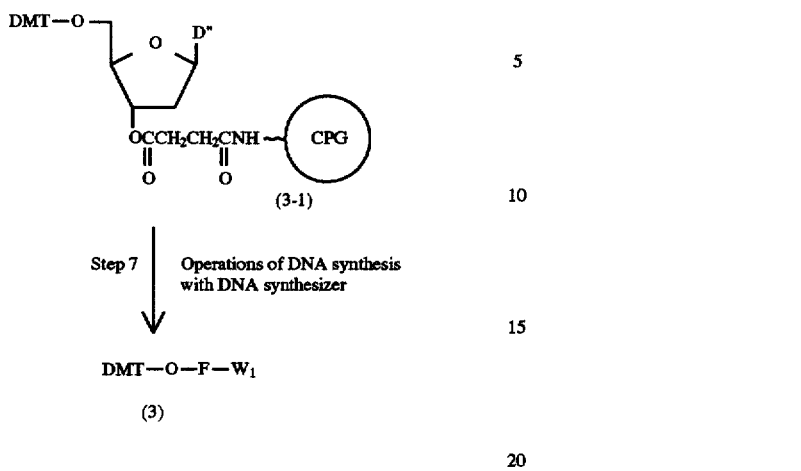
Method B-2
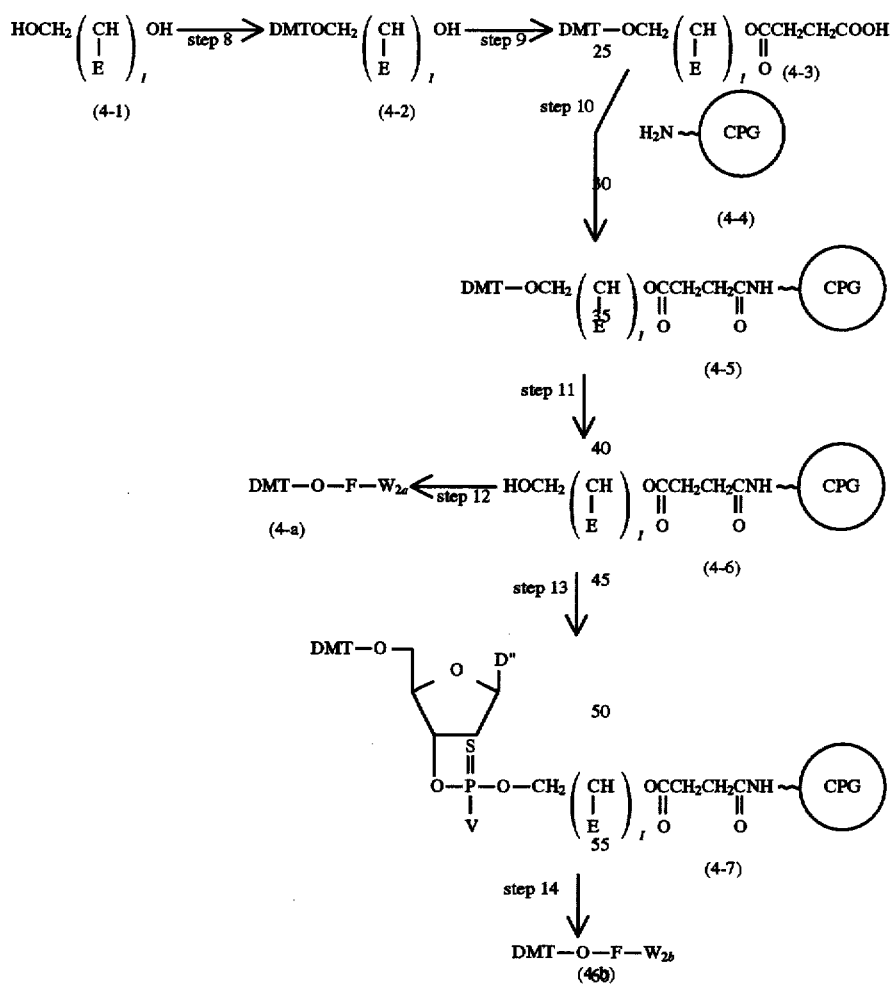

Method B-3

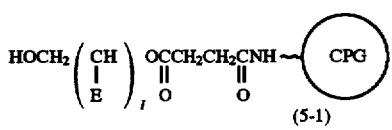
(5-1)

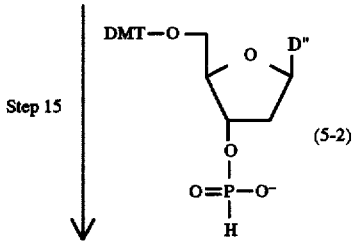

Step 15 ↓

Method B-4

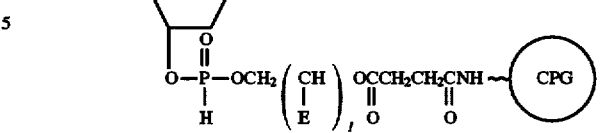
(5-3)

step 16 ↓

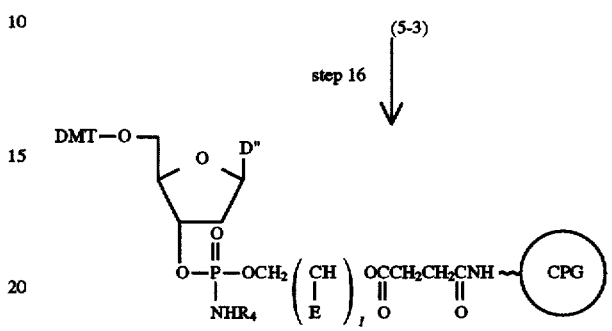
(5-4)

step 17 ↓

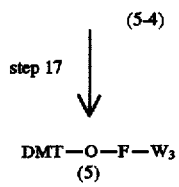

$$\text{H(OCH}_2\text{CH}_2)_6\text{OH} \xrightarrow{\text{Step 18}} \text{DMT−(OCH}_2\text{CH}_2)_6\text{OH} \xrightarrow[\text{Step 19}]{\text{Cl−P}\overset{V}{\underset{U}{\diagup}}\ (6\text{-}3)} \text{DMT−(OCH}_2\text{CH}_2)_6\text{−O−P}\overset{V}{\underset{U}{\diagup}}$$
(6-1)            (6-2)            (6-3)

Step 20 ↓

DMT—(OCH₂CH₂)₆OOCCH₂CH₂COOH   (6-4)

Step 21 ↓    NH₂—(CPG)  (6-5)

DMT—(OCH₂CH₂)₆OOCCH₂CH₂CONH—(CPG)  (6-6)

Step 22 ↓

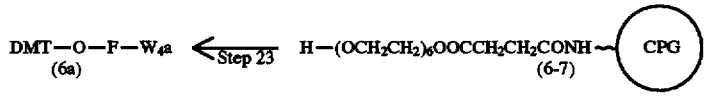
(6a)      Step 23      (6-7)

Step 24 ↓ (6-3)

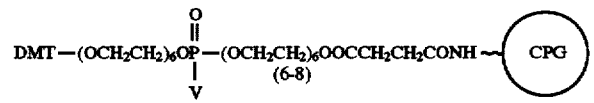
(6-8)

Step 25 ↓

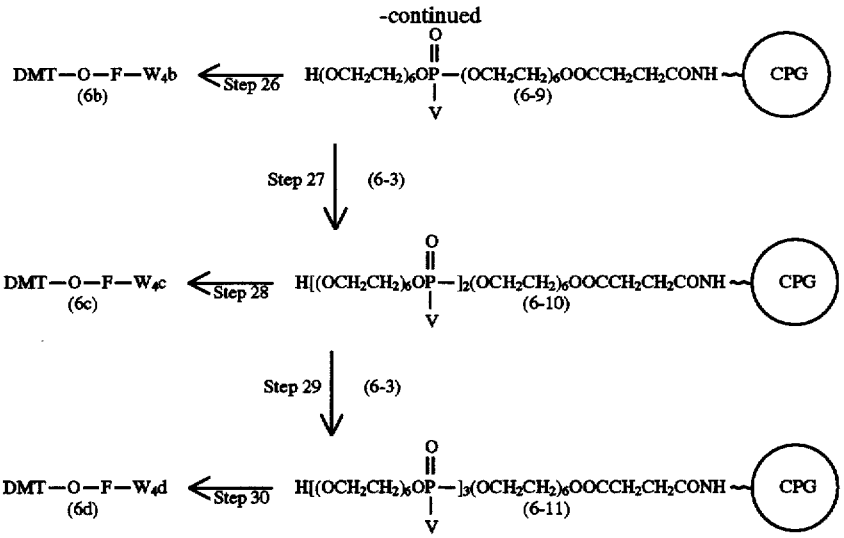
Method B-5
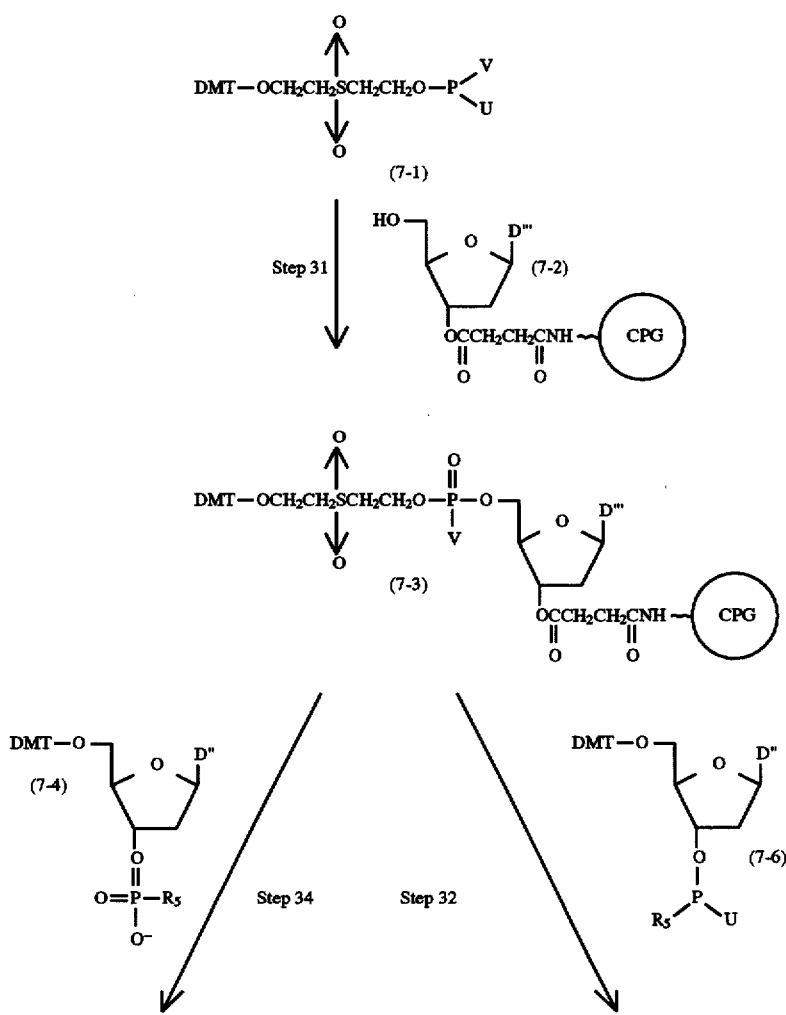

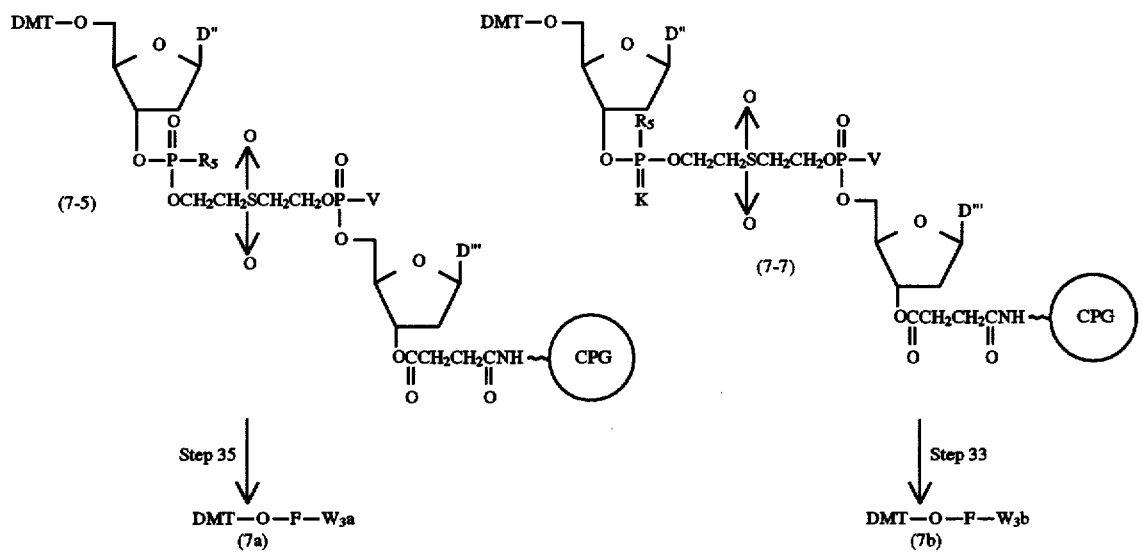
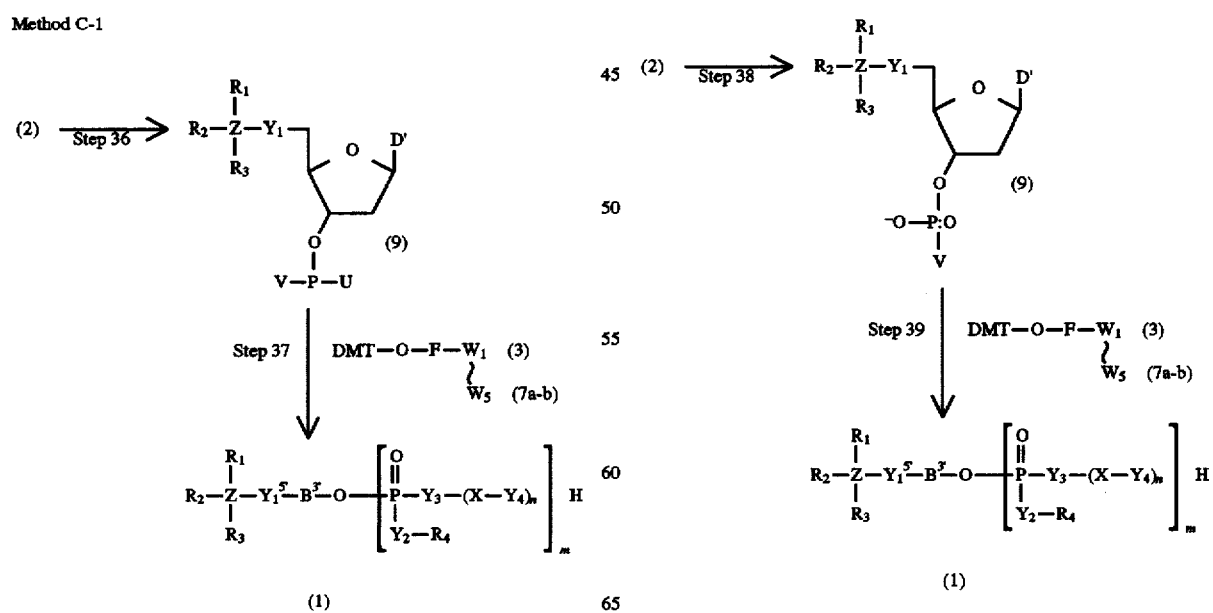

Method C-3

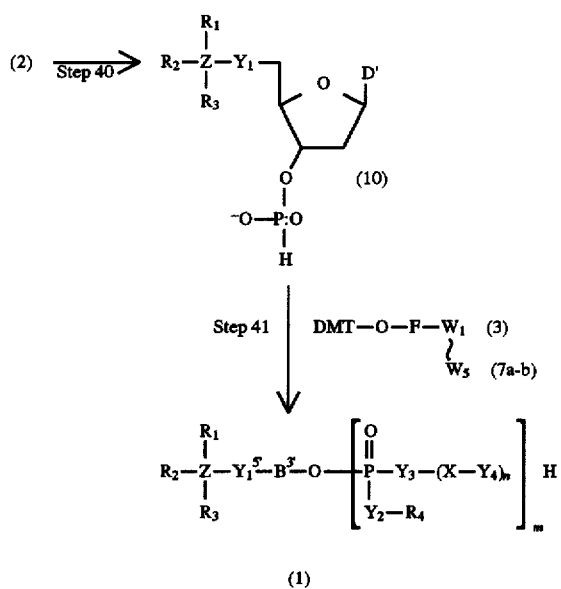

In the various compounds of general formula (2), $R_1$, $R_2$, $R_3$, $Y_1$ and Z are as defined for the said general formula (1); D' represents a base selected from the following "5'-base group" or the corresponding protected base, the base being the base at the 5'-end moiety of the said effective base sequence (hereafter designated as the 5'-end moiety of the said effective base sequence or simply the 5'-end base), where the "5'-base group" is adenine, guanine, cytosine, thymine or 5-methylcytosine.

Method B-1 involves the preparation of a compound (3) lacking one nucleotide fragment from the 5' end of the said effective sequence, synthesized by using controlled pore glass (hereafter designated as CPG) comprizing a linker bonded with a protected nucleoside usable for DNA synthesis of the 3'-end moiety of the said effective base sequence (hereafter designated as a 3'-end nucleoside) and a nucleotide unit commercialized for a DNA synthesizer (hereafter designated as a nucleotide unit).

Method B-2 involves the preparation of a compound (4a) having one nucleotide short fragment from 5' end of the said effective sequence synthesized by protecting one terminal hydroxyl group of $C_2$–$C_{10}$-alkylenediol having hydroxyl groups at the terminal positions or the alkylenediol having protected hydroxyl or amino groups with a dimethoxytrityl (DMT) group, reacting the other hydroxyl group with succinic anhydride to produce a succinic acid monoester, bonding a carboxyl group of the monoester to CPG, removing the terminal DMT group, and finally reacting a nucleotide unit with the CPG-bound alkylene alcohol (4-6) in regular sequence on a DNA synthesizer; and the preparation of a compound (4b) by converting the CPG-bound alkylene alcohol (4-6) to 3'-end nucleoside phosphorothioate supported by CPG (4-7) according to conventional means used in preparing thioate nucleotide on a DNA synthesizer and then reacting with a nucleotide unit in the same way as above.

Method B-3 involves the preparation of a compound (5) having one nucleotide short fragment from 5' end of the said effective sequence synthesized by condensing 3'-end nucleoside phosphonate, which is prepared by reacting a hydroxyl group at the 3'-position of the 3'-end nucleoside with phosphonic acid to produce an ester linkage, with a CPG-bound ethylene glycol (5-1) prepared by the use of succinic anhydride in Method B-2, reacting with alkylamine to produce 3'-end nucleoside phosphoramidite supported by CPG (5-4) and finally reacting with a nucleotide unit in a regular sequence on a DNA synthesizer.

Method B-4 involves the preparation of a known compound (6-3) [M. Durand et al., Nucleic Acids Res., 18, 6353(1990)] by protecting one hydroxyl group of hexaethylene glycol with a DMT group and reacting the other hydroxyl group with a reagent for preparing phosphoramidite group.

Subsequently in analogy with the procedure described in Method B-3, CPG-bound DMT-protected glycol (6—6) can be prepared by condensing the said hexaethylene glycol protected with a DMT group (6—2) to CPG by the use of succinic acid.

After removal of a DMT group from CPG-bound DMT-protecting glycol (6—6) on a DNA synthesizer, the glycol is reacted with a nucleotide unit to give the desired compound (6a) having one nucleotide short fragment from 5' end of the said effective sequence synthesized. The glycol supported on CPG, which is obtained by removal of a DMT group from CPG-bound DMT-protected glycol (6-6) on a DNA synthesizer, is reacted once, twice or thrice with the said phosphoramidite followed by reacting with a nucleotide unit comprizing one nucleotide short fragment from the 5'-end of the said effective base sequence to produce a compound of formulae (6b), (6c) or (6d), respectively.

Method B-5 involves the preparation of a compound (7-3) by deprotecting a DMT group from commercially available protected 2'-deoxynucleoside supported by CPG through a linker (hereafter designated as D"'-CPG) and reacting with (2-cyanoethoxy)-2-(2'-O-4,4'-dimethoxytrityloxyethylsulfonyl)ethoxy-N,N-diisopropylaminophosphine (7-1) reported by T. Horn et al., in Tetrahedron Letters, 27, 4705(1986); the preparation of a compound (7-5) by deprotecting a DMT group from the compound (7-3) prepared above and condensing the deprotected compound with a compound (7-4) having an aryl or alkyl phosphate of a hydroxyl group at the 3'-position of the 3'-end nucleoside using a condensing agent; and the preparation of a compound (7a) by reacting the compound (7-5) prepared above with a nucleotide unit comprizing one nucleotide short fragment from 5' end of the said effective sequence synthesized.

In a similar manner as above a compound (7-7) can be prepared by reacting a compound (7-3) freed from a DMT group with a compound (7-6) having an alkyl or aryl phosphoramidite group at the 3'-position of the 3'-end nucleoside and treating in analogy with the synthesis of phosphoric acid triester or phosphorothioate triester on a DNA synthesizer. The product thus obtained is reacted with a nucleotide unit in regular sequence to produce a compound (7a) having one nucleotide short fragment from the 5'-end of the said effective base sequence.

Method C-1 involves the preparation of the desired compound of general formula (1) by reacting a compound (2) with a phosphitylating agent to produce a 3'-phosphate derivative (8), reacting the product thus obtained with each oligomer of formulae (3, 4a, 4b, 5, 6a to 6d, 7a and 7b) supported on CPG, which is prepared in Methods B-1 to B-5, after deprotection of a DMT group, oxidizing the condensed product by an oxidising agent, cleaving the nucleotide chain from the CPG, and finally removing a protecting group excepting the substituent moiety bonded to a carbon atom at the 5'-position of the 5'-end nucleoside.

Method C-2 involves the preparation of the desired compound (1) by reacting a compound (2) with a phosphorylating agent to produce a 3'-phosphoric acid derivative (9), condensing the product with the said compound each of formulae: (3, 4a, 4b, 5, 6a to 6d, 7a and 7b) after deprotection of a DMT group alone to form a phosphoric acid triester linkage, cleaving the nucleotide chain from the CPG, removing a protecting group excepting the substituent moiety bonded to a carbon atom at the 5'-position of the 5'-end nucleoside; and finally purifying by conventional means.

Method C-3 involves the desired compound (1) by introducing a phosphonic acid group into the 3'-position of a compound (2) to produce a compound (10), condensing the product with the said compound each of formulae: (3, 4a, 4b, 5, 6a to 6d, 7a and 7b) by the use of acid halide in the presence of a base, oxidizing the condensed product by an oxidizing agent to form a phosphoric acid diester linkage, cleaving the nucleotide from CPG, removing a protecting group excepting the substituent moiety bonded to a carbon atom at the 5'-position of the 5'-end nucleoside, and finally purifying by conventional means.

Method A to Method C are explained in great detail as follows.

In the reaction schemes summarized in Methods A to Method C, $R_1$, $R_2$, $R_3$, $R_4$, Z, $Y_1$, $Y_2$, $Y_3$, $Y_4$, X, n, m and B are as defined above; $A_1$ represents a trityl (Tr) group, a monomethoxytrityl (MMT) group or a dimethoxytrity (DMT) group which is generally used for protecting specifically a primary hydroxyl group of nucleoside; and $A_2$ represents a tri-substituted silyl group such as a tert-butyldimethylsilyl (TBDMS) or triisopropylsilyl (TIPS) group; a trihalogenoethoxycarbonyl group such as trichloroethoxycarbonyl (Troc) group; or an aralkyloxycarbonyl group such as a benzyloxycarbonyl (Z) group.

D' represents a base of the 5'-end nucleotide, an amino group of which is protected with an acyl group for synthesizing DNA of the said effective base sequence; D" represents a base moiety of nucleotide at the 3'-end; and D''' represents a base moiety of the optional nucleotide unit to be used in the DNA synthesis, that is, a base selected from the 5'-base group or the corresponding protecting base.

F is an oligonucleotide part having one nucleotide short fragment from 5' end of the said effective sequence and represents a base part or the corresponding oligonucleotide protected with a protecting group of a phosphoric acid part, which is generally used for DNA synthesis but does not contain any hydroxyl gorup at the 5'-position of the 5'-end nucleoside and at the 3'-positions of the 3'-end nucleoside. V represents a protecting group of a phosphoric acid part in the case of DNA synthesis. U represents an amino group of an amidire part. $W_1$ to $W_5$ represent a fragment of from CPG to an oxygen atom of a hydroxyl group at the 3'-position of the 3'-end nucleotide of oligonucleotide (F) of the final desired compound according to the procedure described in Method B-1 to B-5. 1 is an integer of 1 to 9; E represents a hydrogen atom or an optionally protected hydroxyl or amino group; and K represents an oxygen or sulfur atom.

$R_5$ represents a methyl, ethyl, propyl, butyl, phenyl, methoxy, ethoxy, propoxy, butoxy, cyanoethyloxy or optionally substituted phenyloxy group.

Each of the following steps is explained in greater detail as follows. In case the step is capable of conducting in analogy with the procedure described in the preceding one, the first one is explained as a representative.

[Steps 1, 8 and 18]

In these steps a compound (2- 2), in which a hydroxyl group alone at the 5'-position is selectively protected, can be prepared by reacting a compound (2-1) with a hydroxyl-protecting reagent in an inert solvent. Where a base part is A, G or C, amino groups comprizing in the base are protected by acylation in the foregoing stage and the protecting reaction can be carried out in a manner known per se, for example in analogy to the reported procedure [J. Am. Chem. Soc., 104, 1316(1982)]. As an amino-protecting group there comes generally into consideration an aliphatic lower acyl or aromatic acyl group. Examples of acyl groups include: aliphatic lower acyl groups such as a formyl, acetyl, propionyl, butyryl, isobutyryl, pentanoyl, pivaloyl, valeryl or isovaleryl group; and aromatic acyl groups such as a benzoyl, 4-acetoxybenzoyl, 4-methoxybenzoyl, 4-methylbenzoyl or 1-naphthoyl group; preferably in case base part is A or C, a benzoyl group and in case a base part is G, an isobutyryl group.

Examples of preferred solvents to be include: aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitro compounds such as nitroethane or nitrobenzene; nitriles such as acetonitrile or isobutyronitrile; amides such as formamide, dimethylformamide (DMF), dimethylacetamide or hexamethylphosphoric triamide; sulfoxides such as dimethylsulfoxide or sulfolane; aliphatic tertiary amines such as trimethylamine, triethylamine or N-methylmorpholine; and aromatic amines such as pyridine or picoline; more preferably halogenated hydrocarbons (particularly dichloromethane) and amides (particularly DMF).

There is no particular limitation upon the nature of the reagent used for protection, provided that it can be used for specific protection of a hydroxyl group alone at the 5'-position and is capable of removing under acidic or neutral conditions. Example of preferred protecting reagents include triarylmethyl halides such as trityl chloride, monomethoxytrityl chloride or dimethoxytrityl chloride.

Where the protecting reagent is a triarylmethyl halide, the reaction is normally carried out in the presence of a base.

Examples of suitable bases include: heterocyclic a mines such as pyridine, dimethylaminopyridine or pyrrolidinopyridine; and aliphatic tertiary amines such as trimethylamine or triethylamine; preferably organic bases (particularly pyridine, dimethylaminopyridine and pyrrolidinopyridine).

Where organic amines are used as a solvent, it is unnecessary to use the other deacidifying agent because the organic amines themselves act as a deacidifying agent.

The reaction temperature varies depending upon the nature of the starting material and solvent used and other reaction conditions, but the reaction is normally carried out at a temperature from 0° to 150° C., preferably 20° to 100° C.

The time required for the reaction varies depending upon the nature of the starting material and solvent used as well as the reaction temperature, but the reaction is normally complete within a period of 1 to 100 hours, preferably 2 to 24 hours.

After completion of the reaction, the desired compound can be isolated from the reaction mixture, for example, by pouring the reaction mixture into water, extracting with a water-immiscible solvent such as benzene, ether or ethyl acetate, and finally distilling off the solvent from the extract. The product thus obtained can be used in the subsequent reaction without further purification but if desired, can be purified by conventional means, for example, various chromatography or recrystallization.

[Step 2]

In this step a compound (2-3) can be prepared by reacting a compound (2-2) with a hydroxyl-protecting reagent in the presence of an inert solvent.

Examples of preferred solvents include: aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate, diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitro compounds such as nitroethane or nitrobenzene; nitriles such as acetonitrile or isobutyronitrile; amides such as formamide, dimethylformamide, dimethylacetamide or hexamethylphosphoric triamide; sulfoxides such as dimethylsulfoxide or sulfolane; more preferably ethers (particularly tetrahydrofuran), halogenated hydrocarbons (particularly dichloromethane), aromatic hydrocarbons (particularly toluene) and amides (particularly DMF).

There is no particular limitation upon the nature of the hydroxyl-protecting reagent used, provided that the protecting group can be deprotected in distinction from a protecting group at the 5'-position. Examples of such protecting reagents include: silyl halides such as tert-butyldimethylsilyl chloride or triisopropylsilyl chloride; haloalkoxycarbonyl halides such as trichloroethoxycarbonyl chloride; and aralkyloxycarbonyl halides such as benzyloxycarbonyl chloride.

Where the protecting reagent is silyl halides, haloalkoxycarbonyl halides or aralkyloxycarbonyl halides, the reaction for protection is normally carried out in the presence of a base.

Examples of preferred bases include organic bases (particularly triethylamine, pyridine, N-methylmorpholine, DBU and imidazole).

The reaction temperature varies depending upon the nature of the reagent, starting compound and solvent and other reaction conditions, but the reaction is normally carried out at a temperature of $-20°$ to $150°$ C., preferably $-10°$ to $50°$ C.

The time required for the reaction varies depnding upon the nature of the starting compound and solvent used as well as the reaction temperature, but the reaction is normally complete within a period of 1 to 100 hours, preferably 1 to 24 hours.

After completion of the reaction, the desired compound can be isolated from the reaction mixture. An example of one such technique comprises: pouring the reaction mixture into water; extracting with a water-immiscible solvent such as benzene, ether or ethyl acetate; and finally distilling off the solvent from the extract. The product thus obtained can normally be used in the subsequent reaction without further purification but if desired, can be purified by various chromatography, recrystallization or the like means.

[Step 3, 11, 22 and 25]

In these steps, compounds (2-4), (4-6), (6-7) and (6-9) can be prepared by reacting compound (2-3), (4-5), (6—6) and (6-8) with a deprotecting reagent in the presence of an inert solvent to remove selectively the hydroxyl-protecting group at the 5'-position.

Examples of preferred solvents include: aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether, alcohols such as methanol, ethanol, n-propanol, isopropanol, n-butanol, isobutanol, tert-butanol, isoamyl alcohol, diethylene glycol, glycerin, octanol, cyclohexanol or methyl cellosolve; ketones such as acetone, methyl ethyl ketone, methyl isobutyl ketone, isophorone or cyclohexanone; nitro compounds such as nitroethane or nitrobenzen; nitriles such as acetonitrile or isobutyronitrile; amides such as formamide, dimethylformamide, dimethylacetamide or hexamethylphosphoric triamide; and sulfoxides such as dimethylsulfoxide or sulfolane; more preferably alcohols (particularly methanol and ethanol) and dichloromethane, and in case acetic acid is a deprotecting reagent, a mixture of acetic acid and water.

There is no particular limitation upon the nature of the deprotecting reagent used, provided that it can normally be used for conventional deprotection. Where the protecting group is a triarylmethyl group, it can be removed by using acids such as acetic acid, dichloroacetic acid, trifluoroacetic acid, hydrochloric acid or Lewis acids such as zinc bromide, preferably acetic acid, dichloroacetic acid or trifluoroacetic acid.

The reaction temperature varies depending upon the nature of the reagent, starting compound and solvnet used and other reaction conditions, but the reaction is normally carried out at a temperature of $-10°$ to $100°$ C., preferably $0°$ to $50°$ C. The time required for the reaction varies depending upon the nature of the starting compound and solvent used as well as the reaction temperature, but the reaction is normally complete within a period of 1 minute to 50 hours, preferably 1 minute to 24 hours.

After completion of the reaction, the desired compound can be isolated from the reaction mixture. In Step 3, an example of one such technique comprises: neutralizing the reaction mixture, pouring it into water; extracting with a water-immiscible solvent such as benzene, ether or ethyl acetate; and distilling off the solvent from the extract. The product thus obtained can normally be used in the subsequent reaction without further purification but if desired, can be purified by various chromatography, recrystallization or the like means. In Steps 11, 22 and 25, an example of one such technique comprises: separating the desired compound by filtration and washing it with methylene chloride.

[Steps 4 and 6]

In these steps a compound (2-6) or (2) can be prepared by reacting a compound (2-4) or (2-1) with a compound (2-5) (in the formula, Hal signifies a halogen atom) in the presence of an inert solvent and a base. The halide moiety of the compound (2-5) used is exemplified by chlorine, bromine or iodine, preferably chlorine or bromine.

Examples of preferred solvents include: aromatic hydrocarbons such as benzene, toluene or xylene; halogenated hydrocarbons such as dichloromethane, chloroform, carbon tetrachloride, dichloroethane, chlorobenzene or dichlorobenzene; esters such as ethyl formate, ethyl acetate, propyl acetate, butyl acetate or diethyl carbonate; ethers such as diethyl ether, diisopropyl ether, tetrahydrofuran, dioxane, dimethoxyethane or diethylene glycol dimethyl ether; ketones such as acetone, methyl ethyl ketone, methyl isobutyl ketone, isophorone or cyclohexanone; nitro compounds such as nitroethane or nitrobenzen; nitriles such as acetonitrile or isobutyronitrile; amides such as formamide, dimethylformamide, diemthylacetamide or hexamethylphosphoric triamide; and sulfoxides such as dimethylsulfoxide or sulfolane; more preferably ethers (particularly tetrahydrofuran), ketones (particularly acetone), halogenated hydrocarbons (particularly dichloromethane), amides (particularly DMF) and aromatic amines (particularly pyridine).

Examples of preferred bases include: organic bases (particularly triethylamine, pyridine, N-methylmorpholine, DBU and the like base), alkali metal hydrides (particularly sodium hydride) and alkali metal carbonates (particularly sodium carbonate and lithium carbonate), and in case Z of the compound (2-5) is a silicon atom, imidazole is the most preferable organic base.

The reaction temperature is not particularly critical, but the reaction is normally carried out at a temperature of 0° to 100° C., preferably 20° to 60° C.

The time required for the reaction ranges normally from 5 minutes to 30 hours. When the reaction is carried out at 50° C., it is complete within a period of 10 hours.

After completion of the reaction, the desired compound can be isolated from the reaction mixture, for example, by neutralizing properly the reaction mixture of filtering off insoluble materials if any, adding water and a water-immiscible organic solvent such as ethyl acetate thereto, separating the organic layer containing the desired compound, washing the extract with water, drying the extract over anhydrous magnesium sulfate etc., and finally distilling off the solvent. The desired compound thus obtained, if necessary, can be purified by conventional means, for example, recrystallization, reprecipitation, chromatography or the like means.

[Step 5]

In this step a compound (2) can be prepared by reacting a compound (2-6) with a deprotecting reagent in the presence of an inert solvent.

(1) Where a hydroxyl-protecting group at the 3'-position is a silyl group, it can normally be removed by treating with a compound capable of producing a fluoride ion such as tetrabutylammonium fluoride.

There is no particular limitation upon the nature of the solvent used, provided that it has no adverse effect upon the reaction. Preferred examples include ethers such as tetrahydrofuran or dioxane.

The reaction temperature is not particularly critical but the reaction is normally carried out at a temperature of –30° to 100° C., preferably 0° to 30° C.

The time required for the reaction ranges normally from 5 minutes to 30 hours. When the reaction is carried out at 20° C., it is complete within a period of 10 hours.

After completion of the reaction, the desired compound can be isolated from the reaction mixture, for example, by neutralizing properly the reaction mixture of filtering off insoluble materials if any, adding water and a water-immiscible organic solvent such as ethyl acetate thereto, separating the organic layer containing the desired compound, washing the extract with water, drying the extract over anhydrous magnesium sulfate etc., and finally distilling off the solvent. The desired product thus obtained, if necessary, can be purified by conventional means, for example, recrystallization, reprecipitation, chromatography or the like means.

The desired product thus obtained, if necessary, can be further purified by conventional menas, for exmaples, recrystallization, reprecipitation, chromatography or the like means.

(2) Where a hydroxyl-protecting group at the 3'-position is a haloalkoxycarbonyl group, it can normally be removed by treating with zinc dust.

There is no particular limitation upon the nature of the solvent used, provided that it has no adverse effect upon the reaction. Examples of preferred solvents include acetic acid, alcohols or mixtures of water and one or more of these solvents.

The reaction temperature is not particularly critical but the reaction is normally carried out at a temperature of 0° to 100° C., preferably at room temperature.

The time required for the reaction is normally in a range of 5 minutes to 30 hours. Where the reaction is carried out at room temperature, it is complete within a period of 10 hours.

After completion of the reaction, the desired compound can be isolated from the reaction mixture, for example, by neutralizing properly the reaction mixture or filtering off insoluble materials if any, adding water and a water-immiscible organic solvent such as ethyl acetate, separating the organic layer containing the desired compound, washing the extract with water, drying over anhydrous magnesium sulfate etc., and finally distilling off the solvent. The reaction product thus obtained can be further purified by conventional means, for example, recrystallization, reprecipitation, chromatography or the like means.

(3) Where a hydroxyl-protecting group at the 3'-position is an aralkyloxycarbonyl group, it can normally be removed by catalytic reduction or oxidation.

There is no particular limitation upon the nature of the catalyst usable for reduction, provided that it can usually be used in catalytic reduction. Examples of preferred catalysts include palladium on charcoal, Raney nickel, platinum oxide, platinum black, rhodium on alumina, a combination of triphenylphosphine and rhodium chloride and palladium on barium sulfate.

Hydrogen pressure, under which the reaction is carried out, is not particularly critical, but the reaction is normally carried out in a range of 1 to 10 atmospheric pressure.

The reaction temperature and the time required for the reaction vary depending upon the nature of the starting compound and solvent used as well as the type of the catalyst and other reaction conditions, but the reaction is carried out at a temperature of 0° to 100° C. and it is complete within a period of 5 minutes to 24 hours.

There is no particular limitation upon the nature of the solvent to be used in the deprotection by oxidation, provided that it has no adverse effect upon the reaction. Preferred solvent are exemplified by mixtures of water and one or more of organic solvents.

Examples of preferred organic solvents include: ketones such as acetone; halogenated hydrocarbons such as dichloromethane, chloroform or carbon tetrachloride; nitriles such as acetonitrile; ethers such as diethyl ether, tetrahydrofuran or dioxane; amides such as dimethylformamide, dimethylacetamide or hexamethylphosphoric triamide; and sulfoxides such as dimethylsulfoxide.

There is no particular limitation upon the nature of the oxidizing agent used, provided that it can be used in conventional oxidation. Preferred examples are exemplified by potassium persulfate, sodium persulfate, ammonium cerium nitrate (CAN) and 2,3-dichloro-5,6-dicyano-p-benzoquinone (DDQ).

The reaction temperature and the time required for the reaction vary depending upon the nature of the starting compound and solvent as well as the type of the catalyst used and other conditions, but the reaction is normally carried out at a temperature of 0° to 150° C. and it is complete within a period of 10 minutes to 24 hours.

The hydroxyl-protecting group can also be removed by treating with alkali metals such as lithium metal or sodium metal in liquid ammonia or alcohols such as methanol or ethanol at a temperature of −78° to −20° C.

Further the protecting group can be removed by using a combination of aluminium chloride and sodium iodide or alkylsilyl halides such as trimethylsilyl iodide in a solvent.

There is no particular limitation upon the nature of the solvent used, provided that it has no adverse effect upon the reaction. Preferred solvents are exemplified by nitriles such as acetonitrile, halogenated hydrocarbons such as dichloromethane or chloroform and mixtures of two or more of these solvents.

The reaction temperature and the time required for the reaction vary depending upon the nature of the starting compound and solvent and other reaction conditions, but the reaction is normally carried out at a temperature of 0° to 50° C. and it is complete within a period of 5 minutes to 3 days.

Where the substrate contains a sulfur atom, the deprotection can preferably be achieved using a combination of aluminium chloride and sodium iodide.

After completion of the reaction, the desired compound is isolated from the reaction mixture, for example, by neutralizing properly the reaction mixture or filtering off insoluble materials if any, adding water and a water-immiscible organic solvent such as ethyl acetate thereto, separating the organic layer containing the desired compound, washing the extract with water, drying over anhydrous magnesium sulfate etc., and finally distilling off the solvent. The desired compound thus obtained, if necessary, can be further purified by conventional means, for example, recrystallization, reprecipitation, chromatography or the like means.

[Steps 7, 12, 14, 17, 23, 26, 28, 30, 33 and 35]

In these steps, CPG-bond oligodeoxyribonucleotides (3), (4a), (4b), (5), (6a) to (6d), (7a) and (7b) can be prepared by using CPG-bond nucleosides comprizing the 3'-end nucleosides of the said effective base sequence, repeating the elongation step of DNA chain on a DNA synthesizer, and finally preparing one nucleotide short fragment from 5' end of the said effective sequence.

The elongation of DNA chain on a DNA synthesizer is explained according to the "phosphoramidite" approach but it is understood that this method of description of description and not of limitation.

In Step 7 commercially available CPG-bound D" (3-1) is treated with a deprotecting reagent of a DMT group on a DNA synthesizer to remove a 5'-terminal DMT group and then it is condensed with a nucleotide unit commercialized for a DNA synthesizer followed by forming a phosphorous acid triester linkage, which is subsequently oxidized to phosphoric acid triester by using a proper oxidizing agent. After synthesizing one nucleotide short fragment from 5' end of the said effective sequence by repeating these steps, there is prepared CPG-bond ODN (3) having a 5'-terminal DMT group. The CPG-bound ODN of the desired nucleotide base sequence, the 5'-terminal of which is protected with a DMT group, can be synthesized according to the procedure reported by H. Koster et al. in Nucleic Acid Res., 12, 4539(1984) or its modified procedure using a synthesizer based on a phosphoramidite method, for example, Model 380B (a product of Applied Biosystems Inc.) or Cyclon Plus (a product of MilliGen/Biosearch).

A base moiety of the nucleotide unit to be used for synthesizing ODN is those which is protected with an acyl group. Preferred acyl groups are exemplified by a benzoyl group in case the base moiety is A or C and a isobutyryl group in case it is G.

Examples of the acidic substances to be used as a catalyst in the condensing reaction of the step include acidic substances including tetrazoles, preferably tetrazole.

There is no particular limitation upon the nature of the solvent used, provided that it has no adverse effect upon the reaction. Preferred solvents are exemplified by acetonitrile and tetrahydrofuran.

The reaction is carried out at a temperature of from −30° to 50° C., normally at room temperature.

The time required for the reaction varies depending upon the reaction temperature but the reaction is complete within a period of 1 minute to 20 hours. When the reaction is carried out at room temperature, it is complete within 10 minutes.

There is no particular limitation upon the nature of the oxidizing agent used in these steps, provided that it can be used in conventional oxidation as an oxidizing agent. Examples of preferred oxidizing agents include: inorganic metal oxidizing agents including manganese oxides such as potassium permanganate or manganese dioxide; ruthenium oxides such as ruthenium tetraoxide; selenium compounds such as selenium dioxide; iron compounds such as ferric chloride; osmium compounds such as osmium tetraoxide; silver compounds such as silver oxide; mercury compounds such as mercuric acetate; lead oxide compounds such as lead oxide or lead tetraoxide; chromic acid compounds such as potassium chromate, a complex of chromium sulfate and sulfuric acid or a complex of chromic acid and pyridine; cerium compounds such as cerium ammonium nitrite (CAN); inorganic oxidizing agents including halogen molecules such as chlorine, bromine or iodine molecule; periodates such as sodium periodate; ozone; hydrogen peroxide; nitrous compounds such as nitrous acid; chlorous acid compounds such as potassium chlorite or sodium chlorite; persulfuric acid compounds such as potassium persulfate or sodium persulfate; organic oxidizing agents including reagents used in DMSO oxidation (a complex of dimethylsulfoxide and dicyclohexylcarbodiimide, oxalyl chloride, acetic anhydride or phosphorus pentaoxide, or a complex of pyridine and sulfur trioxide); peroxides such as tert-butyl hydroperoxide; stable cations such as triphenylmethyl cation; succinimides such as N-bromosuccinimide; hypochlorous acid compounds such as tert-butyl hypochlorite; azodicarboxylic acid compounds such as azodicarboxylate; a combination of triphenylphosphine and disulfides such as dimethyl disulfide or diphenyl disulfide; nitrous esters such as methyl nitrite; tetrahalogenocarbons such as tetrabromomethane; quinones such as 2,3-dichloro-5,6-dicyano-p-benzoquinone (DDQ); preferably iodine.

There is no particular limitation upon the nature of the solvent used, provided that it has no adverse effect upon the reaction. Examples of preferred solvents include: aromatic hydrocarbons such as benzene, toluene or xylene; halogenated hydrocarbons such as dichloromethane or chloroform; ethers such as ether, tetrahydrofuran, dioxane or dimethoxyethane; amides such as dimethylformamide, dimethylacetamide or hexamethylphosphoric triamide; sulfoxides such as dimethylsulfoxide; alcohols such as methanol, ethanol, n-propanol, isopropanol, n-butanol, isobutanol or isoamyl alcohol; diluted acids such as aqueous sulfric acid; diluted bases such as an aqueous solution of sodium hydroxide; water; ketones such as acetone or methyl ethyl ketone; heterocyclic amines such as pyridine; and nitriles such as acetonitrile; preferably heterocyclic amines (particularly pyridine), nitriles (particularly acetonitrile), ethers (particularly tetrahydrofuran) and halogenated hydrocarbons (particularly dichloromethane).

The reaction is carried out at a temperature from −50° to 100° C. The time required for the reaction varies mainly depending upon the reaction temperature as well as the nature of the starting compound and solvent but the reaction is carried out at a temperature of −50° to 100° C. and it is normally complete within a period of 30 minutes to 15 hours. The oxidation reaction described abvoe is accelerated by adding a phase-transfer catalyst such as triethylbenzylammonium chloride or tributylbenzylammonium bromide.

Steps 12, 14, 17, 23, 26, 28, 30, 33 and 35 are similar.

[Steps 9 and 20]

In these steps a half ester of dicarboxylic acid can be prepared by reacting a free hydroxyl group of a compound (4-2) or (6-2) with an anhydride of dicarboxylic acid such as succinic anhydride in the presence of a base catalyst.

There is no particular limitation upon the nature of the dicarboxylic acid used. Preferred dicarboxylic acids are those which contain 2 to 10 carbon atoms and the most preferred dicarboxylic acid is succinic acid or glutaric acid. Examples of suitable base catalysts include: aminopyridines such as dimethylaminopyridine or pyrrolidinopyridine; tertiary amines such as trimethylamine or triethylamine; sodium hydrogencarbonate; and alkali metal carbonates such as potassium carbonate; most preferably dimethylaminopyridine or pyrrolidinopyridine.

There is no particular limitation upon the nature of the solvent used, provided that it has no adverse effect upon the reaction and is capable of dissolving the starting material in some extent. Examples of preferred solvents include: aromatic hydrocarbons such as benzene, toluene or xylene; halogenated hydrocarbons such as dichloromethane or chloroform; ethers such as ether, tetrahydrofuran, dioxane or dimethoxyethane; amides such as dimethylformamide, dimethylacetamide or hexamethylphosphoric triamide; sulfoxides such as dimethylsulfoxide; alcohols such as methanol, ethanol, n-propanol, isopropanol, n-butanol, isobutanol or isoamyl alcohol; diluted acids such as aqueous sulfuric acid; diluted bases such as an aqueous solution of sodium hydroxide; water; ketones such as acetone or methyl ethyl ketone; heterocyclic amines such as pyridine; and nitriles such as acetonitrile; more preferably nitriles (particularly acetonitrile), ethers (particularly tetrahydrofuran) and halogenated hydrocarbons (particularly dichloromethane).

The reaction is carried out at a temperature of −50° to 100° C. The time required for the reaction varies mainly depending upon the reaction temperature as well as the nature of the starting compound and solvent used, but the reaction is normally complete within a period of 30 minutes to 15 hours.

[Steps 10 and 21]

In these steps the desired compounds (4-5) and (6—6) can be prepared by reacting half esters of succinic acid (4-3) and (6-4) prepared in Steps 9 and 20 with phenols such as pentachlorophenol in the presence of a condensing agent to produce an activated ester and subsequently reacting the product with CPG-amines (4-4) and (6-5) in the presence of a base.

There is no particular limitation upon the nature of phenols used in this reaction. Preferred phenols are exemplified by pentachlorophenol and 4-nitrophenol.

There is no particular limitation upon the nature of the solvent used, provided that it has no adverse effect upon the reaction and is capable of dissolving the starting material in some extent. Examples of suitable solvents include: amides such as dimethylformamide, dimethylacetamide or hexamethylphosphoric triamide; sulfoxides such as dimethylsulfoxide; ketones such as acetone or methyl ethyl ketone; heterocyclic amines such as pyridine; and nitriles such as acetonitrile; preferably amides such as dimethylformamide.

There is no particular limitation upon the nature of the base used, provided that it can be used as a base in conventional reaction. Examples of preferred bases include: organic bases such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO) or 1,8-diazabicyclo[5,4,0]undec-7-ene (DBU); more preferably organic bases, particularly triethylamine, pyridine, N-methylmorpholine and DBU.

The reaction is carried out at a temperature of −50° to 100° C. The time required for the reaction varies mainly depending upon the reaction temperature as well as the nature of the starting compound or solvent used, but when the reaction is carried out at room temperature, it is normally complete within a period of 30 to 50 hours.

[Steps 13 and 32]

In Step 13 CPG-bound nucleoside (4-7) containing a thioate group can be prepared by reacting a compound (4-6) prepared in Step 11 with a commercially available 5'-O-DMT-nucleoside-3'-phosphoramidite reagent on a DNA synthesizer and subsequently reacting with a thioating reagent.

There is no particular limitation upon the nature of the thioating reagent used, provided that it is capable of forming a thioate group by reacting with trivalent phosphorus. Exmaples of preferred thioating reagents include: in addition to sulfur, tetraethylthiuram disulfide (TETD) (a product of Applied Biosystems Inc.) and Beaucage reagent (a product of MilliGen/Biosearch). The desired compound (4-7), in which 3'-end nucleoside of the said effective base sequence is supported on CPG through a thioate group, can be prepared by treating with tetraethylthiuram disulfide (TETD) according to the procedure reported in Tetrahedron Letters, 32, 3005 (1991) or with Beaucage reagent according to the procedure reported in J. Am. Chem. Soc., 112, 1253 (1990) or its modified procedure.

In Step 32 CPG-bound nucleoside (7-7) having a phosphoric triester or thioate grouop can be prepared by reacting a compound (7-3) with a phosphoramidite reagent followed by treating by conventional means or with a thioating agent.

[Step 15]

In the step a CPG-bound compound (5-3) having a phosphonic acid diester group can be prepared by reacting a CPG-bound compound (5-1) freed from a DMT group, which is obtained in analogy with the preparation of a CPG-bound compound (4-6), with a commercially available phosphonic acid monoester compound (5-2) in the presence of a condensing agent and a deacidifying agent. There is no particular limitation upon the nature of the condensing agent used, provided that it can be formed an acid anhydride with phosphonic acid monoester. Examples of preferred condensing agents include adamantane-1-carbonyl chloride and pivaloyl chloride. There is no particular limitation upon the nature of the deacidifying agent used, provided that it can be used as a deacidifying agent in case acylation is carried out using an acid chloride. Examples of preferred deacidifying agents, in general, include aromatic amines such as pyridine. There is no particular limitation upon the nature of the solvent used, provided that it has no adverse effect upon the reaction. Examples of preferred solvents include nitriles such as anhydrous acetonitrile. When the reaction is carried out at room temperature, it is complete within a period of 5 to 60 minutes.

[Step 16]

In the step a phosphonic acid diester group of a CPG-bound compound (5-3) is transformed to a phosphoramidate group by reacting with alkylamine and carbon tetrachloride. As alkylamine there are to be understood the desired alkylamines. There is no particular limitation upon the nature of the solvent used, provided that it has no adverse effect upon the reaction. Examples of preferred solvents include normally non-polar solvents such as carbon tetrachloride. The reaction temperature is not particularly critical and the reaction is normally carried out at a temperature from −50° to 100° C. When the reaction is conducted at room temperature, it is complete within a period 1 to 10 hours.

[Steps 19 and 36]

In these steps 3'-phosphorous acid derivatives (6-3) and (8) can be prepared by reacting compounds (6-2) and (2) with chlorophosphoramidite (6-3'), which is used as a phosphitylating agent, in the presence of an inert solvent and a deacidifying agent. U used in the definition of a compound (6-3') signifies a dialkylamino group such as a dimethylamino or diisopropylamino group or a heterocyclic group having 1 or 2 oxygen and/or nitrogen atoms in the ring. V used in the definition of a compound (6-3') may be any group, provided that it can be removed after forming a phosphate bond. Examples of such groups include preferably lower alkyloxy groups such as a methoxy group and cyanoalkyloxy groups such as cyanoethyloxy group. As the compound (6-3') there are to be understood especially phosphines such as chloromorpholinomethoxyphosphine, chloromorpholinocyanoethoxyphosphine, chlorodimethylaminomethoxyphosphine, chlorodimethylaminocyanoethoxyphosphine, chlorodiisopropylaminomethoxyphosphine and chlorodiisopropylaminocyanoethoxyphosphine; preferably chloromorpholinomethoxyphosphine, chloromorpholinocyanoethoxyphosphine, chlorodiisopropylaminomethoxyphosphine and chlorodiisopropylaminocyanoethoxyphosphine.

There is no particular limitation upon the nature of the solvent used, provided that it has no adverse effect upon the reaction. Preferred solvents are ethers such as tetrahydrofuran, diethyl ether or dioxane. Examples of deacidifying agents include: heterocyclic amines such as pyridine or dimethylaminopyridine and aliphatic amines such as trimethylamine, triethylamine or diisopropylethylamine, preferably aliphatic amines (particularly diisopropylethylamine).

The reaction temperature is not particularly critical, but the reaction is normally carried out at a temperature from −50° to 50° C., preferably at room temperature.

The time required for the reaction varies depending upon the nature of the starting compound and reagent as well as the reaction temperature, but the reaction is normally complete within a period of 5 minutes to 30 hours. When the reaction is preferably carried out at room temperature, it is complete within a period of 30 minutes.

The desired compound can be recovered from the reaction mixture, for example, by neutralizing properly the reaction mixture or filtering off insoluble materials if any, adding water and a water-immiscible solvent such as ethyl acetate, separating the organic layer containing the desired compound, washing the extract with water, drying over anhydrous magnesium sulfate etc., and finally distilling off the solvent.

The desired compound thus obtained, if necessary, can be further purified by conventional means, if necessary, can be further purified by conventional means, for example, recrystallization, reprecipitation, chromatography or the like means.

[Step 24]

In this step a CPG-bound compound (6-8) having a phosphoric triester group can be prepared in analogy with the procedure described in Step 7, but using a compound (6-3) instead of a nucleoside phosphoramidite compound used as a nucleotide unit on a DNA synthesizer.

[Steps 27 and 29]

In these steps CPG-bound compounds (6-10 and 6-11) having 2 or 3 phosphoric triester groups can be prepared from a CPG-bound compound (6-9) prepared in Step 25 by treating in analogy with the procedure described in Step 24.

[Step 31]

In this step a CPG-bound compound (7-3) having a 4,4'-dimethoxytrityloxyethylsulfonylethoxy group can be prepared by treating a commercially available CPG-bound compound (7-2) freed from a 5'-DMT group with (2-cyanoethoxy)-2-[2'-O-(4,4'-dimethoxytrityloxyethylsulfonyl]ethoxy-N,N-diisopropylaminophosphine (7-1) [T. Horn et al., Tetrahedron Letters, 27, 4705(1986)] in analogy with the procedure described in Step 24.

[Step 34]

In the step a CPG-bound compound (7-5) can be preapred by deprotecting a DMT group from a CPG-bound compound (7-3) prepared in Step 31 and then condensing with a nucleotide (7-4) having a DMT group at the 5'-position and a group of alkyl phosphate, phenyl phosphate, alkyl phosphonate or phenyl phosphonate at the 3'-position by the use of a condensing agent.

There is no particular limitation upon the nature of the solvent used, provided that it has no adverse effect upon the reaction. Preferred solvents are aromatic amines such as pyridine. As the condensing agents there come into consideration dicyclohexylcarbodiimide (DCC), mesitylenesulfonyl chloride (Ms-Cl), triisopropylbenzenesulfonyl chloride, mesitylenesulfonyltriazole (MST), mesitylenesulfonyl-3-nitrotriazole (MSNT), triisopropylbenzenesulfonyltetrazole (TPS-Te), triisopropylbenzenesulfonylnitroimidazole (TPS-NI) and triisopropylbenzenesulfonylpyridyltetrazole; preferably MSN, TPS-Te and TPS-NI.

The reaction temperature is not particularly critical but the reaction is carried out at a temperature of −10° to 100° C. The time required for the reaction varies depending upon the nature of the solvent used and the reaction temperature. When the reaction is carried out at room temperature using pyridine as a solvent, it is complete within a period of 30 minutes.

[Step 37]

In this step the final product (1) can be prepared by condensing a compound (8) prepared in Step 36 with CPG-bound ODN (3, 4a, 4b, 5, 6a to 6d, 7a or 7b), which is synthesized on a DNA synthesizer and deprotected a 5'-terminal DMT group alone, using an acid catalyst to form phosphite triester, oxidizing using an appropriate oxidizing agent to produce phosphoric acid triester, cleaving from CPG, removing the protecting groups and finally purifying.

As an acid catalyst used in the condensing reaction there come into consideration acid substances such as tetrazoles; preferably tetrazole.

There is no particular limitation upon the nature of the oxidizing agent used, provided that it can be used as an oxidizing agent in oxidation reactions. Examples of preferred oxidizing agents include: inorganic metal oxides including manganese oxides such as potassium permanganate or manganese dioxide; ruthenium oxides such as ruthenium tetraoxide; selenium oxides such as selenium dioxide; iron compounds such as ferric chloride; osmium compounds such as osmium tetraoxide; silver compounds such as silver oxide; mercuryl compounds such as mercury acetate; lead oxide compounds such as lead oxide or lead tetraoxide; chromic acid compounds such as potassium chromate, a complex of chromic acid and sulfuric acid or a complex of chromic acid and pyridine; and cerium compounds such as cerium ammonium nitrate (CAN); inorganic oxidizing agents including halogen molecules such as a chlorine, bromine or iodine molecule; periodides such as sodium periodide; ozone; hydrogen peroxide; nitrous compounds such as nitrous acid; chlorous acid compounds such as sodium chlorite; persulfate compounds such as potassium persulfate or sodium persulfate; and organic oxidizing agents including reagents used in DMSO oxidation (a combination of dimethylsulfoxide and dicylcohexylcarbodiimide, oxalyl chloride, acetic anhydride or phosphorus pentachloride or a complex of pyridine and sulfuric anhydride); peroxides such as tert-butyl hydroperoxide; stable cations such as triphenylmethyl cation; succinimides such as N-bromosuccinimide; hypochlorous acid compounds such as tert-butyl hypochlorite; azodicarboxylic acid compounds such as azodicarboxylate; a combination of disulfides such as dimethyl disulfide, diphenyl disulfide or dipyridyl disulfide and triphenylphosphine; nitrites such as methyl nitrite; tetrahalogenated compounds such as tetrabromomethane; and quinone compounds such as 2,3-dichloro-5,6-dicyano-p-benzoquinone (DDQ); more preferably iodine.

There is no particular limitation upon the nature of the solvent used, provided that it has no adverse effect upon the reaction and is capable of dissolving the starting materials in some extent. Examples of preferred solvents include: aromatic hydrocarbons such as benzene, toluene or xylene; halogenated hydrocarbons such as dichloromethane or chloroform; ethers such as ether, tetrahydrofuran, dioxane or dimethoxyethane; amides such as dimethylformamide, dimethylacetamide or hexamethylphosphoric triamide; sulfoxides such as dimethylsulfoxide; alcohols such as methanol, ethanol, n-propanol, isopropanol, n-butanol, isobutanol or isoamyl alcohol; diluted acids such as aqueous sulfuric acid; diluted bases such as an aqueous solution of sodium hydroxide; water; ketones such as acetone or methyl ethyl ketone; heterocyclic amines such as pyridine; nitriles such as acetonitrile; preferably heterocyclic amines (particularly pyridine), nitriles (particularly acetonitrile), ethers (particularly tetrahydrofuran) and halogenated hydrocarbons (particularly dichloromethane).

The reaction is conducted at a temperature of −50° to 100° C. The time required for the reaction varies mainly depending upon the reaction temperature and the nature of the starting compound within a period of 30 minutes to 15 hours. The oxidation reaction described above is accelerated by adding a phase transfer catalyst such as triethylbenzylammonium chloride or tributylbenzylammonium bromide.

[Step 38]

In this step an intermediate, mononucleotide (9) can be prepared by reacting a compound (2) with a phosphorylating agent, for example, bistriazolide in the presence of an inert solvent and adding water followed by working-up.

There is no particular limitation upon the nature of the solvent used, provided that it has no adverse effect upon the reaction. The solvent is normally selected from aromatic amines such as pyridine. There is no particular limitation upon the nature of V used in the definition of the phosphorylating agent, provided that it can be removed under the condition removing a protecting group of a base moiety after completion of the condensation reaction of Step 39. V signifies usually a o-chlorophenoxy gorup.

Although the reaction temperature is not particularly critical, the reaction is carried out at a temperature of −20° to 100° C., normally at room temperature. The time required for the reaction varies depending upon the nature of the solvent used and the reaction temperature. When the reaction is carried out at room temperature using pyridine as a solvent, it is complete within a period of an hour.

[Step 39]

In this step the final product (1) can be prepared by condensing a mononucleotide (9) with CPG-bound ODN (3, 4a, 4b, 5, 6a to 6d, 7a or 7b), which is synthesized on a DNA synthesizer and deprotected a 5'-terminal DMT group, having protecting groups in the base and phosphoric acid moieties by the use of a condensing agent to form a phosphoric acid triester group, cleaving from CPG by conventional means, deprotecting a protecting group, and finally purifying. There is no particular limitation upon the nature of the solvent used, provided that it has no adverse effect upon the reaction.

Examples of condensing agents include: dicyclocarbodiimide (DCC), mesitylenesulfonyl chloride (Ms-Cl), triisopropylbenzenesulfonyl chloride, mesitylenesulfonyltriazole (MST), mesitylenesulfonyl-3-nitrotriazole (MSNT), triisopropylbenzenesulfonyltetrazole (TPS-Te), triisopropylbenzenesulfonylnitroimidazole (TPS-NI) and triisopropylbenzenesulfonylpyridyltetrazole; preferably MSNT, TPS-Te and TPS-NI.

The reaction temperature is not particularly critical but the reaction is carried out at a temperature of −10° to 100° C., usually at room temperature. Although the time required for the reaction varies depending upon the nature of the solvent used and the reaction temperature. When the reaction is carried out at room temperature using pyridine as a solvent, it is complete within a period of 30 minutes.

Cleaving ODN from CPG-bound ODN and removing the protecting groups excepting the 5'-terminal substituent are carried out according to the methods known per se (J. Am. Chem. Soc., 103, 3185(1981)]. The reaction mixture containing the compounds of general formula (1) is purified by conventional purification techniques, for example, various chromatography including reverse phase and ion-exchenge chromatography (comprizing high speed liquid chromatography) to produce the compounds having the said general formula (1).

[Step 40]

In this step tris(1,2,4-triazolyl)phosphite which is previously prepared from phosphorus trichloride and 1,2,4-triazole according to the procedure reported by B. C. Freohler, P. G. Ng and M. D. Matteucci in Nucleic Acids Res., 14, 5399(1986) is reacted with a compound (2) in an inert solvent and the reaction is stopped by adding water followed by working-up to produce a nucleoside 3'-H-phosphonate (10). There is no particular limitation upon the nature of the solvent used, provided that it has no adverse effect upon the reaction. A preferred solvent is a halogenated hydrocarbon such as dichloromethane. The reaction temperature is not particularly critical but the reaction is carried out at a temperature of −20° to 100° C., usually at room temperature.

The time required for the reaction varies depending upon the nature of the solvent used and the reaction temperature. When the reaction is carried out at room temperature using dichloromethane as a solvent, it is complete within a period of 30 minutes.

[Step 41]

In this step the final product (1) can be prepared by reacting the nucleoside 3'-H-phosphonate (10) prepared in Step 40 with CPG-bound ODN (3, 4a, 4b, 5, 6a to 6d, 7a or 7b), which is synthesized on a synthesizer and deprotected a 5'-terminal DMT group alone, having protecting groups in the base and phosphoric acid moieties by the use of a condensing agent such as pivaloyl chloride in the presence of a deacidifying agents to produce a H-phosphonic acid diester bond, transforming the H-phosphonic acid group to a phosphoric acid diester group using an oxidizing agent, cleaving ODN from CPG-bound ODN and concurrently removing the protecting group of a base moiety under basic conditions, and finally purifying. There is no particular limitation upon the nature of the solvent used, provided that it has no adverse effect upon the reaction. A preferred solvent is anhydrous acetonitrile. Examples of condensing agents include acid chlorides and phosphoric chloride, preferably pivaloyl chloride.

There is no particular limitation upon the nature of the oxidizing agent used for oxidizing a H-phosphonic acid group of ODN to a phosphoric acid diester group, provided that it can be used as an oxidizing agent in oxidation reactions. Examples of suitable oxidizing agents include: inorganic metal oxides including manganese oxides such as potassium permanganate or manganese dioxide; ruthenium oxides such as ruthenium tetraoxide; selenium oxides such as selenium dioxide; iron compounds such as ferric chloride; osmium compounds such as osmium tetraoxide; silver compounds such as silver oxide; mercuryl compounds such as mercury acetate; lead oxide compounds such as lead oxide or lead tetraoxide; chromic acid compounds such as potassium chromate, a complex of chromic acid and sulfuric acid or a complex of chromic acid and pyridine; and cerium compounds such as cerium ammonium nitrate (CAN); inorganic oxidizing agents including halogen molecules such as a chlorine, bromine or iodine molecule; periodides such as sodium periodide; ozone; hydrogen peroxide; nitrous compounds such as nitrous acid; chlorous acid compounds such as sodium chlorite; and persulfate compounds such as potassium persulfate or sodium persulfate; and organic oxidizing agents including reagent used in DMSO oxidation (a combination of dimethylsulfoxide and dicyclohexylcarbodiimide, oxalyl chloride, acetic anhydride or phosphorus pentachloride or a complex of pyridine and sulfuric anhydride); peroxides such as tert-butyl hydroperoxide; stable cations such as triphenylmethyl cation; succinimides such as N-bromosuccinimide; hypochlorous acid compounds such as tert-butyl hypochlorite; azodicarboxylic acid compounds such as azodicarboxylate; a combination of disulfides such as dimethyl disulfide, diphenyl disulfide or dipyridyl disulfide and triphenylphosphine; nitrites such as methyl nitrite; tetrahalogenated compounds such as tetrabromomethane; and quinone compounds such as. 2,3-dichlor-5,6-dicyano-p-benzoquinone (DDQ); more preferably iodine.

As the deacidifying agent used there come into consideration heterocyclic amines such as pyridine or dimethylaminopyridine and aliphatic amines such as trimethylamine, triethylamine or diisopropylethylamine; preferably aliphatic amines (particularly diisopropylethylamine). The reaction temperature is not particularly critical but the reaction is normally carried out at a temperature of -50° to 50° C., preferably at room temperature.

The time required for the reaction varies depending upon the nature of the starting compound and solvent used as well as the reaction temperature, but the reaction is normally at a temperature of 5 minutes to 30 hours. When the reaction is carried out at room temperature, it is preferably complete within a period of 30 minutes.

Cleaving ODN from CPG-bound ODN and removing protecting groups excepting the 5'-terminal substituent are carried out according to the methods known per se (J. Am. Chem. Soc., 103, 3185(1981)].

The reaction mixture containing the compounds of general formula (1) is purified by conventional purification techniques, for example, various chromatography including reverse phase and ion-exchenge chromatography (comprizing high speed liquid chromatography) to produce the compounds having the said general formula (1).

The present invention further provides a new process for the synthesis of oligodeoxyribonucleotides and oligodeoxyribonucleotide derivatives. The new oligodeoxyribonucleotides of formula (11) prepared by the new process typically include the new compounds of the general formula (1). Furthermore, for use in the new process, the present invention provides new intermediate compounds, as will be more concretely defined.

In the following description, a different set of definitions are employed for the substituent groups, but the correspondence between the respective definitions may be readily recognized. Thus, for example, the similarity can be seen between the substituent group $R_1R_2R_3Z$- of the compounds of general formula (1), and the substituent group $R^4R^5R^6Z$- shown for the compounds employed and produced by the new process. Moreover, it is necessary to note that the groups shown with subscipt identifiers, such as $R_1$, $R_2$, $Y_1$, etc, are not always identical with the groups shown with superscript identifiers, such as $R^1$, $R^2$, $Y^1$, etc.

In this aspect of the invention, the process provided by the invention involves producing an oligodeoxyribonucleotide having a substituted phosphate at the 3'-end. More particularly, the present invention provides novel linker compounds for use with polymer supports in the preparation of solid phase materials for synthesis of oligodeoxyribonucleotides. The solid phase materials can have a protected hydroxy group at the end of the linker to the polymer support, which can then be deprotected and reacted to add nucleotides.

Thus, for example, the present invention provides linker compounds such as the following compounds (12) which with polymer supports can give protected solid phase materials (14) for deprotection to compounds (22) and subsequent reaction to compounds (24), (25) and (27) with added nucleotides.

In one aspect, the present process is for producing a compound represented by the formula (11):

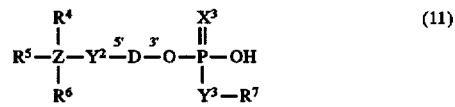

[wherein $R^4$, $R^5$, $R^6$ and a group Z (wherein $R^4$, $R^5$ and $R^6$ may be the same or different from one another and each independently represent a hydrogen atom, an alkyl group having 1 to 4 carbon atoms, an optionally substituted aryl group or an optionally substituted anthraquinonyl group; Z represents a carbon or silicon atom; $R^5$, $R^6$ and Z may together represent a fluorenyl group or a xanthenyl group; or $R^4$, $R^5$, $R^6$ and Z may together represent a hydrogen atom); $R^7$ represents a hydrogen atom, an optionally substituted alkyl group having 1 to 4 carbon atoms, an optionally substituted aryl group or an optionally substituted aralkyl group; $Y^2$ may be the same or different and represents an oxygen atom, a sulfur atom or an NH group; $Y^3$ represents an oxygen atom, a sulfur atom, an NH group, an alkylene group having 1 to 4 carbon atoms or a phenylene group; $X^3$ represents an oxygen or sulfur atom; and D represents an oligodeoxyribonucleotide having a chain length of 2 to 30, provided that the hydroxyl groups at the 5'-and 3'-terminals are not included in D.];
said process comprises:
reacting a compound represented by the formula (12):

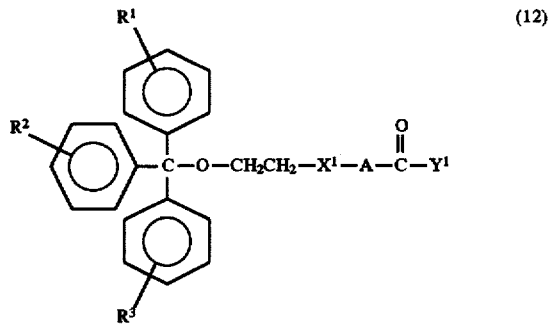

[wherein $R^1$, $R^2$ and $R^3$ may be the same or different from one another and each independently represent a hydrogen atom or an alkoxy group having 1 to 4 carbon atoms; $X^1$ represents a group —S—, —SO— or —SO$_2$; A represents a group —(CH$_2$)$_h$— (wherein h is an integer of 1 to 16), a group —(CH$_2$)$_h$O— (wherein h is an integer of 1 to 16), a group —(CH$_2$)$_j$—O—CO—(CH$_2$)$_k$— (wherein j is a positive integer, k is 0 or a positive integer, and j+k is 2 to 16) or a group —(CH$_2$)$_j$—NH—CO—(CH$_2$)$_k$— (wherein j is a positive integer, k is 0 or a positive integer, and j+k is 2 to 16), a group —(CH$_2$)$_j$—S—CO—(CH$_2$)$_k$— (wherein j is a positive integer, k is 0 or a positive integer, and j+k is 2 to 16) or a group —(CH$_2$)$_n$—O—CO—CH$_2$(OCH$_2$CH$_2$)$_p$—OCH$_2$— (wherein n is a positive integer, p is 0 or a positive integer, and j+k is 2 to 100); and $Y^1$ represents a hydroxyl group, an optionally substituted phenyloxy group or an ethyloxy group which may be substituted by a halogen.]
with a polymeric material represented by the general formula (13):

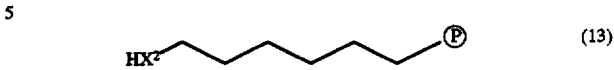

[wherein $X^2$ represents an oxygen atom, a sulfur atom or an NH group; and P represents a polymeric material.] (provided that in the case where $Y^1$ in the general formula (12) is a hydroxyl group, the compound of the general formula (12) is reacted with a carboxylic acid activating agent before reaction with the polymeric material (13)) co form a polymeric material represented by the general formula (14):

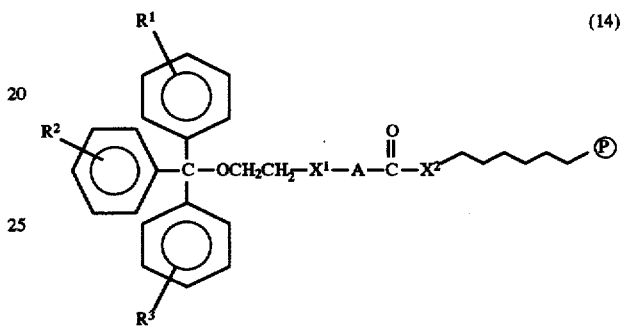

[wherein $R^1$, $R^2$, $R^3$, $X^1$, A, $X^2$ and P have the same meanings as defined above; and
subjecting the resulting polymeric material of the formula (14) to DNA chain extension treatment using a DNA synthesizer.

This process of the present invention is shown in the following flow charts.

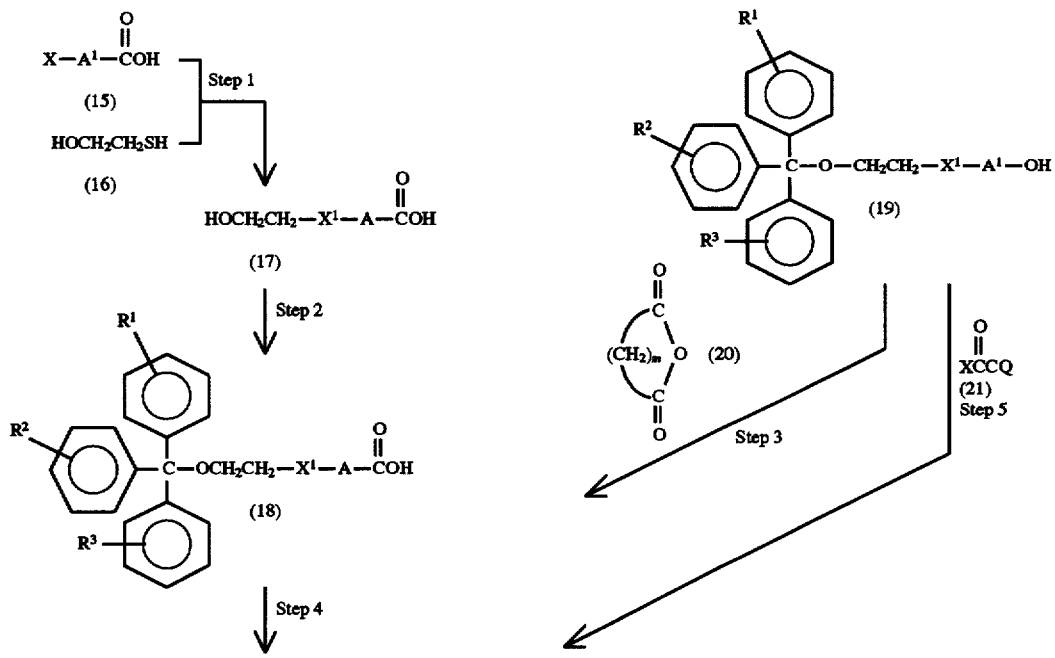

-continued
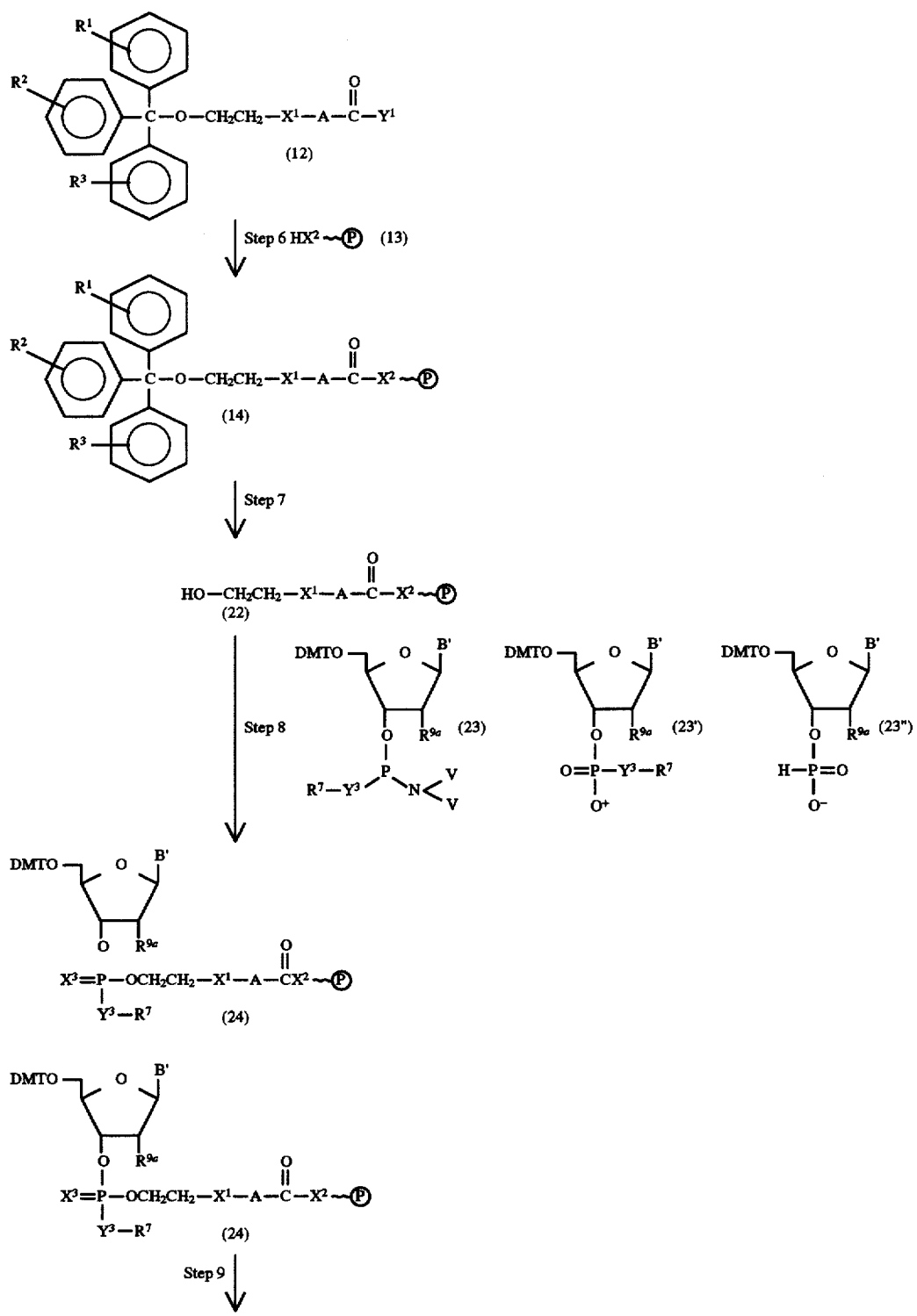

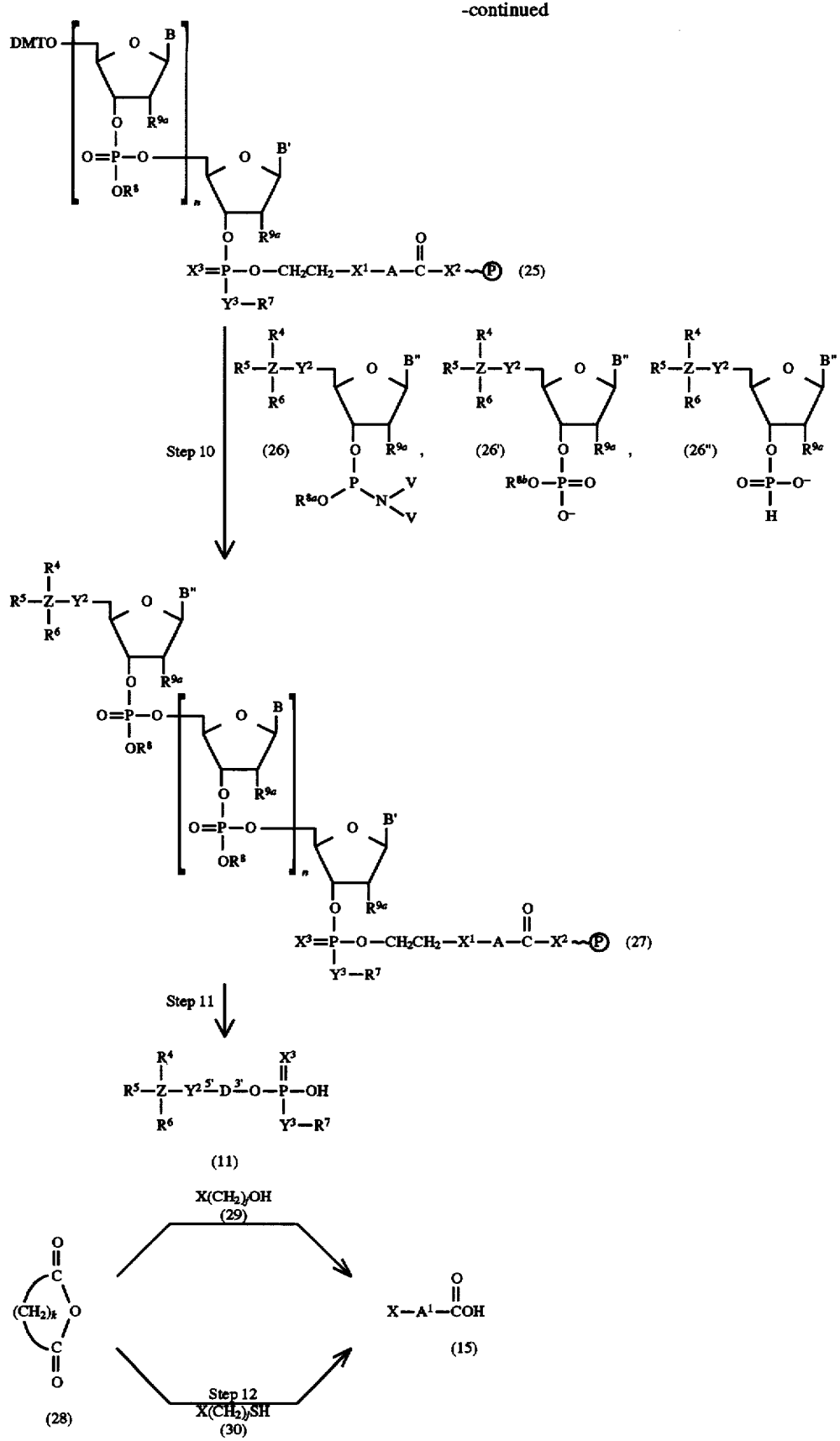

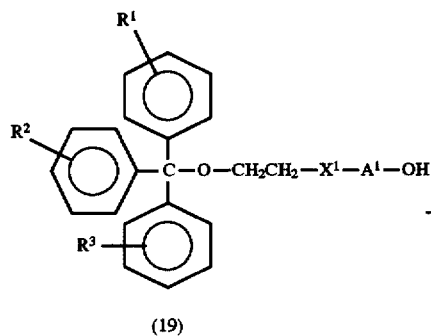

(19)

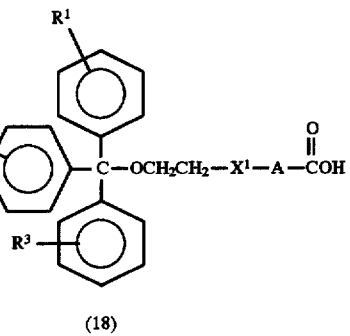

(18)

Step 13
$$\overline{\text{HOOCCH}_2\text{CH}_2(\text{OCH}_2\text{CH}_2)_n\text{OCH}_2\text{COOH}}$$
(31)

In the above flow charts, $R^1$, $R^2$, $R^3$, $R^4$, $R_5$, $R^6$, $R_7$, $X^1$, $X^2$, $X^3$, P, $Y^1$, $Y^2$, $Y^3$, A and Z have the same meanings as defined above (however, in the compounds other than the compound (11), $R^4$, $R^5$, $R^6$ and Z together do not represent a hydrogen atom). $R^{8a}$ represents a methyl group or a cyanoethyl group; $R^{8b}$ represents a phenyl group optionally substituted by a chloro group; $R^8$ represents a methyl group, a cyanoethyl group or a phenyl group optionally substituted by a chloro group; $R^{9a}$ represents a hydrogen atom or a hydrogen group having a protecting group; X represents a halogen atom (preferably chlorine, bromine and iodine); $A^1$ represents an alkylene group having 1 to 20 carbon atoms; m is an integer of 1 to 14; n is an integer of 1 to 28; B, B' and B" each represent the base moiety of adenine nucleotide, guanine nucleotide, thymine nucleotide, uracil nucleotide and cytosine nucleotide protected at the base and phosphate moieties (they should be selected to provide a desired base sequence); with the provide that B' represents the base moiety of the 3'-terminal nucleotide of D having the desired base sequence; B" represents the base moiety of the 5'-terminal nucleotide of D having the desired base sequence; D represents the desired oligodeoxyribonucleotide (provided that the 5'-terminal hydroxyl group and the 3'-terminal hydroxyl group are not included); Q represents a halogenoalkyl group, a halogenophenyl group or a nitrophenyl group such as a 2,2,2-trichloroethyl group, 2,2-dichloroethyl group, 2-chloroethyl group, 2,2,2-tribromoethyl group, 2,2-dibromoethyl group, 2-bromoethyl group, 2-nitrophenyl group, 4-nitrophenyl group, 2,4-dinitrophenyl group, 2,4,5-trichlorophenyl group and 2,3,4, 5,6-pentachlorophenyl group (preferably trichloroethyl group and orthonitrophenyl group); V represents a lower alkyl group (preferably methyl, ethyl and isopropyl groups, particularly isopropyl group).

Next, each step will be described in detail.

(Step 1)

This step is for preparing a compound (17) by reacting 2-mercaptoethanol (16) with a ω-halogenocarboxylic acid (15) in an inert solvent in the presence of an acid binding agent.

The solvent employable is not particularly limited unless it affects the reaction, and it includes aromatic hydrocarbons such as benzene, toluene and xylene; halogenated hydrocarbons such as methylene chloride and chloroform; ethers such as ether, tetrahydrofuran, dioxane and dimethoxyethane; amides such as dimethylformamide, dimethylacetamide and hexamethylphosphorotriamide; sulfoxides such as dimethyl sulfoxide; alcohols such as methanol, ethanol, n-propanol, isopropanol, n-butanol, isobutanol and isoamyl alcohol; dilute acids such as aqueous sulfuric acid; dulute bases such as aqueous sodium hydroxide; water; ketones such as acetone, methyl ethyl ketone; heterocyclic amines such as pyridine; and nitriles such as acetonitrile, preferably ketones such as acetone and alcohols such as ethanol and propanol.

The acid binding agent employable includes alkali metal carbonates such as potassium carbonate and sodium carbonate; alkali metal hydrogencarbonates such as sodium hydrogencarbonate; alkali metal hydroxides such as sodium hydroxide and potassium hydroxide; and organic amines such as triethylamine, preferably alkali metal carbonates (particularly potassium carbonate).

Reaction temperature and reaction time vary depending on the solvent, acid binding agent, etc. employed, the reaction is carried out under reflux with heating for 8 hours when potassium carbonate is used.

After completion of the reaction, the desired compound is isolated from the reaction mixture by conventional procedures.

For example, after the reaction mixture is appropriately neutralized and the insolubles, if present, are removed by filtration, a water-immiscible organic solvent such as ethyl acetate is added to the reaction mixture. After the resulting mixture is washed with water, the organic layer containing the desired compound is separated and dried over anhydrous magnesium sulfate, followed by evaporation of the solvent to give the desired compound.

The desired compound thus obtained may further be purified by conventional procedures such as recrystallization, reprecipitation, chromatography, etc., if necessary.

(Step 2)

This step is for preparing a compound (18), which corresponds to the compound (17) whose hydroxyl group is protected, by reacting the compound (17) with a protecting reagent, which can be eliminated (preferably dimethoxytrityl chloride) under an acidic condition in an inert solvent in the presence of an acid binding agent.

The solvent employable is not particularly limited so long as it does not affect the reaction and can dissolve the starting materials to a certain degree, and it includes aromatic hydrocarbons such as benzene, toluene and xylene; halogenated hydrocarbons such as methylene chloride and chloroform; ethers such as ether, tetrahydrofuran, dioxane and dimethoxyethane; amides such as dimethylformamide, dimethylacetamide and hexamethylphosphorotriamide; sulfoxides such as dimethyl sulfoxide; ketones such as acetone, methyl ethyl ketone; heterocyclic amines such as pyridine; and nitriles such as acetonitrile, preferably heterocyclic amines (especially pyridine).

The protecting reagent employable includes trityl halides such as trityl chloride, monomethoxytrityl chloride, dimethoxytrityl chloride and trimethoxytrityl chloride, preferably dimethoxytrityl chloride.

The acid binding agent employable is not particularly limited unless it affects the reaction and decomposes the product and the starting materials, and it preferably includes aromatic amines such as pyridine and dimethylaminopyridine.

While reaction temperature and reaction time vary depending on the kind of the protecting reagent and acid binding agent employed, the reaction is carried out at room temperature for 2 hours when dimethoxytrityl chloride is used as a protecting reagent and pyridine is used as a solvent and also as an acid binding agent.

After completion of the reaction, the desired compound is isolated from the reaction mixture by conventional procedures.

For example, after the reaction mixture is appropriately neutralized and the insolubles, if present, are removed by filtration, a water-immiscible organic solvent such as ethyl acetate is added to the reaction mixture. After the resulting mixture is washed with water, the organic layer containing the desired compound is separated and dried over anhydrous magnesium sulfate, followed by evaporation of the solvent to give the desired compound.

The desired compound thus obtained may further be purified by conventional procedures such as recrystallization, reprecipitation, chromatography, etc., if necessary.

(Step 3)

This step is for preparing the compound (18) by reacting a compound (19) with a dicarboxylic anhydride (20) in an inert solvent.

The solvent employable is not particularly limited so long as it does not affect the reaction and can dissolve the starting materials to a certain degree, and it includes aromatic hydrocarbons such as benzene, toluene and xylene; halogenated hydrocarbons such as methylene chloride and chloroform; ethers such as ether, tetrahydrofuran, dioxane and dimethoxyethane; amides such as dimethylformamide, dimethylacetamide and hexamethylphosphorotriamide; sulfoxides such as dimethyl sulfoxide;ketones such as acetone, methyl ethyl ketone; heterocyclic amines such as pyridine and nitriles such as acetonitrile, preferably halogenated hydrocarbons such as methylene chloride.

The acid binding agent employable includes pyridines such as pyridine, dimethylaminopyridine and 4-pyrrolidinopyridine, preferably dimethylaminopyridine.

While the dicarboxylic anhydride employable is not particularly limited so long as it is anhydrides of α, ω-alkyldicarboxylic acid having 3 to 16 carbon atoms, it is preferably succinic anhydrides.

While reaction temperature and reaction time vary depending on the kind of the acid anhydride, acid binding agent, etc. employed, the reaction is carried out at room temperature for 30 minutes when succinic anhydride is used and dimethylaminopyridine is used as an acid binding agent.

After completion of the reaction, the desired compound is isolated from the reaction mixture by conventional procedures.

For example, after the reaction mixture is appropriately neutralized and the insolubles, if present, are removed by filtration, a water-immiscible organic solvent such as ethyl acetate is added to the reaction mixture. After the resulting mixture is washed with water, the organic layer containing the desired compound is separated and dried over anhydrous magnesium sulfate, followed by evaporation of the solvent to give the desired compound.

The desired compound thus obtained may further be purified by conventional procedures such as recrystallization, reprecipitation, chromatography, etc., if necessary.

(Step 4)

This step is for forming an active ester (12) by reacting the carboxyl group of the compound (18) having a free carboxyl group with an ester forming reagent, followed by reaction with an optionally substituted phenol.

The solvent employable is not particularly limited unless it affects the reaction, and it includes aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ketones such as acetone, methyl ethyl ketone methyl isobutyl ketone, isophorone and cyclohexanone; nitro compounds such as nitroethane and nitrobenzene; nitriles such as acetonitrile and isobutyronitrile; amides such as formamide, dimethylformamide (DMF), dimethylacetamide and hexamethylphosphorotriamide; and sulfoxides such as dimethyl sulfoxide and sulforane, preferably halogenated hydrocarbons (particularly methylene chloride) and amides (particularly dimethylformamide).

The phenol employable is not particularly limited so long as it can be used as an active ester, and it includes 4-nitrophenol, 2,4-dinitrophenol, 2,4,5-trichlorophenol, pentachlorophenol and 2,3,5,6-tetrafluorophenol, preferably pentachlorophenol.

The ester forming reagent employable includes, for example, N-hydroxy compounds such as N-hydroxysuccinimide, 1-hydroxybenzotriazole and N-hydroxy-5-norbornene-2,3-dicarboxyimide; diimidazole compounds such as 1,1'-oxalyldiimidazole and N,N'-carbonyldiimidazole; disulfide compounds such as 2,2'-dipyridyldisulfide; succinic acid compounds such as N,N'-disuccinimidyl carbonate; phosphinic chloride compounds such as N,N'-bis(2-oxo-3-oxazolidinyl)phosphinic chloride; oxalate compounds such as N,N'-disuccinimidyl oxalate (DSO), N,N-diphthalimidyl oxalate (DPO), N,N'-bis(norbornenylsuccinimidyl) oxalate (BNO), 1,1'-bis(benzotriazolyl) oxalate (BBTO), 1,1'-bis(6-chlorobenzotriazolyl) oxalate (BCTO) and 1,1'-bis(6-trifluoromethylbenzotriazolyl) oxalate (BTBO); and carbodiimides such as dicyclohexylcarbodiimide (DCC), preferably diimidazole compounds and carbodiimides (particularly DCC).

While reaction temperature and reaction time vary depending on the kind of the ester forming reagent and solvent employed, the reaction is carried out at 0° C. to 100° C. for 5 to 50 hours, and particularly when pentachlorophenol and DCC are used in DMF, the reaction is carried out at room temperature for 18 hours.

After completion of the reaction, the desired compound is isolated from the reaction mixture by conventional procedures.

For example, after the reaction mixture is appropriately neutralized and the insolubles, if present, are removed by filtration, a water-immiscible organic solvent such as ethyl acetate is added to the reaction mixture. After the resulting mixture is washed with water, the organic layer containing the desired compound is separated and dried over anhydrous magnesium sulfate, followed by evaporation of the solvent to give the desired compound.

The desired compound thus obtained may further be purified by conventional procedures such as recrystallization, reprecipitation, chromatography, etc., if necessary.

(Step 5)

This step is for preparing a compound (12) by reacting the compound (19) with a compound (21) in an inert solvent in the presence of an acid binding agent.

The solvent employable is not particularly limited unless it affects the reaction, and it includes aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ketones such as acetone, methyl ethyl ketone, methyl isobutyl ketone, isophorone and cyclohexanone; nitro compounds such as nitroethane and nitrobenzene; nitriles such as acetonitrile and isobutyronitrile; amides such as formamide, dimethylformamide (DMF), dimethylacetamide and hexamethylphosphorotriamide; sulfoxides such as dimethyl sulfoxide and sulforane, preferably halogenated hydrocarbons, particularly methylene chloride.

The acid binding agent employable includes organic bases such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) and 1,8-diazabicyclo[5.4.0]undec-7-ene (DBU), preferably organic bases, particularly pyridine and N-methylmorpholine.

While reaction temperature and reaction time vary depending on the kind of the acid binding agent employed, the reaction is usually carried out at 10° C. to 40° C. for 1 to 5 hours.

After completion of the reaction, the desired compound is isolated from the reaction mixture by conventional procedures.

For example, after the reaction mixture is appropriately neutralized and the insolubles, if present, are removed by filtration, a water-immiscible organic solvent such as ethyl acetate is added to the reaction mixture. After the resulting mixture is washed with water, the organic layer containing the desired compound is separated and dried over anhydrous magnesium sulfate, followed by evaporation of the solvent to give the desired compound.

The desired compound thus obtained may further be purified by conventional procedures such as recrystallization, reprecipitation, chromatography, etc., if necessary.

(Step 6)

This step is for preparing a polymer derivative (14) employable as the carrier for synthesizing an oligonucleotide by reacting the compound (12) having an activated carboxyl group obtained in Step 5 with a polymeric material (13) such as controlled pore glass (CPG) to which an amino group, a hydroxyl group, a sulfhydryl group, etc. are bound via an alkylene group in an inert solvent.

While the polymeric material (13) employable in this step is not particularly limited so long as it can usually be used as a carrier, the particle size, the surface area of three-dimentional reticulate structure, the proportion of hydrophilic group site, chemical composition, pressure resistance, etc. of the carrier should be examined.

The carrier employable includes polysaccharide derivatives such as cellulose, dextran and agarose, synthetic polymers such as polyacrylamide gel, polystyrene resins and polyethylene glycol, and inorganic materials such as silica gel, porous glass and metal oxides, typified nonlimitatively by commercially available carriers such as Aminopropyl-CPG and Long-chain aminoalkyl-CPG (manufactured by CPG Inc.); Cosmosil $NH_2$ and Cosmosil Diol (manufactured by Nakarai Tesuku); CPC-Silica Carrier Silane Coated, Aminopropyl-CPG-550A, Aminopropyl-CPG-1400A and polyethylene glycol 5000 monomethyl ether (manufactured by Furuka Co.), p-alkoxybenzyl alcohol resin, aminomethyl resin and hydroxymethyl resin (manufactured by Kokusan Kagaku K. K.); and polyethylene glycol 14000 monomethyl ether (manufactured by Union Carbide).

Further, the functional group bonded to the carrier preferably includes an amino group, a sulfhydryl group and hydroxyl group.

The solvent employable is not particularly limited so long as it does not affect the reaction and can dissolve the starting materials to some extent, and it preferably includes aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ketones such as acetone, methyl ethyl ketone, methyl isobutyl ketone, isophorone and cyclohexanone; nitro compounds such as nitroethane and nitrobenzene; nitriles such as acetonitrile and isobutyronitrile; amides such as formamide, dimethylformamide, dimethylacetamide and hexamethylphosphorotriamide; sulfoxides such as dimethyl sulfoxide and sulforane, preferably halogenated hydrocarbons (particularly methylene chloride) and amides (particularly dimethylformamide).

Reaction temperature is usually from −20° to 150° C., preferably from 0° to 50° C.

While reaction time varies depending on the starting materials, solvent, reaction temperature employed, it is usually 1 to 200 hours, preferably 24 to 100 hours.

After completion of the reaction, the desired compound is isolated from the reaction mixture by conventional procedures.

For example, the desirable polymeric carrier is recovered by filtration from the reaction mixture, washed with an organic solvent such as methylene chloride and dried under reduced pressure to give the desired compound.

(Step 7)

This step is for preparing a compound (22) by reacting the compound (14) with a deprotecting reagent in an inert solvent to eliminate selectively the protecting group of the hydroxyl group.

Incidentally, Step 7 to Step 11 are usually performed in a DNA synthesizer.

The solvent employable preferably includes aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, isobutanol, t-butanol, isoamyl alcohol, diethylene glycol, glycerol, octanol, cyclohexanol and methyl cellosolve; ketones such as acetone, methyl ethyl ketone, methyl isobutyl ketone, isophorone and cyclohexanone; nitro compounds such as nitroethane and nitrobenzene; nitriles such as acetonitrile and isobutyronitrile; amides such as formamide, dimethylformamide, dimethylacetamide and hexamethylphosphorotriamide; sulfoxides such as dimethyl sulfoxide and sulforane, more preferably alcohols (particularly methanol and ethanol) and methylene chloride, and when acetic acid is used as a deprotecting reagent, a mixture of acetic acid and water is included.

While the deprotecting reagent employable is not particularly limited so long as it is customarily used, and if the protecting group is a triarylmethyl group, acetic acid, dichloroacetic acid, trifluoroacetic acid, hydrochloric acid and a Lewis acid such as zinc bromide are exemplified, preferably acetic acid, dichloroacetic acid and trilfuoroacetic acid can be used.

While reaction temperature varies depending on the reagent, starting materials and solvent employed, it is usually from −10° to 100° C., preferably from 0° to 50° C.

While reaction time varies depending on the starting materials, solvent and reaction temperature employed, it is usually from 1 minute to 50 hours, preferably from 1 minute to 24 hours.

After completion of the reaction, the desired compound is isolated from the reaction mixture by conventional procedures.

For example, the polymeric carrier is recovered by filtration from the reaction mixture, washed with an organic solvent such as methylene chloride and dried under reduced pressure to give the desired compound.

(Step 8)

This step is for preparing a compound (24) by reacting a compound (23), (23') or (23") having a dimethoxytrityl group at the 5'-hydroxyl group, in which the base moiety is that of the 3' terminal of a desirable base sequence, and the 3'-hydroxyl group has, via phosphorus bonded thereto a desired alkyloxy, phenyloxy, aralkyloxy, alkyl, aralkyl or phenyl group with the polymeric material (22), followed by thioation or alkylamination, if necessary, to give such compound (24) having the desired 3'-terminal nucleotide unit bonded to a polymeric material such as CPG.

The compounds (23), (23') and (23") employable will be described below, respectively.

(a) If the compound (23) is reacted in this step, an acidic material is employed.

The acidic material employable includes those such as tetrazole etc., preferably tetrazole. While the oxidizing agent employable in the oxidation reaction in this step is not particularly limited so long as it is usually used in oxydation reactions, it preferably includes inorganic metal oxidizing agents such as manganese oxides, e.g. potassium permanganate and manganese dioxide; ruthenium oxides, e.g. ruthenium tetroxide; selenium compounds, e.g. selenium dioxide; iron compounds, e.g. iron(III) chloride; osmium compounds, e.g. osmium tetroxide; silver compounds, e.g. silver oxide; mercury compounds, e.g. mercury acetate; lead oxide compounds, e.g. lead oxide and lead tetroxide; chromic acid compounds, e.g. potassium chromate, chromic acid-sulfuric acid complex and chromic acid-pyridine complex; and cerium compounds e.g. cerium ammonium nitrate (CAN); inorganic oxidizing agents such as halogen molecules, e.g. chlorine molecule, bromine molecule and iodine molecule; periodic acids, e.g. sodium periodate; ozone, aqueous hydrogen proxide; nitrous acid compounds, e.g. nitrous acid; chlorous acid compounds, e.g. potassium chlorite and sodium chlorite; and persulfuric acid compounds, e.g. potassium persulfate and sodium persulfate; and organic oxidizing agents such as reagents employable for DMSO oxidation (a complex of dimethyl sulfoxide and dicyclohexylcarbodiimide, oxalyl chloride, acetic anhydride or phosphorus pentoxide or a complex of pyridine-sulfuric anhydride); peroxides, e.g. t-butyl hydroperoxide; stable cations, e.g. triphenylmethyl cation; succinimides, e.g. N-bromosuccinimide, hypochlorous acid compounds, e.g. t-butyl hypochlorite; azodicarboxylic acid compounds, e.g. azodicarboxylic acid ester; disulfides, e.g. dimethyl disuslfide, diphenyl disulfide and dipyridyl disulfide and triphenylphosphine; nitrous acid esters, e.g. methyl nitrite; carbon tetrahalides, e.g. methane tetrabromide, and quinone compounds, e.g. 2,3-dichloro-5,6-dicyano-p-benzoquinone (DDQ), preferably iodo. The solvent employable is not particularly limited so long as it does not affect the reaction and can dissolve the starting materials to some extent, and it includes aromatic hydrocarbons such as benzene, toluene and xylene; halogenated hydrocarbons such as methylene chloride and chloroform; ethers such as ether, tetrahydrofuran, dioxane and dimethoxyethane; amides such as dimethylformamide, dimethylacetamide and hexamethylphosphorotriamide; sulfoxides such as dimethyl sulfoxide; ketones such as acetone, methyl ethyl ketone; heterocyclic amines such as pyridine; and nitriles such as acetonitrile, preferably heterocyclic amines (particularly pyridine), nitriles (particularly acetonitrile), ethers (particularly tetrahydrofuran) and halogenated hydrocarbons (particularly methylene chloride).

Reaction is carried out at −50° to 100° C., and while reaction time varies depending mainly on the reaction temperature, types of the starting compounds and solvent employed, it is usually 5 minutes to 15 hours.

(b) The solvent employed when the compound (23') is reacted is not particularly limited unless it affects the reaction, and an aromatic amine such as pyridine is preferably used.

In the case where the compound (23') is reacted, a condensation agent is usually used.

The condensation agent employable includes dicyclocarbodiimide (DCC), mesitylenesulfonic acid chloride (Ms-Cl), triisopropylbenzenesulfonic acid chloride, mesitylene-sulfonic acid triazolide (MST), mesitylenesulfonic acid-3-nitrotriazolide (MSNT), triisopropylbenzenesulfonic acid tetrazolide (TPS-Te), triisopropylbenzenesulfonic acid nitroimidazolide (TPS-NI) and triisopropylbenzenesulfonic acid pyridyltetrazolide, preferably MSNT, TPS-Te and TPS-NI. While reaction temperature is not particularly limited in the range of −10° to 100° C., the reaction is usually carried out at room temperature. While the reaction time varies depending on the solvent and reaction temperature employed, it is 30 minutes in the case where the reaction is carried out at room temperature using pyridine as the solvent for the reaction.

(c) While the solvent employable when the compound (23") is reacted is not particularly limited unless it affects the reaction, anhydrous acetonitrile is preferably used. As the reagent used as the condensation agent, acid chlorides of carboxylic acid and phosphoric acid are used, and preferably pivaloyl chloride is used.

While the oxidizing agent for oxidizing an oligonucleotide having a H-phosphonate bond to a phosphodiester type-oligonucleotide is not particularly limited so long as it is usually used for oxidation reactions, it preferably includes inorganic metal oxidizing agents such as manganese oxides, e.g. potassium permanganate and manganese dioxide; ruthenium oxides, e.g. ruthenium tetroxide; selenium compounds, e.g. selenium dioxide; iron compounds, e.g. iron(III) chloride; osmium compounds, e.g. osmium tetroxide; silver compounds, e.g. silver oxide; mercury compounds, e.g. mercury acetate; lead oxide compounds, e.g. lead oxide and lead tetroxide; chromic acid compounds, e.g. potassium chromate, chromic acid-sulfuric acid complex and chromic acid-pyridine complex; and cerium compounds e.g. cerium ammonium nitrate (CAN); inorganic oxidizing agents such as halogen molecules, e.g. chlorine molecule, bromine molecule and iodine molecule; periodic acids, e.g. sodium periodate; ozone; aqueous hydrogen proxide; nitrous acid compounds such as nitrous acid; chlorous acid compounds, e.g. potassium chlorite and sodium chlorite; and persulfuric acid compounds, e.g. potassium persulfate and sodium persulfate; and organic oxidizing agents such as reagents employable for DMSO oxidation (a complex of dimethyl sulfoxide and dicyclohexylcarbodiimide, oxalyl chloride, acetic anhydride or phosphorus pentoxide or a complex of pyridine-sulfuric anhydride); peroxides, e.g. t-butyl hydroperoxide; stable cations, e.g. triphenylmethyl cation; succinimides, e.g. N-bromosuccinimide, hypochlorous acid compounds, e.g. t-butyl hypochlorite; azodicarboxylic acid compounds, e.g. methyl azodicarboxylate; disulfides, e.g. dimethyl disuslfide, diphenyl disulfide and dipyridyl disulfide and triphenylphosphine; nitrous acid esters, e.g. methyl nitrite; carbon tetrahalides, e.g. methane tetrabromide, and quinone compounds, e.g. 2,3-dichloro-5,6-dicyano-p-benzoquinone (DDQ), preferably iodine molecule.

The acid binding agent employable includes heterocyclic amines such as pyridine and diemthylaminopyridine, and aliphatic amines such as trimethylamine, triethylamine and diisopropylethylamine, preferably heterocyclic amines (particularly pyridine). While reaction temperature is not particularly limited, it is usually −50° to 50° C., preferably room temperature.

While reaction time varies depending on the starting materials, reagent, temperature, etc. employed, it is usually 5 minutes to 30 hours, preferably 30 minutes when the reaction is carried out at room temperature.

The thioation which is carried out, if desired, in this step is performed as follows: After the compound (23) is bonded to the compound (22), a thioation reagent is reacted to effect thioation in place of the oxidation with an iodine molecule etc. to give a compound (24) which is a polymeric carrier having a thioate bond such as CPG.

The reagent for thioation is not particularly limited so long as it can form a thioate by reaction with trivalent phosphorous, and it preferably includes sulfur and also tetraethyl thiurum disulfide (TETD) available from Applied Biosystems and Beaucage reagent available from MilliGen/Biosearch. In the case of using the former, the process described in a known literature (Tetrahedron Letters, 32, 3005 (1991) or its variations, and in the case of the latter, the process disclosed in a known literature (J. Am. Chem. Soc. 112, 1253 (1990) or its variations can nonlimitatively be used.

The alkylamination carried out, if desired, in this step can be performed as follows: After the compound (23") is bonded to the compound (22) as described above, a desired alkylamine is reacted therewith at room temperature in place of the oxidizing agent such as an iodine molecule. According to this process, a compound (24), in which the 3'-terminal nucleotide having the desired base sequence is bonded with a polymeric material such as CPG through phosphoramidate bond, can be obtained.

(Step 9)

This step is carried out by 1) treating the polymeric material (24) obtained in Step 8 with an acid to eliminate the DMT group, 2) reacting the thus treated polymeric material with an amidire reagent and an acid catalyst, 3) subjecting the resulting material to an oxidation reaction using an oxidizing agent and 4) subjecting the unreacted moiety to a capping reaction using acetic anhydride. In this step, the above procedures 1) to 4) are repeated to obtain a compound (25) to which only the 5'-terminal nucleotide having the desired base sequence is not yet bonded. The extension reaction of the DNA chain on a DNA synthesizer employed in this step is performed, for example, by a variation of the method of Stec (J. Am. Chem. Soc., 106, 6077–6089 (1984)) using the phosphoroamidite method using Applied Biosystems Model 380B or the phosphoroamidite method (method of H. Koester et al., in Nucleic Acids Res., 12, 4539 (1984)) using the Cyclone Plus DNA synthesizer of MilliGen/Biosearch, but the method is not limited thereto.

(Step 10)

This step is for preparing a polymeric material (27) having the desired base sequence and substituents, and also retaining a protecting group by eliminating the 5'-terminal DMT group of the polymeric material (25) obtained in Step 9 according to the procedures in Step 7, followed by the same treatment as in Step 8 using compounds (26), (26') and (26"), as described below, in place of the compounds (23), (23') and (23").

The compounds (26), (26') and (26") each are 2'-deoxyribonucleoside having a base moiety in which the 5'-terminal nucleotide of the desired base sequence is protected, or a ribonucleoside having a protected hydroxyl group at the 2'-position, with a desired modifying group at the 5'-position. Further, the compound (26) has at the 3'-position thereof a phosphoroamidite bond including the protecting group of the phosphate moiety to be used for ordinary DNA synthesis. Likewise, the compound (26') has a phosphodiester bond, and the compound (26") has a H-phosphonate bond.

(Step 11)

This step is for preparing a desired oligonucleotide (11) by cleaving the oligonucleotide portion from the polymeric material (27), carried on the protected polymeric material obtained in Step 10, has the desired base sequence and substituents at the 5'- and 3'-terminals, and eliminating the protecting groups other than the desired substituents at the 5'-terminal and/or 3'-terminal. The elimination of the protecting group can be carried out by known procedures (J. Am. Chem. Soc., 103, 3185(1981)).

The thus obtained reaction mixture containing the compound of the general formula (11) is purified by means of an ordinary purification treatment employable for purification of nucleic acid, for example, various chromatographies such as reverse phase and/or ion exchange chromatography (including high performance liquid chromatography), etc. to give the compound having the general formula (11).

(Step 12)

This step is for preparing a half ester of dicarboxylic acid, i.e. the compound (15) which is the starting material of the present invention by reacting the free hydroxyl group of a compound (29) or the free sulfhydryl group of a compound (30) with a dicarboxylic anhydride like a compound (28) in an inert solvent in the presence of a basic catalyst.

The dicarboxylic anhydride employable is not particularly limited and preferably includes dicarboxylic anhydrides having 1 to 16 carbon atoms, and most preferably succinic anhydride or glutaric anhydride. The basic catalyst employable includes preferably aminopyridines such as dimethylaminopyridine and pyrrolidinopyridine, tertiary amines such as trimethylamine and triethylamine, and carbonates of alkali metals such as sodium hydrogencarbonate and potassium carbonate, most preferably dimethylaminopyridine and pyrrolidinopyridine.

The solvent employable is not particularly limited so long as it does not affect the reaction and can dissolve the starting materials to some extent, and it preferably includes aromatic hydrocarbons such as benzene, toluene and xylene; halogenated hydrocarbons such as methylene chloride and chloroform; ethers such as ether, tetrahydrofuran, dioxane and dimethoxyethane; amides such as dimethylformamide, dimethylacetamide and hexamethylphosphorotriamide; sulfoxides such as dimethyl sulfoxide; alcohols such as methanol, ethanol, n-propanol, isopropanol, n-butanol, isobutanol and isoamyl alcohol; dilute acids such as aqueous sulfuric acid; dilute bases such as aqueous sodium hydroxide; water; ketones such as acetone, methyl ethyl ketone; heterocyclic amines such as pyridine and nitriles such as acetonitrile, preferably nitriles (particularly acetonitrile), ethers (particularly tetrahydrofuran) and halogenated hydrocarbons (particularly methylene chloride).

The reaction is carried out at −50° to 100° C., and while reaction time varies depending on the reaction temperature, the kind of starting materials and solvent employed, it is usually 30 minutes to 15 hours.

After completion of the reaction, the desired compound is collected from the reaction mixture by conventional procedures.

For example, after the reaction mixture is appropriately neutralized and the insolubles, if present, are removed by filtration, a water-immiscible organic solvent such as ethyl acetate is added to the reaction mixture. After the resulting mixture is washed with water, the organic layer containing the desired compound is separated and dried over anhydrous magnesium sulfate, followed by evaporation of the solvent to give the desired compound.

The desired compound thus obtained may further be purified by conventional procedures such as recrystallization, reprecipitation, chromatography, etc., if necessary.

(Step 13)

This step is for preparing a compound (18) by reacting compound (19) with dicarboxylic acid (31) in an inert solvent in the presence of an ester forming reagent.

The solvent employable is not particularly limited unless it affects the reaction, and it includes aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ketones such as acetone, methyl ethyl ketone methyl isobutyl ketone, isophorone and cyclohexanone; nitro compounds such as nitroethane and nitrobenzene; nitriles such as acetonitrile and isobutyronitrile; amides such as formamide, dimethylformamide (DMF), dimethylacetamide and hexamethylphosphorotriamide; and sulfoxides such as dimethyl sulfoxide and sulforane, preferably halogenated hydrocarbons (particularly methylene chloride) and amides (particularly dimethylformamide).

The ester forming reagent employable includes, for example, N-hydroxy compounds such as N-hydroxysuccinimide, 1-hydroxybenzotriazole and N-hydroxy-5-norbornene-2,3-dicarboxyimide; diimidazole compounds such as 1,1'-oxalyldiimidazole and N,N'-carbonyldiimidazole; disulfide compounds such as 2,2'-dipyridyldisulfide; succinic acid compounds such as N,N'-disuccinimidyl carbonate; phosphinic chloride compounds such as N,N'-bis(2-oxo-3-oxazolidinyl)phosphinic chloride; oxalate compounds such as N,N'-disuccinimidyl oxalate (DSO), N,N-diphthalimidyl oxalate (DPO), N,N'-bis (norbornenylsuccinimidyl) oxalate (BNO), 1,1'-bis (benzotriazolyl) oxalate (BBTO), 1,1'-bis(6-chlorobenzotriazolyl) oxalate (BCTO) and 1,1'-bis(6-trifluoromethylbenzotriazolyl) oxalate (BTBO); and carbodiimides such as dicyclohexylcarbodiimide (DCC), preferably diimidazole compounds and carbodiimides (particularly DCC).

While reaction temperature and reaction time vary depending on the kind of the ester forming reagent and solvent employed, the reaction is carried out at 0° C. to 100° C. for 5 to 50 hours.

After completion of the reaction, the desired compound is isolated from the reaction mixture by conventional procedures.

For example, after the reaction mixture is appropriately neutralized and the insolubles, if present, are removed by filtration, a water-immiscible organic solvent such as ethyl acetate is added to the reaction mixture. After the resulting mixture is washed with water, the organic layer containing the desired compound is separated and dried over anhydrous magnesium sulfate, followed by evaporation of the solvent to give the desired compound.

The desired compound thus obtained may further be purified by conventional procedures such as recrystallization, reprecipitation, chromatography, etc., if necessary.

According to the new process of the present invention, a modified oligonucleotide having a desired substituent at the 3'-terminal of the oligonucleotide via phosphate can easily be synthesized on a DNA synthesizer, thus providing modified oligonucleotide with high purity in a large amount using simple purification procedures at a low cost. Useful oligonucleotide having a substituent at the 3'-terminal is described in Japanese Patent Application No. Hei-301744, which has anti-AIDS activities.

The compounds of the present invention exhibit a specific cytopathic activity against AIDS virus (HIV-1) and can specifically inhibit the proliferation of the virus in infected cells. Accordingly the inventive compounds may be used for the treatment and prevention of AIDS.

The present invention is concretely explained by illustration of the following Examples.

[Test Example 1]

Measurement of anti-HIV-1 activity of modified oligodeoxyribonucleotides

Anti-HIV-1 activity was measured by the method of Pauel et al. (R. Pauel et al., J. Virological Methods, 20, 309–321 (1988)). In summary, MT-4 cells in the exponential growth phase were centrifuged for 5 minutes at 150×g. The cell pellet obtained was suspended in culture media and infected with HIV-1 (Type IIIB) for 1 hour at 37° C. at a concentration of 10 $CCID_{50}$. HIV-1 infected MT-4 cells were obtained by centrifugation in RPMI-1640 culture media containing 10% fetal calf serum (hereafter "serum culture media").

HIV-1 infected MT-4 cells and non-HIV-1 infected MT-4 cells were suspended in serum culture media so that a concentration of $4 \times 10^5$ cells/ml of each was attained. One hundred μl of a solution of stepwise diluted sample compound (dissolved in serum culture media), prepared in advance, was placed in each well of 98-well microtiter plates. Then, 100 μl of each of the above-mentioned cell suspensions was added to each well of microtiter plates, and their cells were cultured for 6 days in the presence of 5% carbon dioxide gas.

As a control, HIV-1 infected MT-4 cells and non-HIV-1 infected MT-4 cells in which no sample compound was added were cultured in the same manner.

After the cultivation, live cell number was measured based on the MTT(3-(4,5-dimethylthiazole-2-yl)-2,5-diphenyltetrazolium bromide) method (L. M. Green et al., J. Immunol, Methods, 70, 257–268 (1984)). Then the cytopathic activity of HIV-1 was measured. With the cytopathic activity of HIV-1 infected MT-4 cells to which no sample compound was added as 100%, and the cytopathic activity of non-HIV-1 (Type IIIB) infected MT-4 cells to which no sample compound was added as 0%, the concentration of the specimen which inhibited the cytopathic activity of HIV-1 infected MT-4 cells by 50% (IC$_{50}$) was calculated. The cytotoxicity of the sample compound was determined as that concentration which inhibited the multiplication of non-HIV-1 infected MT-4 cells by 50% (CC$_{50}$). The results of these measurements are shown in Table 2.

TABLE 21

| Example No | IC$_{50}$ (μg/mol) | CC$_{50}$ (μg/ml) |
|---|---|---|
| 1 | 2.1 | 61 |
| 2 | 5.9 | >100.0 |
| 4 | 1.5 | >100.0 |
| 5 | 2.3 | >100.0 |
| 6 | 1.3 | >100.0 |
| 7 | 1.0 | >100.0 |
| 8 | 4.3 | >100.0 |
| 9 | 8.4 | >100.0 |
| 10 | 1.5 | >100.0 |
| 11 | 4.7 | >100.0 |
| 12 | 0.6 | >100.0 |
| 13 | 1.4 | >100.0 |
| 14 | 0.7 | >100.0 |
| 16 | 4.7 | >100.0 |
| 17 | 3.7 | >100.0 |
| 18 | 4.7 | >100.0 |
| 19 | 6.25 | >100.0 |
| 20 | 4.0 | >100.0 |
| 21 | 1.2 | 100.0 |
| 22 | 0.55 | 50 |
| 23 | 0.8 | 75 |
| 24 | 0.45 | 75 |
| 25 | 4.0 | >100.0 |
| 26 | 6.0 | 80.0 |
| 27 | 5.0 | 95.0 |
| 28 | 5.0 | >100.0 |
| 29 | 3.0 | >100.0 |
| 30 | 1.0 | >100.0 |
| 31 | 1.1 | 90.0 |
| 32 | 3.8 | >100.0 |
| 33 | 5.0 | >100.0 |
| 34 | 5.0 | >100.0 |
| 35 | 5.5 | >100.0 |
| 36 | 1.5 | 100.0 |
| 37 | 6.0 | >100.0 |
| 43 | 3.0 | 100.0 |
| 45 | 0.45 | >100.0 |
| 48 | 0.58 | >100.0 |
| 57 | 1.5 | 100.0 |
| 58 | 7.0 | 50.0 |
| 70 | 1.0 | 60.0 |
| 71 | 1.0 | 37.0 |
| 72 | 1.8 | >100.0 |
| 73 | 3.0 | >100.0 |
| 74 | 4.4 | >100.0 |
| 75 | 6.0 | 40.0 |
| 76 | 7.0 | >100.0 |
| 77 | 9.0 | >100.0 |
| 78 | 9.0 | >50.0 |
| 79 | 9.4 | >100.0 |
| 80 | 9.5 | >100.0 |
| 81 | 10.0 | >100.0 |
| 82 | 0.35 | 100.0 |
| 83 | 0.55 | >50.0 |
| 84 | 0.5 | >50.0 |
| 85 | 0.8 | 60.0 |
| 86 | 0.4 | >100.0 |
| 87 | 0.25 | >100.0 |
| 88 | 0.7 | 75.0 |
| 89 | 0.5 | 38.0 |
| 90 | 0.15 | >100.0 |
| 91 | 0.15 | >100.0 |
| 92 | 0.29 | >100.0 |
| 93 | 0.35 | >100.0 |
| 94 | 0.19 | >100.0 |
| 95 | 0.5 | >100.0 |
| 98 | 0.15 | >100.0 |
| 99 | 0.15 | >100.0 |
| 100 | 0.25 | >100.0 |

TABLE 21-continued

| Example No | IC$_{50}$ (μg/mol) | CC$_{50}$ (μg/ml) |
|---|---|---|
| 101 | 1.5 | >100.0 |
| 102 | 0.7 | >100.0 |
| 103 | 5.0 | >100.0 |
| 104 | 7.0 | >100.0 |
| 105 | 3.0 | >100.0 |
| 106 | 5.0 | >100.0 |
| 107 | 2.5 | >100.0 |
| 108 | 3.5 | >100.0 |
| 109 | 2.0 | >100.0 |
| 110 | 2.3 | >100.0 |

Accordingly it has been definitely shown by the test results that all modified oligodeoxyribonucleotides listed in Table 2 have a particularly intensive anti-(HIV-1) activity at the concentration of less than 10 μg/ml.

Unless otherwise specified, the base sequence (for example TGGGAGG) used in the following chemical structures signifies the triethylamine salt of the appropriate oligodeoxyribonucleotide, not having a hydroxy group at both the 5'- and 3'-positions.

The invention is further illustrated by the following Examples. In the Examples, all mesh sizes employ the Tyler standard, and nuclear magnetic resonance spectra were obtained using trimethylsilane as an internal standard, where indicated by the abbreviation "TMS". The amount of oligodeoxyribonucleotide derivative prepared in each of these Examples was measured by means of the optical density at 260 nm [OD (260 nm)].

EXAMPLE 1

1(a) 5'-O-Tritylthymidine 2-cyanoethyl N,N-diisopropylphosphoramidite

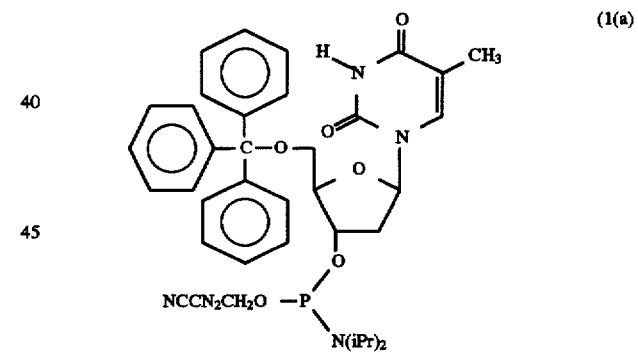

(1(a))

969 mg (2 mmol) of 5'-O-tritylthymidine [J. Am. Chem. Soc., 80, 6212 (1958)] were dried three times by azeotropic distillation with pyridine, after which it was dissolved in 10 ml of tetrahydrofuran. 1.39 ml (8 mmol) of N,N-diisopropyl-N-ethylamine and 0.822 ml (4 mmol) of 2-cyanoethyl N,N-diisopropylchlorophosphoramidite were then added to the solution, and the resulting mixture was stirred at room temperature for 30 minutes in an atmosphere of argon. At the end of this time, the resulting precipitate was filtered off from the reaction mixture, and the filtrate was freed from the solvent by distillation under reduced pressure. The resulting residue was dissolved in 100 ml of ethyl acetate, and the solution was washed twice, each time with 50 ml of an ice-cooled 10% w/v aqueous solution of sodium carbonate. The solution was then dried over anhydrous sodium sulfate, after which the solvent was removed by distillation under reduced pressure. The resulting residue was purified by column chromatography through 40 g of silica gel (70–230 mesh) using a 45:45:10 by volume mixture of methylene chloride, ethyl acetate and triethylamine as the eluent, to give 1.35 g (yield 98%) of the title compound.

¹H Nuclear Magnetic Resonance Spectrum (CDCl₃, 270 MHz, TMS), δ ppm:

7.62, 7.57 (together 1H, two singlets);
7.46–7.20 (15H, multiplet);
6.46–6.37 (1H, multiplet);
4.68 (1H, broad singlet);
4.19, 4.15 (together 1H, two broad singlets);.
3.90–3.30 (6H, multiplet);
2.63–2.28 (4H, multiplet);
1.47 (3H, singlet);
1.23–1.00 (12H, multiplet).

1(b) A Compound of Formula 1(b):

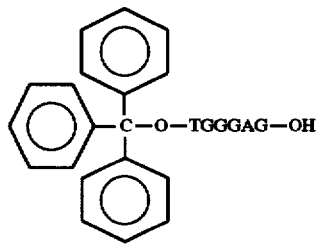

1(b)

Synthesis was effected using a Cyclone Plus (trade mark) DNA/RNA synthesizer manufactured by MilliGen/Biosearch (a division of Millipore Ltd., Japan). Into this were charged the chemical reagents corresponding to the nucleotide residues in the above formula 1(b), to synthesise the above oligonucleotide. A program cartridge for the amidite method was inserted into the machine. The synthesis was carried out on a 15 μmole scale. In this case a 35 mM acetonitrile solution of 5'-O-tritylthymidine 2-cyanoethyl N,N-diisopropylphosphoramidite [prepared as described in step (a) above] was used instead of a 2-cyanoethyl phosphoramidite solution corresponding to thymidine. The reaction column was a column for a 15.0 μmol scale reaction, packed with 5 μmol of G-CPG [i.e. guaninedeoxyribonucleoside (G) coupled to controlled pore glass (CPG)]. The concentration of nucleotide on the glass filler was 35–44 μmol/g, and the CPG filler had an average pore size of 50 nm. The desired base sequence TGGGAG was input (as is conventional, the base sequence quoted here, as well as those referred to hereafter, include the base which has been coupled to the CPG), and the program was nm without acid-treatment after bond-formation with the terminal T, to give a derivative wherein the desired protected oligonucleotide was coupled to the controlled pore glass (CPG). This was dried in vacuo, removed from the column and immersed in about 10 ml of 29% aqueous ammonia. It was then allowed to react at room temperature for about 2 days in a sealed vessel. At the end of this time, the CPG was removed by filtration and washed twice, each time with 10 ml of water; the filtrate and the washings were then combined. The combined mixture was then washed three times, each time with 30 ml of diethyl ether, after which the ammonia and diethyl ether was removed by evaporation in vacuo. The resulting aqueous solution was concentrated to about 3 ml by evaporation under reduced pressure, and the concentrated solution was filtered with the aid of a millipore filter (0.45 μm). The filtrate was divided into 3 portions and each portion was purified by reverse phase high performance liquid chromatography through a 20.0×250 mm column, Inertsil PREP-ODS (trade mark), which had previously been equilibrated with a 0.1M aqueous triethylammonium acetate buffer (TEAA) (pH 7.3), containing 20% by volume of acetonitrile, and monitored by ultraviolet light at 254 nm. The desired product was eluted using a gradient elution method with 0.1M TEAA containing acetonitrile at concentrations ranging from 20 to 50% by volume, with a linear gradient of 8 ml/minute over a period of 30 minutes. Fractions eluted after 17.2 minutes were collected and the solution was freed from acetonitrile by evaporation under reduced pressure, after which the resulting aqueous solution was lyophilized. The product thus obtained was dissolved in 50 ml of water and again lyophilized, to produce 94.80 OD (260 nm) of the compound of formula 1(b) as an amorphous solid.

Ultraviolet Absorption Spectrum (H₂O), $\lambda_{max}$ nm: 254.

Retention time: 23.3 minutes

High performance liquid chromatography (YMC-Pack A-312, S-5, 120A, ODS; eluent A: 0.1M TEAA, pH 7.3; eluent B: acetonitrile; 20→50% B by volume, 30 minutes, linear gradient; 1 ml/minute; 254 nm).

EXAMPLE 2

(2a) 5'-Tritylamino-5'-deoxythymidine 557 mg of trityl chloride were added to a solution of 560 mg (2 mmol) of 3'-O-acetyl-5'-amino-5'-deoxythymidine [which had been prepared by the procedure reported by J. P. Horwitz et al. in J. Org. Chem., 27, 3045 (1962)] in 20 ml of dry pyridine, and the resulting mixture was heated under reflux for 1 hour whilst excluding moisture. After the disappearance of the starting compound had been ascertained by thin layer chromatography (using methylene chloride containing 5% by volume methanol as the developing solvent), the solvent was removed from the reaction mixture by distillation under reduced pressure. The resulting residue was mixed with 10 ml each of methanol and water, and then the mixture was concentrated by distillation under reduced pressure. This operation was repeated three times, after which the residue was dissolved in 30 ml of ethyl acetate, and the resulting solution was washed with 20 ml each of a saturated aqueous solution of sodium chloride, 0.2N aqueous hydrochloric acid and a 5% aqueous solution of sodium hydrogencarbonate. The organic solution was then dried over anhydrous magnesium sulfate, and the solution was then evaporated to dryness under reduced pressure. The residue was dissolved in 30 ml of methanol saturated with ammonia gas and the flask holding the solution was tightly closed. It was then allowed to stand overnight at room temperature. At the end of this time, the reaction mixture was freed from the solvent by distillation under reduced pressure, and the residue was dissolved in 10 ml of methylene chloride. The solution was purified by column chromatography through silica gel, using methylene chloride containing 5% by volume of methanol as the eluent. Fractions containing the desired compound were combined and evaporated to dryness under reduced pressure. By lyophilizing the residue from benzene, 338 mg of the title compound were obtained as a white powder.

¹H Nuclear Magnetic Resonance Spectrum (CDCl₃, 270 MHz, TMS), δ ppm:

8.38 (1H, broad singlet);
7.48–7.18 (15H, multiplet);

7.04 (1H, multiplet);
6.67 (1H, triplet, J=6.60 Hz);
4.35–4.29 (1H, multiplet);
4.01–3.95 (1H, multiplet);
2.62–2.06 (5H, multiplet);
1.84 (3H, singlet).

(2) 5'-Tritylamino-5'-deoxythymidine 2-cyanoethyl N,N-diisopropylphoshoramidite 0.15 g (0.31 mmol) of 5'-tritylamino-5'-deoxythymidine [prepared as described in step (a) above] was dried by azeotropic distillation with pyridine and then dissolved in 2 ml of methylene chloride. 0.23 ml (1.2 mmol) of N,N-diisopropyl-N-ethylamine was then added to the resulting solution, after which 0.08 ml (0.36 mmol) of 2-cyanoethyl N,N-diisopropylchlorophosphoramidite was added over a period of 2 minutes in a stream of nitrogen. The resulting mixture was then stirred at room temperature for 60 minutes. At the end of this time, it was confirmed that the starting compound had disappeared by thin layer chromatography, and the reaction mixture was diluted with 30 ml of ethyl acetate. The resulting organic solution was washed with a saturated aqueous solution of sodium hydrogencarbonate and with a saturated aqueous solution of sodium chloride, in that order. The organic layer was filtered through a 1PS (trade mark) filter paper (Whatman), and the filtrate was freed from the solvent by distillation under reduced pressure. The resulting residue was purified by column chromatography through 15 g of silica gel (70–230 mesh), using ethyl acetate as the eluent, to give 0.19 g (yield 89%) of the title compound as a foamy substance.

$^1$H Nuclear Magnetic Resonance Spectrum (CDCl$_3$, 270 MHz, TMS), δ ppm:

7.50–7.19 (15H, multiplet);
7 15, 7.06 (together 1H, two singlets);
6.30–6.26 (1H, multiplet);
4.55–4.35 (1H, multiplet);
4.12–4.07 (1H, multiplet);
3.84–3.53 (4H, multiplet);
2.64–2.09 (6H, multiplet);
1.86, 1.84 (together 3H, two singlets);
1.19–1.10 (12H, multiplet).

2(c) A Compound of Formula 2(c):

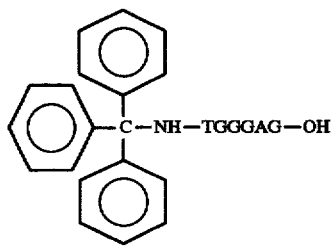

2(c)

Following a procedure similar to that described in Example 1(b), but using 5'-tritylamino-5'-deoxythymidine 2-cyanoethyl N,N-diisopropylphosphoramidite [prepared as described in Preparation 2(b)] in place of the 5'-O-tritylthymidine 2-cyanoethyl N,N-diisopropylphosphoramidite, the title compound was prepared. The reaction product was purified by chromatography through a reverse phase silica gel column (preparative C18, Waters, 1.5×15 cm; 50 mM aqueous trimethylammonium hydrogencarbonate buffer (TEAB), pH 7.5; 20→50% acetonitrile; linear gradient; 254 nm). The eluate was worked up in a similar manner to that described in Example 1b to give 168 OD (260 nm) of the title compound as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minute; linear gradient; 1 ml/minute; 260 nm) showed that the sample had a retention time of 19.20 minutes.

Ultraviolet Absorption Spectrum (H$_2$O), λ$_{max}$ nm: 254.

EXAMPLE 3

3(a) 5'-O-Benzhydrylthymidine 350 mg (8 mmol) of sodium hydride (as a 55% w/w dispersion in mineral oil) were added to a solution of 1.426 g (4 mmol) of 3'-O-[(1,1-dimethylethyl)dimethylsilyl]thymidine [Can. J. Chem., 56, 2768 (1978)] in 8 ml of tetrahydrofuran under an atmosphere of argon, and the resulting mixture was stirred at 60° C. for 2 hours and then allowed to cool to room temperature. A solution of 988 mg (4 mmol) of benzyl bromide in 2 ml of tetrahydrofuran was then added dropwise to the mixture, followed by 300 mg (2 mmol) of sodium iodide. The reaction mixture was then stirred at room temperature for 17 hours, after which it was freed from the solvent by distillation under reduced pressure. The concentrate was dissolved in 50 ml of ethyl acetate, and the resulting solution was washed twice each time with 50 ml of a saturated aqueous solution of sodium chloride. It was then dried over anhydrous magnesium sulfate and the solvent was distilled off under reduced pressure. The residue was dissolved in 4 ml of tetrahydrofuran, and 4 ml of a 1M tetrahydrofuran solution of tetrabutylammonium fluoride were added to the solution. The resulting mixture was then stirred at room temperature for 2 hours. At the end of this time, the solvent was removed by distillation under reduced pressure, and the residue was dissolved in 50 ml of ethyl acetate. The resulting solution was washed twice, each time with 50 ml of a saturated aqueous solution of sodium chloride. The mixture was dried over anhydrous magnesium sulfate, and then the solvent was removed by distillation under reduced pressure. The residue was purified by column chromatography through 60 g of silica gel (230–400 mesh) using a gradient elution method, with methylene chloride containing from 1 to 2.5% by volume methanol as the eluent, to give 377.7 mg (yield 23%) of the title compound.

$^1$H Nuclear Magnetic Resonance Spectrum (CDCl$_3$, 270 MHz, TMS), δ ppm:

9.85 (1H, broad singlet);
7.56 (1H, singlet);
7.38–7.20 (10H, multiplet);
6.45 (1H, triplet, J=6.92 Hz);
5.40 (1H, singlet);
4.62–4.58 (1H, multiplet);
4.17–4.15 (1H, multiplet);
3.75–3.58 (2H, multiplet);
2.47–2.22 (2H, multiplet);
1.36 (3H, singlet).

3(b) 5,'-O-Benzhydrylthymidine 2-cyanoethyl N,N-diisopropylphosphoramidite

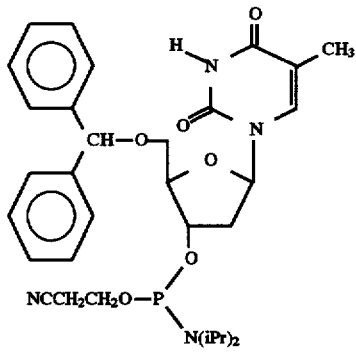

204.2 mg (0.5 mmol) of 5'-O-benzhydrylthymidine [prepared as described in step (a) above] were dried three times by azeotropic distillation with pyridine and then dissolved in 2.5 ml of tetrahydrofuran. 0.348 ml (2 mmol) of N,N-diisopropyl-N-ethylamine and 0.223 ml (1 mmol) of 2-cyanoethyl N,N-diisopropylchlorophosphoramidite were added to the solution under an atmosphere of argon, and the resulting mixture was stirred at room temperature for 30 minutes. At the end of this time, the reaction mixture was freed from precipitates by filtration, and the filtrate was concentrated by evaporation under reduced pressure. The concentrate was dissolved in 50 ml of ethyl acetate, and the resulting solution was washed twice, each time with 50 ml of an ice-cooled 10% w/v aqueous solution of sodium carbonate and dried over anhydrous sodium sulfate. The solvent was then removed by distillation under reduced pressure. The residue was purified by column chromatography through 30 g of silica gel (70–230 mesh), using a 45:45:10 by volume mixture of methylene chloride, ethyl acetate and triethylamine as the eluent. Fractions containing the title compound were combined and the solvent was distilled off. The same chromatography procedure was repeated, to obtain 213.4 mg (yield 70%) of the title compound.

¹H Nuclear Magnetic Resonance Spectrum (CDCl₃, 270 MHz, TMS), δ ppm:

7.55, 7.51 (together 1H, two singlets);
7.43–7.22 (10H, multiplet);
6.48–6.42 (1H, multiplet);
5.44, 5.42 (together 1H, two singlets);
4.73–4.64 (1H, multiplet);
4.25, 4.19 (together 1H, two broad singlets);
3.90–3.55 (6H, multiplet);
2.68–2.24 (4H, multiplet);
1.39 (3H, singlet);
1.30–1.10 (12H, multiplet).

3(c) A compound of formula 3(c):

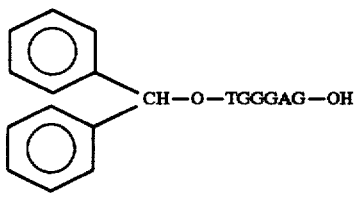

Following a procedure similar to that described in Example 1(b), but using 5'-O-benzhydrylthymidine 2-cyanoethyl N,N-diisopropylphosphoramidite [prepared as described in step (b) above] in place of the 5'-O-tritylthymidine 2-cyanoethyl N,N-diisopropylphosphoramidite, the title compound was prepared. The reaction product was divided into three portions and each portion was purified by chromatography through a reverse phase high performance liquid chromatography column (Inertsil PREP-ODS, 20.0×250 nm; eluent A: 0.1M TEAA, pH 7.3; eluent B: acetonitrile; 15→45% B by volume, 30 minutes, linear gradient; 7 ml/minute; 254 nm). Fractions eluted after 20.2 minutes were combined and worked up in a similar manner to than described in Example 1(b) to produce 76 OD (260 nm) of the title compound as an amorphous solid.

Ultraviolet Absorption Spectrum (H₂O), λ_max nm: 255.
Retention time: 17.3 minutes High performance liquid chromatography (YMC-Pack A-312, S-5, 120A, ODS; eluent A: 0.1M TEAA, pH 7.3; eluent B: acetonitrile; 10→40% B by volume, 30 minutes, linear gradient; 2 ml/minute; 254 nm).

EXAMPLE 4

A Compound of Formula 4(a):

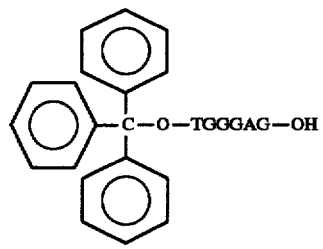

Following a procedure similar to that described in Example 1(b), but inputting the base sequence TGGGAGG the DNA/RNA synthesizer described in Example 1(b), the title compound was prepared. The reaction product was purified by chromatography through a reverse phase silica gel column (preparative C18, Waters, 1.5×15 cm; 50 mM TEAB, pH 7.5; 20→50% acetonitrile; linear gradient; 254 nm). Working up similar to that described in Example 1(b) gave 180 OD (260 nm) of the title compound as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 18.22 minutes.

Ultraviolet Absorption Spectrum (H₂O), λ_max nm: 255.

EXAMPLE 5

5(a) 5'-O-[(1,1-Dimethylethyl)diphenylsilyl]thymidine 1.43 ml (5.5 mmol) of t-butyldiphenylsilyl chloride were added to a solution of 1.21 g (5 mmol) of thymidine and 0.749 g (11 mmol) of imidazole in 10 ml of dimethylformamide under an atmosphere of argon, and the resulting mixture was stirred at room temperature for 140 minutes. At the end of this time, the solvent was removed by distillation under reduced pressure, and the resulting residue was dissolved in 100 ml of methylene chloride. The solution was then washed 5 times, each time with 100 ml of water. The solution was then dried over anhydrous magnesium sulfate, after which the solvent was distilled off under reduced pressure. The residue was purified by column chromatography through 100 g of silica gel (70–230 mesh) using a gradient elution method, with methylene chloride containing from 0.5 to 3% by volume of methanol as the eluent, to give 1.5 g (yield 62%) of the title compound.

¹H Nuclear Magnetic Resonance Spectrum (CDCl₃, 270 MHz, TMS), δ ppm:

10.52 (1H, broad singlet);
7.73–7.32 (10H, multiplet);
7.57 (1H, singlet);
6.53–6.47 (1H, multiplet);
4.63 (1H, broad singlet);
4.48 (1H, broad singlet);
4.11 (1H, broad singlet);
4.04–3.85 (2H, multiplet);
2.58–2.16 (2H, multiplet);
1.59 (3H, singlet);
1.10 (9H, singlet).

5(b) 5'-O-[(1,1-Dimethylethyl)diphenylsilyl]thymidine 2-cyanoethyl N,N-diisopropylphosphoramidite Following a procedure similar to that described in Example 3(b), but using 240 mg (0.5 mmol) of 5'-O-[(1,1-dimethylethyl)diphenylsilyl]thymidine [prepared as described in step (a) above], 254.4 mg (yield 74.7%) of the title compound were obtained.

¹H Nuclear Magnetic Resonance Spectrum (CDCl₃, 270 MHz, TMS), δ ppm:

7.69–7.36 (11H, multiplet);
6.43–6.38 (1H, multiplet);
4.70–4.62 (1H, multiplet);
4.16–4.09 (1H, multiplet);
4.04–3.55 (6H, multiplet);
2.67–2.15 (4H, multiplet);
1.61 (3H, singlet);
1.22–1.05 (12H, multiplet).

5(c) A Compound of Formula 5(c):

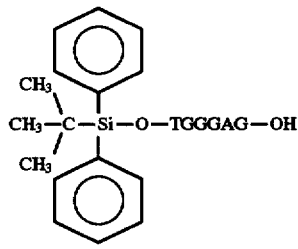

Following a procedure similar to that described in Example 1(b), but using 5'-O-[(1,1-dimethylethyl)diphenylsilyl]thymidine 2-cyanoethyl N,N-diisopropylphosphoramidite [prepared as described in step (b) above] in place of the 5'-Otritylthymidine 2-cyanoethyl N,N-diisopropylphosphoramidite, the title compound was prepared. The reaction product was divided into three portions and each portion was purified by chromatography through a reverse phase high performance liquid chromatography column (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 254 nm). Fractions eluted after 22.4 minutes were combined and worked up in a similar manner to that described in Example 1(b), to give 54 OD (260 nm) of the title compound as an amorphous solid.

Ultraviolet Absorption Spectrum (H₂O), λ_max nm: 255.

Retention time: 22.0 minutes

High performance liquid chromatography (YMC-Pack A-312, S-5, 120A, ODS; eluent A: 0.1M TEAA, pH 7.3; eluent B: acetonitrile; 20→50% B by volume, 30 minutes, linear gradient; 1 ml/minute; 254 nm).

EXAMPLE 6

6(a) 5'-O-(3,5-Dibenzyloxybenzyl)thymidine 175 mg (4 mmol) of sodium hydride (as a 55% w/w dispersion in mineral oil) were added to a solution of 713 mg (2 mmol) of 3'-O-[(1,1-dimethylethyl)dimethylsilyl]thymidine [Can. J. Chem., 56, 2768 (1978)] in 4 ml of tetrahydrofuran under an atmosphere of argon, and the resulting mixture was stirred at 60° C. for 2 hours. At the end of this time, the mixture was allowed to cool to room temperature, and then a solution of 767 mg (2 mmol) of 3,5-dibenzyloxybenzyl bromide [Chem. Ber., 102, 2887 (1969)] in 1 ml of tetrahydrofuran was added dropwise. 149.9 mg (1 mmol) of sodium iodide were then added to the resulting mixture, after which the mixture was stirred at room temperature for 16 hours. At the end of this time, the solvent was removed by distillation under reduced pressure, the residue was dissolved in 50 ml of ethyl acetate and the resulting solution was washed twice, each time with 50 ml of 0.01N aqueous hydrochloric acid. The solution was then dried over anhydrous magnesium sulfate, after which the solvent was distilled off under reduced pressure. The residue was purified by column chromatography through 100 g of silica gel (230–400 mesh), using a gradient elution method, with methylene chloride containing from 0.5 to 3% by volume of methanol as the eluent, to give 637.3 mg of a mixture containing 3'-O-[(1,1-dimethylethyl)dimethylsilyl]-5'-O-(3,5-dibenzyloxybenzyl)thymidine.

The whole of this was dissolved in 1.93 ml of tetrahydrofuran. 1.93 ml of a 1M tetrahydrofuran solution of tetrabutylammonium fluoride were added to the solution, and the resulting mixture was stirred at room temperature for 30 minutes. At the end of this time, the solvent was removed by distillation under reduced pressure, and the resulting residue was dissolved in 50 ml of ethyl acetate. This solution was washed twice, each time with 50 ml of a saturated aqueous solution of sodium chloride. The solution was then dried over anhydrous magnesium sulfate, the solvent was distilled off under reduced pressure and the residue was purified by chromatography through 30 g of silica gel (230–400 mesh), using a gradient elution method, with methylene chloride containing from 1 to 3% by volume of methanol as the eluent, to give 258.5 mg (yield 23.7%) of the title compound.

¹H Nuclear Magnetic Resonance Spectrum (CDCl₃, 270 MHz, TMS), δ ppm:

7.87 (1H, singlet);
7.52 (1H, singlet);
7.43–6.52 (13H, multiplet);
6.37 (1H, triplet, J=6.75 Hz);
5.03 (4H, singlet);
4.51 (2H, doublet, J=3.30 Hz);

4.50–4.44 (1H, multiplet);
4.06–4.03 (1H, multiplet);
3.77–3.63 (2H, multiplet);
2.32–2.12 (2H, multiplet);
1.67 (3H, singlet).

6(b) 5'-O-(3,5-Dibenzyloxybenzyl)thymidine 2-cyanoethyl N,N-diisopropylphosphoramidite Following a procedure similar to that described in Example 3(b), but using 258.5 mg (0.475 mmol) of 5'-O-(3,5-dibenzyloxybenzyl)thymidine [prepared as described in step (a) above], 307.7 mg (87%) of the title compound were obtained.

$^1$H Nuclear Magnetic Resonance Spectrum (CDCl$_3$, 270 MHz, TMS), δ ppm:

7.56, 7.53 (together 1H, two singlets);
7.42–6.56 (13H, multiplet);
6.40 (1H, triplet, J=6.60 Hz);
5.02 (4H, singlet);
4.67–4.58 (1H, multiplet);
4.53, 4.51 (together 2H, two singlets);
4.23, 4.17 (together 1H, two broad singlets);
3.90–3.52 (6H, multiplet);
2.68–2.53 (2H, multiplet);
2.49–2.12 (2H, multiplet);
1.65 (3H, singlet);
1.18 (12H, doublet, J=5.94 Hz).

6(c) A Compound of Formula 6(c):

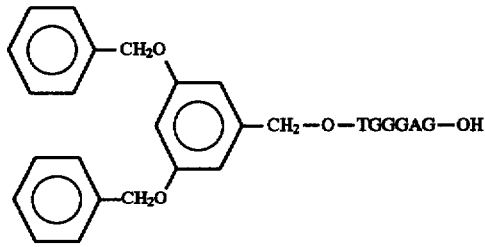

Following a procedure similar to that described in Example 1(b), but using 5'-O-(3,5-dibenzyloxybenzyl)thymidine 2-cyanoethyl N,N-diisopropylphosphoramidite [prepared as described in step (b) above] in place of the 5'-O-tritylthymidine 2-cyanoethyl N,N-diisopropylphosphoramidite, the title compound was obtained. The reaction product was divided into three portions, and each portion was purified by chromatography through a reverse phase high performance liquid chromatography column (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 254 nm). Fractions eluted after 19.8 minutes were combined and worked up in a similar manner to that described in Example 1(b), to give 64.6 OD (260 nm) of the title compound as an amorphous solid.

Ultraviolet Absorption Spectrum (H$_2$O), λ$_{max}$ nm: 255.
Retention time: 22.8 minutes
High performance liquid chromatography (YMC-Pack A-312, S-5, 120A, ODS; eluent A: 0.1M TEAA, pH 7.3; eluent B: acetonitrile; 20→50% B by volume, 30 minutes. linear gradient; 1 ml/minute; 254 nm).

EXAMPLE 7

7(a) 5'-O-(3,4-Dibenzyloxybenzyl)thymidine 713 mg (2 mmol) of 3'-O-[(1,1-dimethylethyl)dimethylsilyl]thymidine [Can. J. Chem., 56, 2768 (1978)] were dissolved in 5 ml of tetrahydrofuran, and 175 mg (4 mmol) of sodium hydride (as a 55% w/w dispersion in mineral oil) were added to the resulting solution under an argon atmosphere. The mixture was then stirred at 60° C. for 2 hours. At the end of this time, the temperature of the mixture was reduced to room temperature, and then 678 mg (2 mmol) of 3,4-dibenzyloxybenzyl chloride was added, followed by 149.9 mg (1 mmol) of sodium iodide, and the resulting mixture was stirred at room temperature for 19 hours, and then at 60° C. for 5 hours. At the end of this time, the solvent was distilled off under reduced pressure, and the residue was dissolved in 50 ml of ethyl acetate. The resulting solution was washed twice, each time with 50 ml of 0.01N aqueous hydrochloric acid; it was then dried over anhydrous magnesium sulfate. The solvent was removed by distillation under reduced pressure. The residue was dissolved in 4 ml of tetrahydrofuran, and 4 ml of a 1M solution of tetrabutylammonium fluoride in tetrahydrofuran was added to the solution. The mixture was then stirred at room temperature for 2 hours. At the end of this time, the solvent was removed by distillation under reduced pressure, and the residue was dissolved in 50 ml of ethyl acetate. The resulting solution was washed twice, each time with 50 ml of a saturated aqueous solution of sodium chloride and dried over anhydrous magnesium sulfate. The solvent was then removed by distillation under reduced pressure, and the residue was applied to a chromatography column [LiChroprep (trade mark) Si60, 40–63 μm, Große C, Merck] and eluted using a gradient elution method, with methylene chloride containing from 1 to 4% by volume of methanol, to give 345.4 mg (yield 31.7%) of the title compound.

$^1$H Nuclear Magnetic Resonance Spectrum (CDCl$_3$, 270 MHz, TMS), δ ppm:

8.26 (1H, singlet);
7.50 (1H, singlet);
7.47–7.28 (10H, multiplet);
6.9–6.79 (3H, multiplet);
6.36 (1H, triplet, J=6.75 Hz);
5.17 (4H, singlet);
4.47, 4.45 (together 2H, two singlets);
4.41–4.36 (1H, multiplet);
4.04–4.01 (1H, multiplet);
3.72–3.56 (2H, multiplet);
2.31–2.05 (2H, multiplet);
1.62 (3H, singlet).

7(b) 5'-O-(3,4-Dibenzyloxybenzyl)thymidine 2-cyanoethyl N,N-diisopropylphosphoramidite 271.7 mg (0.499 mmol) of 5'-O-(3,4-dibenzyloxybenzyl)thymidine [prepared as described in step (a) above] were dried three times by azeotropic distillation with pyridine, after which it was dissolved in 2.5 ml of. tetrahydrofuran. 0.348 ml (2 mmol) of N,N-diisopropyl-N-ethylamine and 0.223 ml (1 mmol) of 2-cyanoethyl N,N-diisopropylchlorophosphoramidite were added to the resulting solution, and the mixture was stirred at room temperature under an argon atmosphere for 2 hours. At the end of this time, the solvent was removed by distillation under reduced pressure. The residue was dissolved in 50 ml of ethyl acetate, and the resulting solution was washed twice, each time with 50 ml of an ice-cooled 10% w/v aqueous solution of sodium carbonate, and then dried over anhydrous sodium sulfate. The solvent was removed by distillation under reduced pressure, and the resulting residue was applied to a column containing 30 g (70–230 mesh) of silica gel. It was then eluted with a 45:45:10 by volume mixture of methylene chloride, ethyl acetate and triethylamine. The fractions containing the desired product were combined, the solvent was removed by distillation under reduced pressure, and the resulting residue was applied to a column containing 30 g (70–230 mesh) of silica gel. It was then eluted with a 6:3:1 by volume mixture of methylene chloride, ethyl acetate and triethylamine, to give 286.9 mg (yield 77%) of the title compound.

¹H Nuclear Magnetic Resonance Spectrum (CDCl₃, 270 MHz, TMS), δ ppm:

8.07 (1H, broad singlet);
7.53, 7.51 (together 1H, two singlets);
7.45–7.25 (10H, multiplet);
6.92–6.81 (3H, multiplet);
6.37 (1H, triplet, J =6.60 Hz);
5.15 (4H, singlet);
4.62–4.53 (1H, multiplet);
4.47 (2H, singlet);
4.22, 4.14 (together 1H, two broad singlets);
3.90–3.53 (6H, multiplet);
2.68–2.53 (2H, multiplet);
2.47–2.05 (2H, multiplet);
1.58 (3H, singlet);
1.17 (12H, doublet, J=5.94 Hz).

7(c) A Compound of Formula 7(c)

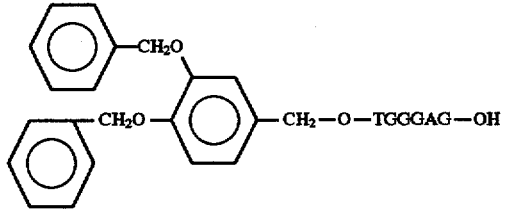

Following a procedure similar to that described in Example 1(b), but using 5'-O-(3,4-dibenzyloxybenzyl)thymidine 2-cyanoethyl N,N-diisoporopylphosphoramidite prepared as described in step (b) above] in place of the 5'-O-tritylthymidine 2-cyanoethyl N,N-diisopropylphosphoramidite, the title compound was prepared. The reaction product was then divided into three portions and each portion was purified by chromatography through a reverse phase high performance liquid chromatography column (Inertsil PREP-ODS, 20.0× 250 nm; eluent A: 0.1M TEAA, pH 7.3; eluent B: acetonitrile; 20→50% B by volume, 30 minutes; linear gradient; 7 ml/minute; 254 nm). Fractions eluted after 22.5 minutes were combined and worked up in a similar manner to that described in Example 1(b), to give 55.7 OD (260 nm) of the title compound as an amorphous solid.

Ultraviolet Absorption Spectrum (H₂O), λ_max nm: 254.

Retention time: 13.6 minutes

High performance liquid chromatography (YMC-Pack A-312, S-5, 120A, ODS; eluent A: 0.1M TEAA, pH 7.3; eluent B: acetonitrile; 20→50% B by volume, 30 minutes, linear gradient; 2 ml/minute; 254 nm).

EXAMPLE 8

A Compound of Formula 8(a)

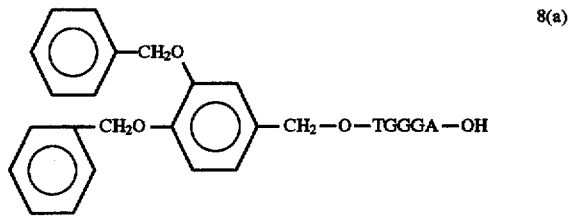

Following a procedure similar to that described in Example 1(b), but using 5'-O-(3,4-dibenzyloxybenzyl)thymidine 2-cyanoethyl N,N-diisopropylphosphoramidite [prepared as described in Example 7(b) above] in place of the 5'-O-tritylthymidine 2-cyanoethyl N,N-diisopropylphosphoramidite, using a column packed with 5 μmol of A-CPG [i.e. adeninedeoxyribonucleoside (A) coupled to controlled pore glass] and inputting a base sequence TGGGA to the synthesizer, the title compound was prepared. The reaction product was divided into three portions and each portion was purified by chromatography through a reverse phase high performance liquid chromatography column (Inertsil PREP-ODS, 20.0×250 nm; eluent A: 0.1M TEAA, pH 7.3; eluent B: acetonitrile; 20→50% B by volume, 30 minutes; linear gradient; 7 ml/minute; 254 nm). Fractions eluted after 23.3 minutes were combined and worked up in a similar manner to that described in Example 1(b), to give 86.2 OD (260 nm) of the title compound as an amorphous solid.

Ultraviolet Absorption Spectrum (H₂O), λ_max nm: 256.

Retention time: 14.2 minutes

High performance liquid chromatography (YMC-Pack A-312, S-5, 120A, ODS; eluent A: 0.1M TEAA, pH 7.3; eluent B: acetonitrile; 20→50% B by volume, 30 minutes, linear gradient; 2 ml/minute; 254 nm).

EXAMPLE 9

A Compound of Formula 9(a)

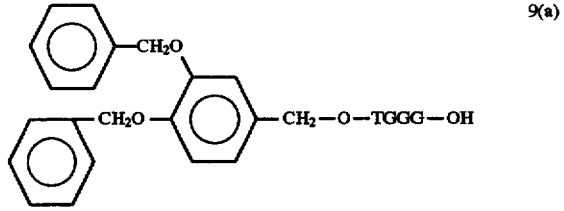

Following a procedure similar to that described in Example 1(b), but using 5'-O-(3,4-dibenzyloxybenzyl)thymidine 2-cyanoethyl N,N-diisopropylphosphoramidite [prepared as described in Example 7(b) above] in place of the 5'-O-tritylthymidine 2-cyanoethyl N,N-diisopropylphosphoramidite, and inputting a base sequence TGGG to the synthesizer, the title compound was prepared. The reaction product was divided into three portions and each portion was purified by chromatography through a reverse phase high performance liquid chromatography column (Inertsil PREP-ODS, 20.0×250 mm; eluent A: 0.1M TEAA, pH 7.3; eluent B: acetonitrile; 25→55% B by volume, 30 minutes; linear gradient; 7 ml/minute; 254 nm). Fractions eluted after 19.5 minutes were combined and worked up in a similar manner to that described in Example 1(b), to give 77.5 OD (260 nm) of the title compound as an amorphous solid.

Ultraviolet Absorption Spectrum (H$_2$O), $\lambda_{max}$ nm: 255.

Retention time: 14.8 minutes

High performance liquid chromatography (YMC-Pack A-312, S-5, 120A, ODS; eluent A: 0.1M TEAA, pH 7.3; eluent B: acetonitrile; 20→50% B by volume, 30 minutes, linear gradient; 2 ml/minute; 254 nm).

EXAMPLE 10

A Compound of Formula 10(a)

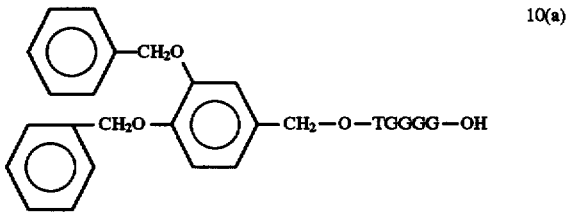

Following a procedure similar to that described in Example 1(b), but using 5'-O-(3,4-dibenzyloxybenzyl)thymidine 2-cyanoethyl N,N-diisopropylphosphoramidite [prepared as described in Example 7(b) above] in place of the 5'-O-tritylthymidine 2-cyanoethyl N,N-diisopropylphosphoramidite, and inputting a base sequence TGGGG to the synthesizer, the title compound was prepared. The reaction product was divided into three portions and each portion was purified by chromatography through a reverse phase high performance liquid chromatography column (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 254 nm). Fractions eluted after 22.9 minutes were combined and worked up in a similar manner to that described in Example 1(b), to give 19.8 OD (260 nm) of the title compound as an amorphous solid.

Ultraviolet Absorption Spectrum (H$_2$O), $\lambda_{max}$ nm: 254.

Retention time: 14.1 minutes

High performance liquid chromatography (YMC-Pack A-312, S-5, 120A, ODS; eluent A: 0.1M TEAA, pH 7.3; eluent B: acetonitrile; 20→50% B by volume, 30 minutes, linear gradient; 2 ml/minute; 254 nm).

EXAMPLE 11

11(a) 5'-O-[(Pyren-1-methyl]thymidine

A mixture of 875 mg of sodium hydride (as a 55% w/w dispersion in mineral oil) in 5 ml of dimethyl sulfoxide was stirred at room temperature for 30 minutes in an atmosphere of nitrogen, and then a solution of 2.42 g (10 mmol) of thymidine in 5 ml of dimethyl sulfoxide was added dropwise to the resulting mixture. The mixture was stirred at room temperature for 30 minutes, after which a suspension of 2.51 g (10 mmol) of 1-(chloromethyl)pyrene [Acta Chem. Scand., 10, 1362 (1956)] in 15 ml of dimethyl sulfoxide was added. The mixture was then stirred at room temperature for 90 minutes. At the end of this time, the reaction mixture was poured into 100 ml of ice-water, and the aqueous mixture was extracted with 100 ml of ethyl acetate and then with 100 ml of methylene chloride. The extract was dried over anhydrous magnesium sulfate, and then the solvent was removed by distillation under reduced pressure. The residue was purified by column chromatography through 150 g of silica gel (230-400 mesh), using a gradient elution method, with mixtures of methylene chloride containing from 0 to 4% by volume of methanol as the eluent, to give 292.4 mg (yield 6.4%) of the title compound.

$^1$H Nuclear Magnetic Resonance Spectrum (hexadeuterated dimethyl sulfoxide, 270 MHz, TMS), δ ppm:

8.44–8.07 (9H, multiplet);

7.44 (1H, singlet);

6.19 (1H, triplet, J=6.75 Hz);

5.33 (1H, doublet, J=5.4 Hz);

5.29 (2H, singlet);

4.37–4.30 (1H, multiplet);

4.00–3.96 (1H, multiplet);

3.92–3.79 (2H, multiplet);

2.10–2.04 (2H, multiplet);

1.20 (3H, singlet).

11(b) 5'-O-[(Pyren-1-yl)methyl]thymidine 2-cyanoethyl N,N-diisopropylphosphoramidite 91.3 mg (0.2 mmol) of 5'-O-[(pyren-1-yl)methyl]thymidine [prepared as described in step (a) above] were dried three times by azeotropic distillation with pyridine, after which it was suspended in 2 ml of tetrahydrofuran. 139 μl (0.8 mmol) of N,N-diisopropyl-N-ethylamine and 89 μl (0.4 mmol) of 2-cyanoethyl N,N-diisopropylchlorophosphoramidite were added to the suspension under an atmosphere of argon, and the resulting mixture was stirred at room temperature for 30 minutes. At the end of this time, the precipitates were removed by filtration, and the filtrate was freed from the solvent by distillation under reduced pressure. The residue was dissolved in 20 ml of ethyl acetate, and the resulting solution was washed twice, each time with 20 ml of an ice-cooled 10% w/v aqueous solution of sodium carbonate. The solution was dried over anhydrous sodium sulfate, and then the solvent was removed by distillation under reduced pressure. The resulting residue was purified by column chromatography through 30 g of silica gel (70–230 mesh), using a 6:3:1 by volume mixture of methylene chloride, ethyl acetate and triethylamine as the eluent, to give 100.2 mg (yield 76%) of the title compound.

$^1$H Nuclear Magnetic Resonance Spectrum (CDCl$_3$, 270 MHz, TMS), δ ppm:

8.36–7.99 (9H, multiplet);

7.50, 7.46 (together 1H, two singlets);

6.35 (1H, triplet, J=6.60 Hz);

5.38–5.22 (2H, multiplet);

4.60–4.50 (1H, multiplet);

4.25–4.17 (1H, multiplet);

4.01–3.77 (2H, multiplet);

3.73–3.44 (4H, multiplet);

2.78–2.09 (4H, multiplet);

1.31, 1.29 (together 3H, two singlets);

1.10–1.05 (12H, multiplet).

11(c) A Compound of Formula 11(c)

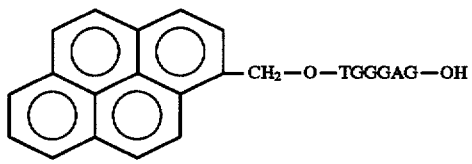

Following a procedure similar to that described in Example 1(b), but using 5'-O-[(pyren-1-yl)methyl]-thymidine 2-cyanoethyl N,N-diisopropylphosphoramidite [prepared as described in step (b) above] in place of the 5'-O-tritylthymidine 2-cyanoethyl N,N-diisopropylphosphoramidite, the title compound was prepared. The reaction product was divided into three portions and each portion was purified by chromatography through a reverse phase high performance liquid chromatography column (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 254 nm). Fractions eluted after 15.4 minutes were combined and worked up in a similar manner to that described in Example 1(b), to give 80 OD (260 nm) of the title compound as an amorphous solid.

Ultraviolet Absorption Spectrum ($H_2O$), $\lambda_{max}$ nm: 243.

Retention time: 16.4 minutes

High performance liquid chromatography (YMC-Pack A-312, S-5, 120A, ODS; eluent A: 0.1M TEAA, pH 7.3; eluent B: acetonitrile; 20→50% B by volume, 30 minutes, linear gradient; 1 ml/minute; 254 nm).

EXAMPLE 12

12(a) O-Dimethoxytrityl ethylene glycol 3.1 g (50 mmol) of ethylene glycol were dried by azeotropic distillation with pyridine and then dissolved in 40 ml of pyridine. 3.38 g (10 mmol) of 4,4'-dimethoxytrityl chloride were added to the solution, and the resulting mixture was stirred at room temperature for 2 hours. After disappearance of the starting compound had been confirmed by thin layer chromatography, 5 ml of methanol were added to the reaction mixture, and the mixture was then concentrated to about one half of its volume by distillation under reduced pressure. The concentrate was dissolved in 100 ml of methylene chloride, and the resulting solution was washed with a saturated aqueous solution of sodium hydrogencarbonate. The organic solution was filtered through a 1PS filter paper (Whatman), and the filtrate was freed from the solvent by distillation under reduced pressure. The residue was purified by column chromatography through 100 g of silica gel (70–230 mesh) using methylene chloride containing 1% by volume of methanol as the eluent, to give 1.97 g of the title compound as a gummy substance.

[1]H Nuclear Magnetic Resonance Spectrum ($CDCl_3$, 270 MHz, TMS), δ ppm:

7.45–6.82 (13H, multiplet);

3.79 (6H, singlet);

3.75 (2H, triplet, J=4.95 Hz);

3.25 (2H, triplet, J=4.62 Hz);

1.95 (1H, triplet).

12(b) A Compound of Formula 12(b)

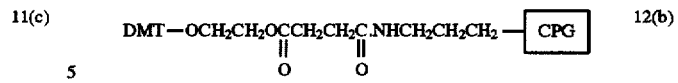

0.18 g (0.5 mmol) of O-dimethoxytrityl ethylene glycol [prepared as described in step (a) above] was dried by azeotropic distillation with pyridine and then dissolved in 2 ml of methylene chloride. 75 mg (0.75 mmol) of succinic anhydride and 92 mg (0.75 mmol) of 4-(dimethylamino) pyridine were then added to the solution, and the resulting mixture was stirred for 1 hour. After the disappearance of the starting material had been confirmed by thin layer chromatography, the reaction mixture was diluted with methylene chloride, and the diluted solution was washed with a 0.5M aqueous solution of potassium dihydrogenphosphate (pH 5.0) and with water in that order. The organic layer was dried over anhydrous sodium sulfate, and the solvent was removed by distillation under reduced pressure, to give O-dimethoxytrityl ethylene glycol monosuccinate.

The whole of this compound was dried by azeotropic distillation with pyridine and then dissolved in 3 ml of dimethylformamide. 0.16 g (0.75 mmol) of pentachlorophenol and 0.16 g (0.75 mmol) of 1,3-dicyclohexylcarbodiimide were then added to the solution, and the resulting mixture was stirred at room temperature for 42 hours. At the end of this time, insoluble materials were filtered off, and the filtrate was concentrated by distillation under reduced pressure. The residue was mixed with benzene, and the resulting insoluble materials were again filtered off, after which the solvent was removed by distillation under reduced pressure.

0.25 g (0.2 mmol) of the residue produced as described above was dissolved in 4 ml of dimethylformamide, and 60 μl (0.44 mmol) of triethylamine and 2.0 g of (3-aminopropyl)-CPG (containing 0.129 mmol/g of amino groups) were added to the solution. The resulting mixture was then allowed to stand at room temperature for 36 hours. At the end of this time, the CPG carrier was collected by filtration, washed with methylene chloride and then dried in vacuo. The CPG carrier was mixed with 10 ml each of cap A and B solutions (Millipore Ltd., Japan) and the mixture was allowed to stand for 10 minutes in order to acetylate any amino group remaining to be reacted. The reaction product was then washed with pyridine and methylene chloride, in that order, after which it was dried in vacuo, to give the title compound of formula 12(b). Cap A solution is a 1:9 by volume mixture of acetic anhydride and tetrahydrofuran, and cap B solution is a 1:4 by volume mixture of N-methylimidazole and tetrahydrofuran.

The proportion of residues derived from O-dimethoxytrityl ethylene glycol introduced into the compound of Example 12(b) was quantitatively analyzed as follows. A mixture of 9.6 mg of the compound of Example 12(b) and a deblock solution (a solution of dichloroacetic acid in methylene chloride; Millipore Ltd., Japan) was shaken for 3 minutes and then sufficient methylene chloride was added to the solution to make the total volume 20 ml. 0.4 ml of this solution was taken in a test-tube and used for measurement. The sample solution was freed from the solvent by distillation under reduced pressure, and the residue was dissolved in a 3:2 by volume mixture of perchloric acid and ethanol. The absorbance of the dimethoxytrityl cation in the solution was determined at 500 nm.

As a result, it was found that the amount of dimethoxytrityl group introduced was 40.0 μmol/g.

12(c) A Compound of Formula 12(c)

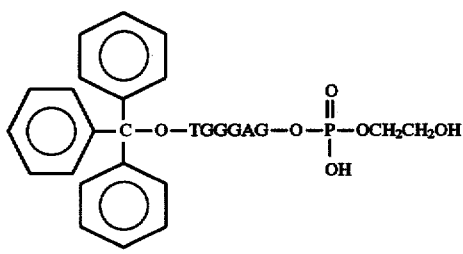

Following a procedure similar to that described in Example 1(b), but using a column packed with 125 mg (5 μmol) of the compound of Example 12(b) and inputting the base sequence TGGGAGZ (in which Z is a dummy code, as explained in Example 17) to the synthesizer, the title compound was prepared using a DNA/RNA synthesizer as described in Example 1(b). The reaction product was purified by chromatography through a reverse phase silica gel column (Preparative C18, Waters, 1.5×15 cm; 50 mM TEAB, pH 7.5; 20→50% acetonitrile; linear gradient; 254 nm) and worked up in a similar manner to that described in Example 1(b), to give 165 OD (260 nm) of the title compound as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample has a retention time of 18.76 minutes.

Ultraviolet Absorption Spectrum ($H_2O$), $\lambda_{max}$ nm: 254.

EXAMPLE 13

A Compound of Formula 13(a)

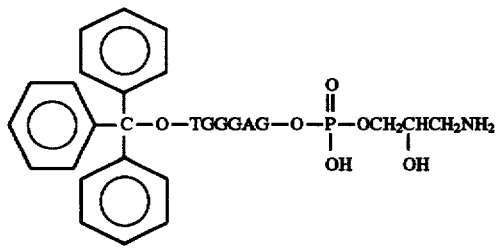

Following a procedure similar to than described in Example 12(c), but using 151 mg (5 μmol) of 3'-amino-ON CPG (trade mark for a product of Clontech), the title compound was prepared. The product was purified by chromatography through a reverse phase silica gel column (Preparative C18, Waters, 1.5×15 cm; 50 mM TEAB, pH 7.5; 20→50% acetonitrile; linear gradient; 254 nm) and worked up in a similar manner to that described in Example 1(b), to give 165 OD (260 nm) of the title compound as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample has a retention time of 18.76 minutes.

Ultraviolet Absorption Spectrum ($H_2O$), $\lambda_{max}$ nm: 255.

EXAMPLE 14

A Compound of Formula 14(a)

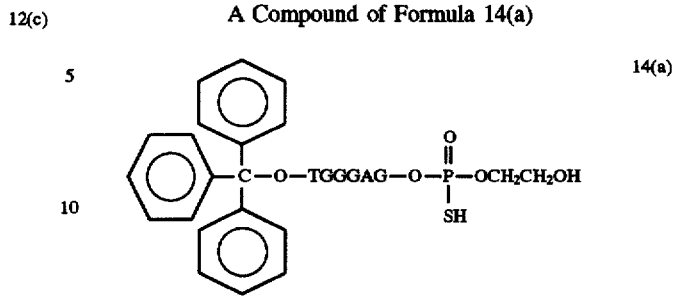

A procedure similar to that described in Example 12(c) was repeated, but with the following modification. The compound of Example 12(b) was first coupled with guaninedeoxyribonucleotide-β-amidite at the terminal 3'-position, and the column was then removed from the synthesizer without oxidation by an oxidizing solution. 5 ml of an acetonitrile solution of tetraethylthiuram disulfide (TETD) (Applied Biosystems) were then added to the column, which was then allowed to stand at room temperature for 15 minutes. The column was then washed with acetonitrile and installed to the synthesizer.

In the purification step, chromatography was carried out through a reverse phase silica gel column (Preparative C18, Waters, 1.5×15 cm; 50 mM TEAB, pH 7.5; 20→50% acetonitrile; linear gradient; 254 nm). By working up in a similar manner to that described in Example 1(b), 33 OD (260 nm) of the title compound was obtained as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 18.92 minutes.

Ultraviolet Absorption Spectrum ($H_2O$), $\lambda_{max}$ nm: 254.

EXAMPLE 15

15(a) 5'-O-Trityl-N-benzoyl-2'-deoxycytidine 3.31 g (10 mmol) of N-benzoyl-2'-deoxycytidine were added to 25 ml of pyridine, and then 3.07 g (11 mmol) of trityl chloride were added to the suspension. The resulting suspension was stirred at 100° C. for 1 hour, after which it was allowed to cool to room temperature. The pyridine was then removed by distillation under reduced pressure. The resulting residue was dissolved in a mixture of ethyl acetate and a saturated aqueous solution of sodium chloride. The organic layer was separated and washed twice, each time with a saturated aqueous solution of sodium chloride. The solution was then dried over anhydrous magnesium sulfate, after which the solvent was removed by distillation under reduced pressure. The resulting residue was purified by column chromatography through silica gel (Lober column Si-60, Size C) using a gradient elution method, with mixtures of methanol and methylene chloride ranging from 2:98 to 5:95 by volume as the eluent, to give 1.47 g (yield 26%) of the title compound.

[1]H Nuclear Magnetic Resonance Spectrum ($CDCl_3$, 270 MHz, TMS), δ ppm:

8.72 (1H, broad singlet);
8.26 (1H, doublet, J=7.3 Hz);
7.89 (1H, doublet, J=7.3 Hz);
7.26–7.64 (20H, multiplet);

6.29 (1H, triplet, J=5.9 Hz);
4.48–4.53 (1H, multiplet);
4.12–4.16 (1H, multiplet);
3.42–3.57 (2H, multiplet);
2.23–2.77 (2H, multiplet);
2.51 (1H, broad singlet).

15(b) 5'-O-Trityl-N-benzoyl-2'-deoxycytidine 2-cyanoethyl N,N-diisopropylphosphoramidite 402 mg (0.7 mmol) of 5'-O-trityl-N-benzoyl-2'-deoxycytidine [prepared as described in step (a) above] were dried by azeotropic distillation with pyridine and then dissolved in 3.5 ml of methylene chloride. 60 mg (0.35 mmol) of diisopropylammonium tetrazolide were added to the solution. 245 µl (0.77 mmol) of 2-cyanoethyl N,N,N',N'-tetraisopropylphosphorodiamidite were then added dropwise, under an atmosphere of argon. The resulting mixture was stirred at room temperature for 3.5 hours under same atmosphere. At the end of this time, the methylene chloride was removed by distillation under reduced pressure. The resulting residue was dissolved in ethyl acetate, and the solution was washed with a 10% w/v aqueous solution of sodium carbonate and with a saturated aqueous solution of sodium chloride, in that order. The solution was then dried over anhydrous magnesium sulfate, after which the solvent was removed by distillation under reduced pressure, and the residue was purified by column chromatography through 23 g of silica gel (70–230 mesh), using ethyl acetate as the eluent, to give 337 mg (yield 62%) of the title compound as a foam substance.

$^1$H Nuclear Magnetic Resonance Spectrum (CDCl$_3$, 270 MHz, TMS), δ ppm:

8.87 (1H, broad singlet);
8.52 & 8.43 (1H, doublet, J=7.3 Hz);
8.12 & 8.11 (1H, doublet, J=7.3 Hz);
7.23–7.86 (20H, multiplet);
6.49–6.55 (1H, multiplet);
4.79–4.91 (1H, multiplet);
4.46–4.47 (1H, multiplet);
3.60–4.10 (6H, multiplet);
2.46–3.08 (4H, multiplet);
1.29–1.40 (12H, multiplet).

15(c) A Compound of Formula 15(c)

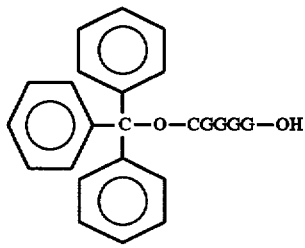

A procedure similar to that described in Example 1(b) was repeated, except that a 35 mM acetonitrile solution of the compound of Example 15(b) was placed in the amidite bottle (referred to as "X") and the base sequence XGGGG was input to the synthesizer. The 90% aqueous formamide solution containing the title compound thus obtained was heated at 95° C. for 5 minutes and then chilled in ice immediately. The reaction mixture was then divided into four portions and each was purified by reverse phase high performance liquid chromatography (Inertsil PREP-ODS 20.0×250 mm; eluent A: 0.1M TEAA pH 7.0; eluent B: acetonitrile; 10 to 60% B by volume, 30 minutes; linear gradient; 7 ml/minute; 260 nm; column temperature 60° C.). Fractions eluted after 20.9 minutes were collected and worked up in a similar manner to that described in Example 1(b), to give 68 OD (260 nm) of the title compound as an amorphous solid.

Ultraviolet Absorption Spectrum (H$_2$O), $\lambda_{max}$ nm: 254.
Retention time: 13.25 minutes
[by high performance liquid chromatography (Inertsil ODS-2: 6×150 mm; eluent A: 0.1M TEAA, pH 7.5; eluent B: acetonitrile; 10 to 60% B by volume, 20 minutes, linear gradient; 1 ml/minute; 260 nm)].

EXAMPLE 16

16(a) A compound of Formula 16(a)

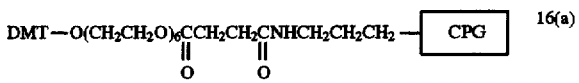

0.26 g (0.5 mmol) of O-dimethoxytrityl hexaethylene glycol [Nucleic Acids Res., 18, 6353 (1990)] was dried by azeotropic distillation with pyridine and then dissolved in 2 ml of methylene chloride. 75 mg (0.75 mmol) of succinic anhydride and 92 mg (0.75 mmol) of 4-(dimethylamino) pyridine were then added to the solution, and the resulting mixture was stirred for 2 hours. After completion of the reaction had been confirmed by thin layer chromatography, the reaction mixture was diluted with methylene chloride, and the diluted mixture was washed with a 0.5M aqueous solution of potassium dihydrogenphosphate (pH 5.0) and with water, in that order. The organic layer was then dried over anhydrous sodium sulfate, and the solvent was removed by distillation under reduced pressure, to give O-dimethoxytrityl hexaethylene glycol monosuccinate.

The whole of this product was dried by azeotropic distillation with pyridine and then dissolved in 3 ml of dimethylformamide. 0.23 g (0.37 mmol) of pentachlorophenol and 0.12 g (0.56 mmol) of 1,3-dicyclohexylcarbodiimide were added to the solution, and the resulting mixture was stirred at room temperature for 16 hours. At the end of this time, the insoluble materials which had precipitated were filtered off, and the filtrate was freed from the solvent by evaporation under reduced pressure. The residue was dissolved in benzene, and the resulting insoluble materials were again filtered off, after which the solvent was removed by distillation under reduced pressure.

30 µl (0.22 mmol) of triethylamine and 1.0 g of (3-aminopropyl)-CPG (containing 0.129 mmol/g of amino groups) were then added to a solution of 0.23 g (0.18 mmol) of the residue in 5 ml of dimethylformamide, and the resulting mixture was allowed to stand at room temperature for 24 hours. At the end of this time, the CPG carrier was collected by filtration and washed with methylene chloride, after which it was dried in vacuo. In order to acetylate the amino groups remaining unreacted, the CPG carrier was mixed with 3 ml each of cap A and B solutions (Millipore Ltd., Japan) and the mixture was allowed to stand for 10 minutes. The reaction product was then washed with pyridine and with methylene chloride, in that order, after which it was dried in vacuo to produce the title compound.

The amount of O-dimethoxytrityl hexaethylene glycol residues introduced into the compound of Example 16(a) was determined as follows. The compound (9.7 mg) of the Example 16(a) was accurately measured and a deblock solution (a methylene chloride solution of dichloroacetic acid; Millipore Ltd., Japan) was added thereto. The mixture was shaken for 3 minutes, and then sufficient methylene chloride was added to make 20 mL. 0.4 ml of this was taken up into a test tube and the solvent was removed by distillation under reduced pressure. 3 ml of a 3:2 by volume mixture of perchloric acid and ethanol were added to the residue, and the absorbance (ε=71,700) of the dimethoxytrityl cation at 500 nm was measured.

The amount of dimethoxytrityl group introduced was 59.1 μmol/g.

16(b) A Compound of Formula 16(b)

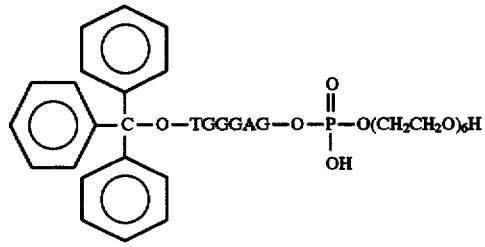

Following a procedure similar to that described in Example 12(c), but using a column packed with 85 mg (5 μmol) of the compound of Example 16(a), the title compound was prepared. The product was purified by chromatography through a reverse phase silica gel column (Preparative C18, Waters, 1.5×15 cm; 50 mM TEAB, pH 7.5; 5→50% by volume acetonitrile; linear gradient; 254 nm). By working up in a similar manner to that described in Example 1(b), the title compound of formula 16(b) was obtained having 151 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 18.50 minutes.

Ultraviolet Absorption Spectrum (H₂O), $\lambda_{max}$ nm: 254.

EXAMPLE 17

A Compond of Formula 17(a)

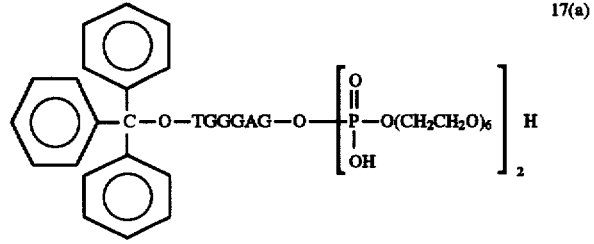

Following a procedure similar to that described in Example 1(b), but using a column packed with 85 mg (5 μmol) of the compound of Example 16(a) and using a 35 mM acetonitrile solution of O-dimethoxytrityl hexaethylene glycol O-(2-cyanoethyl N,N-diisopropylphosphoramidite) [Nucleic Acids Res., 18, 6353 (1990)] placed in the amidite bottle (and referred to herein as "X") and by inputting the base sequence TGGGAGXZ to the synthesizer, the title compound was prepared. In this Example and elsewhere, X is as defined above and Z represents a dummy code, that is a code entered on the synthesizer which does not input an actual base; when inputting the dummy code to the synthesizer, any of the codes A, G, C, T or X may be input, but will not result in a base being added to the sequence. The product was purified by chromatography through a reverse phase silica gel column (Preparative C18, Waters, 1.5×15 cm; 50 mM TEAB, pH 7.5; 5→50% acetonitrile; linear gradient; 254 nm). By working up in a manner similar to that described in Example 1(b), the title compound having 136 OD (260 nm) was obtained as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 18.32 minutes.

Ultraviolet Absorption Spectrum (H₂O), $\lambda_{max}$ nm: 254.

EXAMPLE 18

A Compound of Formula 18(a)

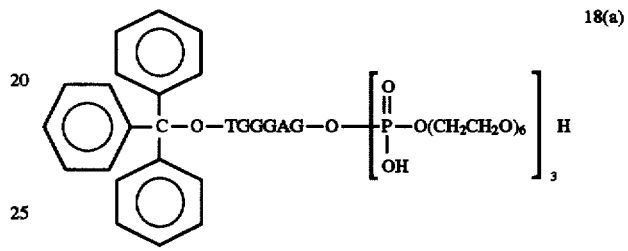

Following a procedure similar to that described in Example 17, but inputting the base sequence TGG-GAGXXZ (in which X and Z are as defined in Example 17) to the synthesizer, the title compound was prepared. The product was purified by chromatography through a reverse phase silica gel column (Preparative C18, waters, 1.5×15 cm; 50 mM TEA , pH 7.5; 5→50% acetonitrile; linear gradient; 254 nm). It was then worked up in a manner similar to that described in Example 1(b), no give 136 OD (260 nm) of the title compound of formula 18(a) as an amorphous solid. Analysis by reverse phase high performance liquid chromatography (Inertsil ODS, 6×150 nm; eluent A: 0.1M TEAA, pH 7.5; eluent B: acetonitrile; 10→60% B by volume, 20 minutes; linear gradient; 1 ml/minute; 260 nm) showed that the sample had a retention time of 18.20 minutes.

Ultraviolet Absorption Spectrum (H₂O), $\mu_{max}$ nm: 255. 19(a)

EXAMPLE 19

A Compound of Formula 19(a)

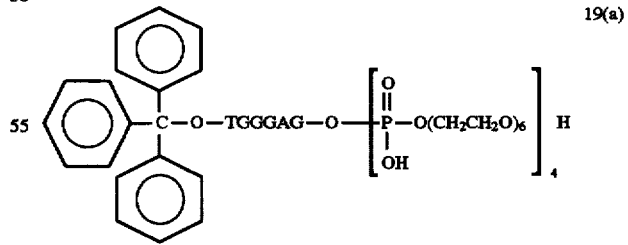

Following a procedure similar to that described in Example 17, but inputting the base sequence TGG-GAGXXXZ (in which X and Z are as defined in Example 17) to the synthesizer, the title compound was prepared. The reaction product was purified by chromatography through a reverse phase silica gel column (Preparative C18, Waters, 1.5×5 cm; 50 mM TEAB, pH 7.5; 5→50% acetonitrile;

linear gradient; 254 nm). It was then worked up in a manner similar to that described in Example 1(b), to give the title compound having 110 OD (260 nm) as an amorphous solid. Analysis by reverse phase high performance liquid chromatography (Inertsil ODS, 6×150 nm; eluent A: 0.1M TEAA, pH 7.5; eluent B: acetonitrile; 10→60% B by volume, 20 minutes; linear gradient; 1 ml/minute; 260 nm) showed that the sample had a retention time of 17.99 minutes.

Ultraviolet Absorption Spectrum (H$_2$O), $\lambda_{max}$ nm: 254.

EXAMPLE 20

A Compound of Formula 2(a)

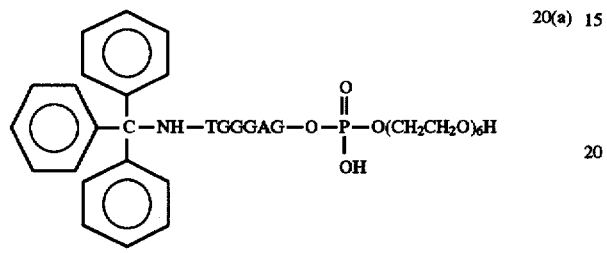

20(a)

Following a procedure similar to that described in Example 2(c), but using a column packed with 85 mg (5 µmol) of the compound of Example 16(a) and inputting the base sequence TGGGAGZ (in which Z is as defined in Example 17) to the DNA/RNA synthesizer described in Example 1(b), the title compound was prepared. The product was purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 177 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 19.10 minutes.

Ultraviolet Absorption Spectrum (H$_2$O), $\lambda_{max}$ nm: 254.

EXAMPLE 21

21(a) A Compound of Formula 21(a)

A solution of 250 mg of 5'-phosphate ON (a trade mark for a product of Clontech) in 5.2 ml of acetonitrile and a column packed with 15 µmol of C-CPG (Millipore Ltd., Japan) were used in the DNA/RNA synthesizer described in Example 1(b), to prepare the title compound quantitatively.

21(b) A Compound of Formula 21(b)

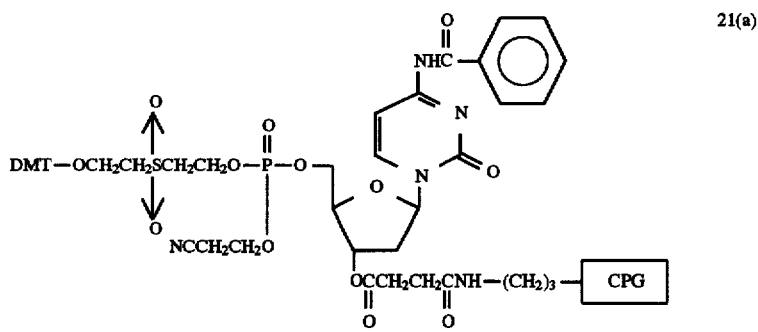

21(a)

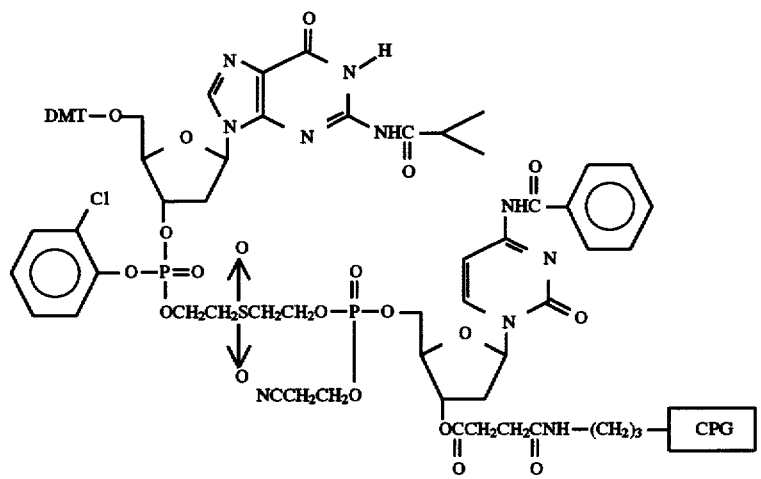

21(b)

5 ml of a deblock solution (Millipore Ltd., Japan) were added to a filter-equipped column packed with 115 mg (4 µmol) of the compound of Example 21(a). It was then allowed to stand for one minute, after which it was washed with 5 ml of methylene chloride, and then treated with a deblock solution for one minute. The mixture was then washed with 5 ml of methylene chloride and with 5 ml of pyridine, in that order, after which it was azeotropically distilled with pyridine. A solution of 20 mg of triethylammonium 5'-O-dimethoxytrityl-2-N-isobutyryl-2'-deoxyguanosine-3'-O-(2-chlorophenyl)-phosphate [Nucleic Acids Res., 8, 546 (1980)] in 0.5 ml of pyridine was then added to the distillate, after which the solvent was removed by distillation under reduced pressure. A solution of 40 mg of 2,4,6-trimethylbenzenesulfonyl-3-nitrotriazole in 0.5 ml of pyridine was added to the residue, and the resulting mixture was heated to 40° C. for 30 minutes. The reaction mixture was then washed three times, each time with 5 ml of pyridine, and then 2.5 ml of cap A solution (Millipore Ltd., Japan) and 2.5 ml of cap B solution (Millipore Ltd., Japan) were added to the mixture. The mixture was allowed to stand for 3 minutes, after which it was washed three times, each time with 5 ml of methylene chloride, to give the title compound.

21(c) A Compound of Formula 21(c)

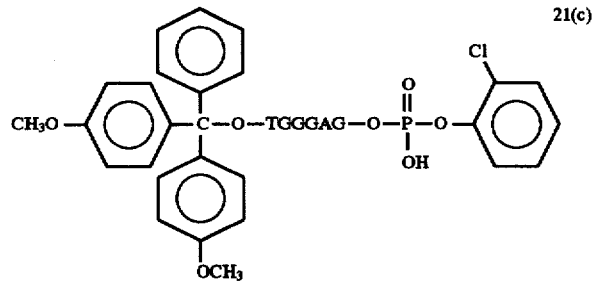

21(c)

Following a procedure similar to that described in Example 1(b) but using a column packed with 115 mg (4 µmol) of the compound of Example 21(b) and thyminedeoxyribonucleotide-β-amidite (Millipore Ltd., Japan) instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 5→50% acetonitrile; linear gradient; 254 nm). It was then worked up in a manner similar to that described in Example 1(b), to give the title compound having 85 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→50% B by volume, 20 minutes; linear gradient; 1 ml/minute; 260 nm) showed that the sample had a retention time of 21.5 minutes.

Ultraviolet Absorption Spectrum ($H_2O$), $\lambda_{max}$ nm: 254.

EXAMPLE 22

22(a) Triethylammonium 5'-O-dimethoxytrityl-2-N-isobutyryl-2'-deoxyguanosine-3'-O-phenylphosphate 0.8 g (11.55 mmol) of 1,2,4-triazole was dried by azeotropic distillation with pyridine and then suspended in 10 ml of dioxane. 0.52 ml (3.5 mmol) of phenyl phosphorodichloridate was added to the suspension, followed by 1.0 ml (7.35 mmol) of triethylamine, whilst ice-cooling and stirring, and the temperature was then allowed to rise to room temperature. The mixture was stirred for 2 hours, after which the hydrochloride deposited was filtered off, to produce a dioxane solution containing 0.35 mmol/ml of phenyl phosphorobis(triazolidate).

1 ml (0.35 mmol) of the dioxane solution of phenyl phosphorobis(triazolidate) prepared as described above was added to 0.15 g (0.23 mmol) of 5'-O-dimethoxytrityl-2-N-isobutyryl-2'-deoxyguanosine [Methods Enzymol., 65, 610 (1980)], and the resulting mixture was stirred at room temperature for 3 hours. At the end of this time, about 10 ml of 30% by volume aqueous pyridine were added. The reaction mixture was then extracted with 30 ml of methylene chloride, and the extract was washed with 0.1M TEAB. The solvent was removed by distillation under reduced pressure, and the resulting residue was dissolved in 1 ml of methylene chloride and triturated with 30 ml of a 1:1 by volume mixture of hexane and diethyl ether, containing 1% by volume triethylamine, to give 81 mg (yield 40%) of the title compound as a powder.

$^1$H Nuclear Magnetic Resonance Spectrum ($CDCl_3$, 270 MHz, TMS), δ ppm:

12.07 (1H, broad singlet);

9.67 (1H, broad singlet);

7.80–7.64 (1H, multiplet);

7.47–6.91 (18H, multiplet);
6.12–6.10 (1H, multiplet);
5.48–5.45 (1H, multiplet);
4.64–4.58 (1H, multiplet);
4.28 (1H, multiplet);
3.74 (6H, singlet);
3.38–3.18 (2H, multiplet);
2.98–2.89 (6H, multiplet);
2.73–2.51 (2H, multiplet);
2.34–2.29 (1H, multiplet);
1.25–1.19 (9H, multiplet);
1.12–0.99 (6H, multiplet).

2(b) A Compound of Formula 22(b)

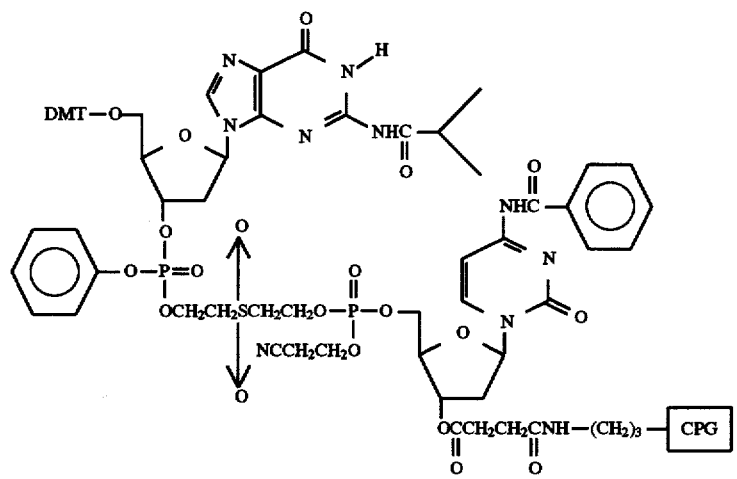

22(b)

Following a procedure similar to that described in Example 21(b), but using 143 mg (5 μmol) of the compound of Example 21(a) and the compound of Example 22(a), the title compound was obtained.

22(c) A Compound of Formula 22(c)

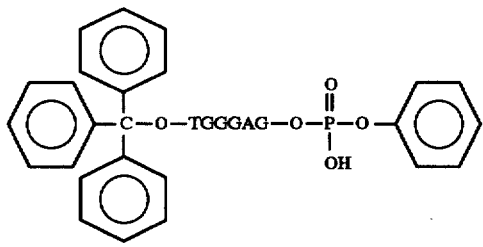

22(c)

Following a procedure similar to that described in Example 1(b), but using a column packed with 43 mg (5 μmol) of the compound of Example 22(b), the title compound was prepared. The reaction product was then purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 66 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 18.22 minutes.

Ultraviolet Absorption Spectrum (H$_2$O), $\lambda_{max}$ nm: 255.

EXAMPLE 23

A Compound of Formula 23(a)

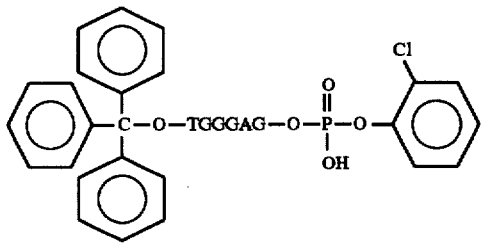

23(a)

Following a procedure similar to that described in Example 1(b), but using a column packed with 115 mg (4 μmol) of the compound of Example 21(b), the title compound was prepared. The reaction product was purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 56 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample has a retention time of 18.38 minutes.

Ultraviolet Absorption Spectrum (H$_2$O), $\lambda_{max}$ nm: 255.

EXAMPLE 24

24(a) A Compound of Formula 24(a)

24(a)

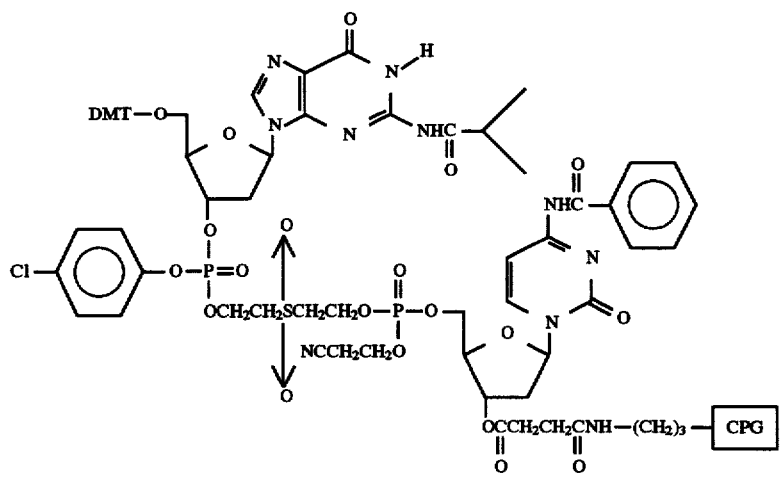

Following a procedure similar to that described in Example 21(b), but using 143 mg (5 μmol) of the compound of Example 21(a) and triethylammonium 5'-O-dimethoxytrityl-2-N-isobutyryl-2'-deoxyguanosine-(3'-(4-chlorophenyl)phosphate [Methods Enzymol., 65, 610 (1980)], the title compound was obtained.

24(b) A Compound of Formula 24(b)

24(b)

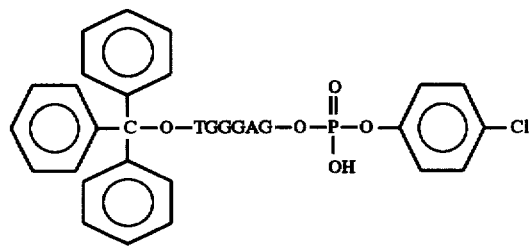

Following a procedure similar to that described in Example 1(b), but using a column packed with 143 mg (4 μmol) of the compound of Example 24(a), the title compound was prepared. The reaction product was purified by chromatography through a reverse phase silica gel column (preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 55 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample has a retention time of 18.55 minutes.

Ultraviolet Absorption Spectrum (H$_2$O), λ$_{max}$ nm: 255.

EXAMPLE 25

DMT-O-TGGGAG-OH

The desired base sequence (5'-TGGGAG-3') was input to a 380B synthesizer (a product of Applied Biosystems Inc.), and a controlled pore glass column (1 μmol scale) bounded with the corresponding nucleoside (2'-deoxyguanosine) at the 3'-terminal was connected to it. The synthesis was conducted on a scale of 1 μmol. The apparatus was set up not to deprotect the DMT group after completion of the reaction, and the product having a DMT group was automatically freed from the resin, to give an oligodeoxyribonucleotide as an ammonia solution. This solution was sealed in a vial and heated at 55° C. for 8 hours, and the ammonia was evaporated off in a stream of nitrogen. The resulting residue was dissolved in a small amount of 0.1M TEAA (pH 7.0). This solution was filtered through a millipore-filter (0.2 μm), and the filtrate was purified by reverse phase high performance liquid chromatography (Cosmosil 5C18-AR, 20×250 mm), under the conditions listed below. Fractions eluted after 13.5 minutes were collected and freed from the solvent (acetonitrile) by distillation under reduced pressure followed by lyophilization, to give 800 μg of the title compound.

Elution time: 17.0 minutes

Conditions for preparative high performance liquid chromatography:

Buffer solution A: 0.1M triethylammonium acetate buffer (pH 7.0);

Buffer solution B: 100% acetonitrile;

Flow rate; 9 ml/min.

| Time (min) | Buffer A (%) | Buffer B (%) |
|---|---|---|
| 0 | 80 | 20 |
| 15 | 55 | 45 |
| 20 | 55 | 45 |

EXAMPLES 26 to 38

Following a procedure similar to that described in Example 25, the compounds of Examples 26 through 38 were synthsized. The compound names and their elution times are listed in Table 3.

TABLE 3

| Example No. | Compound name | Retention time |
|---|---|---|
| 26 | DMT-O-TGGG-OH | 17.5 min |
| 27 | DMT-O-TGGGA-OH | 16.7 min |

TABLE 3-continued

| Example No. | Compound name | Retention time |
|---|---|---|
| 28 | DMT-O-TGGGG-OH | 16.8 min |
| 29 | DMT-O-CGGGAGG-OH | 16.3 min. |
| 30 | DMT-O-TGGGAGG-OH | 16.2 min |
| 31 | DMT-O-TTGGAGG-OH | 18.0 min |
| 32 | DMT-O-TGCGAGG-OH | 17.2 min |
| 33 | DMT-O-GGGGAGG-OH | 15.3 min |
| 34 | DMT-O-mCGGGAGG-OH | 16.3 min |
| 35 | DMT-O-mCGmCGAGG-OH | 16.6 min |
| 36 | DMT-O-TTGGGAGG-OH | 17.1 min |
| 37 | DMT-O-CTGGGAGG-OH | 17.7 min |
| 38 | DMT-O-CTGGT-OH | 17.2 min |

TABLE 3-continued

| Example No. | Compound name | Retention time |
|---|---|---|
| 71 | DMT-O-TAGGAGG-OH | 17.7 min |
| 72 | DMT-O-TGGGAGGT-OH | 16.2 min |
| 73 | DMT-O-TGGGCGCAG-OH | 17.1 min |
| 74 | DMT-O-CCG-OH | 16.7 min |
| 75 | DMT-O-TCGGAGG-OH | 17.5 min |
| 76 | DMT-O-TGmCGAGG-OH | 16.6 min |
| 77 | DMT-O-GTGGGAGG-OH | 15.7 min |
| 78 | DMT-O-TGG-OH | 15.4 min |
| 79 | DMT-O-TGGGAmGG | 16.3 min |
| 80 | DMT-O-TGGGAGA-OH | 16.7 min |
| 81 | DMT-O-AATGGGAGG-OH | 14.9 min |

EXAMPLE 82

82(a) A Compound of Formula 82(a)

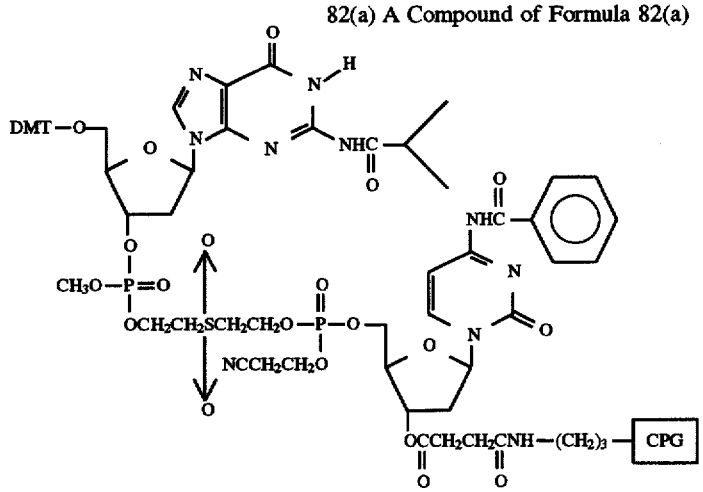

TABLE 3-continued

| Example No. | Compound name | Retention time |
|---|---|---|
| 39 | DMT-O-CTGGC-OH | 17.1 min |
| 40 | DMT-O-CTCGT-OH | 17.6 min |
| 41 | DMT-O-CTCGC-OH | 17.4 min |
| 42 | DMT-O-CTCGG-OH | 17.5 min |
| 43 | DMT-O-CGGGT-OH | 16.1 min |
| 44 | DMT-O-CGGGC-OH | 16.1 min |
| 45 | DMT-O-CGGGG-OH | 16.2 min |
| 46 | DMT-O-CGCGT-OH | 17.8 min |
| 47 | DMT-O-CGCGC-OH | 17.5 min |
| 48 | DMT-O-CGCGG-OH | 18.0 min |
| 49 | DMT-O-TTGGA-OH | 18.6 min |
| 50 | DMT-O-TTGGT-OH | 18.6 min |
| 51 | DMT-O-TTGGC-OH | 18.4 min |
| 52 | DMT-O-TTGGG-OH | 17.7 min |
| 53 | DMT-O-TTCGA-OH | 18.9 min |
| 54 | DMT-O-TTCGT-OH | 18.7 min |
| 55 | DMT-O-TTCGC-OH | 18.6 min |
| 56 | DMT-O-TTCGG-OH | 18.8 min |
| 57 | DMT-O-TGGGT-OH | 17.6 min |
| 58 | DMT-O-TGGGC-OH | 17.4 min |
| 59 | DMT-O-TGCGA-OH | 17.8 min |
| 60 | DMT-O-TGCGT-OH | 17.7 min |
| 61 | DMT-O-TGCGC-OH | 18.3 min |
| 62 | DMT-O-TGCGG-OH | 17.6 min |
| 63 | DMT-O-CTCG-OH | 17.9 min |
| 64 | DMT-O-TTCG-OH | 19.1 min |
| 65 | DMT-O-CTGG-OH | 17.1 min |
| 66 | DMT-O-CGCG-OH | 18.2 min |
| 67 | DMT-O-TGCG-OH | 18.0 min |
| 68 | DMT-O-CGGG-OH | 16.2 min |
| 69 | DMT-O-TTGG-OH | 18.2 min |
| 70 | DMT-O-GGGCGGGC-OH | 15.4 min |

The required reagents for synthesis as detailed below were supplied to a Cyclone (trade mark) Plus DNA/RNA synthesizer of Milligen/biosearch (Millipore Ltd., Japan). Also installed was a program cartridge for the amidite method (15 μmol). There were used an approximately 35 mM acetonitrile solution of 5'-O-dimethoxytrityl-2-N-isobutyryl-2'-deoxyguanosine-3'-O-(methyl N, N-diisopropylphosphoramidite) (Sigma) instead of the β-cyanoethyl amidite corresponding to guanosine. By using an empty column (15.0 μmol) packed with 143 mg (5 μmol) of the compound of Example 21(a), inputting the base sequence GX to the synthesizer and working the program without acid treatment after bonding with a base, G, the title compound was obtained.

82(b) A Compound of Formula 82(b)

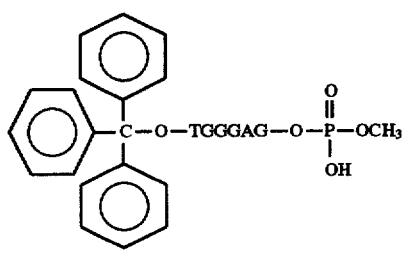

Following a procedure similar to that described in Example 1(b), but using a column packed with 143 mg (5 μmol) of the compound of Example 82(a), the title compound was prepared. The product was purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 66 OD (260 nm) as an amorphous solid. Analysis by reverse phase high performance liquid chromatography (Inertsil ODS, 6×250 mm; eluent A: 0.1M TEAA, pH 7.5; eluent B: acetonitrile; 10→60% B by volume, 20 minutes; linear gradient; 1 ml/minute; 260 nm) showed that the sample has a retention time of 17.54 minutes.

Ultraviolet Absorption Spectrum (H$_2$O), $\lambda_{max}$ nm: 254.

EXAMPLES 83

83(a) A Compound of Formula 83(a)

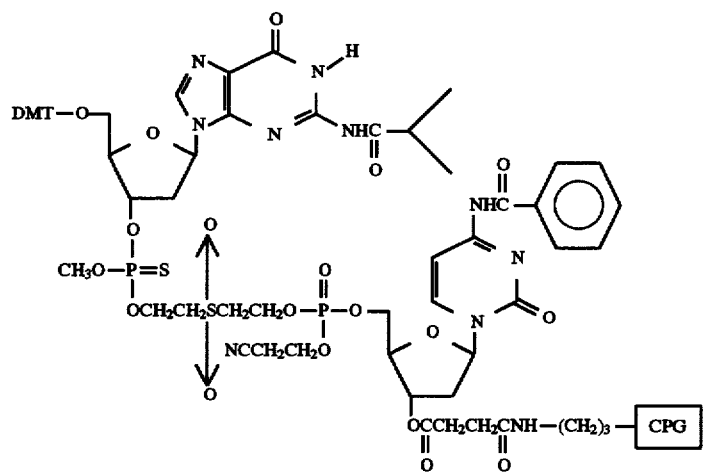

83(a)

Following a procedure similar to that described in Example 82(a), but using 143 mg (5 μmol) of the compound of Example 21(a), the title compound was prepared. In detail, after coupling with 5'-O-dimethoxytrityl-2-N-isobutyryl-2'-deoxyguanosine-3'-O-(methyl N,N-diisopropyl)phosphoramidite, the column was taken away from the DNA/RNA synthesizer without oxidation by an oxidizing solution. 5 ml of an acetonitrile solution of tetraethylthiuram disulfide (TETD) (Applied Biosystems) were added to the column, and the column was allowed to stand at room temperature for 15 minutes. The column was then washed with acetonitrile and installed in the synthesizer.

83(b) A Compound of Formula 83(b)

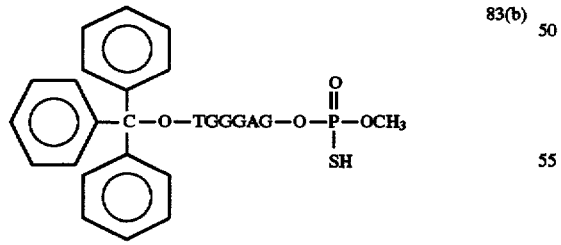

83(b)

Following a procedure similar to that described in Example 1(b), but using a column packed with 143 mg (5 μmol) of the compound of Example 83(a), the title compound was prepared. The reaction product was purified by chromatography through a reverse phase silica gel column (Preparative C18, Waters, 1.5×15 cm; 50 mM TEAB, pH 7.5; 20→50% acetonitrile; linear gradient; 1 ml/minute; 260 nm). It was then worked up in a manner similar to that described in Example 1(b), to give the title compound having 111 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient, 1 ml/minute; 260 nm) showed that the sample has a retention time of 17.72 minute.

Ultraviolet Absorption Spectrum (H$_2$O), $\lambda_{max}$ nm: 254.

EXAMPLE 84

84(a) A Compound of Formula 84(a)

84(a)

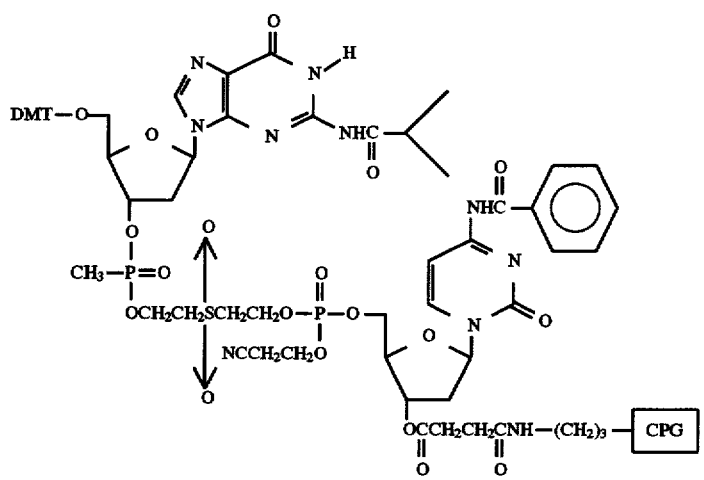

The required reagents for synthesis as detailed below were supplied to a Cyclone (trademark) Plus DNA/RNA synthesizer of Milligen/biosearch (Millipore Ltd., Japan). Also installed was a program cartridge for the amidite method (15 µmol). There was used an approximately 35 mM tetrahydrofuran solution of deoxyguanosine (N-iBu) methyl phosphonamidite (American Bionetic Inc.) instead of a β-cyanoethyl amidite solution corresponding to guanosine. By using an empty column (15.0 µmol) packed with 143 mg (5 µmol) of the compound of Example 21(a) as a solid carrier, inputting a base sequence of GZ (in which Z is as defined in Example 17) and working a program without acid treatment after bonding with a base G, the title compound was obtained.

84(b) A. Compound of Formula 84(b)

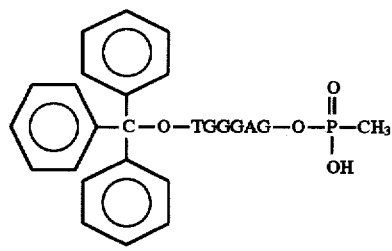

84(b)

Following a procedure similar to that described in Example 1(b), but using a column packed with 143 mg (5 µmol) of the compound of Example 84(a), the title compound was prepared. The reaction product was purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 159 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample has a retention time of 18.03 minutes.

Ultraviolet Absorption Spectrum (H$_2$O), $\lambda_{max}$ nm: 254.

EXAMPLE 85

85(a) A Compound of Formula 85(a)

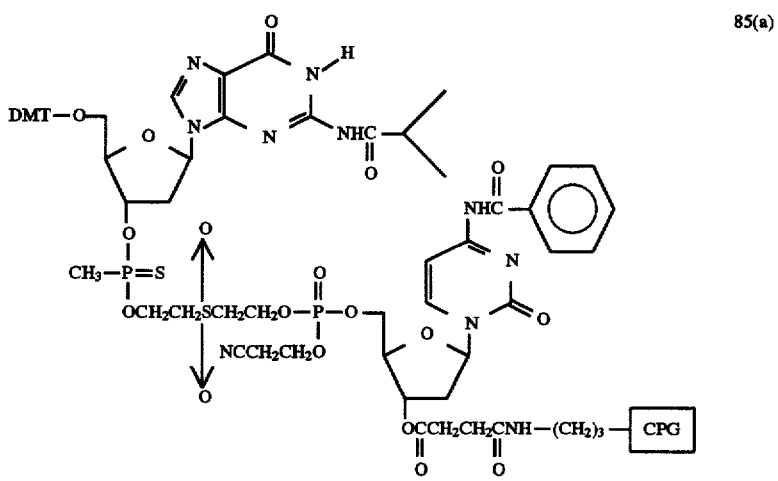

85(a)

Following a procedure similar to that described in Example 84(a), but using a column packed with 143 mg (5 µmol) of the compound of Example 21(a), the title compound was prepared. In more detail, after coupling with deoxyguanosine (N-iBu)methyl phosphonamidite, the column was removed from the synthesizer without oxidation by an oxidizing solution and then 5 ml of an acetonitrile solution of tetraethylthiuram disulfide (TETD) (Applied Biosystems) were added to the column. The column was allowed to stand at room temperature for 15 minutes, after which it was washed with acetonitrile and installed again in the synthesizer.

85(b) A Compound of Formula 85(b)

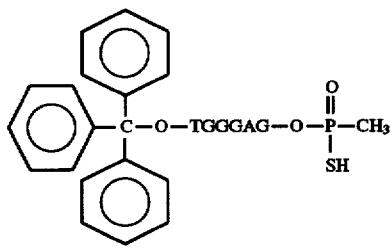

Following a procedure similar to that described in Example 1(b), but using a column packed with 143 mg (5 µmol) of the compound of Example 85(a), the title compound was prepared. The reaction product was purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 124 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 18.07 minutes.

Ultraviolet Absorption Spectrum (H$_2$O), $\lambda_{max}$ nm: 254.

EXAMPLE 86

A Compound of Formula 86(a)

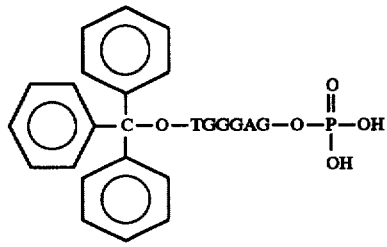

Following a procedure similar to that described in Example 1(b), but using a column packed with 143 mg (5 µmol) of the compound of Example 21(a) and inputting the base sequence TGGGAGZ (in which Z is as defined in Example 17) to the DNA/RNA synthesizer described in Example 1(b), the title compound was prepared. The reaction product was purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 54 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; by volume, 15→65% 20 minutes; linear gradient; 1 ml/minute; 260 nm) showed that the sample had a retention time of 15.20 minutes.

Ultraviolet Absorption Spectrum (H$_2$O), $\lambda_{max}$ nm: 255.

EXAMPLE 87

A Compound of Formula 87(a)

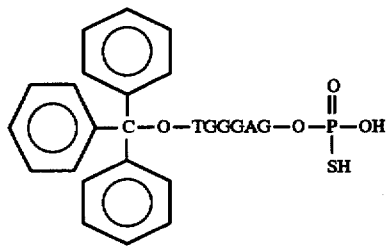

Following a procedure similar to that described in Example 86, but using a column packed with 143 mg (5 µmol) of the compound of Example 21(a), the title compound was prepared. In more detail, after first coupling with G-β-amidite at the 3'-terminal, the column was removed from the DNA/RNA synthesizer without oxidation by an oxidizing solution. 5 ml of an acetonitrile solution of tetraethylthiuram disulfide (TETD) (Applied Biosystems) were added to the column, and the column was allowed to stand at room temperature for 15 minutes, after which it was washed with acetonitrile and installed in the synthesizer.

The reaction product was purified by chromatography through a reverse phase silica gel column (Preparative C18Waters, 1.5×15 cm; 50 mM TEAB, pH 7.5; 20→50% acetonitrile; linear gradient; 254 nm). It was then worked up in a manner similar to that described in Example 1(b), to give the title compound having 136 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minute; linear gradient; 1 ml/minute; 260 nm) showed that the sample had a retention time of 18.02 minutes.

Ultraviolet Absorption Spectrum (H$_2$O), $\lambda_{max}$ nm: 254.

EXAMPLE 88

A Compound of Formula 88(a)

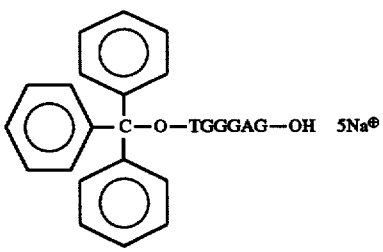

Dowex 50W-X2 ion-exchange resin (a trade mark for a product of Dow Chemical Co.; H-form; about 1 ml) was packed into a column, and 3 ml of 20% v/v aqueous pyridine were passed through the column, which was then washed with water to prepare the pyridinium form of the resin in the column. Following a similar procedure, but using 3 ml of a 1N aqueous solution of sodium hydroxide, the sodium form of the resin was prepared in another column. The compound of Example 1(b) having 27 OD was applied consecutively to a combination of the pyridinium-form resin column and the sodium-form resin column, in that order, and then the columns were eluted with water, to give the title compound (a sodium salt) having 27 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 18.12 minutes.

Ultraviolet Absorption Spectrum (H$_2$O), $\lambda_{max}$ nm: 256.

EXAMPLE 89

A Compound of Formula 89(a)

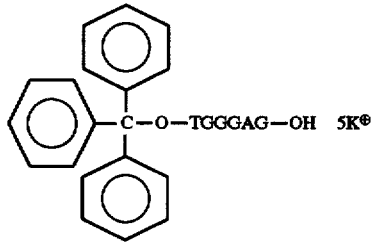

Dowex 50W-X2 ion-exchange resin (a trade mark for a product of Dow Chemical Co.; H-form; about 1 ml) was packed into a column, and 3 ml of 20% v/v aqueous pyridine were passed through the column, which was then washed with water, to prepare a pyridinium form of the resin in the column. Following a similar procedure, but using 3 ml of a 1N aqueous solution of potassium hydroxide, a potassium form of the resin was prepared in another column. The compound of Example 1(b) having 27 OD was applied consecutively to a combination of the pyridinium-form resin column and the potassium-form resin column, and the columns were eluted with water, to gave the title compound (a potassium salt) having 27 OD (260 nm) as an amorphous solid. Analysis by reverse phase high performance liquid chromatography (Inertsil ODS, 6×150 mm; eluent A: 0.1M TEAA, pH 7.5; eluent B: acetonitrile 10→60% B by volume, 20 minute; linear gradient; 1 ml/minute; 260 nm) showed that the sample had a retention time of 18.18 minutes.

Ultraviolet Absorption Spectrum (H$_2$O), $\lambda_{max}$ nm: 254.

EXAMPLE 90

A Compound of Formula 90(a)

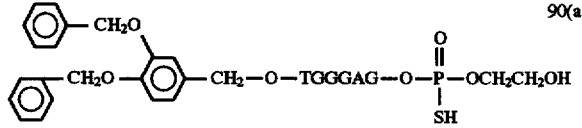

Following a procedure similar to that described in Example 14(a), but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 10→50% acetonitrile; linear gradient; 254 nm). It was then worked up in a manner similar to that described in Example 1(b), to give the title compound having 119 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that this sample had a retention time of 19.20 minutes.

Ultraviolet Absorption Spectrum (H$_2$O), $\lambda_{max}$ nm: 254.

EXAMPLE 91

A Compound of Formula 91(a)

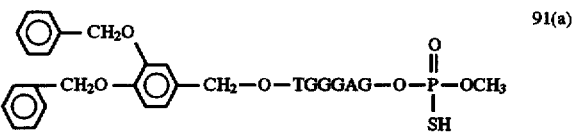

Following a procedure similar to that described in Example 82(b), but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 20→50% acetonitrile; linear gradient; 254 nm). It was then worked up in a manner similar to that described in Example 1(b), to give the title compound having 50 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that this sample had a retention time of 19.15 minutes.

Ultraviolet Absorption Spectrum (H$_2$O), $\lambda_{max}$ nm: 254.

EXAMPLE 92

A Compound of Formula 92(a)

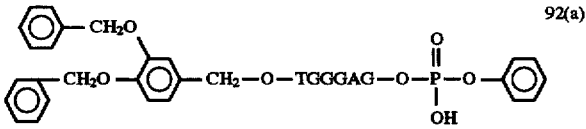

Following a procedure similar to that described in Example 22(c), but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 15→50% acetonitrile; linear gradient; 254 nm). It was then worked up in a manner similar to that described in Example 1(b), to give the title compound having 67 OD (260 nm) as an amorphous solid. Analysis by reverse phase high performance liquid chromatography (Inertsil ODS, 6×150 mm; eluent A: 0.1M TEAA, pH 7.5; eluent B: acetonitrile;

10→60% B by volume, 20 minutes; linear gradient; 1 ml/minute; 260 nm) showed that this sample had a retention time of 19.51 minutes.

Ultraviolet Absorption Spectrum (H₂O), $\lambda_{max}$ nm: 255.

EXAMPLE 93

A Compound of Formula 93(a)

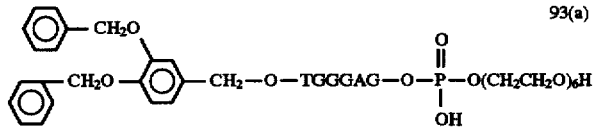

Following a procedure similar to that described in Example 16(b), but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEA, pH 7.5; 15→50% acetonitrile; linear gradient; 254 nm). It was then worked up in a manner similar to that described in Example 1(b), to give the title compound having 96 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that this sample had a retention time of 19.26 minutes.

Ultraviolet Absorption Spectrum (H₂O), $\lambda_{max}$ nm: 254.

EXAMPLE 94

A Compound of Formula 94(a)

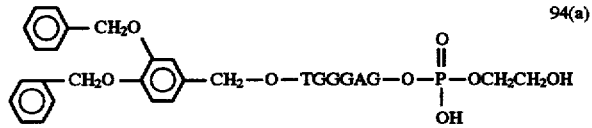

Following a procedure similar to that described in Example 12(c), but using 5,-O-(3,4-dibenzyloxybenzyl)thymidine 2-cyanoethyl N,N-diisopropylphosphoramidite [prepared as described in Example 7(b)] instead of the 5,-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 15→50% acetonitrile; linear gradient; 254 nm). It was then worked up in a manner similar to that described in Example 1(b), to give the title compound having 97 OD (260 nm) as an amorphous solid. Analysis by reverse phase high performance liquid chromatography (Intertsil ODS, 6×150 nm; eluent A: 0.1M TEAA, pH 7.5; eluent B: acetonitrile; 10→60% B by volume, 20 minutes; linear gradient; 1 ml/minute; 260 nm) showed that this sample had a retention time of 19.16 minutes.

Ultraviolet Absorption Spectrum (H₂O), $\lambda_{max}$ nm: 254.

EXAMPLE 95

A Compound of Formula 95(a)

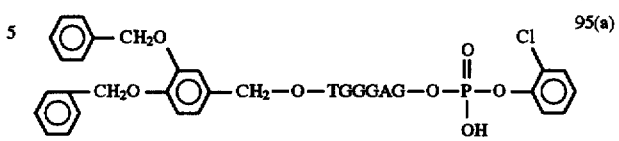

Following a procedure similar to that described in Example 23(a), but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 15→50% acetonitrile; linear gradient; 254 nm). It was then worked up in a manner similar to that described in Example 1(b), to give the title compound having 83 OD (260 nm) as an amorphous solid. Analysis by reverse phase high performance liquid chromatography (Intertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 19.80 minutes.

Ultraviolet Absorption Spectrum (H₂O), $\lambda_{max}$ nm: 255.

EXAMPLE 96

A Compound of Formula 96(a)

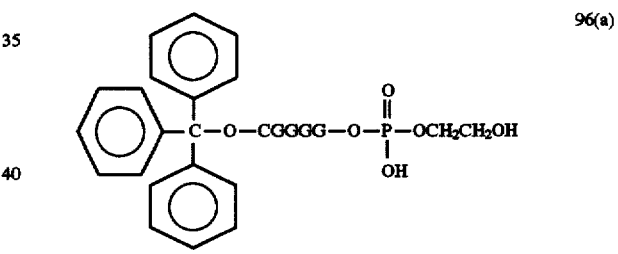

A procedure similar to that described in Example 15(c) was repeated, but using a column packed with 125 mg (5 μmol) of the compound of Example 12(b) and inputting the base sequence XGGGGZ (in which Z is as defined in Example 17) to the synthesizer. The 90% v/v aqueous formamide solution containing the title compound thus obtained was then heated at 95° C. for 5 minutes. After this heating, the solution was cooled rapidly. The reaction mixture was then divided into four portions and each was purified by reverse phase high performance liquid chromatography (Inertsil PREP-ODS 20.0×250 mm; eluent A: 0.1M TEAA pH 7.0; eluent B: acetonitrile; 10 to 60% B by volume, 30 minutes; linear gradient; 7 ml/minute; 260 nm; column temperature 60° C.). Fractions eluted after 20.7 minutes were collected and worked up in a similar manner to that described in Example 1(b), to give 79 OD (260 nm) of the title compound as an amorphous solid.

Ultraviolet Absorption Spectrum (H₂O), $\lambda_{max}$ nm: 253.

Retention time: 13.22 minutes

High performance liquid chromatography (Inertsil ODS-2; 6×150 nm; eluent A: 0.1M TEAA, pH 7.5; eluent B: acetonitrile; 10 to 60% B by volume, 20 minutes; linear gradient; 1 ml/minute; 260 nm).

EXAMPLE 97

A Compound of Formula 97(a)

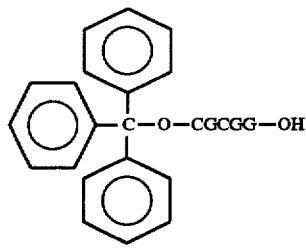

A procedure similar to that described in Example 1(b) was repeated, except that a 35 mM acetonitrile solution of the compound of Example 15(b) in the amidite bottle X was used and the base sequence XGCGG was input to the synthesizer as a program. The 90% formamide aqueous solution containing the title compound thus obtained was heated at 95° C. for 5 minutes. After this heating, the solution was cooled rapidly. The reaction mixture was then divided into four portions, and each was purified by reverse phase high performance liquid chromatography (Inertsil PREP-ODS 20.0×250 mm; eluent A: 0.1M TEAA pH 7.0; eluent B: acetonitrile; 10 to 60% B by volume, 30 minutes; linear gradient; 7 ml/minute; 260 nm; column temperature 60° C.). Fractions eluted after 21.7 minutes were collected and worked up in a similar manner to that described in Example 1(b), to give 123 OD (260 nm) of the title compound as an amorphous solid.

Ultraviolet Absorption Spectrum (H₂O), $\lambda_{max}$ nm: 255.
Retention time: 13.58 minutes high Performance liquid chromatography (Inertsil ODS-2; 6×150 nm; eluent A: 0.1M TEAA, pH 7.5; eluent B: acetonitrile; 10 to 60% B by volume, 20 minutes, linear gradient; 1 ml/minute; 260 nm).

EXAMPLE 98

A Compound of Formula 98(a)

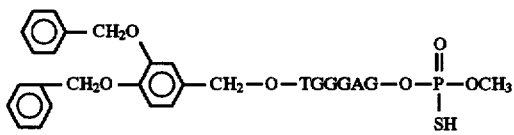

Following a procedure similar to that described in Example 83(b), but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 15→50% acetonitrile; linear gradient; 254 nm). It was then worked up in a manner similar to that described in Example 1(b), to give the title compound having 92 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 1 ml/minute; 260 nm) showed that the sample had a retention time of 19.46 minutes.

Ultraviolet Absorption Spectrum (H₂O), $\lambda_{max}$ nm: 254.

EXAMPLE 99

A Compound of Formula 99(a)

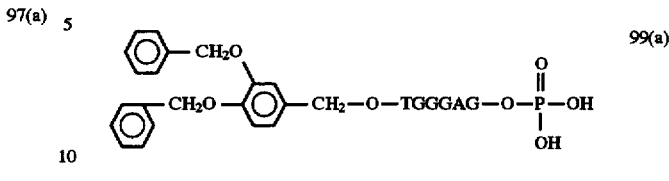

Following a procedure similar to that described in Example 86, but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (preparative C18, Waters, 1.5×15 cm; 50 mM TEAB, pH 7.5; 15→50% acetonitrile; linear gradient; 254 nm). It was then worked up in a manner similar to that described in Example 1(b), to give the title compound having 43 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 260 nm) showed that the sample had a retention time of 19.12 minutes.

Ultraviolet Absorption Spectrum (H₂O), $\lambda_{max}$ nm: 254.

EXAMPLE 100

A Compound of Formula 100(a)

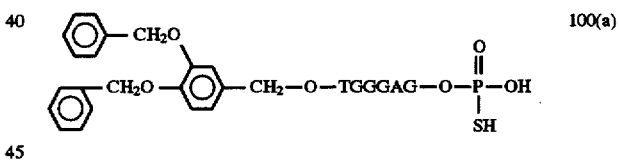

Following a procedure similar to that described in Example 87, but using 5'-O-(3,4-dibenzyloxybenzyl)-thymidine 2-cyanoethyl N,N-diisopropylphosphoramidite [prepared as described in Example 7(b)] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×15 cm; 50 mM TEAB, pH 7.5; 15→50% acetonitrile; linear gradient; 254 nm). It was then worked up in a manner similar to that described in Example 1(b), to give the title compound having 36 OD (260 nm) as an amorphous solid. Analysis by reverse phase high performance liquid chromatography (Inertsil ODS, 6×150 mm; eluent A: 0.1M TEAA, pH 7.5; eluent B: acetonitrile; 10→60% B by volume, 20 minutes; linear gradient; 260 nm) showed that the sample had a retention time of 19.11 minutes.

Ultraviolet Absorption Spectrum (H₂O), $\lambda_{max}$ nm: 255.

EXAMPLE 101

A Compound of Formula 101(a)

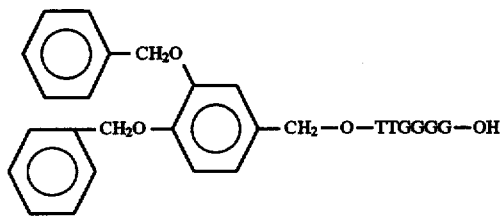

Following a procedure similar to that described in Example 1(b), but using a 35 mM acetonitrile solution of 5'-O-(3,4-dibenzyloxybenzyl)thymidine 2-cyanoethyl N,N-diisopropylphosphoramidite [prepared as described in Example 7(b)] in the amidite bottle X and inputting the base sequence XTGGGG to the synthesizer as a program, the title compound was prepared. The reaction product was divided into three portions, and each was purified by reverse phase high performance liquid chromatography (Inertsil PREP-ODS, 20.0×250 mm; eluent A: 0.1M TEAA, pH 7.3; eluent B: acetonitrile; 25→55% B by volume, 30 minutes; linear gradient; 7 ml/minute; 254 nm). Fractions eluted after 19.8 minutes were collected and worked up in a similar manner to that described in Example 1(b), to give 173.1 OD (260 nm) of the title compound as an amorphous solid.

Ultraviolet Absorption Spectrum (H$_2$O), $\lambda_{max}$ nm: 255.
Retention time: 15.1 minutes High performance liquid chromatography (YMC-Pack A-312, S-5, 120A, ODS; eluent A: 0.1M TEAA, pH 7.3; eluent B: acetonitrile; 20→50% B by volume, 30 minutes; linear gradient; 2 ml/minute; 254 nm).

EXAMPLE 102

A Compound of Formula 102(a)

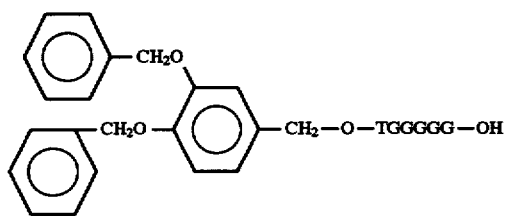

Following a procedure similar to that described in Example 1(b), but using 5'-O-(3,4-dibenzyloxybenzyl)thymidine 2-cyanoethyl N,N-diisopropylphosphoramidite [prepared as described in Example 7(b)] instead of the 5'-O-tritylthymidine 2-cyanoethyl N,N-diisopropylphosphoramidite, and inputting the base sequence TGGGGG to the synthesizer as a program, the title compound was prepared. The reaction product was divided into three portions and each was purified by reverse phase high performance liquid chromatography (Inertsil PREP-ODS, 20.0×250 mm; eluent A: 0.1M TEAA, pH 7.3; eluent B: acetonitrile; 25→55% B by volume, 30 minutes; linear gradient; 7 ml/minute; 254 nm). Fractions eluted after 17.4 minutes were collected and worked up in a similar manner to that described in Example 1(b), to give 120.2 OD (260 nm) of the title compound as an amorphous solid.

Ultraviolet Absorption Spectrum (H$_2$O), $\lambda_{max}$ nm: 254.
Retention time: 13.1 minutes high performance liquid chromatography (YMC-Pack A-312, S-5, 120A, ODS; eluent A: 0.1M TEAA, pH 7.3; eluent B: acetonitrile; 20→50% B by volume, 30 minutes; linear gradient; 2 ml/minute; 254 nm).

EXAMPLE 103

103(a) 5'-O-[(Naphthalen-2-yl)methyl]thymidine

Following a procedure similar to that described in Example 6(a), but using 442 mg (2 mmol) of 2-bromomethylnaphthalene, 253.1 mg (yield 33%) of the title compound were obtained.

$^1$H Nuclear Magnetic Resonance Spectrum (CDCl$_3$, 270 MHz, TMS), δ ppm:

8.12 (1H, broad singlet);
7.88–7.43 (8H, multiplet);
6.40 (1H, triplet, J=6.75 Hz);
4.76 (2H, singlet);
4.61–4.54 (1H, multiplet);
4.12–4.10 (1H, multiplet);
3.88–3.72 (2H, multiplet);
2.40–2.20 (2H, multiplet);
2.05 (1H, broad singlet);
1.58 (3H, singlet).

103(b) 5'-O-[(Naphthalen-2-yl)methyl]thymidine 2-cyanoethyl N,N-diisopropylphosphoramidite Following a procedure similar to that described in Example 11(b), but using 77 mg (0.2 mmol) of 5'-O-[(naphthalen-2-yl)methyl]thymidine [prepared as described in step (a) above], 62.5 mg (yield 54%) of the title compound were obtained.

$^1$H Nuclear Magnetic Resonance Spectrum (CDCl$_3$, 270 MHz, TMS), δ ppm:

7.88–7.43 (8H, multiplet);
6.39 (1H, triplet, J=7.26 Hz);
4.75 (2H, broad singlet);
4.68–4.60 (1H, multiplet);
4.25, 4.20 (together 1H, two broad singlets);
3.90–3.53 (6H, multiplet);
2.68–2.18 (4H, multiplet);
1.57, 1.55 (together 3H, two singlets);
1.17 (12H, doublet, J=6.60 Hz).

103(c) A Compound of Formula 103(c)

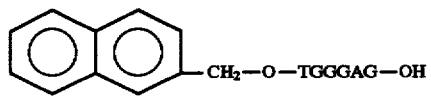

Following a procedure similar to that described in Example 1(b), but using 5'-O-[(naphthalen-2-yl)methyl]-thymidine 2-cyanoethyl N,N-diisopropylphosphoramidite prepared as described in step (b) above] instead of the 5'-O-tritylthymidine 2-cyanoethyl N,N-diisopropylphosphoramidite, the title compound was prepared. The reaction product was divided into three portions and each portion was purified by reverse phase high performance liquid chromatography (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 254 nm). Fractions eluted after 12.8 minutes were collected and worked up in a similar manner to that described in Example 1(b), to give of 257.5 OD (260 nm) the title compound as an amorphous solid.

Ultraviolet Absorption Spectrum (H$_2$O), $\lambda_{max}$ nm: 255.

Retention time: 13.9 minutes

High performance liquid chromatography (YMC-Pack A-312, S-5, 120A, ODS; eluent A: 0.1M TEAA, pH 7.3; eluent B: acetonitrile; 10→40% B by volume, 30 minutes; linear gradient; 2 ml/minute; 254 nm).

EXAMPLE 104

104(a) 5'-O-(4-Phenylbenzyl)thymidine

Following a procedure similar to that described in Example 6(a), but using 405 mg (2 μmol) of 4-phenylbenzyl chloride, 387.8 mg (yield 47%) of the title compound were obtained.

$^1$H Nuclear Magnetic Resonance Spectrum (CDCl$_3$+ CD$_3$OD, 4:1 v/v, TMS, 270 MHz), δ ppm:

7.65–7.33 (10H, multiplet);
6.37 (1H, triplet, J=7.26 Hz);
4.64 (2H, singlet);
4.55–4.48 (1H, multiplet);
4.13–4.09 (1H, multiplet);
3.87–3.70 (2H, multiplet);
2.38–2.15 (2H, multiplet);
1.63 (3H, singlet).

104(b) 5'-O-(4-Phenylbenzyl)thymidine 2-cyanoethyl N,N-diisopropylphosphoramidite Following a procedure similar to that described in Example 11(b), but using 82 mg (0.2 mmol) of 5'-O-(4-phenylbenzyl)thymidine [prepared as described in step (a) above], 71.8 mg (yield 59%) of the title compound were obtained.

$^1$H Nuclear Magnetic Resonance Spectrum (CDCl$_3$, 270 MHz, TMS), δ ppm:

7.62–7.34 (10H, multiplet);
6.40 (1H, triplet, J=6.60 Hz);
4.70–4.60 (3H, multiplet);
4.27, 4.20 (together 1H, two broad singlets);
3.90–3.55 (6H, multiplet);
2.67–2.57 (2H, multiplet);
2.53–2.16 (2H, multiplet);
1.63 (3H, singlet);
1.19 (12H, doublet, J=6.60 Hz).

104(c) A Compound of Formula 104(c)

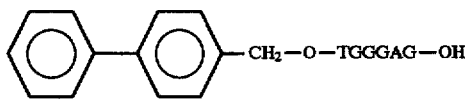

104(c)

Following a procedure similar to that described in Example 1(b), but using 5'-O-(4-Phenylbenzyl)thymidine 2-cyanoethyl N,N-diisopropylphosphoramidite [prepared as described in step (b) above] instead of the 5'-O-tritylthymidine 2-cyanoethyl N,N-diisopropylphosphoramidite, the title compound was prepared. The reaction product was divided into three portions and each portion was purified by reverse phase high performance liquid chromatography (Intertsil PREP-ODS, 20.0× 250 mm; eluent A: 0.1M TEAA, pH 7.3; eluent B: acetonitrile; 20→50% B by volume, 30 minutes; linear gradient; 7 ml/minute; temperature 60° C.; 254 nm). Fractions eluted after 16.1 minutes were collected and worked up in a similar manner to that described in Example 1(b), to give 281.8 OD (260 nm) of the title compound as an amorphous solid.

Ultraviolet Absorption Spectrum (H$_2$O), $\lambda_{max}$ nm: 255.

Retention time: 7.1 minutes

High performance liquid chromatography (YMC-Pack A-312, S-5, 120A, ODS; eluent A: 0.1M TEAA, pH 7.3; eluent B: acetonitrile; 20→50% B by volume, 30 minutes; linear gradient; 2 ml/minute; 60° C.; 254 nm).

EXAMPLE 105

105(a) 5'-O-(2-phenylbenzyl)thymidine

Following a procedure similar to that described in Example 6(a), but using 365 μl (2 mmol) of 2-phenylbenzyl bromide, 133.2 mg (yield 16%) of the title compound were obtained.

$^1$H Nuclear Magnetic Resonance Spectrum (CDCl$_3$, 270 MHz, TMS), δ ppm:

8.13 (1H, broad singlet);
7.50–7.28 (10H, multiplet);
6.34 (1H, triplet, J=6.75 Hz);
4.57, 4.50 (2H, two doublets, J=13.0 Hz);
4.30 (1H, broad singlet);
3.98 (1H, broad singlet);
3.73–3.52 (2H, multiplet);
2.32–2.05 (2H, multiplet);
1.90 (1H, broad singlet);
1.51 (3H, singlet).

105(b) 5'-O-(2-Phenylbenzyl)thymidine 2-cyanoethyl N,N-diisopropylphosphoramidite Following a procedure similar to that described in Example 11(b), but using 82 mg (0.2 mmol) of 5'-O-(2-phenylbenzyl)thymidine [prepared as described in step (a) above], 89.9 mg (yield 73%) of the title compound were obtained.

$^1$H Nuclear Magnetic Resonance Spectrum (CDCl$_3$, 270 MHz, TMS), δ ppm:

7.51–7.29 (10H, multiplet);
6.36 (1H, triplet, J=7.92 Hz);
4.55–4.45 (3H, multiplet);
4.19, 4.11 (together 1H, two singlets);
3.90–3.52 (6H, multiplet);
2.66–2.54 (2H, multiplet);
2.45–2.03 (2H, multiplet);
1.51 (3H, singlet);
1.19 (12H, doublet, J=6.60 Hz).

105(c) A Compound of Formula 105(c)

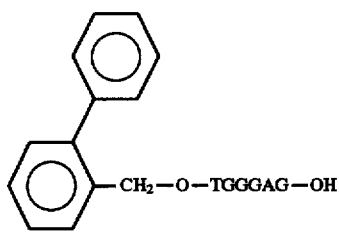

Following a procedure similar to that described in Example 1(b), but using 5'-O-(2-phenylbenzyl)thymidine 2-cyanoethyl N,N-diisopropylphosphoramidite [prepared as described in step (b) above] instead of the 5'-O-tritylthymidine 2-cyanoethyl N,N-diisopropylphosphoramidite, the title compound was prepared. The reaction product was divided into three portions and each portion was purified by reverse phase high performance liquid chromatography (Inertsil PREP-ODS, 20.0× 250 mm; eluent A: 0.1M TEAA, pH 7.3; eluent B: acetonitrile; 20→50% B by volume, 30 minutes; linear gradient; 7 ml/minute; 60° C.; 254 nm). Fractions eluted after 14.8 minutes were collected and worked up in a similar manner to that described in Example 1(b), to give 172.2 OD (260 nm) of the title compound as an amorphous solid.

Ultraviolet Absorption Spectrum (H$_2$O), $\lambda_{max}$ nm: 252.

Retention time: 6.1 minutes

High performance liquid chromatography (YMC-Pack A-312, S-5, 120A, ODS; eluent A: 0.1M TEAA, pH 7.3; eluent B: acetonitrile; 20→50% B by volume, 30 minutes; linear gradient; 2 ml/minute; 60° C.; 254 nm).

EXAMPLE 106

106(a) 3'-O-Triisopropylsilyl-5'-O-(4,4'-dimethoxytrityl)thymidine 1.485 g (2.73 mmol) of 5'-O-(4,4'-dimethoxytrityl)thymidine and 0.37 g (5.45 mmol) of imidazole were first dried by azeotropic distillation under reduced pressure with pyridine and then dissolved in 6 ml of dimethylformamide. 875 µl (4.09 mmol) of triisopropylsilyl chloride were added to this solution, and the resulting mixture was stirred overnight at room temperature. At the end of this time, 875 µl of triisopropylsilyl chloride and 0.37 g of imisazole were added to the mixture, which was then stirred for one day. The reaction mixture was then diluted with 100 ml of ethyl acetate and the diluted mixture was washed twice, each time with 100 ml of a 5% w/v aqueous solution of sodium hydrogencarbonate. The organic layer was dried over anhydrous sodium sulfate and the solvent was removed by distillation under reduced pressure. The resulting residue was purified by column chromatography through 100 g of silica gel (70–230 mesh), using methylene chloride containing from 0 to 3% by volume of methanol as the eluent, to give 1.861 g (yield 97%) of the title compound.

$^1$H Nuclear Magnetic Resonance Spectrum (CDCl$_3$, 270 MHz, TMS), δ ppm:

8.08 (1H, singlet);
7.67 (1H, singlet);
7.42–6.80 (13H, multiplet);
6.39 (1H, triplet, J=5.94 Hz);
4.60–4.55 (1H, multiplet);
4.06–4.03 (1H, multiplet);
3.79 (6H, singlet);
3.53–3.26 (2H, multiplet);
2.42–2.18 (2H, multiplet);
1.50 (3H, singlet);
1.03–0.90 (21H, multiplet).

106(b) 3'-O-(Triisopropylsilyl)thymidine 1.6 ml of trifluoroacetic acid were added dropwise to a solution of 1.861 g (2.655 mmol) of 3'-O-triisopropylsilyl-5'-O-(4,4'-dimethoxytrityl)thymidine [prepared as described in step (a) above] in 80 ml of chloroform, whilst cooling in an ice bath and stirring. The resulting mixture was stirred for 10 minutes and then 2 ml of pyridine were added. The reaction mixture was washed twice, each time with 100 ml of a 5% w/v aqueous solution of sodium hydrogencarbonate and dried over anhydrous sodium sulfate. The solvent was removed by distillation under reduced pressure, and the resulting residue was purified by column chromatography through 50 g of silica gel (70–230 mesh), using methylene chloride containing 4% by volume of methanol as the eluent, to give 0.9965 g (yield 94%) of the title compound.

$^1$H Nuclear Magnetic Resonance Spectrum (CDCl$_3$, 270 MHz, TMS), δ ppm:

8.17 (1H, broad singlet);
7.36 (1H, singlet);
6.12 (1H, triplet, J=5.94 Hz);
4.63–4.59 (1H, multiplet);
4.03–4.00 (1H, multiplet);
3.96–3.74 (2H, multiplet);
2.48 (1H, broad singlet);
2.45–2.21 (2H, multiplet);
1.91 (3H, singlet);
1.15–1.00 (21H, multiplet).

106(c) 3'-O-Triisopropylsilyl-5'-O-[(4-benzyloxy)benzyl]thymidine 88 mg (2 mmol) of sodium hydride (as a 55% w/w dispersion in mineral oil) were added to a solution of 398 mg (1 mmol) of 3'-O-(triisopropylsilyl)thymidine [prepared as described in step (b) above] in 2.5 ml of tetrahydrofuran, and the resulting mixture was allowed to stand at 60° C. for 2 hours and then cooled to room temperature. 232 mg (1 mmol) of 4-benzyloxybenzyl chloride and 75 mg (0.5 mmol) of sodium iodide were added to the mixture, and the reactionmixture was then stirred overnight at room temperature and then at 55° C. for 8 hours. At the end of this time, the solvent was removed by distillation under reduced pressure, and the residue was dissolved in 100 ml of ethyl acetate. The resulting solution was washed twice, each time with 100 ml of 0.01N aqueous hydrochloric acid. The organic layer was dried over anhydrous magnesium sulfate, and the solvent was removed by distillation under reduced pressure. The resulting residue was purified by column chromatography through 30 g of silica gel (230–400 mesh), using methylene chloride containing from 1 to 2% by volume of methanol as the eluent, to give 237 mg (yield 40%) of the title compound.

$^1$H Nuclear Magnetic Resonance Spectrum (CDCl$_3$, 270 MHz, TMS), δ ppm:

8.00 (1H, broad singlet);
7.59 (1H, singlet);
7.48–6.90 (9H, multiplet);
6.36 (1H, triplet, J=6.60 Hz);

5.07 (2H, singlet);
4.56–4.46 (1H, multiplet);
4.50 (2H, singlet);
4.07–4.03 (1H, multiplet);
3.80–3.60 (2H, multiplet);
2.33–2.08 (2H, multiplet);
1.56 (3H, singlet);
1.10–0.97 (21H, multiplet).

106(d) 5'-O-[(4-Benzyloxy)benzyl]thymidine 1.5 ml of a 1M tetrahydrofuran solution of tetrabutylammonium fluoride were added to a solution of 237 mg (0.4 mmol) of 3'-O-triisopropylsilyl-5'-O-[(4-benzyloxy)benzyl] thymidine [prepared as described in step (c) above] in 1.5 ml of tetrahydrofuran, and the resulting mixture was stirred at room temperature for 3 hours. At the end of this time, the reaction mixture was freed from the solvent by distillation under reduced pressure, and the resulting residue was dissolved in 100 ml of ethyl acetate. This solution was washed twice, each time with 100 ml of a saturated aqueous solution of sodium chloride and was then dried over anhydrous magnesium sulfate. The solvent was removed by distillation under reduced pressure, and the resulting residue was purified by column chromatography through 30 g of silica gel (230–400 mesh), using methylene chloride containing from 1 to 4% by volume of methanol as the eluent, to give 108.5 mg (yield 61%) of the title compound.

$^1$H Nuclear Magnetic Resonance Spectrum (CDCl$_3$, 270 MHz, TMS), δ ppm:

8.11 (1H, broad singlet);
7.56 (1H, singlet);
7.47–6.93 (9H, multiplet);
6.38 (1H, triplet, J=7.26 Hz);
5.06 (2H, singlet);
4.57–4.47 (1H, multiplet);
4.52 (2H, singlet);
4.10–4.06 (1H, multiplet);
3.80–3.64 (2H, multiplet);
2.38–2.15 (2H, multiplet);
1.67 (3H, singlet).

106(e) 5'-O-[(4-Benzyloxy)benzyl]thymidine 2-cyanoethyl N,N-diisopropylphosphoramidite Following a procedure similar to that described in Example 11(b), but using 88 mg (0.2 mmol) of 5'-O-[(4-benzyloxy)benzyl]thymidine [prepared as described in step (d) above], 104.8 mg (yield 82%) of the title compound were obtained.

$^1$H Nuclear Magnetic Resonance Spectrum (CDCl$_3$, 270 MHz, TMS), δ ppm:

7.58, 7.56 (together 1H, two singlets);
7.46–6.93 (9H, multiplet);
6.37 (1H, triplet, J=6.60 Hz);
5.06 (2H, singlet);
4.64–4.54 (1H, multiplet);
4.60, 4.59 (2H, 2singlet);
4.25–4.15 (1H, multiplet);
3.90–3.50 (6H, multiplet);
2.66–2.54 (2H, multiplet);
2.50–2.10 (2H, multiplet);
1.65 (3H, singlet);
1.18 (12H, doublet, J=7.26 Hz).

106(f) A Compound of Formula 106(f)

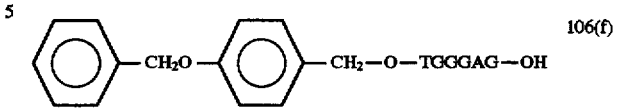

Following a procedure similar to that described in Example 1(b), but using 5'-O-[(4-benzyloxy)benzyl]-thymidine 2-cyanoethyl N,N-diisopropylphosphoramidite [prepared as described in step (e) above] instead of the 5'-O-tritylthymidine 2-cyanoethyl N,N-diisopropylphosphoramidite, the title compound was synthesized. The reaction product was divided into three portions and each portion was purified by reverse phase high performance liquid chromatography (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 60° C.; 254 nm). Fractions eluted after 17.0 minutes were collected and worked up in a similar manner to that described in Example 1(b), to give 208.8 OD (260 nm) the title compound as an amorphous solid.

Ultraviolet Absorption Spectrum (H$_2$O), λ$_{max}$ nm: 254.

Retention time: 8.1 minutes

High performance liquid chromatography (YMC-Pack A-312, S-5, 120A, ODS; aqueous solution of 0.1M TEAA, pH 7.3; eluent B: acetonitrile; 20→50% B by volume, 30 minutes, linear gradient; 2 ml/minute; 60° C.; 254 nm).

EXAMPLE 107

107(a) 5'-O-(9-Phenylxanthen-9-yl)thymidine 585 mg (2 mmol) of 9-chloro-9-phenylxanthene were added to a solution of 484 mg (2 mmol) of thymidine in 20 ml of pyridine, and the resulting mixture was stirred at room temperature for 1 hour whilst shading it from light. The reaction mixture was then diluted with 200 ml of methylene chloride, and the diluted mixture was washed twice, each time with 200 ml of a 5% w/v aqueous solution of sodium hydrogencarbonate. The organic layer was dried over anhydrous sodium sulfate, and the solvent was removed by distillation under reduced pressure. The residue was purified by column chromatography through 35 g of silica gel (70–230 mesh), using methylene chloride containing from 0 to 2.5% by volume of methanol as the eluent, to give 647.8 mg (yield 65%) of the title compound. $^1$H Nuclear Magnetic Resonance Spectrum (CDCl$_3$, 270 MHz, TMS), δ ppm:

8.33 (1H, broad singlet);
7.62 (1H, singlet);
7.45–7.02 (13H, multiplet);
6.36 (1H, triplet, J=5.94 Hz);
4.49–4.41 (1H, multiplet);
4.02–3.96 (1H, multiplet);
3.29–3.12 (2H, multiplet);
2.52–2.24 (2H, multiplet);
1.99 (1H, doublet, J=3.96 Hz);
1.67 (3H, singlet).

107(b) 5,-O-(9-Phenylxanthen-9-yl)thymidine 2-cyanoethyl N,N-diisopropylphosphoramidite Following a procedure similar to that described in Example 11(b), but using 100 mg (0.2 mmol) of 5'-

O-(9-phenylxanthen-9-yl)thymidine [prepared as described in step (a) above], 134.9 mg (yield 99%) of the title compound were obtained.

¹H Nuclear Magnetic Resonance Spectrum (CDCl₃, 270 MHz, TMS), δ ppm:
  8.03 (1H, broad singlet);
  7.69, 7.64 (together 1H, two singlets);
  7.40–7.03 (13H, multiplet);
  6.40–6.32 (1H, multiplet);
  4.58–4.47 (1H, multiplet);
  4.15–4.05 (1H, multiplet);
  3.90–3.10 (6H, multiplet);
  2.82–2.28 (4H, multiplet);
  1.63, 1.62 (together 3H, two singlets);
  1.16 (12H, doublet, J=6.6 Hz).

107(c) A Compound of Formula 107(c)

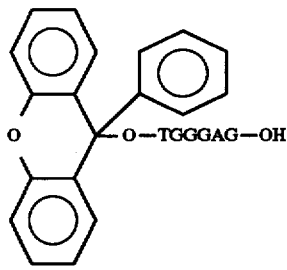

Following a procedure similar to that described in Example 1(b), but using 5'-O-(9-phenylxanthen-9-yl)thymidine 2-cyanoethyl N,N-diisopropylphosphoramidite [prepared as described in step (b) above] instead of the 5'-O-tritylthymidine 2-cyanoethyl N,N-diisopropylphosphoramidite, the title compound was synthesized. The reaction product was divided into three portions and each portion was purified by reverse phase high performance liquid chromatography (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 60° C.; 254 nm). Fractions eluted after 19.7 minutes were collected and worked up in a similar manner to that described in Example 1(b), to give 145.6 OD (260 nm) of the title compound as an amorphous solid.

Ultraviolet Absorption Spectrum (H₂O), $\lambda_{max}$ nm: 249.
Retention time: 10.9 minutes High performance liquid chromatography (YMC-Pack A-312, S-5, 120A, ODS; eluent A: 0.1M TEAA, pH 7.3; eluent B: acetonitrile; 20→50% B by volume, 30 minutes; linear gradient; 2 ml/minute; 60° C.; 254 nm).

EXAMPLE 108

108(a) 5'-O-(9-Phenylfluoren-9-yl)thymidine 770 mg (2.4 mmol) of 9-bromo-9-phenylfluorene were added to a solution of 242 mg (1 mmol) of thymidine in 10 ml of pyridine, and the resulting mixture was stirred at 100° C. for 8 hours. At the end of this time, the reaction mixture was concentrated by evaporation under reduced pressure, and the concentrate was dissolved in 100 ml of methylene chloride. The solution was washed with 100 ml of a 5% w/v aqueous solution of sodium hydrogencarbonate and dried over anhydrous sodium sulfate. The solvent was removed by distillation under reduced pressure, and the resulting residue was purified by column chromatography through 30 g of silica gel (230–400 mesh), using methylene chloride containing from 1 to 3% by volume of methanol as the eluent, to give 194.2 mg (yield 37%) of the title compound.

¹H Nuclear Magnetic Resonance Spectrum (CDCl₃, 270 MHz, TMS), δ ppm:
  8.06 (1H, broad singlet);
  7.76 (1H, singlet);
  7.72–7.20 (13H, multiplet);
  6.41 (1H, triplet, J=6.60 Hz);
  4.64–4.58 (1H, multiplet);
  3.95–3.90 (1H, multiplet);
  3.49–3.13 (2H, multiplet);
  2.45–2.38 (2H, multiplet);
  1.88 (1H, doublet, J=3.96 Hz);
  1.48 (3H, singlet).

108(b) 5'-O-(9-Phenylfluoren-9-yl)thymidine 2-cyanoethyl N,N-diisopropylphosphoramidite Following a procedure similar to that described in Example 11(b), but using 105 mg (0.2 mmol) of 5'-O-(9-phenylfluoren-9-yl)thymidine [prepared as described in step (a) above], 110.8 mg (yield 76%) of the title compound were obtained.

¹H Nuclear Magnetic Resonance Spectrum (CDCl₃, 270 MHz, TMS), δ ppm:
  8.00 (1H, broad singlet);
  7.80 (1H, singlet);
  7.78–7.20 (13H, multiplet);
  6.44–6.37 (1H, multiplet);
  4.72–4.62 (1H, multiplet);
  4.10–4.00 (1H, multiplet);
  3.90–3.10 (6H, multiplet);
  2.75–2.34 (4H, multiplet);
  1.46, 1.45 (together 3H, two singlets);
  1.18 (12H, doublet, J=6.60 Hz).

108(c) A Compound of Formula 108(c)

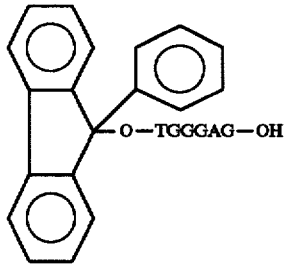

Following a procedure similar to that described in Example 1(b), but using 4'-O-(9-phenylfluoren-9-yl)thymidine 2-cyanoethyl N,N-diisopropylphosphoramidite [prepared as described in step (b) above] instead of the 5'-O-tritylthymidine 2-cyanoethyl N,N-diisopropylphosphoramidite, the title compound was synthesized. The reaction product was divided into three portions and each portion was purified by reverse phase high performance liquid chromatography (Inertsil PREP-ODS, 20.0×250 mm; eluent A: 0.1M TEAA, pH 7.3; eluent B: acetonitrile; 20→50% B by volume, 30 minutes; linear gradient; 7 ml/minute; 60° C.; 254 nm).

Fractions eluted after 19.1 minutes were collected and worked up in a similar manner to that described in Example 1(b), to give 291.2 OD (260 nm) of the title compound as an amorphous solid.

Ultraviolet Absorption Spectrum (H$_2$O), $\lambda_{max}$ nm: 255.

Retention time: 10.4 minutes

High performance liquid chromatography (YMC-Pack A-312, S-5, 120A, ODS; eluent A: 0.1M TEAA, pH 7.3; eluent B: acetonitrile; 20→50% B by volume, 30 minutes; linear gradient; 2 ml/minute; 60° C.; 254 nm).

EXAMPLE 109

109(a) 5'-(S-Triphenylmethyl)thio-5'-deoxythymidine 2-cyanoethyl N,N-diisopropylphosphoramidite Following a procedure similar to that described in Example 11(b), but using 100 mg (0.2 mmol) of 5'-(S-triphenylmethyl)thio-5'-deoxythymidine [B. S. Sproate, B. Beijer, P. Rider, P. Neuner, Nucleic Acids Res., 15, (12) 4837 (1987)], 88 mg (yield 62%) of the title compound were obtained.

$^1$H Nuclear Magnetic Resonance Spectrum (CDCl$_3$, 270 MHz, TMS), δ ppm:

7.45–7.18 (16H, multiplet);
6.23–6.17 (1H, multiplet);
4.31–4.20 (1H, multiplet);
4.11–4.00 (1H, multiplet);
3.85–3.43 (4H, multiplet);
2.62–1.98 (4H, multiplet);
1.56 (3H, singlet);
1.20–1.05 (12H, multiplet).

109(b) A Compound of Formula 109(b)

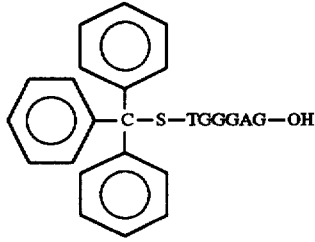

Following a procedure similar to that described in Example 1(b), but using 5'-(S-triphenylmethyl)thio-5'-deoxythymidine 2-cyanoethyl N,N-diisopropylphosphoramidite [prepared as described in step (a) above] instead of the 5'-O-tritylthymidine 2-cyanoethyl N,N-diisopropylphosphoramidite, the title compound was synthesized. The reaction product was purified by chromatography through a reverse phase silica gel column (Preparative C18, Waters, 1.5×15 cm; eluent A: 50 mM TEAB, pH 7.5; eluent B: acetonitrile; 20→50% B by volume, linear gradient; 254 nm). It was then worked up in a similar manner to that described in Example 1(b), to give 122.3 OD (260 nm) of the title compound as an amorphous solid.

Ultraviolet Absorption Spectrum (H$_2$O), $\lambda_{max}$ nm: 254.

Retention time: 19.0 minutes high performance liquid chromatography (Inertsil ODS, 6×150 mm; eluent ; A: 0.1M TEAA, pH 7.5; eluent; B: acetonitrile; 10→60% B by volume, 20 minutes; linear gradient; 1 ml/minute; 60° C.; 260 nm).

EXAMPLE 110

A Compound of Formula 110(a)

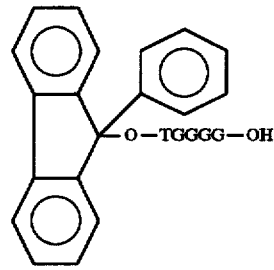

Following a procedure similar to that described in Example 1(b), but using 5'-O-(9-phenylfluoren-9-yl)thymidine 2-cyanoethyl N,N-diisopropylphosphoramidite [prepared as described in Example 108(b)] instead of the 5'-O-tritylthymidine 2-cyanoethyl N,N-diisopropylphosphoramidite and inputting the base sequence TGGGG to a synthesizer, the title compound was prepared. The reaction product was divided into three portions and each portion was purified by reverse phase high performance liquid chromatography (Inertsil PREP-ODS, 20.0 ×250 mm; eluent A: 0.1M TEAA, pH 7.3; eluent B: acetonitrile; 25→55% B by volume, 30 minutes; linear gradient; 7 ml/minute; 60° C.; 254 nm). Fractions eluted after 14.6 minutes were collected and worked up in a similar manner to that described in Example 1(b), to give 28.3 OD (260 nm) of the title compound as an amorphous solid.

Ultraviolet Absorption Spectrum (H$_2$O), $\lambda_{max}$ nm: 256.

Retention time: 10.7 minutes

High performance liquid chromatography (YMC-Pack A-312, S-5, 120A, ODS; eluent A: 0.1M TEAA, pH 7.3; eluent B: acetonitrile; 20→50% B by volume, 30 minutes; linear gradient; 2 ml/minute; 60° C.; 254 nm).

EXAMPLE 111

A Compound of Formula 111(a)

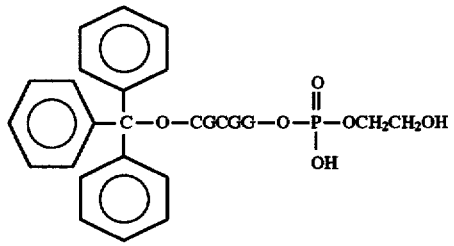

A procedure similar to than described in Example 15(c) was repeated, but using a column packed with 125 mg (5 μmol) of the compound of Example 12(b) and inputting the base sequence XGCGGZ (in which Z is as defined in Example 17) to the DNA/RNA synthesizer described in Example 1(b). The 90% aqueous formamide solution containing the title compound thus obtained was heated at 95° C. for 5 minutes. After this heating, the solution was cooled rapidly. The reaction mixture was divided into four portions and each was purified by reverse phase high performance liquid chromatography (Inertsil PREP-ODS 20.0×250 mm; eluent A: 0.1M TEAA pH 7.0; eluent B: acetonitrile; 10 to 60% B by volume, 30 minutes; linear gradient; 7 ml/minute; 260 nm; column temperature 60° C.). Fractions eluted after 20.8 minutes were collected and worked up in a similar manner to that described in Example 1(b), to give 82 OD (260 nm) of the title compound as an amorphous solid.

Ultraviolet Absorption Spectrum (H$_2$O), $\lambda_{max}$ nm: 254.
Retention time: 13.38 minutes High performance liquid chromatography (Inertsil ODS-2; 6×150 nm; eluent A: 0.1M TEAA, pH 7.5; eluent B: acetonitrile; 10 to 60% B by volume, 20 minutes, linear gradient; 1 ml/minute; 260 nm).

EXAMPLE 112

112(a) 5'-[(3,4-dibenzyloxy)benzylthio]-5'-deoxythymidine 258 mg (1 mmol) of 5'-deoxy-5'-mercaptothymidine was added to 20 ml of acetone. 406 mg (1.2 mmol) of 3,4-dibenzyloxybenzyl chloride and 1 g of anhydrous potassium carbonate were then added to the solution under an atmosphere of nitrogen. The resulting mixture was stirred whilst being heated under reflux for 1 hour. At the end of this time, precipitates were filtered off from the reaction mixture, and the filtrate was freed from the solvent by distillation under reduced pressure. The residue was dissolved a small amount of methylene chloride and purified by column chromatography through 10 g of of silica gel using a 5:95 by volume mixture of methanol and methylene chloride as the eluent, to give 452 mg of the title compound as a colorless caramel-like residue. This residue was lyophilized from benzene, to give 180 mg (yield 32%) of the title compound as white crystals.

$^1$H Nuclear Magnetic Resonance Spectrum (CDCl$_3$, 270 MHz, TMS), δ ppm:

8.26 (1H, broad singlet);
6.78–7.46 (14H, multiplet);
6.20 (1H, triplet, J=6.6 Hz);
5.15 & 5.17 (together 4H, two singlets);
4.20–4.27 (1H, multiplet);
3.87–3.91 (1H, multiplet);
3.67–3.68 (2H, multiplet);
2.61–2.70 (2H, multiplet);
2.09–2.40 (2H, multiplet);
1.91–1.92 (3H, multiplet).

112(b) 5'-[(3,4-Dibenzyloxy)benzylthio]-5'-deoxythymidine 2-cyanoethyl N,N-diisopropylphosphoramidite 112 mg (0.2 mmol) of 5'-[(3,4-dibenzyloxy)benzylthio]-5'-deoxythymidine [prepared as described in step (a) above] were dried by azeotropic distillation with pyridine and then dissolved in 1 ml of methylene chloride. 17 mg (0.1 mmol) of diisopropylammonium tetrazolide were then added to the solution. 70 μl (0.22 mmol) of 2-cyanoethyl N,N,N',N'-tetraisopropylphosphorodiamidite were then added dropwise to the mixture, under an atmosphere of argon. The resulting mixture was stirred at room temperature for 3 hours under the same atmosphere. The methylene chloride was then removed by distillation under reduced pressure. The resulting residue was dissolved in 10 ml of ethyl acetate, and the solution was washed with a 10% w/v aqueous solution of sodium carbonate and with a saturated aqueous solution of sodium chloride, in that order. The solution was then dried over anhydrous sodium sulfate, after which the solvent was removed by distillation under reduced pressure, and the resulting residue was purified by column chromatography through 10 g of silica gel (70–230 mesh), using ethyl acetate as the eluent, to give 115 mg (yield 76%) of the title compound as a caramel-like substance.

$^1$H Nuclear Magnetic Resonance Spectrum (CDCl$_3$, 270 MHz, TMS), δ ppm:

8.16 (1H, broad singlet);
6.76–7.45 (14H, multiplet);
6.23–6.29 (1H, multiplet);
5.14–5.16 (4H, multiplet);
4.38–4.46 (1H, multiplet);
4.08–4.16 (1H, multiplet);
3.50–3.90 (6H, multiplet);
2.09–2.80 (6H, multiplet);
1.91–1.93 (3H, multiplet);
1.08–1.58 (12H, multiplet).

112(c) A Compound of Formula 112(c)

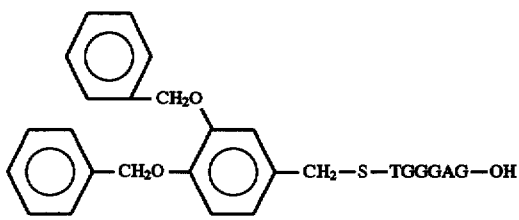

Following a procedure similar to that described in Example 1(b), but using 5'-[(3,4-dibenzyloxy)benzylthio]-5'-deoxythymidine 2-cyanoethyl N,N-diisopropylphosphoramidite [prepared as described in step (b) above] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×150 m; eluent A: 50 mM aqueous triethyl ammonium hydrogencarbonate buffer (TEAB) ; pH 7.5; eluent B: acetonitrile ; 15 to 50% B by volume; linear gradient; 260 nm). The eluted fractions containing the title compound were collected and worked up in a similar manner to that described in Example 1(b), to give 57 OD (260 nm) of the title compound as an amorphous solid.

Ultraviolet Absorption Spectrum (H$_2$O), $\lambda_{max}$ nm: 253.
Retention time: 16.85 minutes High performance liquid chromatography (Inertsil ODS-2; 6×150 nm; eluent A: 0.1M TEAA, pH 7.5; eluent B: acetonitrile; 10 to 60% B by volume, 20 minutes; linear gradient; 1 ml/minute; 260 nm).

EXAMPLE 113

113(a) 5'-[(Anthracen-9-yl)methylthio]-5'-deoxythymidine 258 mg (1 mmol) of 5'-deoxy-5'-mercaptothymidine was added to 20 ml of acetone. 272 mg (1.2 mmol) of 9-chloromethylanthracene and 1 g of anhydrous potassium carbonate were then added to the solution under an atmosphere of nitrogen. The resulting mixture was then stirred whilst being heated under reflux for 2 hours. At the end of this time, precipitates were filtered off from the reaction mixture, and the filtrate was freed from the solvent by distillation under reduced pressure. The residue was crystallized from 10 ml of ethanol, to give 156 mg (yield 35%) of the title compound as pale yellow crystals.

¹H Nuclear Magnetic Resonance Spectrum (hexadeuterated dimethyl sulfoxide, 270 MHz, TMS), δ ppm:

8.56 (1H, singlet);
8.40 (2H, doublet, J=8.7 Hz);
8.09 (2H, doublet, J=8.2 Hz);
7.51–7.61 (5H, multiplet);
6.24–6.28 (1H, multiplet);
5.43 (1H, broad singlet);
4.87–4.89 (2H, multiplet);
4.24–4.25 (1H, triplet, J=2.7 Hz);
4.03–4.07 (1H, multiplet);
3.05 (2H, doublet, J=6.5 Hz);
2.07–2.29 (2H, multiplet);
1.72–1.73 (3H, multiplet).

113(b) 5'-[(Anthracen-9-yl)methylthio]5'-deoxythymidine 2-cyanoethyl N,N-diisopropylphosphoramidite 74 mg (0.165 mmol) of 5'-[(anthracen-9-yl)methylthio]-5'-deoxythymidine [prepared as described in (a) above] were dried by azeotropic distillation with pyridine and then dissolved in 1 ml of tetrahydrofuran. 0.115 ml (0.659 mmol) of N,N-diisopropyl-N-ethylamine was added to the solution. 49 μl (0.22 mmol) of 2-cyanoethyl N,N-diisopropylchlorophosphoramidite were then added dropwise to the mixture, under an atmosphere of argon. The resulting mixture was stirred at room temperature for 1.75 hours under the same atmosphere. The tetrahydrofuran was then removed by distillation under reduced pressure. The resulting residue was dissolved in 10 ml of ethyl acetate, and the solution was washed with a 10% w/v aqueous solution of sodium carbonate and with a saturated aqueous solution of sodium chloride, in that order. The solution was dried over anhydrous sodium sulfate, and then the solvent was removed by distillation under reduced pressure, and the residue was purified by column chromatography through 10 g of silica gel (70–230 mesh), using ethyl acetate as the eluent, to give 85 mg (yield 79%) of the title compound as a foam-like substance.

¹H Nuclear Magnetic Resonance Spectrum (CDCl₃, 270 MHz, TMS, δ ppm:

7.26–8.43 (10H, multiplet);
6.26–6.33 (1H, multiplet);
4.74–4.93 (2H, multiplet);
4.32–4.42 (1H, multiplet);
4.20–4.28 (1H, multiplet);
3.49–3.80 (4H, multiplet);
2.89–3.11 (2H, multiplet);
1.93–2.68 (4H, multiplet);
1.71–1.76 (3H, multiplet);
1.08–1.22 (12H, multiplet).

113(c) A Compound of Formula 113(c)

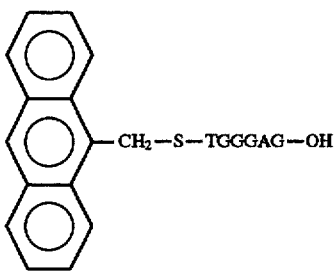

Following a procedure similar to that described in Example 1(b), but using 5'-[(anthracen-9-yl)methylthio]-5'-deoxythymidine 2-cyanoethyl N,N-diisopropylphosphoramidite [prepared as described in step (b) above] instead of the 5'-O-trityl thymidine 2-cyanoethyl N,N-diisopropylphosphoramidite, the title compound was prepared. The reaction product was purified by chromatography through a reverse phase silica gel column (Preparative C18, Waters, 1.5×150 mm; eluent A: 50 mM TEAB; pH 7.5; eluent B: acetonitrile; 15 to 50% B by volume; linear gradient; 260 nm). The eluted fractions containing the title compound were collected and worked up in a similar manner to that described in Example 1(b), to give 30 OD (260 nm) of the title compound as an amorphous solid.

Ultraviolet Absorption Spectrum (H₂O), λ_max nm: 255.
Retention time: 13.52 minutes
High performance liquid chromatography (Inertsil ODS-2; 6×150 nm; eluent A: 0.1M TEAA, pH 7.5; eluent B: acetonitrile; 10 to 60% B by volume, 20 minutes, linear gradient; 1 ml/minute; 260 nm).

EXAMPLE 114

114(a) 5'-[(2-Naphthyl)methylthiol]-5'-deoxythymidine 258 mg (1 mmol) of 5'-deoxy-5'-mercaptothymidine was added to 20 ml of acetone. 265 mg (1.2 mmol) of 2-bromomethylnaphthalene and 1 g of anhydrous potassium carbonate were then added to the solution under an atmosphere of argon. The resulting mixture was stirred whilst being heated under reflux for 2 hours. At the end of this time, precipitates were filtered off from the reaction mixture, and the filtrate was freed from the solvent by distillation under reduced pressure. The residue was crystallized from 10 ml of ethanol, to give 100 mg (yield 25%) of the title compound as white crystals.

¹H Nuclear Magnetic Resonance Spectrum (hexadeuterated dimethyl sulfoxide, 270 MHz, TMS), δ ppm:

7.84–7.90 (1H, broad singlet);
7.78 (1H, singlet);
7.46–7.53 (4H, multiplet);
6.16–6.19 (1H, multiplet);
5.34 (1H, doublet, J=4.4 Hz);
4.14–4.19 (1H, multiplet);
3.92–3.99 (2H, multiplet);
3.83–3.87 (1H, multiplet);
2.62–2.78 (2H, multiplet);
2.02–2.23 (2H, multiplet);
1.75–1.79 (3H, multiplet).

114(b) 5'-[(2-Naphthyl)methylthio]-5'-deoxythymidine 2-cyanoethyl N,N-diisopropylphosphoramidite 79.7 mg (0.2 mmol) of 5'-[(2-naphthyl)methylthio]-5'-deoxythymidine [prepared as described in step (a) above] were dried by azeotropic distillation with pyridine and then dissolved in 2.5 ml of tetrahydrofuran. 0.084 ml (0.48 mmol) of diisopropylamine was then added to the solution. 54 μl (0.24 mmol) of 2-cyanoethyl N,N-diisopropylchlorophosphoramidite were then added dropwise to the mixture, under an atmosphere of argon. The resulting mixture was stirred at room temperature for 1.75 hours under the same atmosphere. The tetrahydrofuran was then removed by distillation under reduced pressure. The resulting residue was dissolved in 10 ml of ethyl acetate, and the solution was washed with a 10% w/v aqueous solution of sodium carbonate and with a saturated aqueous solution of sodium chloride, in that order. The solution was then dried over anhydrous magnesium sulfate, after which the solvent was distilled off under reduced pressure, and the residue was purified by column chromatography through 10 g of silica gel (70–230 mesh), using ethyl acetate as the eluent, to give 67 mg (yield 56%) of the title compound as a foam-like substance.

$^1$H Nuclear Magnetic Resonance Spectrum (CDCl$_3$, 270 MHz, TMS), δ ppm:

8.32 (1H, broad singlet);
7.26–7.85 (8H, multiplet);
6.27 (1H, multiplet);
4.38–4.46 (1H, multiplet);
4.11–4.19 (1H, multiplet);
3.93–3.95 (2H, multiplet);
3.47–3.90 (4H, multiplet);
2.10–2.88 (6H, multiplet);
1.62–1.90 (3H, multiplet);
1.10–1.21 (12H, multiplet).

114(c) A Compound of Formula 114(c)

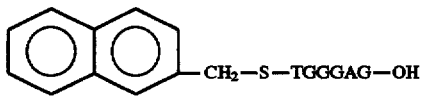

114(c)

Following a procedure similar to that described in Example 1(b), but using 5'-[(2-naphthyl)methylthio]-5'-deoxythymidine 2-cyanoethyl N,N-diisopropylphosphoramidite [prepared as described in step (b) above] instead of the 5'-O-tritylthymidine 2-cyanoethyl N,N-diisopropylphosphoramidite, the title compound was prepared. The reaction product was purified by chromatography through a reverse phase silica gel column (Preparative C18, Waters, 1.5×150 nm; eluent A: 50 mM TEAB; pH 7.5; eluent B: acetonitrile; 15 to 50% B by volume; linear gradient; 260 nm). The eluted fractions containing the title compound were collected and worked up in a similar manner to that described in Example 1(b), to give 165 OD (260 nm) of the title compound as an amorphous solid.

Ultraviolet Absorption Spectrum (H$_2$O), λ$_{max}$ nm: 254.
Retention time: 12.07 minutes
High performance liquid chromatography (Inertsil ODS-2; 6×150 nm; eluent A: 0.1M TEAA, pH 7.5; eluent B: acetonitrile; 10 to 60% B by volume, 20 minutes, linear gradient; 1 ml/minute; 260 nm).

EXAMPLE 115

115(a) 5'-{3,5-Bis[3,5-(dibenzyloxy)benzyloxy]benzylthio}-5'-deoxythymidine 258 mg (1 mmol) of 5'-deoxy-5'-mercaptothymidine was added to 20 ml of acetone. 969 mg (1.2 mmol) of 3,5-bis[3,5-(dibenzyloxy)benzyloxy]benzyl bromide and 1 g of anhydrous potassium carbonate were then added to the solution under an atmosphere of argon. The resulting mixture was stirred whilst being heated under reflux for hours. At the end of this time, precipitates were filtered off from the reaction mixture, and the filtrate was freed from the solvent by distillation under reduced pressure. The residue was lyophilized from benzene, to give 365 mg (yield 37%) of the title compound as a white powder.

$^1$H Nuclear Magnetic Resonance Spectrum (CDCl$_3$, 270 MHz, TMS), δ ppm:

7.99 (1H, broad singlet);
23–7.42 (21H, multiplet);
6.49–6.68 (9H, multiplet);
4.98–5.03 (12H, multiplet);
4.18–4.26 (1H, multiplet);
3.87–3.91 (1H, multiplet);
3.64–3.71 (2H, multiplet);
2.67 (2H, doublet, J=5.7 Hz);
2.00–2.64 (2H, multiplet);
1.86–1.92 (3H, multiplet).

115(b) 5'-{[3,5-(dibenzyloxy)benzyloxy]benzylthio}-5'-deoxythymidine 2-cyanoethyl N,N-diisopropylphosphoramidite 197 mg (0.2 mmol) of 5'-{3,5-bis[3,5-(dibenzyloxy)benzyloxy]benzylthio}-5'-deoxythymidine [prepared as described in step (a) above] were dried by azeotropic distillation with pyridine and then dissolved in 1 ml of methylene chloride. 0.017 g (0.1 mmol) of diisopropylammonium tetrazolide was then added to the solution. 70 μl (0.22 mmol) of 2-cyanoethyl N,N,N',N'-tetraisopropylphosphorodiamidite were then added dropwise to the mixture, under an atmosphere of argon. The resulting mixture was stirred at room temperature for 3 hours under the same atmosphere. The tetrahydrofuran was then removed by distillation under reduced pressure. The resulting residue was dissolved in 10 ml of ethyl acetate, and the solution was washed with a 10% w/v aqueous solution of sodium carbonate and with a saturated aqueous solution of sodium chloride, in that order. The solution was then dried over anhydrous magnesium sulfate, after which the solvent was removed by distillation under reduced pressure, and the residue was purified by column chromatography through 10 g of silica gel (70–230 mesh), using ethyl acetate as the eluent, to give 103 mg (yield 43%) of the title compound as a caramel-like substance.

$^1$H Nuclear Magnetic Resonance Spectrum (CDCl$_3$, 270 MHz, TMS), δ ppm:

7.27–7.44 (20H, multiplet);
6.51–6.69 (10H, multiplet);
4.98–5.05 (12H, multiplet);
4.44–4.51 (1H, multiplet);
4.13–4.18 (1H, multiplet);
3.47–3.87 (6H, multiplet);
2.17–2.84 (6H, multiplet);
1.92 (3H, singlet);

1.08–1.34 (12H, multiplet);

115(c) A Compound of Formula 115(c)

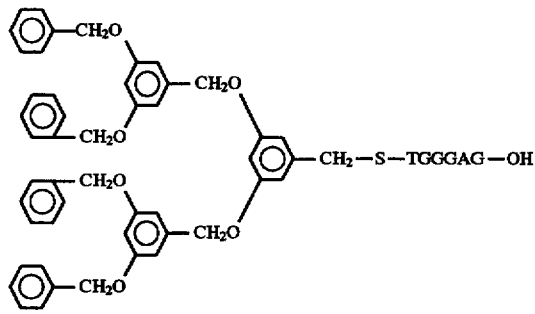

Following a procedure similar to that described in Example 1(b), but using 5'-{3,5-bis[3,5-(dibenzyloxy)benzyloxy]benzyl thio]-5'-deoxythymidine 2-cyanoethyl N,N-diisopropylphosphoramidite [prepared as described in step (b) above] instead of the 5'-O-tritylthymidine 2-cyanoethyl N,N-diisopropylphosphoramidite, the title compound was prepared. The reaction product was purified by chromatography through a reverse phase high performance liquid chromatography (Intertsil PREP-ODS 20.0× 250 mm; eluent A: 0.1M TEAA pH 7.0; eluent B: acetonitrile; 30 to 100% B by volume, 30 minutes; linear gradient; 7 ml/minute; 260 nm; column temperature 60° C.). Fractions eluted after 26.5 minutes were collected and worked up in a similar manner to that described in Example 1(b), to give 86 OD (260 nm) of the title compound as an amorphous solid.

Ultraviolet Absorption Spectrum (H$_2$O), $\lambda_{max}$ nm: 257.

Retention time: 18.44 minutes

High performance liquid chromatography (Inertsil ODS-2; 6×150 nm; eluent A: 0.1M TEAA, pH 7.5; eluent B: acetonitrile; 40 to 100% B by volume, 25 minutes, linear gradient; 1 ml/minute; 260 nm).

PREPARATIONS

The following Preparations illustrate the preparation of alternative starting materials for the preparation of the compounds of the present invention.

Preparation 1

2-[2-O-(4,4'-Dimethoxytrityloxy)ethylsulfonyl]-ethyl monosuccinate 1.37 g (3.0 mmol) of 2-[2-O-(4,4'-dimethoxytrityloxy)ethylsulfonyl]ethanol [Tetrahedron Lett. 27, 4705 (1986)] was dried by azeotropic distillation under reduced pressure with pyridine and then dissolved in 12 ml of methylene chloride. 315 mg (3.15 mmol) of succinic anhydride and 384 mg (3.15 mmol) of 4-(dimethylamino)pyridine were added to the resulting solution, which was then stirred for 30 minutes. After the completion of the reaction had been confirmed by thin layer chromatography, 80 ml of methylene chloride were added to the reaction mixture. The resulting mixture was then washed with a 0.5M aqueous solution of potassium dihydrogen phosphate (pH 5.0) and with water, in that order, and the organic layer was dried over anhydrous anhydrous sodium sulfate. The solvent was then removed by distillation under reduced pressure, to give 1.60 g (yield 96%) of the title compound.

$^1$H Nuclear Magnetic Resonance Spectrum (CDCl$_3$, 270 MHz, TMS), δ ppm:

7.40–6.83 (13H, multiplet);
4.58–4.53 (2H, triplet, J=5.94 Hz);
3.79 (6H, singlet);
3.68–3.64 (2H, triple n, J=5.61 Hz);
3.50–3.45 (2H, triplet, J=5.94 Hz);
3.18–3.14 (2H, triplet, J=5.61 Hz);
2.71–2.61 (4H, multiplet).

Preparation 2

A Compound of Formula 2(p):

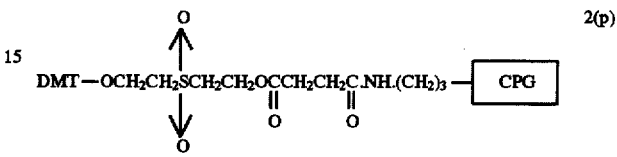

1.60 g (2.87 mmol) of 2-[2-O-(4,4'-dimethoxytrityloxy)ethylsulfonyl]ethyl monosuccinate (prepared as described in Preparation 1) were dissolved in 18 ml of dimethylformamide, and 0.96 g (3.6 mmol) of pentachlorophenol and 0.96 g (4.5 mmol) of 1,3-dicyclohexylcarbodiimide were added to the resulting solution, which was then stirred for 18 hours. The insolubles which precipitated were separated by filtration, and the solvent was removed from the filtrate by evaporation under reduced pressure. Benzene was added to the residue, and further insolubles which precipitated were separated by filtration. The solvent was again removed from the filtrate by evaporation under reduced pressure.

The residue (0.16 g, 0.2 mmol) was dissolved in 4 ml of dimethylformamide, and 15 μl (0.11 mmol) of triethylamine and 1.0 g of aminopropyl-CPG (85.7 μmol/g of amino groups are introduced thereto) were added to the solution, which was then left to stand at room temperature for 24 hours. At the end of this time, the CPG carrier was collected by filtration, washed with methylene chloride and then dried under by evaporation reduced pressure. 5 ml each of Cap A and B solutions (Nippon Millipore Limited) were added to the CPG carrier, and the mixture was left to stand for 5 minutes. The mixture was then washed with pyridine and with methylene chloride, in that order, and dried by evaporation under reduced pressure, to give the title compound.

The amount of the compound of Preparation 1 introduced into the title compound was determined according to the following method. A deblock solution (a 3% by volume solution of dichloroacetic acid in methylene chloride, Nippon Millipore Limited) was added to 11.4 mg of the title compound, and the mixture was shaken for 3 minutes, after which sufficient methylene chloride was added to make up the total amount to 20 ml. 0.4 ml of the solvent was distilled off, and then 3 ml of a 3:2 by volume solution of perchloric acid in ethanol was added to the residue, and the absorbance of the dimethoxytrityl cation at 500 nm was measured (ε=71700).

The amount of dimethoxytrityl groups introduced was 53.1 μmol/g.

Preparation 3

2-[2-O-(4,4'-Dimethoxytrityloxy)ethylsulfonyl]-ethyl 2,2,2-trichloroethoxycarbonate 1.1 g (2.4 mmol) of 2-[2-O-(4,4'-dimethoxytrityloxy)ethylsulfonyl]ethanol [Tetrahedrom Lett. 27, 4705 (1986)] were dried by azeotropic distillation under reduced pressure with pyridine and then dissolved in 12 ml of methylene chloride. 0.35 ml (2.6 mmol) of 2,2,2-trichloroethoxycarbonyl chloride was added to the solution, which was then stirred for 2 hours. After the completion of the reaction had been confirmed by thin layer chromatography, the reaction mixture was poured into a mixture of 100 ml of methylene chloride and 100 ml of a 5% w/v aqueous solution of sodium hydrogencarbonate to effect phase separation. The organic layers were washed with a 5% w/v aqueous solution of sodium hydrogencarbonate, and they were then collected and dried over anhydrous sodium sulfate. The solvent was then removed by distillation under reduced pressure, and the residue was purified by reverse phase column chromatography (Preparative C18, Waters, φ2.2×7.0 cm, solvent: 60% v/v aqueous acetonitrile), to give 1.35 g (yield 89%) of the title compound as an amorphous powder.

$^1$H Nuclear. Magnetic Resonance Spectrum (CDCl$_3$, 270 MHz, TMS). δ ppm:

7.41–6.83 (13H, multiplet);

4.75 (2H, singlet);

4.70–4.66 (2H, triplet, J=5.94 Hz);

3.80 (6H, singlet);

3.68–3.64 (2H, triplet, J=5.28 Hz);

3.61–3.56 (2H, triplet, J=6.27 Hz);

3.23–3.19 (2H, triplet, J=5.28 Hz).

Preparation 4

A Compound of Formula 4(p):

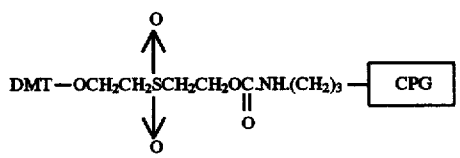

0.126 g (0.2 mmol) of 2-[2-O-(4,4'-dimethoxytrityloxy)ethylsulfonyl]ethyl 2,2,2-trichloroethoxycarbonate (prepared as described in Preparation 3) was dissolved in 5 ml of dimethylformamide, and 15 μl (0.11 mmol) of triethylamine and 1.0 g of a minopropyl-CPG (85.7 μmol/g of amino groups are introduced thereto) were added to the resulting solution and washed with a 1% v/v solution of triethylamine in dimethylformamide. The mixture was then left to stand at room temperature for 4 days. At the end of this time, the CPG carrier was collected by filtration and washed with methylene chloride, after which it was dried by evaporation under reduced pressure. 5 ml each of Cap A and B solutions (Nippon Millipore Limited) were added to the CPG carrier, and the mixture was left to stand for 5 minutes. The mixture was then washed with pyridine and with methylene chloride, in that order, and dried by evaporation under reduced pressure, to give the title compound.

The amount of the compound of Preparation 3 introduced into the title compound was determined according to the following method. A deblock solution (a 3% v/v solution of dichloroacetic acid in methylene chloride, Nippon Millipore Limited) was added to 11.4 mg of the title compound, and the mixture was shaken for 3 minutes, after which sufficient methylene chloride was added to make up a total amount of 20 ml. 0.4 ml of the solvent was distilled off, and then 3 ml of a 3:2 by volume solution of perchloric acid in ethanol were added to the residue, and the absorbance of the dimethoxytrityl cation at 500 nm was measured (ε=71700).

The amount of dimethoxytrityl groups introduced was 24.0 μmol/g.

Preparation 5

A Compound of Formula 5(p):

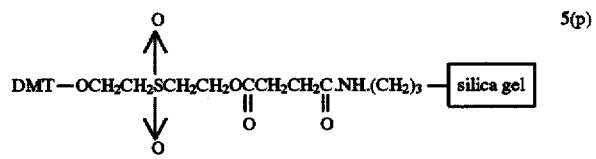

1.60 g (2.87 mmol) of 2-[2-O-(4,4'-dimethoxytrityloxy)ethylsulfonyl]ethyl monosuccinate (prepared as described in Preparation 1) were dissolved in 18 ml of dimethylformamide, and 0.96 g (3.6 mmol) of pentachlorophenol and 0.96 g (4.5 mmol) of 1,3-dicyclohexylcarbodiimide were added to the solution. The resulting mixture was then stirred at room temperature for 18 hours. At the end of this time, precipitates were filtered off from the reaction mixture, and the filtrate was free from the solvent by distillation under reduced pressure. Benzene was added to the residue. The resulting precipitates were filtered off, and the filtrate was again freed from the solvent by distillation under reduced pressure. 1.0 g (0.92 mmol) of the residue was used in the following step.

1.0 g (0.92 mmol) of this residue, 75 μl (0.55 mmol) of triethylamine and Cosmosil 150 NH$_2$-300 (having 450 μmol of amino groups per 1 g of the silica gel surface; produced by Nacalai Tesque Co. Ltd.) were added to 20 ml of dimethylformamide. The resulting mixture was then stirred at room temperature for 20 hours. The desired carrier, namely substituted Cosmosil 150 NH$_2$-300 was collected, washed with methylene chloride and dried by evaporation under reduced pressure. 10 ml each of Cap A and B solutions (Nippon Millipore limited) were added to the carrier, and the mixture was left to stand for 10 minutes. The mixture was then washed with pyridine and with methylene chloride, in that order, and dried by evaporation under reduced pressure, to give the title compound.

The amount of the compound of Preparation 1 introduced into the title compound was determined according to the following method. A deblock solution (a 3% v/v solution of dichloroacetic acid in methylene chloride, Nippon Millipore Limited) was added to 5.4 mg of the title compound, and the mixture was shaken for 3 minutes, after which sufficient methylene chloride was added to make up a total amount of 20 ml. 0.4 ml of the solvent was distilled off under reduced pressure, and 3 ml of a 3:2 by volume solution of perchloric acid in ethanol was added to the residue, and the absorbance of the dimethoxytrityl cation at 500 nm was measured (ε=71700).

The amount of dimethoxytrityl groups introduced was found to be 51.8 μmol/g.

Preparation 6

A Compound of Formula 6(p):

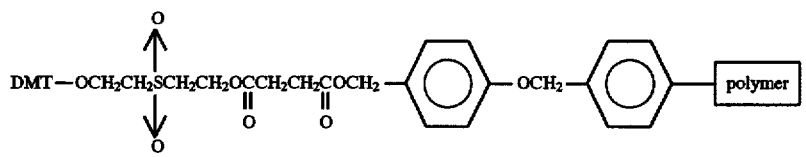

1.60 g (2.87 mmol) of 2-[2-O-(4,4'-dimethoxytrityloxy)ethylsulfonyl]ethyl monosuccinate (prepared as described in Preparation 1) were dissolved in 18 ml of dimethylformamide, and 0.96 g (3.6 mmol) of pentachlorophenol and 0.96 g (4.5 mmol) of 1,3-dicyclohexylcarbodiimide were added to the solution. The resulting mixture was then stirred at room temperature for 18 hours. At the end of this time, precipitates were filtered off from the reaction mixture and the filtrate was freed from the solvent by distillation under reduced pressure. Benzene was added to the residue. The resulting precipitates were filtered off and the filtrate was freed from the solvent by distillation under reduced pressure. 0.48 g (0.6 mmol) of the residue were used in the following step.

0.48 g (0.6 mmol) of this residue, 110 mg (0.9 mmol) of 4-(dimethylamino)pyridine and 1.0 g of a p-alkoxybenzyl alcohol resin (having 0.9 mmol of amino groups per 1 g of the silica gel surface; produced by Kokusan Kagaku Co. Ltd.) were added to 15 ml of dimethylformamide, and the resulting mixture was stirred at room temperature for 25 hours. At the end of this time, the desired carrier, namely the substituted p-alkoxybenzyl alcohol resin was collected, washed with methylene chloride, with methanol and with diethyl ether, in that order, and dried under by evaporation reduced pressure. 10 ml each of Cap A and B solutions (Nippon Millipore Limited) were added to the carrier, and the mixture was left to stand for 15 minutes. The mixture was then washed with methylene chloride, with methanol and with diethyl ether, in that order, and dried by evaporation under reduced pressure, to give the title compound.

The amount of the compound of Preparation 1 introduced into the title compound was determined according to the following method. A deblock solution (a 3% v/v solution of dichloroacetic acid in methylene chloride, Nippon Millipore Limited) was added to 10.6 mg of the title compound, and the mixture was shaken for 3 minutes, after which sufficient methylene chloride was added to make up a total amount of 20 ml. 0.4 ml of the solvent was distilled off, and then 6 ml of a 3:2 by volume solution of perchloric acid in ethanol were added to the residue, and the absorbance of the dimethoxytrityl cation at 500 nm was measured ($\varepsilon=71700$.)

The amount of dimethoxytrityl groups introduced was found to be 302 μmol/g.

Preparation 7

A Compound of Formula 7(p):

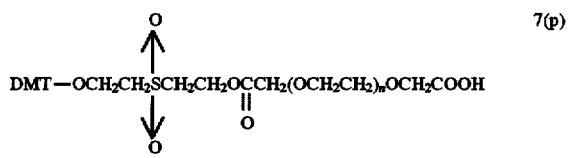

9.9 g (3.3 mmol) of poly(oxyethylene) diglycol were dried by azeotropic distillation with pyridine and then dissolved in 10 ml of methylene chloride. 226 mg (1.1 mmol) of 1,3-dicyclohexylcarbodiimide were then added to the solution, whilst ice-cooling. The resulting mixture was then stirred whilst ice-cooling for 15 minutes. At the end of this time, 2 ml of a methylene chloride solution containing 0.5 g (1.1 mmol) of 2-[2-O-(4,4'-dimethoxytrityloxy)ethylsulfonyl]ethanol [Tetrahedron Lett., 27, 4705 (1986)] and 0.13 g (1.1 mmol) of 4-(dimethylamino)pyridine were added to the solution. The resulting mixture was stirred at room temperature for 18 hours. Precipitates were filtered off. The reaction mixture was then concentrated to 50 ml by evaporation under reduced pressure. 500 ml of cold diethyl ether were then added to the concentrated solution, and the precipitates obtained were collected and dried by evaporation under reduced pressure. The resulting precipitates were dissolved in methylene chloride and purified by column chromatography through 200 g of silica gel (70–230 mesh) using a 2:8 by volume mixture of methanol and methylene chloride as the eluent, to give 2.77 g (yield 72%) of the title compound.

$^1$H Nuclear Magnetic Resonance Spectrum (CDCl$_3$, 270 MHz, TMS) , δ ppm:

7.09–7.43 (multiplet);
6.81–6.88 (multiplet);
4.58–4.64 (multiplet);
3.65 (singlet);
3.50–3.53 (multiplet);
3.46–3.49 (multiplet);
3.31–3.34 (multiplet).

Preparation 8

A Compound of Formula 8(p):

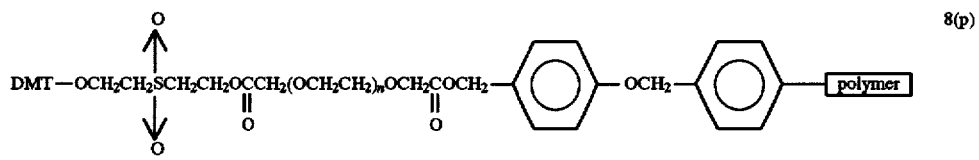

0.7 g (0.2 mmol) of the compound of Preparation 7 was dissolved in 6 ml of methylene chloride, and 2 ml of a dimethylformamide solution containing 63 mg (0.24 mmol) of pentachlorophenol and 64 mg (0.3 mmol) of 1,3-dicyclohexylcarbodiimide were added to the solution, whilst ice-cooling. The resulting solution was then stirred at room temperature for 7 days. At the end of this time, precipitates were filtered off from the reaction mixture, and the filtrate was freed from the solvent by distillation under reduced pressure. The resulting residue was dissolved in 10 ml of methylene chloride. 100 ml of diethyl ether were added to the solution, whilst ice-cooling, and the resulting precipitates were filtered off. The filtrate was freed from the solvent by distillation under reduced pressure. The filtrate, 37 mg (0.3 mmol) of 4-(dimethylamino)pyridine and 0.25 g of a p-alkoxybenzyl alcohol resin (having 0.9 mmol of amino groups per 1 g of the silica gel surface; produced by Kokusan Kagaku Co. Ltd.) were added to 6 ml of dimethylformamide. The resulting mixture was left at room temperature for 24 hours. The desired carrier, namely a substituted p-alkoxybenzyl alcohol resin was collected, washed with pyridine, with methylene chloride and with diethyl ether, in that order, and dried by evaporation under reduced pressure. 10 ml each of Cap A and B solutions (Nippon Millipore limited) were added to the carrier, and the mixture was left to stand for 15 minutes. The mixture was then washed with methylene chloride, with methanol and with diethyl ether, in that order, and dried by evaporation under reduced pressure, to give the title compound.

The amount of the compound of Preparation 1 introduced into the title compound was determined according to the following method. A deblock solution (a 3% v/v solution of dichloroacetic acid in methylene chloride, Nippon Millipore Limited) was added to 6.7 mg of the title compound, and the mixture was shaken for 3 minutes, after which sufficient methylene chloride was added to make up a total amount of 20 ml. 0.4 ml of the solvent was removed by distillation under reduced pressure, and then 20 ml of a 3:2 by volume solution of perchloric acid in ethanol were added to the residue, and the absorbance of the dimethoxytrityl cation at 500 nm was measured ($\epsilon$=71700).

The amount of dimethoxytrityl groups introduced was found to be 16 µmol/g

Formulation Example 1

Injection Formulation

An injection formulation was prepared by stirring 1.5% by weight of the compound of Example 25 in 10% by volume of propylene glycol, adding sufficient water for injections to give the required final volume and sterilizing.

Formulation Example 2

Tablet Formulation

| | | |
|---|---|---|
| 1) Compound of Example 25 | | 200 |
| 2) Sodium pyrophosphate | | 5 |
| 3) Aerosil 200 | | 5 |
| 4) Magnesium stearate | | 5 |
| 5) Lactose | | 495 |
| 6) Corn starch | | 154 |
| 7) Apicel | | 123 |
| 8) HPL (L) | | 10 |
| | Total | 997 mg |

Tablets, each containing 100 mg of the ingredients, were prepared by adding a ground mixture of the above Items No. 1 through 4 to a pregranulated mixture of Items No. 5 through 8 and then compressing the mixture produced above on a suitable tabletting machine.

Formulation Example 3

Capsule Formulation

| | | |
|---|---|---|
| 1) Compound of Example 25 | | 200 |
| 2) Calcium phosphate | | 200 |
| 3) Aluminium silicate | | 345 |
| 4) Crystalline cellulose | | 250 |
| 5) Magnesium stearate | | 2 |
| | Total | 997 mg |

According to conventional means, capsules comprising 200 mg of the above ingredients were prepared by pulverizing a mixture of the ingredients in a suitable mixer, passing the mixture through a screen and finally mixing well.

FORMULATION EXAMPLE 4

Hard Capsule Formulation

Unit capsules were prepared by mixing 100 mg of the powdery compound of Example 25, 150 mg of lactose, 50 mg of cellulose and 6 mg of magnesium stearate, filling the above mixture into standard 2-piece hard gelatin capsules, washing and finally drying.

Formulation Example 5

Soft Capsule Formulation

Soft capsules comprising 100 mg of the active ingredient were prepared by mixing the compound of Example 25 in a digestible oil (such as soy bean oil, cottonseed oil or olive oil), filling this mixture into suitable gelatine capsules by means of a motor pump, washing and finally drying.

Formulation Example 6

Tablet Formulation

According to conventional means, tablets were prepared by granulating a mixture of 100 mg of the compound of Example 25, 0.2 mg of colloidal silicon dioxide, 5 mg of magnesium stearate, 275 mg of fine crystalline cellulose, 11 mg of starch and 98.8 mg of lactose.

[Sequence table]

SEQ ID No.: 1
Sequence length: 4
Sequence type: Nucleic acid
Strandedness: Single
Topology: Linear
Hypothetical sequence: No
Anti-sense: No
Sequence: TGGG
SEQ ID No.: 2
Sequence length: 5
Sequence type: Nucleic acid
Strandedness: Single
Topology: Linear
Hypothetical sequence: No
Anti-sense: No
Sequence: TGGGG
SEQ ID No.: 3
Sequence length: 5
Sequence type: Nucleic acid
Strandedness: Single
Topology: Linear
Hypothetical sequence: No Anti-sense: No
Sequence: TGGGA
SEQ ID No.: 4
Sequence length: 6
Sequence type: Nucleic acid
Strandedness: Single
Topology: Linear
Hypothetical sequence: No
Anti-sesce: No
Sequence: TGGGAG
SEQ ID No.: 5
Sequence length: 7
Sequence type: Nucleic acid
Strandedness: Single
Topology: Linear
Hypothetical sequence: No
Anti-sesce: No
Sequence: TGGGAGG
SEQ ID No.: 6
Sequence length: 7
Sequence type: Nucleic acid
Strandedness: Single
Topology: Linear
Hypothetical sequence: No
Anti-sense: No
Sequence: CGGGAGG
SEQ ID No.: 7
Sequence length: 7
Sequence type: Nucleic acid
Strandedness: Single
Topology: Linear
Hypothetical sequence: No
Anti-sense: No
Sequence: TTGGAGG
SEQ ID No.: 8
Sequence length: 7
Sequence type: Nucleic acid
Strandedness: Single
Topology: Linear
Hypothetical sequence: No
Anti-sense: No
Sequence: TGCGAGG
SEQ ID No.: 9
Sequence length: 7
Sequence type: Nucleic acid
Strandedness: Single
Topology: Linear
Hypothetical sequence: No
Anti-sense: No
Sequence: GGGGAGG
SEQ ID No.: 10
Sequence length: 7
Sequence type: Nucleic acid
Strandedness: Single
Topology: Linear
Hypothetical sequence: No
Anti-sense: No
Sequence: mCGGGAGG
SEQ ID No.: 11
Sequence length: 7
Sequence type: Nucleic acid
Strandedness: Single
Topology: Linear
Hypothetical sequence: No
Anti-sense: No
Sequence: mCGmCGAGG
SEQ ID No.: 12
Sequence length: 8
Sequence type: Nucleic acid
Strandedness: Single
Topology: Linear
Hypothetical sequence: No
Anti-sense: No
Sequence: TTGGGAGG
SEQ ID No.: 13
Sequence length: 8
Sequence type: Nucleic acid
Strandedness: Single
Topology: Linear
Hypothetical sequence: No
Anti-sense: No
Sequence: CTGGGAGG
SEQ ID No.: 14
Sequence length: 5
Sequence type: Nucleic acid
Strandedness: Single
Topology: Linear
Hypothetical sequence: No
Anti-sense: No
Sequence: CTCGT
SEQ ID No.: 15
Sequence length: 5
Sequence type: Nucleic acid
Strandedness: Single
Topology: Linear
Hypothetical sequence: No
Anti-sense: No
Sequence: CTCGC
SEQ ID No.: 16
Sequence length: 5
Sequence type: Nucleic acid
Strandedness: Single
Topology: Linear
Hypothetical sequence: No
Anti-sense: No
Sequence: CTCGG
SEQ ID No.: 17
Sequence length: 5
Sequence type: Nucleic acid
Strandedness: Single
Topology: Linear
Hypothetical sequence: No
Anti-sense: No
Sequence: CGGGT
SEQ ID No.: 18
Sequence length: 5
Sequence type: Nucleic acid
Strandedness: Single
Topology: Linear
Hypothetical sequence: No
Anti-sense: No
Sequence: CGGGC
SEQ ID No.: 19
Sequence length: 5
Sequence type: Nucleic acid
Strandedness: Single
Topology: Linear
Hypothetical sequence: No
Anti-sense: No
Sequence: CGGGG
SEQ ID No.: 20
Sequence length: 5
Sequence type: Nucleic acid
Strandedness: Single
Topology: Linear
Hypothetical sequence: No
Anti-sense: No
Sequence: CGOGT
SEQ ID No.: 21
Sequence length: 5
Sequence type: Nucleic acid
Strandedness: Single
Topology: Linear
Hypothetical sequence: No
Anti-sense: No
Sequence: CGCGC
SEQ ID No.: 22
Sequence length: 5
Sequence type: Nucleic acid
Strandedness: Single
Topology: Linear
Hypothetical sequence: No
Anti-sense: No
Sequence: CGCGG
SEQ ID No.: 23
Sequence length: 5

[Sequence table]

Sequence type: Nucleic acid
Strandedness: Single
Topology: Linear
Hypothetical sequence: No
Anti-sense: No
Sequence: TTGGA
SEQ ID No.: 24
Sequence length: 5
Sequence type: Nucleic acid
Strandedness: Single
Topology: Linear
Hypothetical sequence: No
Anti-sense: No
Sequence: TTGGT
SEQ ID No.: 25
Sequence length: 5
Sequence type: Nucleic acid
Strandedness: Single
Topology: Linear
Hypothetical sequence: No
Anti-sense: No
Sequence: TTGGC
SEQ ID No.: 26
Sequence length: 5
Sequence type: Nucleic acid
Strandedness: Single
Topology: Linear
Hypothetical sequence: No
Anti-sense: No
Sequence: TTGGG
SEQ ID No.: 27
Sequence length: 5
Sequence type: Nucleic acid
Strandedness: Single
Topology: Linear
Hypothetical sequence: No
Anti-sense: No
Sequence: TTCGA
SEQ ID No.: 28
Sequence length: 5
Sequence type: Nucleic acid
Strandedness: Single
Topology: Linear
Hypothetical sequence: No
Anti-sense: No
Sequence: TTCGT
SEQ ID No.: 29
Sequence length: 5
Sequence type: Nucleic acid
Strandedness: Single
Topology: Linear
Hypothetical sequence: No
Anti-sense: No
Sequence: TTCGC
SEQ ID No.: 30
Sequence length: 5
Sequence type: Nucleic acid
Strandedness: Single
Topology: Linear
Hypothetical Sequence: No
Anti-sense: No
Sequence: TTCGG
SEQ ID No.: 31
Sequence length: 5
Sequence type: Nucleic acid
Strandedness: Single
Topology: Linear
Hypothetical sequence: No
Anti-sense: No
Sequence: TGGGT
SEQ ID No.: 32
Sequence length: 5
Sequence type: Nucleic acid
Strandedness: Single
Topology: Linear
Hypothetical sequence: No
Anti-sense: No
Sequence: TGGGC

[Sequence table]

SEQ ID No.: 33
Sequence length: 5
Sequence type: Nucleic acid
Strandedness: Single
Topology: Linear
Hypothetical sequence: No
Anti-sense: No
Sequence: TGCGA
SEQ ID No.: 34
Sequence length: 5
Sequence type: Nucleic acid
Strandedness: Single
Topology: Linear
Hypothetical sequence: No
Anti-sense: No
Sequence: TGCGT
SEQ ID No.: 35
Sequence length: 5
Sequence type: Nucleic acid
Strandedness: Single
Topology: Linear
Hypothetical sequence: No
Anti-sense: No
Sequence: TGCGC
SEO ID No.: 36
Sequence length: 5
Sequence type: Nucleic acid
Strandedness: Single
Topology: Linear
Hypothetical sequence: No
Anti-sense: No
Sequence: TGCGG
SEQ ID No.: 37
Sequence length: 5
Sequence type: Nucleic acid
Strandedness: Single
Topology: Linear
Hypothetical sequence: No
Anti-sense: No
Sequence: CTGGT
SEQ ID No.: 38
Sequence length: 5
Sequence type: Nucleic acid
Strandedness: Single
Topology: Linear
Hypothetical sequence: No
Anti-sense: No
Sequence: CTGGC
SEQ ID No.: 39
Sequence length: 4
Sequence type: Nucleic acid
Strandedness: Single
Topology: Linear
Hypothetical sequence: No
Anti-sense: No
Sequence: CTCG
SEQ ID No.: 40
Sequence length: 4
Sequence type: Nucleic acid
Strandedness: Single
Topology: Linear
Hypothetical sequence: No
Anti-sense: No
Sequpnce: TTCG
SEQ ID No.: 41
Sequence length: 4
Sequence type: Nucleic acid
Strandedness: Single
Topology: Linear
Hypothetical sequence: No
Anti-sense: No
Sequence: CTGG
SEQ ID.No.: 42
Sequence length: 4
Sequence type: Nucleic acid
Strandedness: Single
Topology: Linear
Hypothetical sequence: No

[Sequence table]

Anti-sense: No
Sequence: CGCG
SEQ ID No.: 43
Sequence length: 4
Sequence type: Nucleic acid
Strandedness: Single
Topology: Linear
Hypothetical sequence: No
Anti-sense: No
Sequence: TGCG
SEQ ID No.: 44
Sequence length: 4
Sequence type: Nucleic acid
Strandedness: Single
Topology: Linear
Hypothetical sequence: No
Anti-sense: No
Sequence: CGGG
SEQ ID No.: 45
Sequence length: 4
Sequence type: Nucleic acid
Strandedness: Single
Topology: Linear
Hypothetical sequence: No
Anti-sense: No
Sequence: TTGG
SEQ ID No.: 46
Sequence length: 9
Sequence type: Nucleic acid
Strandedness: Single
Topology: Linear
Hypothetical sequence: No
Anti-sense: No
Sequence: GGGCGGGGC
SEQ ID No.: 47
Sequence length: 7
Sequence type: Nucleic acid
Strandedness: Single
Topology: Linear
Hypothetical sequence: No
Anti-sense: No
Sequence: TAGGAGG
SEQ ID No.: 48
Sequence length: 8
Sequence type: Nucleic acid
Strandedness: Single
Topology: Linear
Hypothetical sequence: No
Anti-sense: No
Sequence: TGGGAGGT
SEQ ID No.: 49
Sequence length: 9
Sequence type: Nucleic acid
Strandedness: Single
Topology: Linear
Hypothetical sequence: No
Anti-sense: No
Sequence: TGGGCGCAG
SEQ ID No.: 50
Sequence length: 3
Sequence type: Nucleic acid
Strandedness: Single
Topology: Linear
Hypothetical sequence: No
Anti-sense: No
Sequence: CCG
SEQ ID No.: 51
Sequence length: 7
Sequence type: Nucleic acid
Strandedness: Single
Topology: Linear
Hypothetical sequence: No
Anti-sense: No
Sequence: TCGGAGG
SEQ ID No.: 52
Sequence length: 7
Sequence type: Nucleic acid
Strandedness: Single

[Sequence table]

Topology: Linear
Hypothetical sequence: No
Anti-sense: No
Sequence: TGmCGAGG
SEQ ID No.: 53
Sequence length: 8
Sequence type: Nucleic acid
Strandedness: Single
Topology: Linear
Hypothetical sequence: No
Anti-sense: No
Sequence: GTGGGAGG
SEQ ID No.: 54
Sequence length: 3
Sequence type: Nucleic acid
Strandedness: Single
Topology: Linear
Hypothetical sequence: No
Anti-sense: No
Sequence: TGG
SEQ ID No.: 55
Sequence length: 7
Sequence type: Nucleic acid
Strandedness: Single
Topology: Linear
Hypothetical sequence: No
Anti-sense: No
Sequence: TGGGAMGG
SEQ ID No.: 56
Sequence length: 7
Sequence type: Nucleic acid
Strandedness: Single
Topology: Linear
Hypothetical sequence: No
Anti-sense: No
Sequence: TGGGAGA
SEQ ID No.: 57
Sequence length: 9
Sequence type: Nucleic acid
Strandedness: Single
Topology: Linear
Hypothetical sequence: No
Anti-sense: No
Sequence: AATGGGAGG

We claim:

1. A compound of the formula (1):

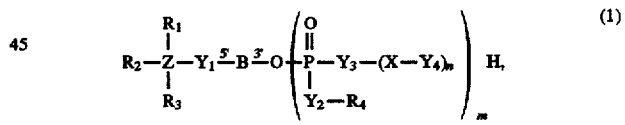

wherein the group of formula $R_1R_2R_3Z\text{-}Y_1$ is selected from the group consisting of a triphenylmethyloxy, 3,4-(dibenzyloxy)benzyloxy, 3,5-(dibenzyloxy)benzyloxy, 3,5-bis(3,5-(dibenzyloxy)benzyloxy)benzyloxy, tert-butyldiphenylsilyloxy, phenylfluorenyloxy and phenylxanthenyloxy group; the group of formula $(P(O)(Y_2R_4)\text{-}Y_3\text{-}(X\text{-}Y_4)_n)_mH$ is selected from the group consisting of a hydrogen atom, a methylphosphoryl, 2-chlorophenylphosphoryl, —O-methylthiophosphoryl, methylphosphonyl, methylthiophosphonyl, phenylphosphonyl, 2-hydroxyethylphosphoryl, —O-(2-hydroxyethyl)thiophosphoryl, phenylphosphoryl, 4-chlorophenylphosphoryl, 2-nitrophenylphosphoryl, 4-nitrophenylphosphoryl, ethylphosphoryl and —O-ethylthiophosphoryl group; and B is selected from the group consisting of TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, GGGCGGGGC, TAGGAGG, TGGGAGGT, TGGGCGCAG, CCG, TCGGAGG, TGmCGAGG, CTGGGAGG, TGG, TGGGAmGG, TGGGAGA, AATGGGAGG, TTGGGG, TGGGGG, CGGGG, CGCGG, CGGGT, TGGGC and TGGGT, wherein mC is 5-methylcytosinedeoxyribonucleotide; and mG is $O^6$-methylguaninedeoxyribonucleotide wherein said compound has the ability to inhibit replication of foreign nucleic acids normal cells.

2. The compounds of claim 1, wherein the oligodeoxyribonucleotide B has a chain length of 4 to 8.

3. The compounds of claim 2, wherein the oligodeoxyribonucleotide B has a chain length of 5 or 6.

4. The compound of claim 1, wherein the group of formula $R_1R_2R_3Z-Y_1$ is selected from the group consisting of a triphenylmethyloxy, 3,4-(dibenzyloxy)benzyloxy and 3,5-(dibenzyloxy)benzyloxy group; the group of formula $[P(O)(Y_2R_4)-Y_3-(X-Y_4)_n]_mH$ is selected from the group consisting of a hydrogen atom, a methylphosphoryl, 2-chlorophenylphosphoryl, —O-methylthiophosphoryl, methylphosphonyl, methylthiophosphonyl, phenylphosphonyl, 2-hydroxyethylphosphoryl and —O-(2-hydroxyethyl)thiophosphoryl group; and B is selected from the group consisting of TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, TTGGGG, TGGGGG, CGGGG and CGCGG.

5. The compound of claim 1, wherein the group of formula $R_1R_2R_3Z-Y_1$ represents a 3,4-(dibenzyloxy) benzyloxy group; and B represents TGGGAG.

6. The compound of claim 1, wherein the group of formula $R_1R_2R_3Z-Y_1$ represents a 3,4-(dibenzyloxy) benzyloxy group; and B represents TGGGAG.

7. The compound of claim 1, wherein the group of formula $R_1R_2R_3Z-Y_1$ represents a 3,4-(dibenzyloxy) benzyloxy group; and B represents TGGGAG.

8. The compound of claim 1, wherein the group of formula $R_1R_2R_3Z-Y_1$ represents a 3,4-(dibenzyloxy) benzyloxy group; and B represents TGGGAG.

9. The compound of claim 1, wherein the group of formula $R_1R_2R_3Z-Y_1$ represents a triphenylmethyloxy group; and B represents TGGGAG.

10. The compound of claim 1, wherein the group of formula $R_1R_2R_3Z-Y_1$ represents a trimethylphenyloxy group; and B represents TGGGAG.

11. The compound of claim 1, wherein the group of formula $R_1R_2R_3Z-Y_1$ represents a trimethylphenyloxy group; and B represents TGGGAG.

12. The compound of claim 1, wherein the group of formula $R_1R_2R_3Z-Y_1$ represents a trimethylphenyloxy group; and B represents TGGGAG.

13. The compound of claim 1, wherein the group of formula $R_{R2}R_3Z-Y_1$ represents a 3,4-(dibenzyloxy) benzyloxy group; and B represents CGGGG.

14. The compound of claim 1, wherein the group of formula $R_1R_2R_3Z-Y_1$ represents a 3,4-(dibenzyloxy) benzyloxy group; and B represents CGGGG.

15. The compound of claim 1, wherein the group of formula $R_1R_2R_3Z-Y_1$ represents a 3,4-(dibenzyloxy) benzyloxy group; and B represents CGGGG.

16. The compound of claim 1, wherein the group of formula $R_1R_2R_3Z-Y_1$ represents a 3,4-(dibenzyloxy) benzyloxy group; and B represents CGGGG.

17. The compound of claim 1, wherein the group of formula $R_1R_2R_3Z-Y_1$ represents a triphenylmethyloxy group; and B represents CGGGG.

18. The compound of claim 1, wherein the group of formula $R_1R_2R_3Z-Y_1$ represents a trimethylphenyloxy group; and B represents CGGGG.

19. The compound of claim 1, wherein the group of formula $R_1R_2R_3Z-Y_1$ represents a trimethylphenyloxy group; and B represents CGGGG.

20. The compound of claim 1, wherein the group of formula $R_1R_2R_3Z-Y_1$ represents a trimethylphenyloxy group; and B represents CGGGG.

21. The compound of claim 1, wherein the group of formula $R_1R_2R_3Z-Y_1$ represents a 3,4-(dibenzyloxy) benzyloxy group; and B represents CGCGG.

22. The compound of claim 1, wherein the group of formula $R_1R_2R_3Z-Y_1$ represents a 3,4-(dibenzyloxy) benzyloxy group; and B represents CGCGG.

23. The compound of claim 1, wherein the group of formula $R_1R_2R_3Z-Y_1$ represents a 3,4-(dibenzyloxy) benzyloxy group; and B represents CGCGG.

24. The compound of claim 1, wherein the group of formula $R_1R_2R_3Z-Y_1$ represents a 3,4-(dibenzyloxy) benzyloxy group; and B represents CGCGG.

25. The compound of claim 1, wherein the group of formula $R_1R_2R_3Z-Y_1$ represents a triphenylmethyloxy group; and B represents CGCGG.

26. The compound of claim 1, wherein the group of formula $R_1R_2R_3Z-Y_1$ represents a trimethylphenyloxy group; and B represents CGCGG.

27. The compound of claim 1, wherein the group of formula $R_1R_2R_3Z-Y_1$ represents a trimethylphenyloxy group; and B represents CGCGG.

28. The compound of claim 1, wherein the group of formula $R_1R_2R_3Z-Y_1$ represents a trimethylphenyloxy group; and B represents CGCGG.

29. The compound of claim 1, wherein B is selected from group consisting of TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, TTGGGG, TGGGGG, CGGGG and CGCGG.

30. The compound of claim 1, wherein the group of formula $(P(O)(Y_2R_4)-Y_3-(X-Y_4)_n)_mH$ is selected from the group consisting of a hydrogen atom, a methylphosphoryl, 2-chlorophenylphosphoryl, —O-methylthiophosphoryl, methylphosphonyl, methylthiophosphonyl, phenylphosphonyl, 2-hydroxyethylphosphoryl, —O-(2-hydroxyethyl) thiophosphoryl group; and B is selected from the group consisting of TGGGAG, TGGGA, TGGGG, TGGG, TGGGAGG, CGGGAGG, TTGGAGG, TTGGGAGG, TGCGAGG, GGGGAGG, mCGGGAGG, mCGmCGAGG, CTGGGAGG, TTGGGG, TGGGGG, CGGGG and CGCGG.

31. The compound of claim 1, wherein the group of formula $R_1R_2R_3Z-Y_1$ is selected from the group consisting of a triphenylmethyloxy, 3,4-(dibenzyloxy)benzyloxy and 3,5-(dibenzyloxy)benzyloxy group; and B is selected from the group consisting of TGGGAG, TGGGA, TGGGG, TGGG, TGGGAGG, CGGGAGG, TTGGAGG, TTGGGAGG TGCGAGG, GGGGAGG, mCGGGAGG, mCGmCGAGG, CTGGGAGG, TTGGGG, TGGGGG, CGGGG and CGCGG.

32. The compound of claim 1, wherein the group of formula $R_1R_2R_3Z-Y_1$ is a tert-butyldiphenylsilyloxy group and B is TGGGAG.

* * * * *

UNITED STATES PATENT AND TRADEMARK OFFICE
CERTIFICATE OF CORRECTION

PATENT NO. : 5,674,856       Page 1 of 2
DATED : October 7, 1997
INVENTOR(S) : Hidehiko FURUKAWA ET AL.

It is certified that error appears in the above-indentified patent and that said Letters Patent is hereby corrected as shown below:

Title Page: Item [56] "References Cited", under "FOREIGN PATENT DOCUMENTS", after "WO92/08729  5/1992", replace "Japan" with --WIPO--.

Title Page: Item [56] "References Cited", under "OTHER PUBLICATIONS", line 2, replace "phite    esters: Synthesis    of" with --phite esters: Synthesis of--.

Title Page: Item [56] "References Cited", under "OTHER PUBLICATIONS", COLUMN 2, Paragraph No. 6 from the top, replace "Taunton-Riby" with --Taunton-Rigby--.

UNITED STATES PATENT AND TRADEMARK OFFICE
CERTIFICATE OF CORRECTION

PATENT NO. : 5,674,856
DATED : October 7, 1997
INVENTOR(S) : Hidehiko FURUKAWA ET AL.

It is certified that error appears in the above-identified patent and that said Letters Patent is hereby corrected as shown below:

Column 211, line 8 (Claim 1, last line),
after "acids" insert --in--.

Columns 211 and 212 (Claims 10, 11, 12, 18, 19, 20, 26, 27 and 28,
line 2 of each of said claims, replace "trimethylphenyloxy" with --triphenylmethyloxy--.

Signed and Sealed this

Tenth Day of March, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,674,856
DATED : October 7, 1997
INVENTOR(S) : FURUKAWA et al

It is certified that error appears in the above-indentified patent and that said Letters Patent is hereby corrected as shown below:

Column 137, line 8: Replace "(2)" with --2(b)--.

Column 161, line 16: Replace "2(b)" with --22(b)--.

Column 211, line 9 (Claim 2): replace "compounds" with --compound--.

Column 211, line 11 (Claim 3): replace "compounds" with --compound--.

Signed and Sealed this

Twenty-eighth Day of July, 1998

Attest:

BRUCE LEHMAN

*Attesting Officer*  *Commissioner of Patents and Trademarks*